(12) United States Patent
Liao et al.

(10) Patent No.: US 8,298,798 B2
(45) Date of Patent: Oct. 30, 2012

(54) PRODUCTION OF C5-C8 ALCOHOLS USING EVOLVED ENZYMES AND METABOLICALLY ENGINEERED MICROORGANISMS

(75) Inventors: James C. Liao, Los Angeles, CA (US); Kechun Zhang, Minneapolis, MN (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/089,164

(22) Filed: Apr. 18, 2011

(65) Prior Publication Data

US 2011/0201083 A1 Aug. 18, 2011

Related U.S. Application Data

(63) Continuation of application No. PCT/US2009/061116, filed on Oct. 18, 2009.

(60) Provisional application No. 61/119,308, filed on Dec. 2, 2008, provisional application No. 61/106,564, filed on Oct. 18, 2008, provisional application No. 61/106,563, filed on Oct. 18, 2008, provisional application No. 61/106,562, filed on Oct. 18, 2008, provisional application No. 61/106,561, filed on Oct. 18, 2008.

(51) Int. Cl.
*C12N 9/88* (2006.01)

(52) U.S. Cl. ........................................ 435/193

(58) Field of Classification Search .................... 435/193
See application file for complete search history.

(56) References Cited

U.S. PATENT DOCUMENTS

| 6,403,342 B1 * | 6/2002 | Gusyatiner et al. ........... 435/116 |
| 2003/0167513 A1 | 9/2003 | Mourad |

FOREIGN PATENT DOCUMENTS

| JP | 2005-296010 A | 10/2005 |
| WO | 2008/098227 A2 | 8/2008 |

OTHER PUBLICATIONS

"Alpha-Ketoisovalerate Decarboxylase [*Lactococcus lactis* subsp. *lactis*]," GenBank Accession No. CAG34226, Apr. 15, 2005, 2 pages.
International Preliminary Report on Patentability, issued Apr. 19, 2011, with Written Opinion, completed Jun. 28, 2010, in corresponding International Application No. PCT/US2009/061116, filed Oct. 18, 2009, 6 pages.
International Search Report mailed Jun. 28, 2010, issued in corresponding International Application No. PCT/US2009/061116, filed Oct. 18, 2009, 4 pages.
"2-Isopropylmalate Synthase" [*Escherichia coli* O157:H7 str. EC4113], NCBI Reference Sequence ZP_02776439.1, May 13, 2008, 2 pages.

* cited by examiner

*Primary Examiner* — Tekchand Saidha
(74) *Attorney, Agent, or Firm* — Christensen O'Connor Johnson Kindness PLLC

(57) ABSTRACT

Provided herein are metabolically-modified microorganisms useful for producing biofuels. More specifically, provided herein are methods of producing higher alcohols including C5-C8 alcohol from a suitable substrate.

2 Claims, 18 Drawing Sheets

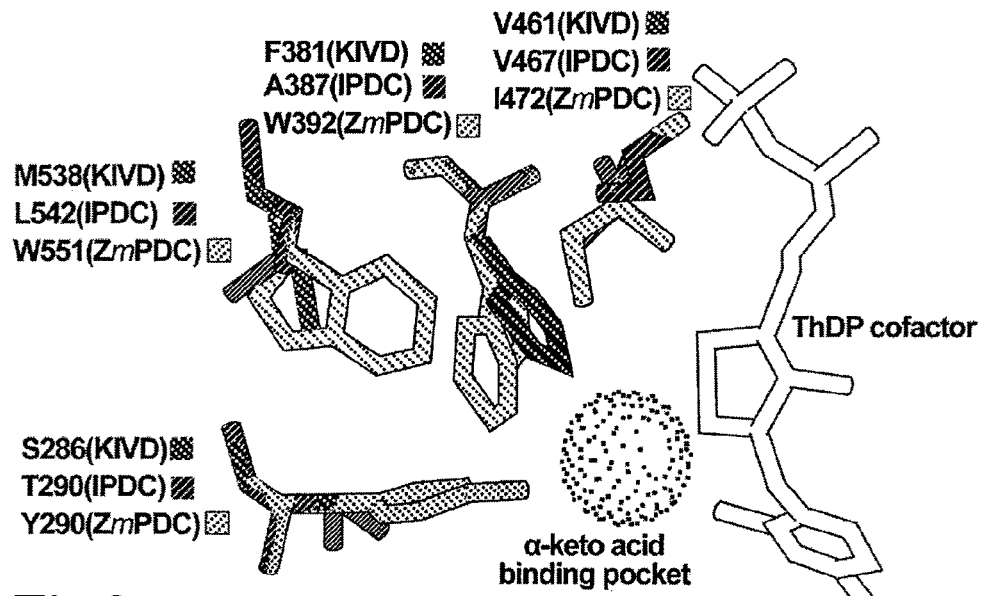
*Fig.2.*
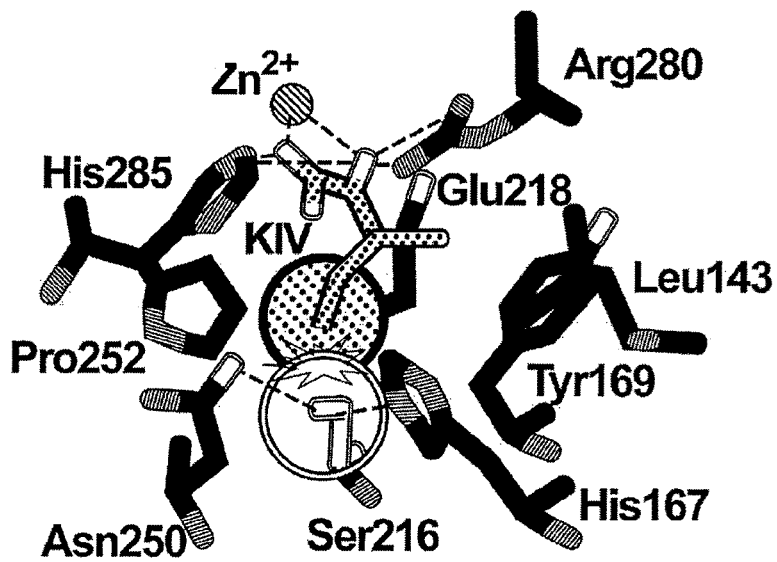
*Fig.3A.*
|  | His97 | Ser139 | Asn167 |
|---|---|---|---|
| E. coli | RIHTFIATS | DVEFSCE | INIPDTV |
| S. typhimurium | RIHTFIATS | DVEFSCE | INIPDTV |
| M. tuberculosis | IVHFYNSTS | RFEYSPE | FNLPATV |
|  | His167 | Ser216 | Asn250 |
*Fig.3B.*

**kivd   alpha ketoisovalarate decarboxylase (*Lactococcus lactis*)**

```
atgtatacagtaggagattacctattagaccgattacacgagttaggaattgaagaaattttggagtccct
ggagactataacttacaattttagatcaaattatttcccgcaaggatatgaaatgggtcggaaatgctaat
gaattaaatgcttcttatatggctgatggctatgctcgtactaaaaaagctgccgcatttcttacaacctt
ggagtaggtgaattgagtgcagttaatggattagcaggaagttacgccgaaaatttaccagtagtagaata
gtgggatcacctacatcaaaagtccaaaatgaaggaaaatttgttcatcatacgctggctgacggtgatttt
aaacactttatgaaaatgcacgaacctgttacagcagctcgaacttactgacagcagaaaatgcaaccgtt
gaaattgaccgagtactttctgcactactaaaagaaagaaacctgtctatatcaacttaccagttgatgtt
gctgctgcaaaagcagagaaacccctcactcccttttgaaaaaagaaaatccaacttcaaatacaagtgaccaa
gagatttgaataaaattcaagaaagcttgaaaaatgccaaaaaaccaatcgtgattacaggacatgaaata
attagctttggcttagaaaatacagtcactcaatttatttcaaagacaaaactccctattacgacattaaac
tttggaaaaagttcagttgatgaaactctcccttcatttttaggaatctataatggtaaactctcagagcct
aatcttaaagaattcgtggaatcagccgacttcatcctgatgcttggagttaaactcacagactcttcaaca
ggagcatttacccatcatttaaatgaaaataaaatgatttcactgaacatagacgaaggaaaaatatttaac
gaaagcatccaaaattttgattttgaatccctcatctcctctctcttagacctaagcggaatagaatacaaa
ggaaaatatatcgataaaaagcaagaagactttgttccatcaaatgcgcttttatcacaagaccgcctatgg
caagcagttgaaaacctaactcaaagcaatgaaacaatcgttgctgaacaagggacatcattctttggcgct
tcatcaattttcttaaaaccaaagagtcatttttattggtcaacccttatggggatcaattggatatacattc
ccagcagcattaggaagccaaattgcagataaagaaagcagacaccttttatttattggtgatggttcactt
caacttacagtgcaagaattaggattagcaatcagagaaaaaattaatccaatttgctttattatcaataat
gatggttatacagtcgaaagagaaattcatggaccaaatcaaagctacaatgatattccaatgtggaattac
tcaaaattaccagaatcatttggagcaacagaagaacgagtagtctcgaaaatcgttagaactgaaaatgaa
tttgtgtctgtcatgaagaagctcaagcagatccaaatagaatgtactggattgagttagttttggcaaaa
gaagatgcaccaaaagtactgaaaaaaatgggtaaactatttgctgaacaaaataaatcataa
```

**PDC6   (*Saccharomyces cerevisiae*)**

```
atgtctgaaattactcttggaaaatacttatttgaaagattgaagcaagttaatgttaacaccattttgggcta
ccaggcgacttcaacttgtccctattggacaagatttacgaggtagatggattgagatgggctggtaatgcaaat
gagctgaacgccgcctatgccgccgatggttacgcacgcatcaaggggttttatctgtgctggtaactactttggc
gtaggtgaattatccgccttgaatggtattgcaggatcgtatgcagaacacgtcggtgtactgcatgttgttggt
gtcccctctatctccgctcaggctaagcaattgttgttgcatcataccttgggtaacggtgattttaccgtttt
cacagaatgtccgccaatatctcagaaactacatcaatgattacagacattgctacagcccttcagaaatcgat
aggttgatcaggacaacatttataacacaaaaggcctagctacttggggttgccagcgaatttggtagatctaaag
gttcctggttctcttttggaaaaaccgattgatctatcattaaaacctaacgatcccgaagctgaaaaggaagtt
attgataccgtactagaattgatccagaattcgaaaaaccctgttatactatcggatgcctgtgcttctaggcac
aacgttaaaaaagaaacccagaagttaattgatttgacgcaattcccagcttttgtgacacctctaggtaaaggg
tcaatagatgaacagcatccagatatggcggtgtttatgtgggaacgctgtccaaacaagacgtgaaacaggcc
gttgagtcggctgatttgatcctttcggtcggtgctttgctctctgattttaacacaggttcgttttcctactcc
tacaagactaaaaatgtagtggagtttcattccgattacgtaaaggtgaagaacgctacgttcctcggtgtacaa
atgaaatttgcactacaaaacttactgaaggttattcccgatgttgttaagggctacaagagcgttcccgtacca
accaaaaactcccgcaaacaaaggtgtacctgctagcacgcccttgaaacaagagtggttgtggaacgaattgtcc
aaattcttgcaagaaggtgatgttatcatttccgagaccggcacgtctgccttcggtatcaatcaaactatcttt
cctaaggacgcctacggtatctcgcaggtgttgtgggggtccatcggttttacaacaggagcaactttaggtgct
gcctttgccgctgaggagattgaccccaacaagagagtcatcttattcatggtgacgggtctttgcagttaacc
gtccaagaaatctccaccatgatcagatgggggttaaagccgtatcttttgtccttaacaacgacggctacact
atcgaaaagctgattcatgggcctcacgcagagtacaacgaaatccagacctgggatcacctcgcctgttgccc
gcatttggtgcgaaaaagtacgaaaatcacaagatcgccactacgggtgagtgggatgccttaaccactgattca
gagttccagaaaaactcggtgatcagactaattgaactgaaactgcccgtctttgatgctccggaaagtttgatc
aaacaagcgcaattgactgc cgctacaaatgccaaacaataa
```

*Fig. 5.*

*ARO10 (Saccharomyces cerevisiae)*
atggcacctgttacaattgaaaagttcgtaaatcaagaagaacgacaccttgtttccaaccgatcagcaacaatt
ccgtttggtgaatacatatttaaaagattgttgtccatcgatacgaaatcagttttcggtgttcctggtgacttc
aacttatctctattagaatatctctattcacctagtgttgaatcagctggcctaagatgggtcggcacgtgtaat
gaactgaacgccgcttatgcggccgacggatattcccgttactctaataagattggctgtttaataaccacgtat
ggcgttggtgaattaagcgccttgaacggtatagccggttcgttcgctgaaaatgtcaaagtttttgcacattgtt
ggtgtggccaagtccatagattcgcgttcaagtaactttagtgatcggaacctacatcatttggtcccacagcta
catgattcaaattttaaaggggccaaatcataaagtatatcatgatatggtaaaagatagagtcgcttgctcggta
gcctacttggaggatattgaaactgcatgtgaccaagtcgataatgttatccgcgatatttacaagtattctaaa
cctggttatatttttgttcctgcagattttgcggatatgtctgttacatgtgataatttggttaatgttccacgt
atatctcaacaagattgtatagtataccttctgaaaaccaattgtctgacataatcaacaagattactagttgg
atatattccagtaaaacacctgcgatccttggagacgtactgactgataggtatggtgtgagtaacttttttgaac
aagcttatctgcaaaactgggatttggaattttttccactgttatgggaaaatctgtaattgatgagtcaaaccca
acttatatgggtcaatataatggtaaagaaggtttaaaacaagtctatgaacattttgaactgtgcgacttggtc
ttgcattttggagtcgacatcaatgaaattaataatgggcattatactttttacttataaaccaaatgctaaaatc
attcaatttcatccgaattatattcgccttgtggacactaggcagggcaatgagcaaatgttcaaaggaatcaat
tttgcccctattttaaaagaactatacaagcgcattgacgtttctaaactttctttgcaatatgattcaaatgta
actcaatatacgaacgaaacaatgcggttagaagatcctaccaatggacaatcaagcattattacacaagttcac
ttacaaaagacgatgcctaaattttgaaccctggtgatgttgtcgtttgtgaaacaggctcttttcaattctct
gttcgtgatttcgcgtttccttcgcaattaaaatatatatcgcaaggattttcctttccattggcatggccctt
cctgccgccctaggtgttggaattgccatgcaagaccactcaaacgctcacatcaatggtggcaacgtaaaagag
gactataagccaagattaattttgtttgaaggtgacggtgcagcacagatgacaatccaagaactgagcaccatt
ctgaagtgcaatattccactagaagttatcatttggaacaataacggctacactattgaaagagccatcatgggc
cctaccaggtcgtataacgacgttatgtcttggaaatggaccaaactatttgaagcattcggagacttcgacgga
aagtatactaatagcactctcattcaatgtccctctaaattagcactgaaattggaggagcttaagaattcaaac
aaaagaagcgggatagaacttttagaagtcaaattaggcgaattggatttccccgaacagctaaagtgcatggtt
gaagcagcggcacttaaaagaaataaaaaatag

*THI3 (Saccharomyces cerevisiae)*
atgaattctagctatacacagagatatgcactgccgaagtgtatagcaatatcagattatcttttccatcggctc
aaccagctgaacatacataccatatttggactctccggagaatttagcatgccgcgttgctggataaactatacaac
attccgaacttacgatgggccggtaattctaatgagttaaatgctgcctacgcagcagatggatactcacgacta
aaaggcttgggatgtctcataacaacctttggtgtaggcgaattatcggcaatcaatggcgtggccggatcttac
gctgaacatgtaggaatacttcacatagtgggtatgccgccaacaagtgcacaaacgaaacaactactactgcat
catactctgggcaatggtgatttcacggtatttcatagaatagccagtgatgtagcatgctatacaacattgatt
attgactctgaattatgtgccgacgaagtcgataagtgcatcaaaaaggcttggatagaacagaggccagtatac
atgggcatgcctgtcaaccaggtaaatctcccgattgaatcagcaaggcttaatacacctctggatttacaattg
cataaaaacgacccagacgtagagaaagaagttatttctcgaatattgagttttatatacaaaagccagaatccg
gcaatcatcgtagatgcatgtactagtcgacagaattttaatcgaggagactaaagagctttgtaataggcttaaa
tttccagttttttgttacacctatgggtaagggtacagtaaacgaaacagaccccgcaatttgggggcgtattcacg
ggctcgatatcagccccagaagtaagagaagtagttgattttgccgatttttatcatcgtcattggttgcatgctc
tccgaattcagcacgtcaactttccacttccaatataaaactaagaattgtgcgctactatattctacatctgtg
aaattgaaaaatgccacatatcctgacttgagcattaaattactactacagaaaatattagcaaatcttgatgaa
tctaaactgtcttaccaaccaagcgaacaacccagtatgatggttccaagaccttacccagcaggaaatgtcctc
ttgagacaagaatgggtctgtaatgaaatatcccattggttccaaccaggtgacataatcataacagaaactgt
gcttctgcatttggagttaaccagaccagatttccggtaaatacactaggtatttcgcaagctctttggggatct
gtcggatatacaatgggggcgtgtcttgggcagaatttgctgttcaagagataaacaaggataaattccccgca
actaaacatagagttattctgtttatggtgacggtgctttccaattgacagttcaagaattatccacaattgtt
aagtggggattgacaccttatattttgtgatgaataaccaaggttactctgtggacaggttttgcatcacagg
tcagatgctagttattacgatatccaaccttggaactacttgggattattgcgagtatttggttgcacgaactac
gaaacgaaaaaattattactgttggagaattcagatccatgatcagtgacccaaactttgcgaccaatgacaaa
attcggatgatagagattatgctaccaccaagggatgttccacaggctctgcttgacaggtgggtggtagaaaaa
gaacagagcaaacaagtgcaagaggagaacgaaaattctagcgcagtaaatacgccaactccagaattccaacca
cttctaaaaaaaaatcaagttggatactga

*Fig.6.*

*pdc (Clostridium acetobutylicum)*
ttgaagagtgaatacacaattggaagatatttgttagaccgtttatcagagtttgggtattcggcatatctttggt
gtacctggagattacaatctatccttttagactatataatggagtacaaagggatagattgggttggaaattgc
aatgaattgaatgctgggtatgctgctgatggatatgcaagaataaatggaattggagccatacttacaacattt
ggtgttggagaattaagtgccattaacgcaattgctggggcatacgctgagcaagttccagttgttaaaattaca
ggtatccccacagcaaaagttagggacaatggattatatgtacaccacacattaggtgacggaaggtttgatcac
ttttttgaaatgtttagagaagtaacagttgctgaggcattactaagcgaagaaaatgcagcacaagaaattgat
cgtgttcttatttcatgctggagacaaaaacgtcctgttcttataaatttaccgattgatgtatatgataaacca
attaacaaaccattaaagccattactcgattatactatttcaagtaacaaagaggctgcatgtgaatttgttaca
gaaatagtacctataataaatagggcaaaaaagcctgttattcttgcagattatggagtatatcgttaccaagtt
caacatgtgcttaaaaacttggccgaaaaaaccggatttcctgtggctacactaagtatgggaaaaggtgttttc
aatgaagcacaccctcaatttattggtgtttataatggtgatgtaagttctccttatttaaggcagcgagttgat
gaagcagactgcattattagcgttggtgtaaaattgacggattcaaccacagggggatttttctcatggattttct
aaaaggaatgtaattcacattgatcctttttcaataaaggcaaaaggtaaaaaatatgcacctattacgatgaaa
gatgctttaacagaattaacaagtaaaattgagcatagaaactttgaggatttagatataaagccttacaaatca
gataatcaaaagtattttgcaaaagagaagccaattacacaaaaacgttttttttgagcgtattgctcactttata
aaagaaaaagatgtattattagcagaacagggtacatgctttttttggtgcgtcaaccatacaactacccaaagat
gcaacttttattggtcaacctttatggggatctattggatacacacttcctgctttattaggttcacaattagct
gatcaaaaaggcgtaatattcttttaattggggatggtgcatttcaaatgacagcacaagaaatttcaacaatg
cttcgtttacaaatcaaacctattatttttttaattaataacgatggttatacaattgaacgtgctattcatggt
agagaacaagtatataacaatattcaaatgtggcgatatcataatgttccaaaggttttaggtcctaaagaatgc
agcttaacctttaaagtacaaagtgaaactgaacttgaaaaggctcttttagtggcagataaggattgtgaacat
ttgatttttatagaagttgttatggatcgttatgataaacccgagcctttagaacgtctttcgaaacgttttgca
aatcaaaataattag

*ADH2: alchohol dehydrogenase (Saccharomyces cerevisiae)*
atgccttcgcaagtcattcctgaaaaacaaaaggctattgtcttttatgagacagatggaaaattggaatataaa
gacgtcacagttccggaacctaagcctaacgaaattttagtccacgttaaatattctggtgtttgtcatagtgac
ttgcacgcgtggcacggtgattggccatttcaattgaaatttccattaatcggtggtcacgaaggtgctggtgtt
gttgttaagttgggatctaacgttaagggctggaaagtcggtgattttgcaggtataaaatggttgaatgggact
tgcatgtcctgtgaatattgtgaagtaggtaatgaatctcaatgtccttatttggatggtactggcttcacacat
gatggtacttttcaagaatacgcaactgccgatgccgttcaagctgcccatattccaccaaacgtcaatcttgct
gaagttgccccaatcttgtgtgcaggtatcactgtttataaggcgttgaaaagagccaatgtgataccaggccaa
tgggtcactatatccggtgcatgcggtggcttgggttctctggcaatccaatacgcccttgctatgggttacagg
gtcattggtatcgatggtggtaatgccaagcgaaagttatttgaacaattaggcggagaaatattcatcgatttc
acggaagaaaaagacattgttggtgctataaataaggccactaatggcggttctcatgagttattaatgtgtct
gtttctgaagcagctatcgaggcttctacgaggtattgtaggcccaatggtactgtcgtcctggttggtatgcca
gctcatgcttactgcaattccgatgttttcaatcaagttgtaaaatcaatctccatcgttggatcttgtgttgga
aatagagctgatacaagggaggctttagatttcttcgccagaggtttgatcaaatctccgatccacttagctggc
ctatcggatgttcctgaaatttttgcaaagatggagaagggtgaaattgttggtagatatgttgttgagacttct
aaatga

*Fig. 7.*

*ilvI (E. coli)*
atggagatgttgtctggagccgagatggtcgtccgatcgcttatcgatcagggcgttaaacaagtattcggttat
cccggaggcgcagtccttgatatttatgatgcattgcataccgtgggtggtattgatcatgtattagttcgtcat
gagcaggcggcggtgcatatggccgatggcctggcgcgcgcgaccggggaagtcggcgtcgtgctggtaacgtcg
ggtccaggggcgaccaatgcgattactggcatcgccaccgcttatatggattccattccattagttgtcctttcc
gggcaggtagcgaccctcgttgataggttacgatgcctttcaggagtgcgacatggtggggattcgcgaccggtg
gttaaacacagttttctggttaagcaaacggaagacattccgcaggtgctgaaaaaggctttctggctggcggca
agtggtcgcccaggaccagtagtcgttgatttaccgaaagatattcttaatccggcgaacaaattaccctatgtc
tggccggagtcggtcagtatgcgttcttacaatcccactactaccggacataaagggcaaattaagcgtgctctg
caaacgctggtagcggcaaaaaaaccggttgtctacgtaggcggtggggcaatcacggcgggctgccatcagcag
ttgaaagaaacggtggaggcgttgaatctgcccgttgtttgctcattgatggggctggggcgtttccggcaacg
catcgtcaggcactgggcatgctgggaatgcacggtacctacgaagccaatatgacgatgcataacgcggatgtg
atttttcgccgtcggggtacgatttgatgaccgaacgacgaacaatctggcaaagtactgcccaaatgccactgtt
ctgcatatcgatattgatcctacttccatttctaaaaccgtgactgcggatatcccgattgtggggatgctcgc
caggtcctcgaacaaatgcttgaactcttgtcgcaagaatccgcccatcaaccactggatgagatccgcgactgg
tggcagcaaattgaacagtggcgcgctcgtcagtgcctgaaatatgacactcacagtgaaagattaaaccgcag
gcggtgatcgagactctttggcggttgacgaaggggagacgcttacgtgacgtccgatgtcgggcagcaccagatg
tttgctgcactttattatccattcgacaaaccgcgtcgctggatcaattccggtggcctcggcacgatgggttt
ggtttacctgcggcactgggcgtcaaaatggcgttgccagaagaaaccgtggtttgcgtcactggcgacggcagt
attcagatgaacatccaggaactgtctaccgcgttgcaatacgagttgccgtactggtggtgaatctcaataac
cgctatctggggatggtgaagcagtggcaggacatgatctattccggccgtcattcacaatcttatatgcaatcg
ctacccgatttcgtccgtctggcggaagcctatgggcatgtcgggatccagatttctcatccgcatgagctggaa
agcaaacttagcgaggcgctggaacaggtgcgcaataatcgcctggtgtttgttgatgttaccgtcgatggcagc
gagcacgtctacccgatgcagattcgcgggggcggaatggatgaaatgtggttaagcaaaacggagagaacctga

*ilvH (E. coli)*
atgcgccggatattatcagtcttactcgaaaatgaatcaggcgcgttatcccgcgtgattggccttttttcccag
cgtggctacaacattgaaagcctgaccgttgcgccaaccgacgatccgacattatcgcgtatgaccatccagacc
gtgggcgatgaaaaagtacttgagcagatcgaaaagcaattacacaaactggtcgatgtcttgcgcgtgagtgag
ttggggcagggcgcgcatgttgagcgggaaatcatgctggtgaaaattcaggccagcggttacgggcgtgacgaa
gtgaaacgtaatacggaaatattccgtgggcaaattatcgatgtcacaccctcgctttataccgttcaattagca
ggcaccagcggtaagcttgatgcattttttagcatcgattcgcgatgtggcgaaaattgtggaggttgctcgctct
ggtgtggtcggactttcgcgcggcgataaaataatgcgttga

*ilvC (E. coli)*
atggctaactacttcaatacactgaatctgcgccagcagctggcacagctgggcaaatgtcgctttatgggccgc
gatgaattcgccgatggcgcgagctaccttcagggtaaaaaagtagtcatcgtcggctgtggcgcacagggtctg
aaccagggcctgaacatgcgtgattctggtctcgatatctcctacgctctgcgtaaagaagcgattgccgagaag
cgcgcgtcctggcgtaaagcgaccgaaaatggttttaaagtgggtacttacgaagaactgatcccacaggcggat
ctggtgattaacctgacgccggacaagcagcactctgatgtagtgcgcaccgtacagccactgatgaaagacggc
gcggcgctggctactcgcacggtttcaacatcgtcgaagtgggcgagcagatccgtaaagatatcaccgtagtg
atggttgcgccgaaatgcccaggcaccgaagtgcgtgaagagtacaaacgtgggttcggcgtaccgacgctgatt
gccgttcacccggaaaacgatccgaaaggcgaaggcatggcgattgccaaagcctgggcggctgcaaccggtggt
caccgtgcgggtgtgctggaatcgtccttcgttgcggaagtgaaatctgacctgatgggcgagcaaaccatcctg
tgcggtatgttgcaggctggctctctgctgtgcttcgacaagctggtggaagaaggtaccgatccagcatacgca
gaaaaactgattcagttcggtggaaaccatcaccgaagcactgaaacagggcggcatcaccctgatgatggac
cgtctctctaaccggcgaaactgcgtgcttatgcgcttcgtgaacagctgaaagagatcatggcaccctgttc
cagaaacatatggacgacatcatctccggcgaattctcttccggtatgatggcggactgggccaacgatgataag
aaactgctgacctggcgtgaagagaccggcaaaaccgcgtttgaaaccgcgccgcagtatgaaggcaaatcggc
gagcaggagtacttcgataaaggcgtactgatgattgcgatggtgaaagcgggcgttgaactggcgttcgaaacc
atggtcgattccggcatcattgaagagtctgcatattatgaatcactgcacgagctgccgctgattgccaacacc
atcgcccgtaagcgtctgtacgaaatgaacgtggttatctctgataccgctgagtacggtaactatctgttctct
tacgcttgtgtgccgttgctgaaaccgtttatggcagagctgcaaccgggcgacctgggtaaagctattccggaa
ggcgcggtagataacgggcaactgcgtgatgtgaacgaagcgattcgcagccatgcgattgagcaggtaggtaag
aaactgcgcggctatatgacagatatgaaacgtattgctgttgcgggttaa

*Fig.8.*

*ilvD: (E. coli)*
atgcctaagtaccgttccgccaccaccactcatggtcgtaatatggcgggtgctcgtgcgctgtggcgcgccacc
ggaatgaccgacgccgatttcggtaagccgattatcgcggttgtgaactcgttcacccaatttgtaccgggtcac
gtccatctgcgcgatctcggtaaactggtcgccgaacaaattgaagcggctggcggcgttgccaaagagttcaac
accattgcggtggatgatgggattgccatgggccacggggggatgctttattcactgccatctcgcgaactgatc
gctgattccgttgagtatatggtcaacgccactgcgccgacgccatggtctgcatctctaactgcgacaaaatc
accccggggatgctgatggcttccctgcgcctgaatattccggtgatctttgtttccggcggcccgatggaggcc
gggaaaaccaaactttccgatcagatcatcaagctcgatctggttgatgcgatgatccagggcgcagacccgaaa
gtatctgactcccagagcgatcaggttgaacgttccgcgtgtccgacctgcggttcctgctccgggatgtttacc
gctaactcaatgaactgcctgaccgaagcgctgggcctgtcgcagccgggcaacggctcgctgctggcaacccac
gccgaccgtaagcagctgttccttaatgctggtaaacgcattgttgaattgaccaaacgttattacgagcaaaac
gacgaaagtgcactgccgcgtaatatcgccagtaaggcggcgtttgaaaacgccatgacgctggatatcgcgatg
ggtggatcgactaacaccgtacttcacctgctggcggcggcgcaggaagcggaaatcgacttcaccatgagtgat
atcgataagctttcccgcaaggttccacagctgtgtaaagttgcgccgagcacccagaaataccatatggaagat
gttcaccgtgctggtggtgttatcggtattctcggcgaactggatcgcgcggggttactgaaccgtgatgtgaaa
aacgtacttggcctgacgttgccgcaaacgctggaacaatacgacgttatgctgacccaggatgacgcggtaaaa
aatatgttccgcgcaggtcctgcaggcattcgtaccacacaggcattctcgcaagattgccgttgggatacgctg
gacgacgatcgcgccaatggctgtatccgctcgctggaacacgcctacagcaaagacggcggcctggcggtgctc
tacggtaactttgcggaaaacggctgcatcgtgaaaacggcaggcgtcgatgacagcatcctcaaattcaccggc
ccggcgaaagtgtacgaaagccaggacgatgcggtagaagcgattctcggcggtaaagttgtcgccggagatgtg
gtagtaattcgctatgaaggcccgaaaggcggtccggggatgcaggaaatgctctacccaaccagcttcctgaaa
tcaatgggtctcggcaaagcctgtgcgctgatcaccgacggtcgtttctctggtggcacctctggtctttccatc
ggccacgtctcaccggaagcggcaagcggcggcagcattggcctgattgaagatggtgacctgatcgctatcgac
atcccgaaccgtggcattcagttacaggtaagcgatgccgaactggcggcgcgtcgtgaagcgcaggacgctcga
ggtgacaaagcctggacgccgaaaaatcgtgaacgtcaggtctcctttgccctgcgtgcttatgccagcctggca
accagcgccgacaaaggcgcggtgcgcgataaatcgaaactgggggggttaa

*ilvA: (E. coli)*
atggctgactcgcaacccctgtccggtgctccggaaggtgccgaatatttaagagcagtgctgcgcgcgccggtt
tacgaggcggcgcaggttacgccgctacaaaaaatggaaaaactgtcgtcgcgtcttgataacgtcattctggtg
aagcgcgaagatcgccagccagtgcacagctttaagctgcgcggcgcatacgccatgatggcgggcctgacggaa
gaacagaaagcgcacgcgtgatcactgcttctgcgggtaaccacgcgcaggcgtcgcgttttcttctgcgcgg
ttaggcgtgaaggccctgatcgttatgccaaccgccaccgccgacatcaaagtcgacgcggtgcgcggcttcggc
ggcgaagtgctgctccacggcgcgaactttgatgaagcgaaagccaaagcgatcgaactgtcacagcagcagggg
ttcacctgggtgccgccgttcgaccatccgatggtgattgccgggcaaggcacgctggcgctggaactgctccag
caggacgcccatctcgaccgcgtatttgtgccagtcggcggcggcggtctggctgctggcgtggcggtgctgatc
aaacaactgatgccgcaaatcaaagtgatcgccgtagaagcggaagactccgcctgcctgaaagcagcgctggat
gcgggtcatccggttgatctgccgcgcgtagggctatttgctgaaggcgtagcggtaaaacgcatcggtgacgaa
accttccgtttatgccaggagtatctcgacgacatcatcaccgtcgatagcgatgcgatctgtgcggcgatgaag
gatttattcgaagatgtgcgcgcggtggcggaaccctctggcgcgctggcgctggcgggaatgaaaaaatatatc
gccctgcacaacattcgcggcgaacggctggcgcatattctttccggtgccaacgtgaacttccacgcctgcgc
tacgtctcagaacgctgcgaactgggcgaacagcgtgaagcgttgttggcggtgaccattccggaagaaaaaggc
agcttcctcaaattctgccaactgcttggcgggcgttcggtcaccgagttcaactaccgttttgccgatgccaaa
aacgcctgcatctttgtcggtgtgcgcctgagccgcggcctcgaagagcgcaaagaaattttgcagatgctcaac
gacggcggctacagcgtggttgatctctccgacgacgaaatgcgaagctacacgtgcgctatatggtcggcgga
cgtccatcgcatccgttgcaggaacgcctctacagcttcgaattcccggaatcaccgggcgcgctgctgcgcttc
ctcaacacgctgggtacgtactggaacatttctttgttccactatcgcagccatggcaccgactacggcgcgta
ctggcggcgttcgaacttggcgaccatgaaccggatttcgaaacccggctgaatgagctgggctacgattgccac
gacgaaaccaataacccggcgttcaggttcttttttggcggggttag

*Fig. 9.* leuA (E. coli)
atgagccagcaagtcattatttttcgataccacattgcgcgacggtgaacaggcgttacaggcaagcttgagtgtg
aaagaaaaactgcaaattgcgctggcccttgagcgtatgggtgttgacgtgatggaagtcggtttccccgtctct
tcgccgggcgattttgaatcggtgcaaaccatcgcccgccaggttaaaaacagccgcgtatgtgcgttagctcgc
tgcgtggaaaaagatatcgacgtggcggccgaatccctgaaagtcgccgaagccttccgtattcatacctttatt
gccacttcgccaatgcacatcgccaccaagctgcgcagcacgctggacgaggtgatcgaacgcgctatctatatg
gtgaaacgcgcccgtaattacaccgatgatgttgaattttcttgcgaagatgccgggcgtacacccattgccgat
ctggcgcgagtggtcgaagcggcgattaatgccggtgccaccaccatcaacattccggacaccgtgggctacacc
atgccgtttgagttcgccggaatcatcagcggcctgtatgaacgcgtgcctaacatcgacaaagccattatctcc
gtacatacccacgacgatttgggcctggcggtcggaaactcactggcggcggtacatgccggtgcacgccaggtg
gaaggcgcaatgaacgggatcggcgagcgtgccggaaactgttccctggaagaagtcatcatggcgatcaaagtt
cgtaaggatattctcaacgtccacaccgccattaatcaccaggagatatggcgcaccagccagttagttagccag
atttgtaatatgccgatcccggcaaacaaagccattgttggcagcggcgcattcgcacactcctccggtatacac
caggatggcgtgctgaaaaaccgcgaaaactacgaaatcatgacaccagaatctattggtctgaaccaaatccag
ctgaatctgacctctcgttcggggcgtgcggcggtgaaacatcgcatggatgagatggggtataaagaaagtgaa
tataatttagacaatttgtacgatgctttcctgaagctggcggacaaaaaaggtcaggtgtttgattacgatctg
gaggcgctggccttcatcggtaagcagcaagaagagccggagcatttccgtctggattacttcagcgtgcagtct
ggctctaacgatatcgccaccgccgcgtcaaactggcctgtggcgaagaagtcaaagcagaagccgccaacggt
aacggtccggtcgatgccgtctatcaggcaattaaccgcatcactgaatataacgtcgaactggtgaaatacagc
ctgaccgccaaaggccacggtaaagatgcgctgggtcaggtggatatcgtcgctaactacaacggtcgccgcttc
cacggcgtcggcctggctaccgatattgtcgagtcatctgccaaagccatggtgcacgttctgaacaatatctgg
cgtgccgcagaagtcgaaaaagagttgcaacgcaaagctcaacacaacgaaaacaacaaggaaaccgtgtga

LeuA (E. coli)
MSQQVIIFDTTLRDGEQALQASLSVKEKLQIALALERMGVDVMEVGFPVSSPGDFESVQTIARQVKNSRVCALAR
CVEKDIDVAAESLKVAEAFRIHTFIATSPMHIATKLRSTLDEVIERAIYMVKRARNYTDDVEFSCEDAGRTPIAD
LARVVEAAINAGATTINIPDTVGYTMPFEFAGIISGLYERVPNIDKAIISVHTHDDLGLAVGNSLAAVHAGARQV
EGAMNGIGERAGNCSLEEVIMAIKVRKDILNVHTAINHQEIWRTSQLVSQICNMPIPANKAIVGSGAFAHSSGIH
QDGVLKNRENYEIMTPESIGLNQIQLNLTSRSGRAAVKHRMDEMGYKESEYNLDNLYDAFLKLADKKGQVFDYDL
EALAFIGKQQEEPEHFRLDYFSVQSGSNDIATAAVKLACGEEVKAEAANGNGPVDAVYQAINRITEYNVELVKYS
LTAKGHGKDALGQVDIVANYNGRRFHGVGLATDIVESSAKAMVHVLNNIWRAAEVEKELQRKAQHNENNKETV* leuB (E. coli)
gtgatgtcgaagaattaccatattgccgtattgccggggacggtattggtccggaagtgatgacccaggcgctg
aaagtgctggatgccgtgcgcaaccgctttgcgatgcgcatcaccaccagccattacgatgtaggcggcgcagcc
attgataaccacgggcaaccactgccgcctgcgacggttgaaggttgtgagcaagccgatgccgtgctgtttggc
tcggtaggcggcccgaagtgggaacatttaccaccagaccagcaaccagaacgcggcgcgctgctgcctctgcgt
aagcacttcaaattattcagcaacctgcgcccggcaaaactgtatcaggggctggaagcattctgtccgctgcgt
gcagacattgccgcaaacggcttcgacatcctgtgtgtgcgcgaactgaccggcggcatctatttcggtcagcca
aaaggccgcgaaggtagcggacaatatgaaaaagcctttgataccgaggtgtatcaccgttttgagatcgaacgt
atcgcccgcatcgcgttttgaatctgctcgcaagcgtcgccacaaagtgacgtcgatcgataaagccaacgtgctg
caatcctctatttatgcggggagatcgttaacgagatcgccacggaataccggatgtcgaactggcgcatatg
tacatcgacaacgccaccatgcagctgattaaagatccatcacagtttgacgttctgctgtgctccaacctgttt
ggcgacattctgtctgacgagtgcgcaatgatcactggctcgatggggatgttgccttccgccagcctgaacgag
caaggttttggactgtatgaaccggcggcggctcggcaccagatatcgcaggcaaaaacatcgccaacccgatt
gcacaaatcctttcgctggcactgctgctgcgttacagcctggatgccgatgatgcggcttgcgccattgaacgc
gccattaaccgcgcattagaagaaggcattcgcaccggggatttagcccgtggcgctgccgccgttagtaccgat
gaaatgggcgatatcattgcccgctatgtagcagaagggggtgtaa

*Fig.10.*

*leuC (E. coli)*
atggctaagacgttatacgaaaaattgttcgacgctcacgttgtgtacgaagccgaaaacgaaaccccactgtta
tatatcgaccgccacctggtgcatgaagtgacctcaccgcaggcgttcgatggtctgcgcgcccacggtcgcccg
gtacgtcagccgggcaaaaaccttcgctaccatggatcacaacgtctctacccagaccaaagacattaatgcctgc
ggtgaaatggcgcgtatccagatgcaggaactgatcaaaaactgcaaagaatttggcgtcgaactgtatgacctg
aatcacccgtatcaggggatcgtccacgtaatggggccggaacagggcgtcaccttgccggggatgaccattgtc
tgcggcgactcgcataccgccaccacggcgcgtttggcgcactggcctttggtatcggcacttccgaagttgaa
cacgtactggcaacgcaaaccctgaaacagggcgcgcaaaaaccatgaaaattgaagtccagggcaaagccgcg
ccgggcattaccgcaaaagatatcgtgctggcaattatcggtaaaaccggtagcgcaggcggcaccgggcatgtg
gtggagttttgcggcgaagcaatccgtgatttaagcatggaaggtcgtatgaccctgtgcaatatggcaatcgaa
atgggcgcaaaagccggtctggttgcaccggacgaaaccacctttaactatgtcaaaggccgtctgcatgcgccg
aaaggcaaagatttcgacgacgccgttgcctactggaaaaccctgcaaaccgacgaaggcgcaactttcgatacc
gttgtcactctgcaagcagaagaaatttcaccgcaggtcacctgggcaccaatcccggccaggtgatttccgtg
aacgacaatattcccgatccggcttcgtttgccgatccggttgaacgcgcgtcggcagaaaaagcgctggcctat
atgggcgaaaccgggtattccgctgaccgaagtggctatcgacaaagtgtttatcggttcctgtaccaactcg
cgcattgaagatttacgcgcggcagcggagatcgccaaaggcgaaaagtcgcgccaggcgtgcaggcactggtg
gttcccggctctggccggtaaaagcccaggcggaagcggaaggtctggataaaatctttattgaagccggtttt
gaatggcgcttgcctggctgctcaatgtgtctggcgatgaacaacgaccgtctgaatccgggcgaacgttgtgcc
tccaccagcaaccgtaactttgaaggccgccaggggcgcggcgggcgcacgcatctggtcagcccggcaatggct
gccgctgctgctgtgaccggacatttcgccgacattcgcaacattaaataa

*leuD (E. coli)*
atggcagagaaatttatcaaacacacaggcctggtggttccgctggatgccgccaatgtcgataccgatgcaatc
atcccgaaacagttttttgcagaaagtgacccgtacgggttttggcgcgcatctgtttaacgactggcgttttctg
gatgaaaaaggccaacagccaaaccgggacttcgtgctgaacttcccgcagtatcagggcgcttccatttttgctg
gcacgagaaaacttcggctgtggctcttcgcgtgagcacgcgccctgggcattgaccgactacggttttaaagtg
gtgattgcgccgagttttgctgacatcttctacggcaatagcttaacaaccagctgctgccggtgaaattaagc
gatgcagaagtggacgaactgtttgcgctggtgaaagctaatccggggatccatttcgacgtggatctggaagcg
caagaggtgaaagcgggagagaaaacctatcgctttaccatcgatgccttccgccgccactgcatgatgaacggt
ctggacagtattgggcttaccttgcagcacgacgacgccattgccgcttatgaagcaaaacaacctgcgtttatg
aattaa

*ilvM (E. coli)*
atgatgcaacatcaggtcaatgtatcggctcgcttcaatccagaaaccttagaacgtgttttacgcgtggtgcgt
catcgtggtttccacgtctgctcaatgaatatggccgccgccagcgatgcacaaaatataaatcgaattgacc
gttgccagcccacggtcggtcgacttactgtttagtcagttaaataaactggtggacgtcgcacacgttgccatc
tgccagagcacaaccacatcacaacaaatccgcgcctga

*ilvG (E. coli)*
ttgttgttaaaacaactgtcggatcgtaaacctgcggattgcgtcgtgaccacagatgtggggcagcaccagatg
tgggctgcgcagcacatcgcccacactcgcccgaaaatttcatcacctccagcggtttaggtaccatgggttttt
ggtttaccggcggcggttggcgcacaagtcgcgcgaccgaacgataccgttgtctgtatctccggtgacggctct
ttcatgatgaatgtgcaagagctgggcaccgtaaaacgcaagcagttaccgttgaaaatcgtcttactcgataac
caacggttagggatggttcgacaatggcagcaactgttttttcaggaacgatacagcgaaaccaccctactgat
aaccccgatttcctcatgttagccagcgcgccttcggcatccatggccaacacatcacccggaaagaccaggttga
gcggcactcgacaccatgctgaacagtgatgggccataccctgcttcatgtctcaatcgacgaacttgagaacgtc
tggccgctggtgccgcctggcgcgccagtaattcagaaatgttggagaaattatcatga

*ilvN (E. coli)*
atgcaaaacacaactcatgacaacgtaattctggagctcaccgttcgcaaccatccgggcgtaatgacccacgtt
tgtggccttttttgccgccgcgcttttaacgttgaaggcattctttgtctgccgattcaggacagcgacaaaagc
catatctggctactggtcaatgacgaccagcgtctggagcagatgataagccaaatcgataagctggaagatgtc
gtgaaagtgcagcgtaatcagtccgatccgacgatgtttaacaagatcgcggtgttttttcagtaa

*Fig.11.*

*ilvB (E. coli)*
atggcaagttcgggcacaacatcgacgcgtaagcgctttaccggcgcagaatttatcgttcatttcctggaacag
cagggcattaagattgtgacaggcattccgggcggttctatcctgcctgtttacgatgccttaagccaaagcacg
caaatccgccatattctggcccgtcatgaacagggcgcgggctttatcgctcagggaatggcgcgcaccgacggt
aaaccggcggtctgtatggcctgtagcggaccgggtgcgactaacctggtgaccgccattgccgatgcgcggctg
gactccatcccgctgatttgcatcactggtcaggttcccgcctcgatgatcggcaccgacgccttccaggaagtg
gacacctacggcatctctatccccatcaccaaacacaactatctggtcagacatatcgaagaactcccgcaggtc
atgagcgatgccttccgcattgcgcaatcaggccgcccaggcccggtgtggatagacattcctaaggatgtgcaa
acggcagtttttgagattgaaacacagcccgctatggcagaaaaagccgccgcccccgcctttagcgaagaaagc
attcgtgacgcagcggcgatgattaacgctgccaaacgcccggtgctttatctgggcggcggtgtgatcaatgcg
cccgcacgggtgcgtgaactggcggagaaagcgcaactgcctaccaccatgactttaatggcgctgggcatgttg
ccaaaagcgcatccgttgtcgctgggtatgctggggatgcacggcgtgcgcagcaccaactatattttgcaggag
gcggatttgttgatagtgctcggtgcgcgttttgatgaccgggcgattggcaaaaccgagcagttctgtccgaat
gccaaaatcattcatgtcgatatcgaccgtgcagagctgggtaaaatcaagcagccgcacgtggcgattcaggcg
gatgttgatgacgtgctggcgcagttgatcccgctggtggaagcgcaaccgcgtgcagagtggcaccagttggta
gcggatttgcagcgtgagtttccgtgtccaatcccgaaagcgtgcgatccgttaagccattacggcctgatcaac
gccgttgccgcctgtgtcgatgacaatgcaattatcaccaccgacgttggtcagcatcagatgtggaccgcgcaa
gcttatccgctcaatcgcccacgccagtggctgacctccggtgggctgggcacgatggttttggcctgcctgcg
gcgattggcgctgcgctggcgaacccggatcgcaaagtgttgtgtttctccggcgacggcagcctgatgatgaat
attcaggagatggcgaccgccagtgaaaatcagctggatgtcaaaatcattctgatgaacaacgaagcgctgggg
ctggtgcatcagcaacagagtctgttctacgagcaaggcgttttgccgccacctatccgggcaaaatcaacttt
atgcagattgccgccggattcggcctcgaaacctgtgatttgaataacgaagccgatccgcaggcttcattgcag
gaaatcatcaatcgccctggcccggcgctgatccatgtgcgcattgatgccgaagaaaaagtttacccgatggtg
ccgccaggtgcggcgaatactgaaatggtgggggaataa

*Fig.12.*

*adhE2 (Clostridium acetobutylicum)*
atgaaagttacaaatcaaaagaactaaaacaaaagctaaatgaattgagagaagcgcaaaagaagtttgcaacc
tatactcaagagcaagttgataaaattttaaacaatgtgccatagccgcagctaaagaagaataaacttagct
aaattagcagtagaagaaacaggaataggtcttgtagaagataaaattataaaaaatcattttgcagcagaatat
atatacaataaatataaaaatgaaaaaacttgtggcataatagaccatgacgattctttaggcataacaaaggtt
gctgaaccaattggaattgttgcagccatagttcctactactaatccaacttccacagcaattttcaaatcatta
atttctttaaaaacaagaaacgcaatattcttttcaccacatccacgtgcaaaaaaatctacaattgctgcagca
aaattaattttagatgcagctgttaaagcaggagcacctaaaaatataataggctggatagatgagccatcaata
gaactttctcaagatttgatgagtgaagctgatataatattagcaacaggaggtccttcaatggttaaagcggcc
tattcatctggaaaacctgcaattggtgttggagcaggaaatacaccagcaataatagatgagagtgcagatata
gatatggcagtaagctccataattttatcaaagacttatgacaatggagtaatatgcgcttctgaacaatcaata
ttagttatgaattcaatatacgaaaaagttaaagaggaatttgtaaaacgaggatcatatatactcaatcaaaat
gaaatagctaaaataaaagaaactatgtttaaaaatggagctattaatgctgacatagttggaaaatctgcttat
ataattgctaaaatggcaggaattgaagttcctcaaactacaaagatacttataggcgaagtacaatctgttgaa
aaaagcgagctgttctcacatgaaaaactatcaccagtacttgcaatgtataaagttaaggattttgatgaagct
ctaaaaaaggcacaaaggctaatagaattaggtggaagtggacacacgtcatctttatatatagattcacaaaac
aataaggataaagttaaagaatttggattagcaatgaaaacttcaaggacatttattaacatgccttcttcacag
ggagcaagcggagatttatacaatttctgcgatagcaccatcattctcttggatgcggcacttggggaggaaac
tctgtatcgcaaaatgtagagcctaaacatttattaaatattaaaagtgttgctgaaagaagggaaaatatgctt
tggtttaaagtgccacaaaaatatattttaaatatggatgtcttagattgcattaaaagaattaaaagatatg
aataagaaagagcctttatagtaacagataaagatctttttaaacttggatatgttaataaaataacaaaggta
ctagatgagatagatattaaatacagtatatttacagatattaaatctgatccaactattgattcagtaaaaaaa
ggtgctaaagaaatgcttaactttgaacctgatactataatctctattggtggtggatcgccaatggatgcagca
aaggttatgcacttgttatatgaatatccagaagcagaaattgaaaatctagctataaactttatggatataaga
aagagaatatgcaatttccctaaattaggtacaaaggcgatttcagtagctattcctacaactgctggtaccggt
tcagaggcaacaccttttgcagttataactaatgatgaaacaggaatgaaatacccttaacttcttatgaattg
accccaaacatggcaataatagatactgaattaatgttaaatatgcctagaaaattaacagcagcaactggaata
gatgcattagttcatgctatagaagcatatgtttcggttatggctacggattatactgatgaattagccttaaga
gcaataaaaaatgatattttaaatatttgcctagagcctataaaaatgggactaacgacattgaagcaagagaaaa
atggcacatgcctctaatattgcggggatggcatttgcaaatgcttcttaggtgtatgccattcaatggctcat
aaacttggggcaatgcatcacgttccacatgaattgcttgtgctgtattaatagaagaagttattaaatataac
gctacagactgtccaacaaagcaaacagcattccctcaatataaatctcctaatgctaagagaaaatatgctgaa
attgcagagtatttgaatttaaagggtactagcgataccgaaaaggtaacagccttaatagaagctatttcaaag
ttaaagatagatttgagtattccacaaaatataagtgccgctggaataaataaaaagattttataatacgcta
gataaaatgtcagagcttgcttttgatgaccaatgtacaacagctaatcctaggtatccacttataagtgaactt
aaggatatctatataaaatcatttttaa

*Li-leuC (Leptospira interrogans)*
atgaag

**Li-leuD (*Leptospira interrogans*)**

atgaaaccctttactatattaaatggaattgccgccttactggacagacccaacgtggatacggatca
gatcattccaaaacaattttacggaagatagaacgaaccggtttcggagttcatctgtttcacgatt
ggagatacttagacgacgcgggtaccaaactcaatcctgattttccctcaatcaagaacgatataag
ggagcttctatccttatcaccagagataactttggttgtggatcttccagagaacacgctccttgggc
tttagaagactacgggtttagggcaatcattgctccttcttacgcggatatttttttcaacaactgct
ttaaaaacggaatgcttccagtcattttaaaatcggaagaagtagaagagctgttccatttggtttcg
actaacgtaggagcgaaagtcatagtggatctggacaaacaaactgtaaccggaccgactggaaaaat
atattattttgaagtggattcttttcgtaaatactgtctttataacggacttgatgacataggtctaa
ctctaaaacaagaaagtaaaattggagagtttgaaaaaaagcagaaagaagttgaaccttggttatac
gccatataa

**Li-leuB (*Leptospira interrogans*)**

atgaagaatgtagcagtactttcaggagacggaatcggaccggaagtcatggagatagccatctccgt
tttgaaaaaggctctcggtgcaaaagtttccgagtttcaatttaaagaaggatttgtaggtggaatcg
caatcgataaaactggacacccacttccaccggaaactcttaaactatgtgaagaatcttccgcaatt
cttttcggaagtgtgggaggtcctaaatgggaaacactccctccggaaaaacaaccggaacgagggc
acttctacctttgagaaaacattttgatctatttgcaaacttaagacctgcgatcatttatccagagt
tgaaaaatgcttctccagttcgttctgatattattggaaacggattagatattctcatattaagagag
ttaaccggaggaatttattttggacaaccaaaaggaagagaaggatcaggtcaggaagaatttgcata
cgacacgatgaagtattccagaagagaaatcgaaaggattgctaaagtcgcattccaggcggccagaa
aaagaaataataaagtgactagtatcgataaagcaaacgtcttgactacttccgtttttttggaaggaa
gtagtaatcgaattgcataagaaagaattttcagacgtccaattgaatcatctttatgtggacaatgc
ggcgatgcagttaatcgtaaatccgaaacaattcgacgtggttctttgtgagaatatgtttggtgata
ttctttcggacgaggcttccatcattacgggttcaatcggaatgcttccttctgcctctctttccgaa
tctggatttggattgtatgaaccttctggtggttctgcgccggacatagccggaaaaggagtggcaaa
tccgattgctcaagtattgagtgcggcgttgatgttacgttattctttttctatggaagaagaagcaa
acaagatagaaaccgccgtgcgtaaaacgattgcctccggaaaaagaaccagagacatagcggaagta
ggatctacgatcgtaggaactaaagaaatcggtcaattgatcgaatcctttctctaa

**TyrA (*E. coli*)**

Atggttgctgaattgaccgcattacgcgatcaaattgatgaagtcgataaagcgctgctgaatttatt
agcgaagcgtctggaactggttgctgaagtgggcgaggtgaaaagccgctttggactgcctatttatg
ttccggagcgcgaggcatctatgttggcctcgcgtcgtgcagaggcggaagctctgggtgtaccgcca
gatctgattgaggatgttttgcgtcgggtgatgcgtgaatcttactccagtgaaaacgacaaaggatt
taaaacactttgtccgtcactgcgtccggtggttatcgtcggcggtggcggtcagatgggacgcctgt
tcgagaagatgctgaccctctcgggttatcaggtgcggattctggagcaacatgactgggatcgagcg
gctgatattgttgccgatgccggaatggtgattgttagtgtgccaatccacgttactgagcaagttat
tggcaaattaccgcctttaccgaaagattgtattctggtcgatctggcatcagtgaaaaatgggccat
tacaggccatgctggtggcgcatgatggtccggtgctggggctacacccgatgttcggtccggacagc
ggtagcctggcaaagcaagttgtggtctggtgtgatggacgtaaaccggaagcataccaatggtttct
ggagcaaattcaggtctggggcgctcggctgcatcgtattagcgccgtcgagcacgatcagaatatgg
cgtttattcaggcactgcgccactttgctacttttgcttacgggctgcacctggcagaagaaaatgtt
cagcttgagcaacttctggcgctctcttcgccgatttaccgccttgagctggcgatggtcgggcgact
gtttgctcaggatccgcagctttatgccgacatcattatgtcgtcagagcgtaatctggcgttaatca
aacgttactataagcgtttcggcgaggcgattgagttgctggagcagggcgataagcaggcgtttatt
gacagtttccgcaaggtggagcactggttcggcgattacgcacagcgttttcagagtgaaagccgcgt
gttattgcgtcaggcgaatgacaatcgccagtaa

*Fig. 14.*

PRODUCTION OF C5-C8 ALCOHOLS USING EVOLVED ENZYMES AND METABOLICALLY ENGINEERED MICROORGANISMS

CROSS-REFERENCES TO RELATED APPLICATIONS

This application is a continuation of International Patent Application No. PCT/US2009/061116, filed Oct. 18, 2009, which claims priority to U.S. Provisional Application Ser. Nos. 61/106,561, filed Oct. 18, 2008; 61/106,562, filed Oct. 18, 2008; 61/106,563, filed Oct. 18, 2008; 61/106,564, filed Oct. 18, 2008; and 61/119,308, filed Dec. 2, 2008, the disclosures of all of which applications are expressly incorporated herein by reference.

TECHNICAL FIELD

Metabolically-modified microorganisms and methods of producing such organisms are provided. Also provided are methods of producing biofuels by contacting a suitable substrate with a metabolically-modified microorganism and enzymatic preparations there from.

BACKGROUND

Demand for biofuels as a substitute for petroleum is expected to increase because of economic and environmental concerns.

SUMMARY

Nature uses a limited set of metabolites such as organic acids, amino acids, nucleotides, lipids and sugars as building blocks for biosynthesis. These chemicals support the biological functions of all organisms. The disclosure provides a strategy to produce seven-(C7) to nine-carbon (C9) 2-keto acids which can lead to useful nonnatural alcohols comprising five to eight carbon (C5-C8) as well as nonnatural amino acids.

Aliphatic alcohols with carbon chain of C5 or greater are attractive biofuel targets since they have higher energy density, and lower water solubility (1-pentanol 23 g/L, 1-hexanol 6.2 g/L, 1-heptanol 1.2 g/L) that could facilitate post-production purification from culture medium through an aqueous/organic two-phase separation process. The only well-characterized mechanism for aliphatic alcohol production is through the Ehrlich pathway, which converts branched-chain amino acids into alcohols. The carbon number (up to five) of the alcohols derived from this type of pathway is limited by the carbon number in the branched chain amino acid pathways.

The disclosure provides a recombinant microorganism that produces a higher alcohol comprising a C5, C6, C7, or C8 alcohol. In one embodiment, the C5 alcohol comprises 2-methyl-1-butanol or 3-methyl-1-butanol or 1-pentanol. In another embodiment, the C6 alcohol is 3-methyl-1-pentanol or 1-hexanol. In one embodiment, the C7 alcohol is 2-isopropyl-1-butanol. In another embodiment, the C8 alcohol is a 5-methyl-1-heptanol. In another embodiment, the alcohol is produced from a metabolite comprising L-threonine. In one embodiment, the microorganism comprises a mutant 2-isopropylmalate synthase (LeuA), wherein the mutant is capable utilizing a C7 to C9 keto acid as a substrate. In a further embodiment, the microorganism comprises a mutant keto acid decarboxylase. In one embodiment, the microorganism comprises reduced ethanol production capability compared to a parental microorganism. In yet another embodiment, the microorganism comprises a reduction or inhibition in the conversion of acetyl-CoA to ethanol. In one embodiment, the microorganism comprises elevated expression of a 2-keto-acid decarboxylase (e.g., Pdc, Pdc 1, Pdc5, Pdc6, Aro10, Thi3, Kivd, KdcA, a homolog or variant of any of the foregoing, and a polypeptide having at least 60% identity to any one of the foregoing and having 2-keto-acid decarboxylase activity). In another embodiment, the 2-keto-acid decarboxylase is encoded by a polynucleotide having at least 60% identity to a polynucleotide selected from the group consisting of pdc, pdc1, pdc5, pdc6, aro10, thi3, kivd, kdcA, a homolog or variant of any of the foregoing, or a fragment thereof and wherein the polynucleotide encodes a polypeptide having 2-keto acid decarboxylase activity. In a specific embodiment, the 2-keto-acid decarboxylase is encoded by a polynucleotide derived from a kivd gene, or homolog thereof. In one embodiment, the microorganism comprises elevated expression or activity of a 2-keto-acid decarboxylase and an alcohol dehydrogenase, as compared to a parental microorganism. In one embodiment, the alcohol dehydrogenase is selected from the group consisting of Adh1, Adh2, Adh3, Adh4, Adh5, Adh6, Sfa1, a homolog or variant of any of the foregoing, and a polypeptide having at least 60% identity to any one of the foregoing and having alcohol dehydrogenase activity. In yet another embodiment, the alcohol dehydrogenase is encoded by a polynucleotide having at least 60% identity to a nucleic acid selected from the group consisting of an adh1, adh2, adh3, adh4, adh5, adh6, sfa1 gene, and a homolog of any of the foregoing and wherein the polynucleotide encodes a protein having 2-alcohol dehydrogenase activity.

Provided herein are metabolically-modified microorganisms that include recombinant biochemical pathways useful for producing higher alcohols comprising C5, C6, C7, or C8 alcohols such as 1-pentanol, 1-hexanol, 3-methyl-1-pentanol, 4-methyl-1-pentanol, 4-methyl-1-hexanol, 2-isopropyl-1-butanol, and 5-methyl-1-heptanol. Also provided are methods of producing biofuels using microorganisms described herein. In one embodiment, the microorganism comprises a mutant 2-isopropylmalate synthase (LeuA), wherein the mutant is capable utilizing a C7 to C9 keto acid as a substrate. In a further embodiment, the microorganism comprises a mutant keto acid decarboxylase. The disclosure comprises a recombinant microorganism that produces a C5, C6, C7, or C8 alcohols such as 1-pentanol, 1-hexanol, 3-methyl-1-pentanol, 4-methyl-1-pentanol, 4-methyl-1-hexanol, 2-isopropyl-1-butanol, and 5-methyl-1-heptanol. In one embodiment, the microorganism comprises an *E. coli*. In another embodiment, the microorganism comprises a nonnatural metabolic pathway for the production of a C5, C6, C7, or C8 alcohol such as 1-pentanol, 1-hexanol, 3-methyl-1-pentanol, 4-methyl-1-pentanol, 4-methyl-1-hexanol, 2-isopropyl-1-butanol, and 5-methyl-1-heptanol. In another embodiment, the microorganism comprises a mutant LeuA or a mutant LeuA and a mutant Kivd. In another embodiment, the microorganism comprises a nonnatural metabolic pathway that comprises an increase in one or more polynucleotides encoding an enzyme selected from the group consisting of tdcB, ilvG, ilvM, ilvC, ilvD, leuA, a mutant leuA, leuD, leuC, leuB, kivD, a mutant kivD, and adh6.

The disclosure provides a recombinant microorganism comprising a metabolic pathway for producing a C5, C6, C7, or C8 alcohol such as 1-pentanol, 1-hexanol, 3-methyl-1-pentanol, 4-methyl-1-pentanol, 4-methyl-1-hexanol, 2-isopropyl-1-butanol, and 5-methyl-1-heptanol. In one embodiment, the microorganism is *E. coli*. In one embodiment, the microorganism comprises a mutant 2-isopropylmalate synthase (LeuA), wherein the mutant LeuA produces or enhances production of 2-keto-4-methylhexanoate. In a further embodiment, the microorganism comprises a mutant keto acid decarboxylase. In one embodiment, the foregoing enzymes are derived from *E. coli*. The metabolic intermediate, 2-keto-4-methylhexanoate can then be converted to 3-methyl-1-pentanol by ketoisovalerate decarboxylase (Kivd or a mutant Kivd) and alcohol dehydrogenase (adh6). Alternatively, 2-keto-4-methylhexanoate can be converted to 2-keto-5-methylheptanoate by the actions of LeuABCD. The 2-keto-5-methylheptanoate can then be converted to 4-methyl-1-hexanol by ketoisovalerate decarboxylase (Kivd or a mutant Kivd) and alcohol dehydrogenase (adh6). Alternatively, 2-keto-5-methylheptanoate can be converted to 2-keto-6-methylheptanoate by the actions of LeuABCD. The 2-keto-6-methylheptanoate can then be converted to 5-methyl-1-heptanol by ketoisovalerate decarboxylase (Kivd or a mutant Kivd) and alcohol dehydrogenase (adh6). In yet a further alternative, 2-ketoisocaproate can be converted to 2-keto-5-methylhexanoate by the action of the mutant LeuA. The 2-keto-5-methylhexanoate can then be converted to 4-methyl-1-pentanol by the action of ketoisovalerate decarboxylase (Kivd or a mutant Kivd) and alcohol dehydrogenase (adh6). In one embodiment the kivd is derived from *L. lactis*. In another embodiment, the adh6 is derived from *S. cerevisiae*. In one embodiment the Kivd has a F381L and V461A mutation compared to a wild-type.

The disclosure provides a substantially purified polypeptide comprising at least 80% identical to SEQ ID NO:2, having a mutation in any of the following residues D430, A453, A460, or G462 to remove leucine feedback inhibition and may include at least one additional mutation selected from the group consisting of S139G, N167A, N167L, and H97A, wherein the polypeptide is capable of initiating the conversion of 2-keto-3-methylvalerate to a C6-C9 keto acid. In one embodiment, the polypeptide comprises SEQ ID NO:2 with 1-50 conservative amino acid substitutions and a mutation in any of the following residues D430, A453, A460 or G462 to remove leucine feedback inhibition. In another embodiment, the polypeptide comprises a sequence that is at least 80%, 90%, 95%, 98%, or 99% identical to a sequence selected from the group consisting of SEQ ID NO:4, 6, 8, 10, 12, 14, or 16 that when expressed with a LeuB, C, and D is capable of converting 2-keto-3-methylvalerate to 2-keto-4-methylhexanoate. In yet a further embodiment, the G462 mutation is a G462A mutation.

The disclosure also provides a recombinant microorganism that expresses a polypeptide comprising at least 80% identical to SEQ ID NO:2, having a mutation in any of the following residues D430, A453, A460, or G462 to remove leucine feedback inhibition and may include at least one additional mutation selected from the group consisting of S139G, N167A, N167L, and H97A, wherein the polypeptide is capable of initiating the conversion of 2-keto-3-methylvalerate to a C6-C9 keto acid. In one embodiment, the polypeptide comprises SEQ ID NO:2 with 1-50 conservative amino acid substitutions and a mutation in any of the following residues D430, A453, A460 or G462 to remove leucine feedback inhibition. In another embodiment, the polypeptide comprises a sequence that is at least 80%, 90%, 95%, 98%, or 99% identical to a sequence selected from the group consisting of SEQ ID NO:4, 6, 8, 10, 12, 14, or 16 that when expressed with a LeuB, C, and D is capable of converting 2-keto-3-methylvalerate to 2-keto-4-methylhexanoate. In yet a further embodiment, the G462 mutation is a G462A mutation.

The disclosure also provides an isolated polynucleotide encoding a polypeptide comprising at least 80% identity to SEQ ID NO:2, having a mutation in any of the following residues D430, A453, A460, or G462 to remove leucine feedback inhibition and may include at least one additional mutation selected from the group consisting of S139G, N167A, N167L, and H97A, wherein the polypeptide is capable of initiating the conversion of 2-keto-3-methylvalerate to a C6-C9 keto acid. In one embodiment, the polypeptide comprises SEQ ID NO:2 with 1-50 conservative amino acid substitutions and a mutation in any of the following residues D430, A453, A460, or G462 to remove leucine feedback inhibition. In another embodiment, the polypeptide comprises a sequence that is at least 80%, 90%, 95%, 98%, or 99% identical to a sequence selected from the group consisting of SEQ ID NO:4, 6, 8, 10, 12, 14, or 16 that when expressed with a LeuB, C, and D is capable of converting 2-keto-3-methylvalerate to 2-keto-4-methylhexanoate. In yet a further embodiment, the G462 mutation is a G462A mutation. In one embodiment, the isolated polynucleotide comprises a sequence that hybridizes to a sequence consisting of SEQ ID NO:1, 3, 5, 7, 9, 11, 13, or 15, wherein the polynucleotide encodes a polypeptide that promotes the conversion of 2-keto-3-methylvalerate to 2-keto-4-methylhexanoate. In yet another embodiment, the polynucleotide encodes a polypeptide that is at least 80%, 90%, 95%, 98%, or 99% identical to a LeuA polypeptide of SEQ ID NO:4, 6, 8, 10, 12, 14, or 16. In a yet a further embodiment, the polynucleotide comprises a sequence that is at least 80%, 90%, 95%, 98% or 99% identical to SEQ ID NO:1, 3, 5, 7, 9, 11, 13, or 15 and encodes a polypeptide that promotes the conversion of 2-keto-3-methylvalerate to 2-keto-4-methylhexanoate. In another embodiment, the polynucleotide is part of an operon comprising LeuBCD, wherein the operon converts 2-keto-3-methylvalerate to 2-keto-4-methylhexanoate. In a further embodiment, the disclosure provides a vector comprising a polynucleotide as described above alone or as part of an operon. The vector can be an expression vector suitable for expression in a desired host cell.

The disclosure also provides a recombinant microorganism comprising the polynucleotide or vector described above.

The disclosure also provides a substantially purified polypeptide comprising at least 80% identical to SEQ ID NO:18, having a V461A mutation and may include at least one additional mutation selected from the group consisting of M538A, M538L, F381A, and F381L, wherein the polypeptide is capable of initiating the conversion of a C6-C9 keto acid to a C5-C8 alcohol. In one embodiment, the polypeptide comprises SEQ ID NO:18 with 1-50 conservative amino acid substitutions and a V461A mutation and may further comprise at least one additional mutation at M538 or F381. In yet another embodiment, the polypeptide comprises a sequence that is at least 80%, 90%, 95%, 98%, or 99% identical to a sequence as set forth in SEQ ID NO:18, 20, 22, 24, 26, or 28 and that is capable of promoting the conversion of a C6-C9 keto acid to a C5-C8 alcohol.

The disclosure also provides an isolated polynucleotide encoding the polypeptide comprising at least 80% identical to SEQ ID NO:18, having a V461A mutation and may include at least one additional mutation selected from the group consisting of M538A, M538L, F381A and F381L, wherein the polypeptide is capable of initiating the conversion of a C6-C9 keto acid to a C5-C8 alcohol. In one embodiment, the polypeptide comprises SEQ ID NO:18 with 1-50 conservative amino acid substitutions and a V461A mutation and may further comprise at least one additional mutation at M538 or F381. In yet another embodiment, the polypeptide comprises a sequence that is at least 80%, 90%, 95%, 98%, or 99% identical to a sequence as set forth in SEQ ID NO:18, 20, 22, 24, 26 or 28 and that is capable of promoting the conversion of a C6-C9 keto acid to a C5-C8 alcohol. The disclosure also provides an isolated polynucleotide comprising a sequence that encodes a polypeptide of SEQ ID NO:18 having a V461A mutation. In one embodiment, the polynucleotide comprises a sequence that hybridizes to a sequence consisting of SEQ ID NO:17, 19, 21, 23, 25 or 27, wherein the polynucleotide encodes a polypeptide that promotes the conversion of C6-C9 keto acid to the corresponding C5-C8 alcohol. In yet another embodiment, the polynucleotide encodes a polypeptide that is at least 80%, 90%, 95%, 98% or 99% identical to a Kivd polypeptide of SEQ ID NO:20, 22, 24, 26, or 28 and which promotes the conversion of a C6-C9 keto acid to the corresponding C5-C8 alcohol. In another embodiment, the polynucleotide comprises a sequence that is at least 80%, 90%, 95%, 98%, or 99% identical to SEQ ID NO:17, 19, 21, 23, 25, or 27 and encodes a polypeptide that promotes the conversion of a C7-C9 keto acid to a C6-C8 alcohol.

The disclosure further provides a microorganism that expresses the polypeptide above. The disclosure further provides a microorganism that comprises the isolated polynucleotide as described above.

The disclosure provides a recombinant microorganism that expresses a polypeptide comprising at least 80% identical to SEQ ID NO:2, having a mutation in any of the following residues D430, A453, A460, or G462 to remove leucine feedback inhibition and may include at least one additional mutation selected from the group consisting of S139G, N167A, N167L, and H97A, wherein the polypeptide is capable of initiating the conversion of 2-keto-3-methylvalerate to a C6-C9 keto acid and also expresses a polypeptide comprising at least 80% identity to SEQ ID NO:18, having a V461A mutation and may include at least one additional mutation selected from the group consisting of M538A, M538L, F381A and F381L, wherein the polypeptide is capable of initiating the conversion of a C6-C9 keto acid to a C5-C8 alcohol.

The disclosure provides a recombinant microorganism that produces a C5, C6, C7, or C8 alcohol comprising a recombinant metabolic pathway and a mutant 2-isopropylmalate synthase that converts a 2-keto-3-methylvalerate to a C6-C9 keto acid. In one embodiment, the mutant 2-isopropylmalate synthase has a larger binding pocket compared to a wild-type 2-isopropylmalate synthase. In yet another embodiment, the microorganism is selected from a genus of *Corynebacterium, Lactobacillus, Lactococcus, Salmonella, Enterobacter, Pseudomonas, Enterococcus, Erwinia, Pantoea, Morganella, Pectobacterium, Proteus, Serratia, Shigella, Klebsiella, Citrobacter, Saccharomyces, Dekkera, Klyveromyces, Escherchia,* and *Pichia*. In yet another embodiment, the biosynthetic pathway for the production of an amino acid in the organism is modified for production of the alcohol. In a further embodiment, the microorganism comprises reduced ethanol production capability compared to a parental microorganism. In a specific embodiment, the microorganism is derived from *E. coli*. In yet another embodiment, the microorganism comprises a keto-acid decarboxylase selected from the group consisting of Pdc, Pdc1, Pdc5, Pdc6, Aro10, Thi3, Kivd, and KdcA, a homolog or variant of any of the foregoing, and a polypeptide having at least 60% identity to any one of the foregoing and having 2-keto-acid decarboxylase activity. In a further embodiment, the keto-acid decarboxylase is encoded by a polynucleotide having at least 60% identity to a nucleic acid selected from the group consisting of pdc, pdc1, pdc5, pdc6, aro10, thi3, kivd, kdcA, a homolog or variant of any of the foregoing, or a fragment thereof and wherein the polynucleotide encodes a polypeptide having 2-keto acid decarboxylase activity. In yet another embodiment, the 2-keto-acid decarboxylase is encoded by a polynucleotide derived from a kivd gene, or homolog thereof. In yet a further embodiment, the 2-keto-acid decarboxylase comprises a sequence that encodes a polypeptide of SEQ ID NO:18 having a V461A mutation. In one embodiment, the microorganism comprises an alcohol dehydrogenase selected from the group consisting of Adh1, Adh2, Adh3, Adh4, Adh5, Adh6, Sfa1, a homolog or variant of any of the foregoing, and a polypeptide having at least 60% identity to any one of the foregoing and having alcohol dehydrogenase activity. The alcohol dehydrogenase is encoded by a polynucleotide having at least 60% identity to a nucleic acid selected from the group consisting of an adh1, adh2, adh3, adh4, adh5, adh6, sfa1 gene, and a homolog of any of the foregoing and wherein the polynucleotide encodes a protein having 2-alcohol dehydrogenase activity. In one embodiment, the microorganism comprises a feedback resistant ThrA*. In a specific embodiment, the microorganism comprise an *E. coli* LeuA having one or more mutations at D430, A453, A460 or G462. In a specific embodiment, the microorganism comprise an *E. coli* LeuA having one or more mutations selected from the group consisting of G462D, S139G, H97A, and N167A. In yet another embodiment, the microorganism comprises a G462D/S139G/N167A triple mutant or a G462D/S139G/H97A/N167A quadruple mutant to an *E. coli* LeuA of SEQ ID NO:2. In another embodiment, the microorganism comprises a mutant 2-isopropylmalate synthase derived from *E. coli* comprising a G462D/S139G/N167A triple mutant or a G462D/S139G/H97A/N167A quadruple mutant.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the disclosure and, together with the detailed description, serve to explain the principles and implementations of the invention.

FIG. 2 shows stereo view of active site of *Z. mobilis* pyruvate decarboxylase ZmPDC and the corresponding homology model of *Enterobacter cloacae* indolepyruvate decarboxylase IPDC and KIVD using ZmPDC as the template. The multiple sequence alignment was performed with ClustalW. Residues Y290, W392, and W551 of ZmPDC restrict the size of the binding pocket and prevent activating substrates larger than pyruvate. Residues F381, V461, and M538 of KIVD were mutated to smaller hydrophobic residues such as alanine and leucine in order to allow the enzyme to accept substrates larger than 2-ketoisovalerate.

FIG. 3A-B shows a LeuA sequences and structural information. (A) Binding pocket of *Mycobacterium tuberculosis* LeuA (PDB: 1SR9) complexed with its natural substrate 2-ketoisovalerate. (S)-2-Keto-3-methylvalerate has one more methyl group that would cause steric conflict with Ser 216, His167, and Asn250. (B) Multiple sequence alignment of *Mycobacterium tuberculosis, E. coli,* and *Salmonella typhimurium* LeuA. The binding pocket is conserved, and the corresponding residues of *E. coli* LeuA are His97, Ser139, and Asn167. These residues were subjected to site-specific mutagenesis.

FIG. 5: polynucleotide sequence of kivd: keto isovalerate decarboxylase (*Lactococcus lactis*) (SEQ ID NO: 17); polynucleotide sequence of PDC6 (*Saccharomyces cerevisiae*) (SEQ ID NO: 69).

FIG. 6: polynucleotide sequence of ARO10 (*Saccharomyces cerevisiae*), SEQ ID NO: 71; polynucleotide sequence of THI3 (*Saccharomyces cerevisiae*), SEQ ID NO: 73.

FIG. 7: polynucleotide sequence of pdc (*Clostridium acetobutylicum*), SEQ ID NO: 75; polynucleotide sequence of ADH2: alcohol dehydrogenase (*Saccharomyces cerevisiae*), SEQ ID NO: 77.

FIG. 8: polynucleotide sequence of ilvI (*E. coli*), SEQ ID NO: 79; polynucleotide sequence of ilvH (*E. coli*), SEQ ID NO: 81; polynucleotide sequence of ilvC (*E. coli*), SEQ ID NO: 83.

FIG. 9: polynucleotide sequence of ilvD (*E. coli*), SEQ ID NO: 85; polynucleotide sequence of ilvA (*E. coli*), SEQ ID NO: 87.

FIG. 10: polynucleotide sequence of leuA (*E. coli*), SEQ ID NO: 1; polypeptide sequence of LeuA (*E. coli*), SEQ ID NO: 2; polynucleotide sequence of leuB (*E. coli*), SEQ ID NO: 89.

FIG. 11: polynucleotide sequence of leuC (*E. coli*), SEQ ID NO: 91; polynucleotide sequence of leuD (*E. coli*), SEQ ID NO: 93; polynucleotide sequence of leuM (*E. coli*), SEQ ID NO: 95; polynucleotide sequence of ilvG (*E. coli*), SEQ ID NO: 97; polynucleotide sequence of ilvN (*E. coli*), SEQ ID NO: 99.

FIG. 12: polynucleotide sequence of ilvB (*E. coli*); polynucleotide sequence of ilvB (*E. Coli), SEQ ID NO:* 102.

FIG. 13: polynucleotide sequence of adhE2 (*Clostridium acetobutylicum*), SEQ ID NO: 103; polynucleotide sequence of Li-leuC (*Leptospira interrogans*), SEQ ID NO: 105.

FIG. 14: polynucleotide sequence of Li-leuD (*Leptospira interrogans*), SEQ ID NO: 107; polynucleotide sequence of Li-leuB (*Leptospira interrogans*), SEQ ID NO: 109; polynucleotide sequence of TyrA (*E. coli*), SEQ ID NO: 111.

DETAILED DESCRIPTION

As used herein and in the appended claims, the singular forms "a," "and," and "the" include plural referents unless the context clearly dictates otherwise. Thus, for example, reference to "a polynucleotide" includes a plurality of such polynucleotides and reference to "the microorganism" includes reference to one or more microorganisms, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Any publications discussed above and throughout the text are provided solely for their disclosure prior to the filing date of the present application. Nothing herein is to be construed as an admission that the inventors are not entitled to antedate such disclosure by virtue of prior disclosure.

The disclosure demonstrates that by combining protein engineering and metabolic engineering approaches, it is possible to expand the intermediary metabolism of *E. coli* to produce various C5 to C8 alcohols and amino acids that are not readily produced by microorganisms. Due to their specific physical and chemical properties, these long chain alcohols are good candidates as biofuels or renewable chemical reagents.

Figure 1A:
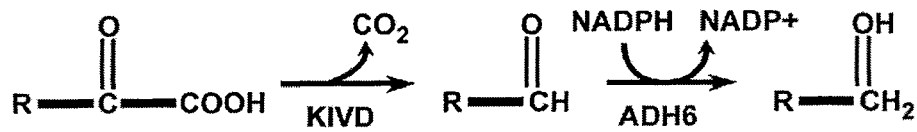
FIG. 1A-E depicts pathways useful in understanding the disclosure. (A) Conversion of 2-keto acids to alcohols by a broad-substrate range 2-keto-acid decarboxylase (KIVD) and an alcohol dehydrogenase (ADH6). (B) Schematic representation of the biosynthetic pathway of 3-methyl-1-pentanol. Similar to 2-ketoisovalerate, 2-keto-3-methylvalerate adds one more carbon to its side chain by the leucine biosynthesis enzymes. (C) Synthetic operons for gene expression. Overexpression of ThrABC, TdcB, and IlvGMCD drives the carbon flux towards 2-keto-3-methylvalerate. (D) shows a further diagram of the alcohols that can be generated by the pathways of the disclosure. (E) shows a cloning strategy used in the disclosure.
Figure 1B:
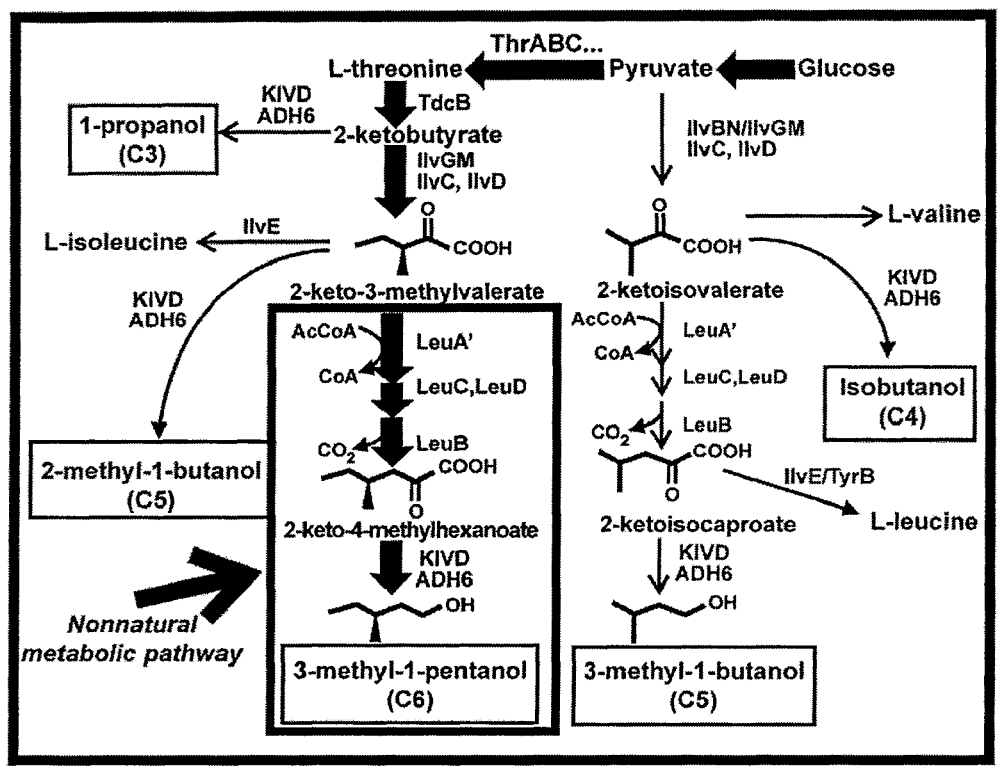

Acetyl-CoA is a common chemical unit for carbon chain elongation, such as reactions in tricarboxylic acid cycle, glyoxylate cycle, mevalonate pathway, and leucine biosynthesis. To explore the possibility of using acetyl-CoA related chemistry to produce C5-C8 alcohols, the disclosure provides an engineered nonnatural metabolic pathway (FIG. 1B). The pathway can be recombinantly produced in a number of microorganisms as discussed more fully herein.

The disclosure utilizes a pathway comprising a mutant enzyme that provides or improves the synthesis and production C5-C8 alcohols. In one embodiment, a mutant 2-isopropylmalate synthase (LeuA) enzyme is provided. The mutant LeuA is capable of utilizing longer chain keto acids precursors as a substrate thereby allowing for the generation C7-C9 2-keto acids, which are ultimately converted to C5-C8 alcohols. In yet another embodiment, the disclosure utilizes a mutant keto acid decarboxylase (e.g., kivd). The mutant keto acid decarboxylase is capable of utilizing longer chain 2-keto acids as a substrate. For example, the mutant keto acid decarboxylase can utilize 2-keto-4-methylhexanoate as a substrate in the generation of an alcohol.

The existing metabolic capability of *E. coli* to synthesize 2-keto-3-methylvalerate, the 2-keto acid precursor of amino acid L-isoleucine was used as a starting point. The chemical structure of 2-keto-3-methylvalerate is very similar to 2-ketoisovalerate (the 2-keto acid precursor of amino acid L-valine), containing only one more methyl group on the side chain. Since 2-ketoisovalerate is converted to 2-ketoisocaproate through a three-step chain elongation cycle by 2-isopropylmalate synthase (LeuA), isopropylmalate isomerase complex (LeuC, LeuD), and 3-isopropylmalate dehydrogenase (LeuB), it was reasoned that LeuA, LeuB, LeuC, and LeuD are promiscuous enough to allow 2-keto-3-methylvalerate to go through the same elongation cycle and produce a 2-keto-4-methylhexanoate, 2-keto-5-methylhexanoate, 2-keto-5-methylheptanoate, a 2-keto-6-methyloctanoate and the like. Analogous to the Ehrlich pathway for production of fusel alcohols (FIG. 1A), it was further determined that 2-keto-4-methylhexanoate, 2-keto-5-methylheptanoate, a 2-keto-6-methyloctanoate could be converted to the corresponding aldehyde and then to a five-, six-, seven-, or eight-carbon alcohol (e.g., 1-pentanol, 1-hexanol, 3-methyl-1-pentanol, 4-methyl-1-pentanol, 4-methyl-1-hexanol, 2-isopropyl-1-butanol, and 5-methyl-1-heptanol) by the broad-substrate-range 2-ketoisovalerate decarboxylase (KIVD) from *Lactococcus lactis* and alcohol dehydrogenase VI (ADH6) from *Saccharomyces cerevisiae* or homologs or mutants thereof.

The disclosure provides a LeuA polypeptide comprising a sequence that is at least 80% identical to SEQ ID NO:2, having a mutation in any of the following residues D430, A453, A460, or G462 to remove leucine feedback inhibition. In one embodiment, the polypeptide has a G462D mutation and may include at least one additional mutation selected from the group consisting of S139G, N167A, N167L, and H97A, wherein the LeuA polypeptide is capable of initiating the conversion of 2-keto-3-methylvalerate to a C7-C9 keto acid. In one embodiment, the LeuA polypeptide comprises SEQ ID NO:2 with 1-50 conservative amino acid substitutions and having a mutation in any of the following residues D430, A453, A460, or G462 to remove leucine feedback inhibition. In one embodiment, the polypeptide has a G462D mutation. In yet another embodiment, the LeuA polypeptide comprises a sequence that is at least 80%, 90%, 95%, 98%, or 99% identical to a sequence as set forth in SEQ ID NO:4, 6, 8, 10, 12, 14, or 16 that is capable of converting 2-keto-3-methylvalerate to 2-keto-4-methylhexanoate. In one embodiment, the polypeptide is part of an expressed operon comprising a LeuB, LeuC, and LeuD.

The disclosure further provides a LeuA polynucleotide encoding a LeuA polypeptide of the disclosure. In one embodiment, the polynucleotide comprises a sequence that encodes a polypeptide of SEQ ID NO:2 having a mutation in any of the following residues D430, A453, A460, or G462 to remove leucine feedback inhibition. In another embodiment, the polynucleotide comprises a sequence that encodes a polypeptide of SEQ ID NO:2 having a G462D mutation. In another embodiment, the polynucleotide comprises a sequence that hybridizes to a sequence consisting of SEQ ID NO:1, 3, 5, 7, 9, 11, 13, or 15, wherein the polynucleotide encodes a polypeptide that promotes the conversion of 2-keto-3-methylvalerate to 2-keto-4-methylhexanoate. In yet another embodiment, the polynucleotide encodes a polypeptide that is at least 80%, 90%, 95%, 98%, or 99% identical to a LeuA polypeptide of SEQ ID NO:4, 6, 8, 10, 12, 14, or 16. In yet another embodiment, the polynucleotide comprises a sequence that is at least 80%, 90%, 95%, 98%, or 99% identical to SEQ ID NO:1, 3, 5, 7, 9, 11, 13, or 15 and encodes a polypeptide the promotes the conversion of 2-keto-3-methylvalerate to 2-keto-4-methylhexanoate. In one embodiment, the LeuA polynucleotide is part of an operon comprising LeuABCD, wherein the operon converts 2-keto-3-methylvalerate to 2-keto-4-methylhexanoate.

The disclosure also provides a recombinant microorganism comprising a non-naturally occurring LeuA of the disclosure. In one embodiment, the recombinant microorganism comprises a polynucleotide having a sequence that encodes a polypeptide of SEQ ID NO:2 having a mutation in any of the following residues D430, A453, A460, or G462 to remove leucine feedback inhibition. In one embodiment, the mutant comprises a G462D mutation in SEQ ID NO:2. In another embodiment, the microorganism comprises a polynucleotide having a sequence that hybridizes to a sequence consisting of SEQ ID NO:1, 3, 5, 7, 9, 11, 13, or 15, wherein the polynucleotide encodes a polypeptide that promotes the conversion of 2-keto-3-methylvalerate to 2-keto-4-methylhexanoate. In yet another embodiment, the microorganism comprises a polynucleotide that encodes a polypeptide that is at least 80%, 90%, 95%, 98% or 99% identical to a LeuA polypeptide of SEQ ID NO:4, 6, 8, 10, 12, 14, or 16 and which promotes conversion of 2-keto-3-methylvalerate to 2-keto-4-methylhexanoate. In yet another embodiment, the microorganism comprises a polynucleotide having a sequence that is at least 80%, 90%, 95%, 98%, or 99% identical to SEQ ID NO:1, 3, 5, 7, 9, 11, 13, or 15 and encodes a polypeptide the promotes the conversion of 2-keto-3-methylvalerate to 2-keto-4-methylhexanoate. In yet another embodiment, the microorganism comprises a LeuA polynucleotide that is part of an operon comprising LeuABCD, wherein the operon converts 2-keto-3-methylvalerate to 2-keto-4-methylhexanoate.

As used herein a "Kivd polypeptide" refers to a wild-type polypeptide as well as mutant polypeptides that are capable of promoting the conversion of a keto acid to an alcohol. In one specific embodiment, a mutant kivd polypeptide refers to a polypeptide that promotes the conversion of C7-C9 keto acids to a C6-C8 alcohol. The disclosure provides a Kivd polypeptide comprising a sequence that is at least 80% identical to SEQ ID NO:18, having a V461A mutation and may include at least one additional mutation selected from the group consisting of M538A, M538L, F381A, and F381L, wherein the Kivd polypeptide is capable of initiating the conversion of C7-C9 keto acid to a C6-C8 alcohol. In one embodiment, the Kivd polypeptide comprises SEQ ID NO:18 with 1-50 conservative amino acid substitutions and a V461A mutation and may further comprise at least one additional mutation at M538 or F381. In yet another embodiment, the Kivd polypeptide comprises a sequence that is at least 80%, 90%, 95%, 98%, or 99% identical to a sequence as set forth in SEQ ID NO:18, 20, 22, 24, 26, or 28 that is capable of promoting the conversion of a C7-C9 keto acid to a C6-C8 alcohol.

The disclosure further provides a Kivd polynucleotide encoding a Kivd polypeptide of the disclosure. In one embodiment, the polynucleotide comprises a sequence that encodes a polypeptide of SEQ ID NO:18 having a V461A mutation. In another embodiment, the polynucleotide comprises a sequence that hybridizes to a sequence consisting of SEQ ID NO:17, 19, 21, 23, 25, or 27, wherein the polynucleotide encodes a polypeptide that promotes the conversion of C7-C9 keto acid to the corresponding C6-C8 alcohol. In yet another embodiment, the polynucleotide encodes a polypeptide that is at least 80%, 90%, 95%, 98%, or 99% identical to a Kivd polypeptide of SEQ ID NO:20, 22, 24, 26, or 28 and which promotes the conversion of a C7-C9 keto acid to the corresponding C6-C8 alcohol. In yet another embodiment, the polynucleotide comprises a sequence that is at least 80%, 90%, 95%, 98%, or 99% identical to SEQ ID NO:17, 19, 21, 23, 25, or 27 and encodes a polypeptide that promotes the conversion of a C7-C9 keto acid to a C6-C8 alcohol.

The disclosure also provides a recombinant microorganism comprising a non-naturally occurring Kivd of the disclosure. In one embodiment, the recombinant microorganism comprises a polynucleotide having a sequence that encodes a polypeptide of SEQ ID NO:18 having a V461A mutation. In another embodiment, the microorganism comprises a polynucleotide having a sequence that hybridizes to a sequence consisting of SEQ ID NO:18, 20, 22, 24, 26, or 28, wherein the polynucleotide encodes a polypeptide that promotes the conversion of a C7-C9 keto acid to a C6-C8 alcohol. In yet another embodiment, the microorganism comprises a polynucleotide that encodes a polypeptide that is at least 80%, 90%, 95%, 98%, or 99% identical to a Kivd polypeptide of SEQ ID NO:20, 22, 24, 26, or 28 and which promotes conversion of C7-C9 keto acid to a C6-C8 alcohol. In yet another embodiment, the microorganism comprises a polynucleotide having a sequence that is at least 80%, 90%, 95%, 98%, or 99% identical to SEQ ID NO:17, 19, 21, 23, 25, or 27 and encodes a polypeptide the promotes the conversion of a C7-C9 keto acid to a C6-C8 alcohol.

The disclosure provides metabolically engineered microorganisms comprising biochemical pathways for the production of higher alcohols including C5 to C8 alcohols such as, for example, 1-pentanol, 1-hexanol, 3-methyl-1-pentanol, 4-methyl-1-pentanol, 4-methyl-1-hexanol, 2-isopropyl-1-butanol, and 5-methyl-1-heptanol. A metabolically engineered microorganism of the disclosure comprises one or more recombinant polynucleotides within the genome of the organism or external to the genome within the organism. The microorganism can comprise a reduction, disruption or knockout of a gene found in the wild-type organism and/or introduction of a heterologous polynucleotide.

The disclosure also includes metabolically engineered biosynthetic pathways that utilize an organism's native amino acid pathway. Biofuel production utilizing the organism's native amino acid pathways offers several advantages. Not only does it avoid the difficulty of expressing a large set of foreign genes but it also minimizes the possible accumulation of toxic intermediates. The disclosure provides a much more host-friendly biofuel production system utilizing the organism's native metabolites in the amino acid biosynthetic pathway to produce biofuels.

In one embodiment, the disclosure provides a recombinant microorganism comprising elevated expression of at least one target enzyme as compared to a parental microorganism or encodes an enzyme not found in the parental organism. In another or further aspect, the microorganism comprises a reduction, disruption or knockout of at least one gene encoding an enzyme that competes with a metabolite necessary for the production of a desired higher alcohol product. The recombinant microorganism produces at least one metabolite involved in a biosynthetic pathway for the production of a C5, C6, C7, or C8 alcohol such as 1-pentanol, 1-hexanol, 3-methyl-1-pentanol, 4-methyl-1-pentanol, 4-methyl-1-hexanol, 2-isopropyl-1-butanol, and 5-methyl-1-heptanol. In general, the recombinant microorganism comprises at least one recombinant metabolic pathway that comprises a target enzyme and may further include a reduction in activity or expression of an enzyme in a competitive biosynthetic pathway. The pathway acts to modify a substrate or metabolic intermediate in the production of a C5, C6, C7, or C8 alcohol. The target enzyme is encoded by, and expressed from, a polynucleotide derived from a suitable biological source. In some embodiments, the polynucleotide comprises a gene derived from a bacterial or yeast source and recombinantly engineered into the microorganism of the disclosure. In a more specific embodiment, the microorganism comprises an engineered LeuA or LeuA and Kivd polypeptide that generate C7-C9 keto acids and promote the conversion of the C7-C9 keto acids to a corresponding C5-C8 alcohol.

As used herein, the term "metabolically engineered" or "metabolic engineering" involves rational pathway design and assembly of biosynthetic genes, genes associated with operons, and control elements of such polynucleotides, for the production of a desired metabolite in a microorganism. "Metabolically engineered" can further include optimization of metabolic flux by regulation and optimization of transcription, translation, protein stability and protein functionality using genetic engineering and appropriate culture conditions including the reduction of, disruption, or knocking out of, a competing metabolic pathway that competes with an intermediate leading to a desired pathway. A biosynthetic gene can be heterologous to the host microorganism, either by virtue of being foreign to the host, or being modified by mutagenesis, recombination, and/or association with a heterologous expression control sequence in an endogenous host cell. In one embodiment, where the polynucleotide is xenogenetic to the host organism, the polynucleotide can be codon optimized.

The term "biosynthetic pathway", also referred to as "metabolic pathway", refers to a set of anabolic or catabolic biochemical reactions for converting (transmuting) one chemical species into another. Gene products belong to the same "metabolic pathway" if they, in parallel or in series, act on the same substrate, produce the same product, or act on or produce a metabolic intermediate (i.e., metabolite) between the same substrate and metabolite end product.

The leuABCD operon includes leuA, leuB, leuC, and leuD genes. Among them, leuA encodes α-isopropylmalate synthase, leuB encodes β-isopropylmalate dehydrogenase, and leuC and leuD encode α-isopropylmalate isomerase. Of these enzymes, α-isopropylmalate synthase catalyzes the synthetic reaction from α-ketoisovalerate to α-isopropylmalate, α-isopropylmalate isomerase catalyzes the isomerization reaction from α-isopropylmalate to β-isopropylmalate and β-isopropylmalate dehydrogenase catalyzes the dehydrogenation reaction from β-isopropylmalate to α-ketoisocaproic acid which is the final intermediate of L-leucine biosynthesis. The disclosure takes advantage of the promiscuity of α-isopropylmalate synthase and modifies the capacity of the α-isopropylmalate synthase to convert 2-keto-3-methylvalerate to a C7-C9 keto acid. Although not wanting to be bound by any particular mechanism of action, it is believed that the mutant LeuA polypeptides of the disclosure have an enlarged substrate binding domain compared to the wild-type LeuA thereby allowing for the generation of longer chain keto acids.

Escherichia possess four kinds of transaminases, namely, transaminase A (aspartate-glutamate aminotransferase) encoded by aspC gene, transaminase B (BCAA aminotransferase) encoded by ilvE gene which is included in the ilvGMEDA operon, transaminase C (alanine-valine aminotransferase) encoded by avtA gene and transaminase D (tyrosine aminotransferase) encoded by tyrB gene. These enzymes participate in various amination reactions. Of these enzymes, transaminase B and transaminase D catalyze the above-mentioned amination reaction from α-ketoisocaproic acid to L-leucine. Transaminase C and transaminase D catalyze the final step of L-valine biosynthetic pathway, which includes a common pathway among the L-valine biosynthesis and L-leucine biosynthesis.

Also, the expression of leuABCD operon is repressed by L-leucine. Expression of ilvBN gene encoding acetohydroxy acid synthase I suffers concerted repression by L-valine and L-leucine, expression of ilvGM gene encoding acetohydroxy acid synthase II suffers concerted repression by L-isoleucine, L-valine and L-leucine, and expression of ilvIH gene encoding acetohydroxy acid synthase III suffers repression by L-leucine.

The term "substrate" or "suitable substrate" refers to any substance or compound that is converted or meant to be converted into another compound by the action of an enzyme. The term includes not only a single compound, but also combinations of compounds, such as solutions, mixtures and other materials which contain at least one substrate, or derivatives thereof. Further, the term "substrate" encompasses any biomass derived sugar, but also intermediate and end product metabolites used in a pathway associated with a metabolically engineered microorganism as described herein. A "biomass derived sugar" includes, but is not limited to, molecules such as glucose, sucrose, mannose, xylose, and arabinose. The term biomass derived sugar encompasses suitable carbon substrates ordinarily used by microorganisms, such as 6 carbon sugars, including but not limited to glucose, lactose, sorbose, fructose, idose, galactose, and mannose all in either D or L form, or a combination of 6 carbon sugars, such as glucose and fructose, and/or 6 carbon sugar acids including, but not limited to, 2-keto-L-gulonic acid, idonic acid (IA), gluconic acid (GA), 6-phosphogluconate, 2-keto-D-gluconic acid (2 KDG), 5-keto-D-gluconic acid, 2-ketogluconatephosphate, 2,5-diketo-L-gulonic acid, 2,3-L-diketogulonic acid, dehydroascorbic acid, erythorbic acid (EA), and D-mannonic acid.

Recombinant microorganisms provided herein can express a plurality of target enzymes involved in pathways for the production of, for example, C5, C6, C7, and C8 alcohols such as 1-pentanol, 1-hexanol, 3-methyl-1-pentanol, 4-methyl-1-pentanol, 4-methyl-1-hexanol, 2-isopropyl-1-butanol, and 5-methyl-1-heptanol from using a suitable carbon substrate. In one embodiment, at least one enzyme in the plurality of target enzymes is a mutant LeuA polypeptide or a mutant LeuA and mutant Kivd polypeptide.

Accordingly, metabolically "engineered" or "modified" microorganisms are produced via the introduction of genetic material into a host or parental microorganism of choice thereby modifying or altering the cellular physiology and biochemistry of the microorganism. Through the introduction of genetic material the parental microorganism acquires new properties, e.g., the ability to produce a new, or greater quantities of, an intracellular metabolite. In an illustrative embodiment, the introduction of genetic material into a parental microorganism results in a new or modified ability to produce a C7-C9 keto acid or an alcohol such as C5, C6, C7, and C8 alcohols including, e.g., 1-pentanol, 1-hexanol, 3-methyl-1-pentanol, 4-methyl-1-pentanol, 4-methyl-1-hexanol, 2-isopropyl-1-butanol, and 5-methyl-1-heptanol. The genetic material introduced into the parental microorganism contains gene(s), or parts of genes, coding for one or more of the enzymes involved in a biosynthetic pathway for the production of an alcohol and may also include additional elements for the expression and/or regulation of expression of these genes, e.g., promoter sequences.

An engineered or modified microorganism can also include, in the alternative or in addition to, the introduction of a genetic material into a host or parental microorganism, or the disruption, deletion, or knocking out of a gene or polynucleotide to alter the cellular physiology and biochemistry of the microorganism. Through the reduction, disruption, or knocking out of a gene or polynucleotide the microorganism acquires new or improved properties (e.g., the ability to produce a new or greater quantities of an intracellular metabolite, improve the flux of a metabolite down a desired pathway, and/or reduce the production of undesirable by-products).

The disclosure demonstrates that the expression of one or more heterologous polynucleotide or over-expression of one or more heterologous polynucleotide encoding a polypeptide having ketoacid decarboxylase and a polypeptide having alcohol dehydrogenase in the presence of a polypeptide having modified α-isopropylmalate synthase capable of promoting synthesis of C7-C9 keto acids, a polypeptide having β-isopropylmalate dehydrogenase, a polypeptide having α-isopropylmalate isomerase, and a polypeptide having threonine synthase activity. For example, the disclosure demonstrates that with over-expression of the heterologous kivd and adh6 and the E. coli leuA (or mutant thereof), leuB, leuC, leuD (or a Leu operon, e.g., leuABCD (wherein leuA is a mutant leuA), the production of C5-C8 alcohols can be obtained (e.g., 1-pentanol, 1-hexanol, 3-methyl-1-pentanol, 4-methyl-1-pentanol, 4-methyl-1-hexanol, 2-isopropyl-1-butanol, and 5-methyl-1-heptanol) can be obtained.

Microorganisms provided herein are modified to produce metabolites in quantities not available in the parental microorganism. A "metabolite" refers to any substance produced by metabolism or a substance necessary for or taking part in a particular metabolic process. A metabolite can be an organic compound that is a starting material (e.g., glucose or pyruvate), an intermediate (e.g., 2-keto acid, 2-keto-4-methylhexanoate, 2-keto-5-methylheptanoate, 2-keto-6-methyloctanoate, or 2-keto-5-methylhexanoate) in, or an end product (e.g., 1-pentanol, 1-hexanol, 3-methyl-1-pentanol, 4-methyl-1-pentanol, 4-methyl-1-hexanol, 2-isopropyl-1-butanol, and 5-methyl-1-heptanol) of metabolism. Metabolites can be used to construct more complex molecules, or they can be broken down into simpler ones. Intermediate metabolites may be synthesized from other metabolites, perhaps used to make more complex substances, or broken down into simpler compounds, often with the release of chemical energy.

Accordingly, provided herein are recombinant microorganisms that produce C5, C6, C7, or C8 alcohols and in some aspects may include the elevated expression of target enzymes such as a 2-keto-acid decarboxylase (e.g., PDC6, ARO10, THI3, kivd, or pdc), and alcohol dehydrogenase (e.g., ADH6) in combination with mutant LeuA polypeptides.

As previously noted the target enzymes described throughout this disclosure generally produce metabolites. For example, the enzymes 2-isopropylmalate synthase (leuA) or mutants thereof, beta-isopropylmalate dehydrogenase (leuB), and isopropylmalate isomerase (leuC, leuD, or leuCD operon) may produce 2-keto-4-methylhexanoate, 2-keto-5-methylheptanoate, 2-keto-6-methyloctanoate, or 2-keto-5-methylhexanoate from a substrate that includes 2-ketobutyrate or 2-keto-3-methylvalerate. In addition, the target enzymes described throughout this disclosure are encoded by polynucleotides. For example, threonine dehydratase can be encoded by a polynucleotide derived from an ilvA gene. Acetohydroxy acid synthase can be encoded by a polynucleotide derived from an ilvIH operon. Acetohydroxy acid isomeroreductase can be encoded by a polynucleotide derived from an ilvC gene. Dihydroxy-acid dehydratase can be encoded by a polynucleotide derived from an ilvD gene. 2-Keto-acid decarboxylase can be encoded by a polynucleotide derived from a PDC6, ARO10, THI3, kivd, and/or pdc gene. Alcohol dehydrogenase can be encoded by a polynucleotide derived from an ADH6 gene. Additional enzymes and exemplary genes are described throughout this document. Homologs of the various polypeptides and polynucleotides can be derived from any biologic source that provides a suitable polynucleotide encoding a suitable enzyme. Homologs, for example, can be identified by reference to various databases.

The disclosure identifies specific genes useful in the methods, compositions and organisms of the disclosure; however it will be recognized that absolute identity to such genes is not necessary. For example, changes in a particular gene or polynucleotide comprising a sequence encoding a polypeptide or enzyme can be performed and screened for activity. Typically such changes comprise conservative mutation and silent mutations. Such modified or mutated polynucleotides and polypeptides can be screened for expression of a functional enzyme activity using methods known in the art.

Due to the inherent degeneracy of the genetic code, other polynucleotides which encode substantially the same or a functionally equivalent polypeptide can also be used to clone and express the polynucleotides encoding such enzymes.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17: 477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al. (1996) Nucl. Acids Res. 24: 216-218). Methodology for optimizing a nucleotide sequence for expression in a plant is provided, for example, in U.S. Pat. No. 6,015,891, and the references cited therein.

Those of skill in the art will recognize that, due to the degenerate nature of the genetic code, a variety of DNA compounds differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA compounds of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as they modified or variant polypeptides have the enzymatic anabolic or catabolic activity of the reference polypeptide. Furthermore, the amino acid sequences encoded by the DNA sequences shown herein merely illustrate embodiments of the disclosure.

In addition, homologs of enzymes useful for generating metabolites (e.g., keto thiolase, acetyl-CoA acetyltransferase, hydroxybutyryl CoA dehydrogenase, crotonase, crotonyl-CoA reductase, butyryl-coA dehydrogenase, alcohol dehydrogenase (ADH)) are encompassed by the microorganisms and methods provided herein. The term "homologs" used with respect to an original enzyme or gene of a first family or species refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as a homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences).

As used herein, two proteins (or a region of the proteins) are substantially homologous when the amino acid sequences have at least about 30%, 40%, 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences. For example, reference to a kivd gene includes homologs (e.g., pdc6, aro10, thI3, pdc, kdcA, pdc1, pdc5) from other organisms encoding an enzyme having substantially similar enzymatic activity, as well as genes having at least 30, 40, 50, 60, 70, 80, 85, 90, 95, 98, or 99% identity to the referenced gene and which encodes an enzyme having substantially similar enzymatic activity as the referenced gene. For example, pyruvate decarboxylase of *Kluyveromyces lactis* has 37% identity to Kivd at the amino acids level; kivd and thI3 are 32% identical at the nucleic acid level; Alcohol dehydrogenase of *Schizosaccharomyces pombe* has 52% identity to ADH2 of *Saccharomyces cerevisiae* at the amino acid sequence level; *S. cerevisiae* adh2 and *Lactococcus lactis* adh are 49% identical; KIVD (*Lactococcus lactis*) and PDC6 (*Saccharomyces cerevisiae*) share 36% identity (Positives=322/562 (57%), Gaps=24/562 (4%)); KIVD (*Lactococcus lactis*) and THI3 (*Saccharomyces cerevisiae*) share 32% identity (Positives=307/571 (53%), Gaps=35/571 (6%)); kivd (*Lactococcus lactis*) and ARO10 (*Saccharomyces cerevisiae*) share 30% identity (Positives=296/598 (49%), Gaps=65/598 (10%)); ARO10 (*Saccharomyces cerevisiae*) and PDC6 (*Saccharomyces cerevisiae*) share 34% identity (Positives=320/616 (51%), Gaps=61/616 (9%)); ARO10 (*Saccharomyces cerevisiae*) and THI3 (*Saccharomyces cerevisiae*) share 30% identity (Positives=304/599 (50%), Gaps=48/599 (8%)); ARO10 (*Saccharomyces cerevisiae*) and Pyruvate decarboxylase (*Clostridium acetobutylicum* ATCC 824) share 30% identity (Positives=291/613 (47%), Gaps=73/613 (11%)); PDC6 (*Saccharomyces cerevisiae*) and THI3 (*Saccharomy-*

*ces cerevisiae*) share 50% identity (Positives=402/561 (71%), Gaps=17/561 (3%)); PDC6 (*Saccharomyces cerevisiae*) and Pyruvate decarboxylase (*Clostridium acetobutylicum* ATCC 824) share 38% identity (Positives=328/570 (57%), Gaps=30/570 (5%)); and THI3 (*Saccharomyces cerevisiae*) and Pyruvate decarboxylase (*Clostridium acetobutylicum* ATCC 824) share 35% identity (Positives=284/521 (54%), Gaps=25/521 (4%)). Sequence for each of the genes and polypeptides/enzymes listed herein can be readily identified using databases available on the World-Wide-Web. In addition, the amino acid sequence and nucleic acid sequence can be readily compared for identity using commonly used algorithms in the art.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al., 1994, hereby incorporated herein by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A typical algorithm used comparing a molecule sequence to a database containing a large number of sequences from different organisms is the computer program BLAST (Altschul, 1990; Gish, 1993; Madden, 1996; Altschul, 1997; Zhang, 1997), especially blastp or tblastn (Altschul, 1997). Typical parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

When searching a database containing sequences from a large number of different organisms, it is typical to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (Pearson, 1990, hereby incorporated herein by reference). For example, percent sequence identity between amino acid sequences can be determined using FASTA with its default parameters (a word size of 2 and the PAM250 scoring matrix), as provided in GCG Version 6.1, hereby incorporated herein by reference.

As demonstrated herein, mutants of enzymes of the disclosure can be used in the engineered pathways of the disclosure. For example, mutant Kivd and LeuA are useful either independently or in combination for the production of various alcohols.

Mutant Kivd, LeuA or other enzymes in the metabolic pathway can be derived by error prone PCR, directed mutagenesis and directed evolution techniques known in the art. The result mutants can then be assayed for their ability to convert a substrate to a product.

The disclosure provides accession numbers for various genes, homologs and variants useful in the generation of recombinant microorganisms described herein as well as for the generation of mutant enzymes (e.g., Kivd mutants or LeuA mutants). It is to be understood that homologs and variants described herein are exemplary and non-limiting. Additional homologs, variants and sequences are available to those of skill in the art using various databases including, for example, the National Center for Biotechnology Information (NCBI) access to which is available on the World-Wide-Web. It will be recognized that although various mutations in LeuA and Kivd have been identified, similar mutations in homologs can be obtained and identified using techniques known in the art. For example, an alignment of homologs will identify corresponding amino acids and thus codons in each homolog that can be mutated and assayed for activity. Such homolog variants are encompassed by the disclosure.

Ethanol Dehydrogenase (also referred to as Aldehyde-alcohol dehydrogenase) is encoded in *E. coli* by adhE. adhE comprises three activities: alcohol dehydrogenase (ADH); acetaldehyde/acetyl-CoA dehydrogenase (ACDH); pyruvate-formate-lyase deactivase (PFL deactivase); PFL deactivase activity catalyzes the quenching of the pyruvate-formate-lyase catalyst in an iron, NAD, and CoA dependent reaction. Homologs are known in the art (see, e.g., aldehyde-alcohol dehydrogenase (*Polytomella* sp. Pringsheim 198.80) gi|40644910|emb|CAD42653.2|(40644910); aldehyde-alcohol dehydrogenase (*Clostridium botulinum* A str. ATCC 3502) gi|148378348|ref|YP_001252889.1|(148378348); aldehyde-alcohol dehydrogenase (*Yersinia pestis* CO92) gi|16122410|ref|NP_405723.1|(16122410); aldehyde-alcohol dehydrogenase (*Yersinia pseudotuberculosis* IP 32953) gi|51596429|ref|YP_070620.1|(51596429); aldehyde-alcohol dehydrogenase (*Yersinia pestis* CO92) gi|115347889|emb|CAL20810.1|(115347889); aldehyde-alcohol dehydrogenase (*Yersinia pseudotuberculosis* IP 32953) gi|51589711|emb|CAH21341.1|(51589711); Aldehyde-alcohol dehydrogenase (*Escherichia coli* CFT073) gi|26107972|gb|AAN80172.1|AE016760_31(26107972); aldehyde-alcohol dehydrogenase (*Yersinia pestis* biovar Microtus str. 91001) gi|45441777|ref|NP_993316.1| (45441777); aldehyde-alcohol dehydrogenase (*Yersinia pestis* biovar Microtus str. 91001) gi|45436639|gb|AAS62193.1| (45436639); aldehyde-alcohol dehydrogenase (*Clostridium perfringens* ATCC 13124) gi|110798574|ref|YP_697219.1| (110798574); aldehyde-alcohol dehydrogenase (*Shewanella oneidensis* MR-1) gi|24373696|ref|NP_717739.1| (24373696); aldehyde-alcohol dehydrogenase (*Clostridium* botulinum A str. ATCC 19397) gi|153932445|ref|YP_001382747.1|(153932445); aldehyde-alcohol dehydrogenase (*Yersinia pestis* biovar Antigua str. E1979001) gi|165991833|gb|EDR44134.1|(165991833); aldehyde-alcohol dehydrogenase (*Clostridium botulinum* A str. Hall) gi|153937530|ref|YP_001386298.1|(153937530); aldehyde-alcohol dehydrogenase (*Clostridium perfringens* ATCC 13124) gi|110673221|gb|ABG82208.1|(110673221); aldehyde-alcohol dehydrogenase (*Clostridium botulinum* A str. Hall) gi|152933444|gb|ABS38943.1|(152933444); aldehyde-alcohol dehydrogenase (*Yersinia pestis* biovar Orientalis str. F1991016) gi|165920640|gb|EDR37888.1|(165920640); aldehyde-alcohol dehydrogenase (*Yersinia pestis* biovar Orientalis str. IP275) gi|165913933|gb|EDR32551.1|(165913933); aldehyde-alcohol dehydrogenase (*Yersinia pestis* Angola) gi|162419116|ref|YP_001606617.1|(162419116); aldehyde-alcohol dehydrogenase (*Clostridium botulinum* F str. Langeland) gi|153940830|ref|YP_001389712.1|(153940830); aldehyde-alcohol dehydrogenase (*Escherichia coli* HS) gi|157160746|ref|YP_001458064.1|(157160746); aldehyde-alcohol dehydrogenase (*Escherichia coli* E24377A) gi|157155679|ref|YP_001462491.1|(157155679); aldehyde-alcohol dehydrogenase (*Yersinia enterocolitica* subsp. *enterocolitica* 8081) gi|123442494|ref|YP_001006472.1|(123442494); aldehyde-alcohol dehydrogenase (*Synechococcus* sp. JA-3-3Ab) gi|86605191|ref|YP_473954.1|(86605191); aldehyde-alcohol dehydrogenase (*Listeria monocytogenes* str. 4b F2365) gi|46907864|ref|YP_014253.1|(46907864); aldehyde-alcohol dehydrogenase (*Enterococcus faecalis* V583) gi|29375484|ref|NP_814638.1|(29375484); aldehyde-alcohol dehydrogenase (*Streptococcus agalactiae* 2603V/R) gi|22536238|ref|NP_687089.1|(22536238); aldehyde-alcohol dehydrogenase (*Clostridium botulinum* A str. ATCC 19397) gi|152928489|gb|ABS33989.1|(152928489); aldehyde-alcohol dehydrogenase (*Escherichia coli* E24377A) gi|157077709|gb|ABV17417.1|(157077709); aldehyde-alcohol dehydrogenase (*Escherichia coli* HS) gi|157066426|gb|ABV05681.1|(157066426); aldehyde-alcohol dehydrogenase (*Clostridium botulinum* F str. Langeland) gi|152936726|gb|ABS42224.1|(152936726); aldehyde-alcohol dehydrogenase (*Yersinia pestis* CA88-4125) gi|149292312|gb|EDM42386.1|(149292312); aldehyde-alcohol dehydrogenase (*Yersinia enterocolitica* subsp. *enterocolitica* 8081) gi|122089455|emb|CAL12303.1|(122089455); aldehyde-alcohol dehydrogenase (*Chlamydomonas reinhardtii*) gi|92084840|emb|CAF04128.1|(92084840); aldehyde-alcohol dehydrogenase (*Synechococcus* sp. JA-3-3Ab) gi|86553733|gb|ABC98691.1|(86553733); aldehyde-alcohol dehydrogenase (*Shewanella oneidensis* MR-1) gi|24348056|gb|AAN55183.1|AE015655_9(24348056); aldehyde-alcohol dehydrogenase (*Enterococcus faecalis* V583) gi|293429441gb|AAO80708.1|(29342944); aldehyde-alcohol dehydrogenase (*Listeria monocytogenes* str. 4b F2365) gi|46881133|gb|AAT04430.1|(46881133); aldehyde-alcohol dehydrogenase (*Listeria monocytogenes* str. 1/2a F6854) gi|47097587|ref|ZP_00235115.1|(47097587); aldehyde-alcohol dehydrogenase (*Listeria monocytogenes* str. 4b H7858) gi|47094265|ref|ZP_00231973.1|(47094265); aldehyde-alcohol dehydrogenase (*Listeria monocytogenes* str. 4b H7858) gi|47017355|gb|EAL08180.1|(47017355); aldehyde-alcohol dehydrogenase (*Listeria monocytogenes* str. 1/2a F6854) gi|47014034|gb|EAL05039.1|(47014034); aldehyde-alcohol dehydrogenase (*Streptococcus agalactiae* 2603V/R) gi|22533058|gb|AAM98961.1|AE014194_6(22533058)p; aldehyde-alcohol dehydrogenase (*Yersinia pestis* biovar Antigua str. E1979001) gi|166009278|ref|ZP_02230176.1|(166009278); aldehyde-alcohol dehydrogenase (*Yersinia pestis* biovar Orientalis str. IP275) gi|165938272|ref|ZP_02226831.1|(165938272); aldehyde-alcohol dehydrogenase (*Yersinia pestis* biovar Orientalis str. F1991016) gi|165927374|ref|ZP_02223206.1|(165927374); aldehyde-alcohol dehydrogenase (*Yersinia pestis* Angola) gi|162351931|gb|ABX85879.1|(162351931); aldehyde-alcohol dehydrogenase (*Yersinia pseudotuberculosis* IP 31758) gi|153949366|ref|YP_001400938.1|(153949366); aldehyde-alcohol dehydrogenase (*Yersinia pseudotuberculosis* IP 31758) gi|152960861|gb|ABS48322.1|(152960861); aldehyde-alcohol dehydrogenase (*Yersinia pestis* CA88-4125) gi|149365899|ref|ZP_01887934.1|(149365899); Acetaldehyde dehydrogenase (acetylating) (*Escherichia coli* CFT073) gi|26247570|ref|NP_753610.1|(26247570); aldehyde-alcohol dehydrogenase (includes: alcohol dehydrogenase; acetaldehyde dehydrogenase (acetylating) (EC 1.2.1.10) (acdh); pyruvate-formate-lyase deactivase (pfl deactivase)) (*Clostridium botulinum* A str. ATCC 3502) gi|148287832|emb|CAL81898.1|(148287832); aldehyde-alcohol dehydrogenase (Includes: Alcohol dehydrogenase (ADH); Acetaldehyde dehydrogenase (acetylating) (ACDH); Pyruvate-formate-lyase deactivase (PFL deactivase)) gi|71152980|sp|P0A9Q7.2|ADHE_ECOLI(71152980); aldehyde-alcohol dehydrogenase (includes: alcohol dehydrogenase and acetaldehyde dehydrogenase, and pyruvate-formate-lyase deactivase (*Erwinia carotovora* subsp. *atroseptica* SCRI1043) gi|50121254|ref|YP_050421.1|(50121254); aldehyde-alcohol dehydrogenase (includes: alcohol dehydrogenase and acetaldehyde dehydrogenase, and pyruvate-formate-lyase deactivase (*Erwinia carotovora* subsp. *atroseptica* SCRI1043) gi|49611780|emb|CAG75229.1|(49611780); Aldehyde-alcohol dehydrogenase (Includes: Alcohol dehydrogenase (ADH); Acetaldehyde dehydrogenase (acetylating) (ACDH)) gi|19858620|sp|P33744.3|ADHE_CLOAB(19858620); Aldehyde-alcohol dehydrogenase (Includes: Alcohol dehydrogenase (ADH); Acetaldehyde dehydrogenase (acetylating) (ACDH); Pyruvate-formate-lyase deactivase (PFL deactivase)) gi|71152683|sp|P0A9Q8.2|ADHE_ECO57(71152683); aldehyde-alcohol dehydrogenase (includes: alcohol dehydrogenase; acetaldehyde dehydrogenase (acetylating); pyruvate-formate-lyase deactivase (*Clostridium difficile* 630) gi|126697906|ref|YP_001086803.1|(126697906); aldehyde-alcohol dehydrogenase (includes: alcohol dehydrogenase; acetaldehyde dehydrogenase (acetylating); pyruvate-formate-lyase deactivase (*Clostridium difficile* 630) gi|115249343|emb|CAJ67156.1|(115249343); Aldehyde-alcohol dehydrogenase (includes: alcohol dehydrogenase (ADH) and acetaldehyde dehydrogenase (acetylating) (ACDH); pyruvate-formate-lyase deactivase (PFL deactivase)) (*Photorhabdus luminescens* subsp. *laumondii* TTO1) gi|37526388|ref|NP_929732.1|(37526388); aldehyde-alcohol dehydrogenase 2 (includes: alcohol dehydrogenase; acetaldehyde dehydrogenase) (*Streptococcus pyogenes* str. Manfredo) gi|134271169emb|CAM29381.1|(134271169); Aldehyde-alcohol dehydrogenase (includes: alcohol dehydrogenase (ADH) and acetaldehyde dehydrogenase (acetylating) (ACDH); pyruvate-formate-lyase deactivase (PFL deactivase)) (*Photorhabdus luminescens* subsp. *laumondii* TTO1) gi|36785819|emb|CAE14870.1|(36785819); aldehyde-alcohol dehydrogenase (includes: alcohol dehydrogenase and pyruvate-formate-lyase deactivase (*Clostridium difficile* 630) gi|126700586|ref|YP_

001089483.1|(126700586); aldehyde-alcohol dehydrogenase (includes: alcohol dehydrogenase and pyruvate-formate-lyase deactivase (*Clostridium difficile* 630) gi|115252023|emb|CAJ69859.1|(115252023); aldehyde-alcohol dehydrogenase 2 (*Streptococcus pyogenes* str. Manfredo) gi|139472923|ref|YP_001127638.1|(139472923); aldehyde-alcohol dehydrogenase E (*Clostridium perfringens* str. 13) gi|18311513|ref|NP_563447.1|(18311513); aldehyde-alcohol dehydrogenase E (*Clostridium perfringens* str. 13) gi|18146197|dbj|BAB82237.1|(18146197); Aldehyde-alcohol dehydrogenase, ADHE1 (*Clostridium acetobutylicum* ATCC 824) gi|15004739|ref|NP_149199.1| (15004739); Aldehyde-alcohol dehydrogenase, ADHE1 (*Clostridium acetobutylicum* ATCC 824) gi|14994351|gb|AAK76781.1|AE001438_34(14994351); Aldehyde-alcohol dehydrogenase 2 (Includes: Alcohol dehydrogenase (ADH); acetaldehyde/acetyl-CoA dehydrogenase (ACDH)) gi|2492737|sp|Q24803.1|ADH2_ENTHI (2492737); alcohol dehydrogenase (*Salmonella enterica* subsp. *enterica* serovar Typhi str. CT18) gi|16760134|ref|NP_455751.1|(16760134); and alcohol dehydrogenase (*Salmonella enterica* subsp. *enterica* serovar Typhi) gi|16502428|emb|CAD08384.1|(16502428)), each sequence associated with the accession number is incorporated herein by reference in its entirety.

Alpha isopropylmalate synthase (EC 2.3.3.13, sometimes referred to as 2-isopropylmalate synthase, alpha-IPM synthetase) catalyzes the condensation of the acetyl group of acetyl-CoA with 3-methyl-2-oxobutanoate (2-oxoisovalerate) to form 3-carboxy-3-hydroxy-4-methylpentanoate (2-isopropylmalate). Alpha isopropylmalate synthase is encoded in *E. coli* by leuA. LeuA homologs and variants are known. Additionally mutant LeuA polypeptides are provided by the disclosure. Such mutants can be used to identify conserved and non-conserved amino acids in homologs. For example, such homologs and variants include, for example, 2-isopropylmalate synthase (*Corynebacterium glutamicum*) gi|452382|emb|CAA50295.1|(452382); 2-isopropylmalate synthase (*Escherichia coli* K12) gi|16128068|ref|NP_414616.1|(16128068); 2-isopropylmalate synthase (*Escherichia coli* K12) gi|1786261|gb|AAC73185.1|(1786261); 2-isopropylmalate synthase (*Arabidopsis thaliana*) gi|15237194|ref|NP_197692.1|(15237194); 2-isopropylmalate synthase (*Arabidopsis thaliana*) gi|42562149|ref|NP_173285.2|(42562149); 2-isopropylmalate synthase (*Arabidopsis thaliana*) gi|15221125|ref|NP_177544.1|(15221125); 2-isopropylmalate synthase (*Streptomyces coelicolor* A3(2)) gi|32141173|ref|NP_733575.1|(32141173); 2-isopropylmalate synthase (*Rhodopirellula baltica* SH 1) gi|32477692|ref|NP_870686.1|(32477692); 2-isopropylmalate synthase (*Rhodopirellula baltica* SH 1) gi|32448246|emb|CAD77763.1|(32448246); 2-isopropylmalate synthase (*Akkermansia muciniphila* ATCC BAA-835) gi|166241432|gb|EDR53404.1|(166241432); 2-isopropylmalate synthase (*Herpetosiphon aurantiacus* ATCC 23779) gi|159900959|ref|YP_001547206.1|(159900959); 2-isopropylmalate synthase (*Dinoroseobacter shibae* DFL 12) gi|159043149|ref|YP_001531943.1|(159043149); 2-isopropylmalate synthase (*Salinispora arenicola* CNS-205) gi|159035933|ref|YP_001535186.1|(159035933); 2-isopropylmalate synthase (*Clavibacter michiganensis* subsp. *michiganensis* NCPPB 382) gi|148272757|ref|YP_001222318.1|(148272757); 2-isopropylmalate synthase (*Escherichia coli* B) gi|124530643|ref|ZP_01701227.1| (124530643); 2-isopropylmalate synthase (*Escherichia coli* C str. ATCC 8739) gi|124499067|gb|EAY46563.1| (124499067); 2-isopropylmalate synthase (*Bordetella pertussis* Tohama I) gi|33591386|ref|NP_879030.1| (33591386); 2-isopropylmalate synthase (*Polynucleobacter necessarius* STIR1) gi|164564063|ref|ZP_02209880.1| (164564063); 2-isopropylmalate synthase (*Polynucleobacter necessarius* STIR1) gi|164506789|gb|EDQ94990.1| (164506789); and 2-isopropylmalate synthase (*Bacillus weihenstephanensis* KBAB4) gi|163939313|ref|YP_001644197.1|(163939313), any sequence associated with the accession number is incorporated herein by reference in its entirety. Of particular interest are mutants comprising a LeuA wherein the binding pocket is enlarged relative to the wild-type. For example, multiple protein sequence alignment shows that *E. coli* LeuA shares 92% and only 21% sequence identity with *Salmonella typhimurium* LeuA and *Mycobacterium tuberculosis* LeuA respectively. Fortunately, the binding pocket is well conserved and the corresponding residues of *E. coli* LeuA are His97, Ser139, and Asn167 (FIG. 3B). In one embodiment, the mutant LeuA comprises one or more mutations in an amino acid comprising or having alignment with *E. coli* LeuA at G462 (e.g., G462D), S139 (e.g., S139G), H97 (e.g., H97A), and N167 (e.g., N167A).

BCAA aminotransferases catalyze the formation of branched chain amino acids (BCAA). A number of such aminotransferases are known and are exemplified by ilvE in *E. coli*. Exemplary homologs and variants include sequences designated by the following accession numbers: ilvE (*Microcystis aeruginosa* PCC 7806) gi|159026756|emb|CAO86637.1|(159026756); IlvE (*Escherichia coli*) gi|87117962|gb|ABD20288.1|(87117962); IlvE (*Escherichia coli*) gi|87117960|gb|ABD20287.1| (87117960); IlvE (*Escherichia coli*) gi|87117958|gb|ABD20286.1|(87117958); IlvE (*Shigella flexneri*) gi|87117956|gb|ABD20285.1|(87117956); IlvE (*Shigella flexneri*) gi|87117954|gb|ABD20284.1| (87117954); IlvE (*Shigella flexneri*) gi|87117952|gb|ABD20283.1|(87117952); IlvE (*Shigella flexneri*) gi|87117950|gb|ABD20282.1|(87117950); IlvE (*Shigella flexneri*) gi|87117948|gb|ABD20281.1| (87117948); IlvE (*Shigella flexneri*) gi|87117946|gb|ABD20280.1|(87117946); IlvE (*Shigella flexneri*) gi|87117944|gb|ABD20279.1|(87117944); IlvE (*Shigella flexneri*) gi|87117942|gb|ABD20278.1| (87117942); IlvE (*Shigella flexneri*) gi|87117940|gb|ABD20277.1|(87117940); IlvE (*Shigella flexneri*) gi|87117938|gb|ABD20276.1|(87117938); IlvE (*Shigella dysenteriae*) gi|87117936|gb|ABD20275.1| (87117936); IlvE (*Shigella dysenteriae*) gi|87117934|gb|ABD20274.1|(87117934); IlvE (*Shigella dysenteriae*) gi|87117932|gb|ABD20273.1|(87117932); IlvE (*Shigella dysenteriae*) gi|87117930|gb|ABD20272.1| (87117930); and IlvE (*Shigella dysenteriae*) gi|87117928|gb|ABD20271.1|(87117928), each sequence associated with the accession number is incorporated herein by reference.

L-threonine 3-dehydrogenase (EC 1.1.1.103) catalyzes the conversion of L-threonine to L-2-amino-3-oxobutanoate. The gene tdh encodes an L-threonine 3-dehydrogenase. There are approximately 700 L-threonine 3-dehydrogenases from bacterial organisms recognized in NCBI. Various homologs and variants of tdh include, for example, L-threonine 3-dehydrogenase gi|135560|sp|P07913.1|TDH_ECOLI (135560); L-threonine 3-dehydrogenase gi|166227854|sp|A4TSC6.1|TDH_YERPP(166227854); L-threonine 3-dehydrogenase gi|166227853|sp|A1JHX8.1|TDH_YERE8(166227853); L-threonine 3-dehydrogenase L-threonine 3-dehydrogenase gi|166227852|sp|A6UBM6.1|TDH_SINMW(166227852); L-threonine 3-dehydrogenase gi|166227851|sp|A1RE07.1|TDH_SHESW(166227851); L-threonine 3-dehydrogenase gi|166227850|sp|A0L2Q3.1|TDH_SHESA(166227850); L-threonine 3-dehydrogenase gi|166227849|sp|A4YCC5.1|TDH_SHEPC(166227849); L-threonine 3-dehydrogenase gi|166227848|sp|A3QJC8.1|TDH_SHELP(166227848); L-threonine 3-dehydrogenase gi|166227847|sp|A6WUG6.1|TDH_SHEB8 (166227847); L-threonine 3-dehydrogenase gi|166227846|sp|A3CYN0.1|TDH_SHEB5 (166227846); L-threonine 3-dehydrogenase gi|166227845|sp|A1S1Q3.1|TDH_SHEAM(166227845); L-threonine 3-dehydrogenase gi|166227844|sp|A4FND4.1|TDH_SACEN(166227844); L-threonine 3-dehydrogenase gi|166227843|sp|A1SVW5.1|TDH_PSYIN(166227843); L-threonine 3-dehydrogenase gi|166227842|sp|A5IGK7.1|TDH_LEGPC(166227842); L-threonine 3-dehydrogenase gi|166227841|sp|A6TFL2.1|TDH_KLEP7(166227841); L-threonine 3-dehydrogenase gi|166227840|sp|A4IZ92.1|TDH_FRATW(166227840); L-threonine 3-dehydrogenase gi|166227839|sp|A0Q5K3.1|TDH_FRATN(166227839); L-threonine 3-dehydrogenase gi|166227838|sp|A7NDM9.1|TDH_FRATF(166227838); L-threonine 3-dehydrogenase gi|166227837|sp|A7MID0.1|TDH_ENTS8(166227837); and L-threonine 3-dehydrogenase gi|166227836|sp|A1AHF3.1|TDH_ECOK1 (166227836), the sequences associated with each accession number are incorporated herein by reference.

Acetohydroxy acid synthases (e.g. ilvH) and acetolactate synthases (e.g., alsS, ilvB, ilvI) catalyze the synthesis of the branched-chain amino acids (valine, leucine, and isoleucine). IlvH encodes an acetohydroxy acid synthase in *E. coli* (see, e.g., acetohydroxy acid synthase AHAS III (IlvH) (*Escherichia coli*) gi|40846|emb|CAA38855.1|(40846), incorporated herein by reference). Homologs and variants as well as operons comprising ilvH are known and include, for example, ilvH (*Microcystis aeruginosa* PCC 7806) gi|159026908|emb|CAO89159.1|(159026908); IlvH (*Bacillus amyloliquefaciens* FZB42) gi|154686966|ref|YP_001422127.1|(154686966); IlvH (*Bacillus amyloliquefaciens* FZB42) gi|154352817|gb|ABS74896.1|(154352817); IlvH (*Xenorhabdus nematophila*) gi|131054140|gb|ABO32787.1|(131054140); IlvH (*Salmonella typhimurium*) gi|7631124|gb|AAF65177.1|AF117227_2(7631124), ilvN (*Listeria innocua*) gi|16414606|emb|CAC97322.1| (16414606); ilvN (*Listeria monocytogenes*) gi|16411438|emb|CAD00063.1|(16411438); acetohydroxy acid synthase (*Caulobacter crescentus*) gi|408939|gb|AAA23048.1|(408939); acetohydroxy acid synthase I, small subunit (*Salmonella enterica* subsp. *enterica* serovar Typhi) gi|16504830|emb|CAD03199.1| (16504830); acetohydroxy acid synthase, small subunit (*Tropheryma whipplei* TW08/27) gi|28572714|ref|NP_789494.1|(28572714); acetohydroxy acid synthase, small subunit (*Tropheryma whipplei* TW08/27) gi|28410846|emb|CAD67232.1|(28410846); acetohydroxy acid synthase I, small subunit (*Salmonella enterica* subsp. *enterica* serovar Paratyphi A str. ATCC 9150) gi|56129933|gb|AAV79439.1|(56129933); acetohydroxy acid synthase small subunit; acetohydroxy acid synthase, small subunit gi|551779|gb|AAA62430.1|(551779); acetohydroxy acid synthase I, small subunit (*Salmonella enterica* subsp. *enterica* serovar Typhi Ty2) gi|29139650|gb|AAO71216.1|(29139650); acetohydroxy acid synthase small subunit (*Streptomyces cinnamonensis*) gi|5733116|gb|AAD49432.1|AF175526_1(5733116); acetohydroxy acid synthase large subunit; and acetohydroxy acid synthase, large subunit gi|400334|gb|AAA62429.1| (400334), the sequences associated with the accession numbers are incorporated herein by reference.

Acetolactate synthase genes include alsS and ilvI. Homologs of ilvI and alsS are known and include, for example, acetolactate synthase small subunit (*Bifidobacterium longum* NCC2705) gi|23325489|gb|AAN24137.1| (23325489); acetolactate synthase small subunit (*Geobacillus stearothermophilus*) gi|19918933|gb|AAL99357.1| (19918933); acetolactate synthase (*Azoarcus* sp. BH72) gi|119671178|emb|CAL95091.1|(119671178); Acetolactate synthase small subunit (*Corynebacterium diphtheriae*) gi|38199954|emb|CAE49622.1|(38199954); acetolactate synthase (*Azoarcus* sp. BH72) gi|119669739|emb|CAL93652.1|(119669739); acetolactate synthase small subunit (*Corynebacterium jeikeium* K411) gi|68263981|emb|CAI37469.1|(68263981); acetolactate synthase small subunit (*Bacillus subtilis*) gi|1770067|emb|CAA99562.1|(1770067); Acetolactate synthase isozyme 1 small subunit (AHAS-I) (Acetohydroxy-acid synthase I small subunit) (ALS-I) gi|83309006|sp|P0ADF8.1|ILVN_ECOLI(83309006); acetolactate synthase large subunit (*Geobacillus stearothermophilus*) gi|19918932|gb|AAL99356.1|(19918932); and Acetolactate synthase, small subunit (*Thermoanaerobacter tengcongensis* MB4) gi|20806556|ref|NP_621727.1| (20806556), the sequences associated with the accession numbers are incorporated herein by reference. There are approximately 1120 ilvB homologs and variants listed in NCBI.

Acetohydroxy acid isomeroreductase is the second enzyme in parallel pathways for the biosynthesis of isoleucine and valine. IlvC encodes an acetohydroxy acid isomeroreductase in *E. coli*. Homologs and variants of ilvC are known and include, for example, acetohydroxyacid reductoisomerase (*Schizosaccharomyces pombe* 972h-) gi|162312317|ref|NP_001018845.21(162312317); acetohydroxyacid reductisomerase (*Schizosaccharomyces pombe*) gi|3116142|emb|CAA18891.1|(3116142); acetohydroxyacid reductoisomerase (*Saccharomyces cerevisiae* YJM789) gi|151940879|gb|EDN59261.1|(151940879); Ilv5p: acetohydroxyacid reductoisomerase (*Saccharomyces cerevisiae*) gi|609403|gb|AAB67753.1|(609403); ACL198Wp (*Ashbya gossypii* ATCC 10895) gi|45185490|ref|NP_983206.1|(45185490); ACL198Wp (*Ashbya gossypii* ATCC 10895) gi|44981208|gb|AAS51030.1|(44981208); acetohydroxyacid isomeroreductase; Ilv5x (*Saccharomyces cerevisiae*) gi|957238|gb|AAB33579.1|||bbm|369068|bbs|165406 (957238); acetohydroxy-acid isomeroreductase; Ilv5g (*Saccharomyces cerevisiae*) gi|957236|gb|AAB33578.1|||bbm|369064|bbs|165405 (957236); and ketol-acid reductoisomerase (*Schizosaccharomyces pombe*) gi|2696654|dbj|BAA24000.1|(2696654), each sequence associated with the accession number is incorporated herein by reference.

Dihydroxy-acid dehydratases catalyzes the fourth step in the biosynthesis of isoleucine and valine, the dehydration of 2,3-dihydroxy-isovaleic acid into alpha-ketoisovaleric acid.

IlvD and ilv3 encode a dihydroxy-acid dehydratase. Homologs and variants of dihydroxy-acid dehydratases are known and include, for example, IlvD (*Mycobacterium leprae*) gi|21045941|emb|CAB08798.1|(2104594); dihydroxy-acid dehydratase (*Tropheryma whipplei* TW08/27) gi|28410848|emb|CAD67234.1|(28410848); dihydroxy-acid dehydratase (*Mycobacterium leprae*) gi|13093837|emb|CAC32140.1|(13093837); dihydroxy-acid dehydratase (*Rhodopirellula baltica* SH 1) gi|32447871|emb|CAD77389.1|(32447871); and putative dihydroxy-acid dehydratase (*Staphylococcus aureus* subsp. *aureus* MRSA252) gi|49242408|emb|CAG41121.1| (49242408), each sequence associated with the accession numbers are incorporated herein by reference.

2-Ketoacid decarboxylases catalyze the conversion of a 2-ketoacid to the respective aldehyde. For example, 2-ketoisovalerate decarboxylase catalyzes the conversion of 2-ketoisovalerate to isobutyraldehyde. A number of 2-ketoacid decarboxylases are known and are exemplified by the pdc, pdc1, pdc5, pdc6, aro10, thI3, kdcA and kivd genes. Exemplary homologs and variants useful for the conversion of a 2-ketoacid to the respective aldehyde comprise sequences designated by the following accession numbers and identified enzymatic activity: gi|44921617|gb|AAS49166.1| branched-chain alpha-keto acid decarboxylase (*Lactococcus lactis*); gi|15004729|ref|NP_149189.1| Pyruvate decarboxylase (*Clostridium acetobutylicum* ATCC 824); gi|82749898|ref|YP_415639.1| probable pyruvate decarboxylase (*Staphylococcus aureus* RF122); gi|77961217|ref|ZP_00825060.1| COG3961: Pyruvate decarboxylase and related thiamine pyrophosphate-requiring enzymes (*Yersinia mollaretii* ATCC 43969); gi|71065418|ref|YP_264145.1| putative pyruvate decarboxylase (*Psychrobacter arcticus* 273-4); gi|16761331|ref|NP_456948.1| putative decarboxylase (*Salmonella enterica* subsp. *enterica* serovar Typhi str. CT18); gi|93005792|ref|YP_580229.1| Pyruvate decarboxylase (*Psychrobacter cryohalolentis* K5); gi|23129016|ref|ZP_00110850.1| COG3961: Pyruvate decarboxylase and related thiamine pyrophosphate-requiring enzymes (*Nostoc punctiforme* PCC 73102); gi|6417060|gb|AAL18557.1|AF354297_1 pyruvate decarboxylase (*Sarcina ventriculi*); gi|15607993|ref|NP_215368.1|PROBABLE PYRUVATE OR INDOLE-3-PYRUVATE DECARBOXYLASE PDC (*Mycobacterium tuberculosis* H37Rv); gi|41406881|ref|NP_959717.1| Pdc (*Mycobacterium avium* subsp. *paratuberculosis* K-10); gi|91779968|ref|YP_555176.1| putative pyruvate decarboxylase (*Burkholderia xenovorans* LB400); gi|15828161|ref|NP_302424.1| pyruvate (or indolepyruvate) decarboxylase (*Mycobacterium leprae* TN); gi|118616174|ref|YP_904506.1| pyruvate or indole-3-pyruvate decarboxylase Pdc (*Mycobacterium ulcerans* Agy99); gi|67989660|ref|NP_001018185.1| hypothetical protein SPAC3H8.01 (*Schizosaccharomyces pombe* 972h-); gi|21666011|gb|AAM73540.1|AF282847_1 pyruvate decarboxylase PdcB (*Rhizopus oryzae*); gi|69291130|ref|ZP_00619161.1| Pyruvate decarboxylase: Pyruvate decarboxylase (*Kineococcus radiotolerans* SRS30216); gi|66363022|ref|XP_628477.1| pyruvate decarboxylase (*Cryptosporidium parvum* Iowa II); gi|70981398|ref|XP_731481.1| pyruvate decarboxylase (*Aspergillus fumigatus* Af293); gi|121704274|ref|XP_001270401.1| pyruvate decarboxylase, putative (*Aspergillus clavatus* NRRL 1); gi|119467089|ref|XP_001257351.1| pyruvate decarboxylase, putative (*Neosartorya fischeri* NRRL 181); gi|26554143|ref|NP_758077.1| pyruvate decarboxylase (*Mycoplasma penetrans* HF-2); gi|21666009|gb|AAM73539.1|AF282846_1 pyruvate decarboxylase PdcA (*Rhizopus oryzae*). The sequences associated with the forgoing accession numbers are incorporated herein by reference. The disclosure provides mutant Kivd polypeptide having the ability to convert a C6-C9 keto acid to a C5-C8 alcohol in combination with Adh6. Mutant homologs can be prepare and assayed using the sequences provided above and identifying the corresponding amino acids in the homologs to those in SEQ ID NO:18 at position V461 and F381 and M538.

Alcohol dehydrogenases (adh) catalyze the final step of amino acid catabolism, conversion of an aldehyde to a long chain or complex alcohol. Various adh genes are known in the art. As indicated herein adh1 homologs and variants include, for example, adh2, adh3, adh4, adh5, adh6 and sfa1 (see, e.g., SFA (*Saccharomyces cerevisiae*) gi|1288591|emb|CAA48161.1| (288591); the sequence associated with the accession number is incorporated herein by reference).

Citramalate synthase catalyzes the condensation of pyruvate and acetate. CimA encodes a citramalate synthase. Homologs and variants are known and include, for example, citramalate synthase (*Leptospira biflexa* serovar Patoc) gi|116664687|gb|ABK13757.1|(116664687); citramalate synthase (*Leptospira biflexa* serovar Monteralerio) gi|116664685|gb|ABK13756.1|(116664685); citramalate synthase (*Leptospira interrogans* serovar Hebdomadis) gi|116664683|gb|ABK13755.1|(116664683); citramalate synthase (*Leptospira interrogans* serovar Pomona) gi|116664681|gb|ABK13754.1|(116664681); citramalate synthase (*Leptospira interrogans* serovar Australis) gi|116664679|gb|ABK13753.1|(116664679); citramalate synthase (*Leptospira interrogans* serovar Autumnalis) gi|116664677|gb|ABK13752.1|(116664677); citramalate synthase (*Leptospira interrogans* serovar Pyrogenes) gi|116664675|gb|ABK13751.1|(116664675); citramalate synthase (*Leptospira interrogans* serovar Canicola) gi|116664673|gb|ABK13750.1|(116664673); citramalate synthase (*Leptospira interrogans* serovar Lai) gi|116664671|gb|ABK13749.1|(116664671); CimA (*Leptospira meyeri* serovar Semaranga) gi|119720987|gb|ABL98031.1|(119720987); (R)-citramalate synthase gi|2492795|sp|Q58787.1|CIMA_METJA (2492795); (R)-citramalate synthase gi|22095547|sp|P58966.1|CIMA_METMA (22095547); (R)-citramalate synthase gi|22001554|sp|Q8TJJ1.1|CIMA_METAC(22001554); (R)-citramalate synthase gi|22001553|sp|O26819.1|CIMA_METTH(22001553); (R)-citramalate synthase gi|22001555|sp|Q8TYB1.1|CIMA_METKA(22001555); (R)-citramalate synthase (*Methanococcus maripaludis* S2) gi|45358581|ref|NP_988138.1|(45358581); (R)-citramalate synthase (*Methanococcus maripaludis* S2) gi|44921339|emb|CAF30574.1|(44921339); and similar to (R)-citramalate synthase (*Candidatus Kuenenia stuttgartiensis*) gi|91203541|emb|CAJ71194.1|(91203541), each sequence associated with the foregoing accession numbers is incorporated herein by reference.

It is understood that a range of microorganisms can be modified to include a recombinant metabolic pathway suitable for the production of C5-C8 alcohols e.g., 3-methyl-1-pentanol, 4-methyl-1-hexanol, 5-methyl-1-heptanol, and 4-methyl-1-pentanol. It is also understood that various microorganisms can act as "sources" for genetic material encoding target enzymes suitable for use in a recombinant microorganism provided herein. The term "microorganism" includes prokaryotic and eukaryotic microbial species from the Domains Archaea, Bacteria, and Eucarya, the latter including yeast and filamentous fungi, protozoa, algae, or higher Protista. The terms "microbial cells" and "microbes" are used interchangeably with the term microorganism.

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the prokaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt (NaCl)); and extreme (hyper) thermophilus (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria", or "eubacteria", refers to a domain of prokaryotic organisms. Bacteria include at least 11 distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus, Staphylococci, Streptococci, Mycoplasmas*); (2) Proteobacteria, non-photosynthetic Gram-negative bacteria (includes most "common" Gram-negative bacteria); (3) Spirochetes and related species; (4) Planctomyces; (5) *Bacteroides, Flavobacteria*; (6) *Chlamydia*; (7) Green sulfur bacteria; (8) Green non-sulfur bacteria (also anaerobic phototrophs); (9) Radioresistant micrococci and relatives; (10) Thermotoga and Thermosipho thermophiles.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter,* Spirilla, *Serratia, Vibrio, Rhizobium, Chlamydia, Rickettsia, Treponema,* and *Fusobacterium.*

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus,* and *Streptomyces.*

The term "recombinant microorganism" and "recombinant host cell" are used interchangeably herein and refer to microorganisms that have been genetically modified to express or over-express endogenous polynucleotides, or to express non-endogenous polypeptide or polynucleotides, such as those included in a vector, or which have a reduction in expression of an endogenous gene. The polynucleotide generally encodes a target enzyme involved in a metabolic pathway for producing a desired metabolite as described above. Accordingly, recombinant microorganisms described herein have been genetically engineered to express or over-express target enzymes not previously expressed or over-expressed by a parental microorganism. It is understood that the terms "recombinant microorganism" and "recombinant host cell" refer not only to the particular recombinant microorganism but to the progeny or potential progeny of such a microorganism.

A "parental microorganism" refers to a cell used to generate a recombinant microorganism. The term "parental microorganism" describes a cell that occurs in nature, i.e. a "wild-type" cell that has not been genetically modified. The term "parental microorganism" also describes a cell that has been genetically modified but which does not express or over-express a target enzyme, e.g., an enzyme involved in the biosynthetic pathway for the production of a desired metabolite such as, for example, 3-methyl-1-pentanol, 4-methyl-1-hexanol, 5-methyl-1-heptanol, and 4-methyl-1-pentanol. For example, a wild-type microorganism can be genetically modified to express or over express a first target enzyme such as LeuA or a mutant LeuA of the disclosure. This microorganism can act as a parental microorganism in the generation of a microorganism modified to express or over-express a second target enzyme such as Kivd or a mutant Kivd of the disclosure. In turn, the microorganism can be modified to express or over express e.g., in addition to a mutant LeuA and mutant Kivd, a third target enzyme e.g., Adh6. Accordingly, a parental microorganism functions as a reference cell for successive genetic modification events. Each modification event can be accomplished by introducing a nucleic acid molecule in to the reference cell. The introduction facilitates the expression or over-expression of a target enzyme. It is understood that the term "facilitates" encompasses the activation of endogenous polynucleotides encoding a target enzyme through genetic modification of e.g., a promoter sequence in a parental microorganism. It is further understood that the term "facilitates" encompasses the introduction of exogenous polynucleotides encoding a target enzyme in to a parental microorganism.

In another embodiment a method of producing a recombinant microorganism that converts a suitable carbon substrate to a C5, C6, C7, or C8 alcohol is provided. In one embodiment, the microorganism is derived from an *E. coli* parental species. The method includes transforming a microorganism with one or more recombinant polynucleotides encoding polypeptides that include, for example, acetohydroxy acid isomeroreductase (e.g., ilvC), dihydroxy-acid dehydratase (e.g., ilvD), 2-keto-acid decarboxylase (e.g., PDC6, ARO10, THI3, kivd, or pdc), 2-isopropylmalate synthase (e.g., leuA or a mutant thereof), beta-isopropylmalate dehydrogenase (e.g., leuB), isopropylmalate isomerase (e.g., leuCD operon), beta-isopropylmalate dehydrogenase (e.g., leuB), acetolactate synthase (e.g., ilvMG or ilvNB), dihydroxy-acid dehydratase (e.g., ilvD), and alcohol dehydrogenase activity. Polynucleotides that encode enzymes useful for generating metabolites including homologs, variants, fragments, related fusion proteins, or functional equivalents thereof, are used in recombinant nucleic acid molecules that direct the expression of such polypeptides in appropriate host cells, such as bacterial or yeast cells. It is understood that the addition of sequences which do not alter the encoded activity of a polynucleotide, such as the addition of a non-functional or non-coding sequence, is a conservative variation of the basic nucleic acid. The "activity" of an enzyme is a measure of its ability to catalyze a reaction resulting in a metabolite, i.e., to "function", and may be expressed as the rate at which the metabolite of the reaction is produced. For example, enzyme activity can be represented as the amount of metabolite produced per unit of time or per unit of enzyme (e.g., concentration or weight), or in terms of affinity or dissociation constants.

A "protein" or "polypeptide", which terms are used interchangeably herein, comprises one or more chains of chemical building blocks called amino acids that are linked together by chemical bonds called peptide bonds. An "enzyme" means any substance, composed wholly or largely of protein, that catalyzes or promotes, more or less specifically, one or more chemical or biochemical reactions. The term "enzyme" can also refer to a catalytic polynucleotide (e.g., RNA or DNA). A "native" or "wild-type" protein, enzyme, polynucleotide, gene, or cell, means a protein, enzyme, polynucleotide, gene, or cell that occurs in nature.

It is understood that the polynucleotides described above include "genes" and that the nucleic acid molecules described above include "vectors" or "plasmids." For example, a polynucleotide encoding a keto thiolase can be encoded by an atoB gene or homolog thereof, or a fadA gene or homolog thereof. Accordingly, the term "gene", also called a "structural gene" refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence. The term "nucleic acid" or "recombinant nucleic acid" refers to polynucleotides such as deoxyribonucleic acid (DNA), and, where appropriate, ribonucleic acid (RNA). The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence.

The term "operon" refers two or more genes which are transcribed as a single transcriptional unit from a common promoter. In some embodiments, the genes comprising the operon are contiguous genes. It is understood that transcription of an entire operon can be modified (i.e., increased, decreased, or eliminated) by modifying the common promoter. Alternatively, any gene or combination of genes in an operon can be modified to alter the function or activity of the encoded polypeptide. The modification can result in an increase in the activity of the encoded polypeptide. Further, the modification can impart new activities on the encoded polypeptide. Exemplary new activities include the use of alternative substrates and/or the ability to function in alternative environmental conditions.

A "vector" is any means by which a nucleic acid can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes," that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an *agrobacterium* or a bacterium.

"Transformation" refers to the process by which a vector is introduced into a host cell. Transformation (or transduction, or transfection), can be achieved by any one of a number of means including electroporation, microinjection, biolistics (or particle bombardment-mediated delivery), or *agrobacterium* mediated transformation.

Those of skill in the art will recognize that, due to the degenerate nature of the genetic code, a variety of DNA compounds differing in their nucleotide sequences can be used to encode a given amino acid sequence of the disclosure. The native DNA sequence encoding the biosynthetic enzymes described above are referenced herein merely to illustrate an embodiment of the disclosure, and the disclosure includes DNA compounds of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with alternate amino acid sequences, and the amino acid sequences encoded by the DNA sequences shown herein merely illustrate embodiments of the disclosure.

The disclosure provides nucleic acid molecules in the form of recombinant DNA expression vectors or plasmids, as described in more detail below, that encode one or more target enzymes. Generally, such vectors can either replicate in the cytoplasm of the host microorganism or integrate into the chromosomal DNA of the host microorganism. In either case, the vector can be a stable vector (i.e., the vector remains present over many cell divisions, even if only with selective pressure) or a transient vector (i.e., the vector is gradually lost by host microorganisms with increasing numbers of cell divisions). The disclosure provides DNA molecules in isolated (i.e., not pure, but existing in a preparation in an abundance and/or concentration not found in nature) and purified (i.e., substantially free of contaminating materials or substantially free of materials with which the corresponding DNA would be found in nature) forms.

The various components of an expression vector can vary widely, depending on the intended use of the vector and the host cell(s) in which the vector is intended to replicate or drive expression. Expression vector components suitable for the expression of genes and maintenance of vectors in *E. coli*, yeast, *Streptomyces*, and other commonly used cells are widely known and commercially available. For example, suitable promoters for inclusion in the expression vectors of the disclosure include those that function in eukaryotic or prokaryotic host microorganisms. Promoters can comprise regulatory sequences that allow for regulation of expression relative to the growth of the host microorganism or that cause the expression of a gene to be turned on or off in response to a chemical or physical stimulus. For *E. coli* and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (bla), bacteriophage lambda PL, and T5 promoters. In addition, synthetic promoters, such as the tac promoter (U.S. Pat. No. 4,551,433), can also be used. For *E. coli* expression vectors, it is useful to include an *E. coli* origin of replication, such as from pUC, pIP, pI, and pBR.

Thus, recombinant expression vectors contain at least one expression system, which, in turn, is composed of at least a portion of PKS and/or other biosynthetic gene coding sequences operably linked to a promoter and optionally termination sequences that operate to effect expression of the coding sequence in compatible host cells. The host cells are modified by transformation with the recombinant DNA expression vectors of the disclosure to contain the expression system sequences either as extrachromosomal elements or integrated into the chromosome.

A nucleic acid of the disclosure can be amplified using cDNA, mRNA or alternatively, genomic DNA, as a template and appropriate oligonucleotide primers according to standard PCR amplification techniques and those procedures described in the Examples section below. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer.

It is also understood that an isolated nucleic acid molecule encoding a polypeptide homologous to the enzymes described herein can be created by introducing one or more nucleotide substitutions, additions or deletions into the nucleotide sequence encoding the particular polypeptide, such that one or more amino acid substitutions, additions or deletions are introduced into the encoded protein. Mutations can be introduced into the polynucleotide by standard techniques, such as site-directed mutagenesis and PCR-mediated mutagenesis. In contrast to those positions where it may be desirable to make a non-conservative amino acid substitutions (see above), in some positions it is preferable to make conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In another embodiment, a method for producing e.g., 3-methyl-1-pentanol, 4-methyl-1-hexanol, 5-methyl-1-heptanol, or 4-methyl-1-pentanol is provided. The method includes culturing a recombinant microorganism as provided herein in the presence of a suitable substrate and under conditions suitable for the conversion of the substrate to C5, C6, C7, or C8 alcohol. The alcohol produced by a microorganism provided herein can be detected by any method known to the skilled artisan. Culture conditions suitable for the growth and maintenance of a recombinant microorganism provided herein are described in the Examples below. The skilled artisan will recognize that such conditions can be modified to accommodate the requirements of each microorganism.

As previously discussed, general texts which describe molecular biological techniques useful herein, including the use of vectors, promoters and many other relevant topics, include Berger and Kimmel, Guide to Molecular Cloning Techniques, Methods in Enzymology Volume 152 (Academic Press, Inc., San Diego, Calif.) ("Berger"); Sambrook et al., Molecular Cloning—A Laboratory Manual, 2d ed., Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel"). Examples of protocols sufficient to direct persons of skill through in vitro amplification methods, including the polymerase chain reaction (PCR), the ligase chain reaction (LCR), Qβ-replicase amplification and other RNA polymerase mediated techniques (e.g., NASBA), e.g., for the production of the homologous nucleic acids of the disclosure are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levenson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Nat'l Acad. Sci. USA 87: 1874; Lomell et al. (1989) J. Clin. Chem. 35: 1826; Landegren et al. (1988) Science 241: 1077-1080; Van Brunt (1990) Biotechnology 8: 291-294; Wu and Wallace (1989) Gene 4: 560; Barringer et al. (1990) Gene 89: 117; and Sooknanan and Malek (1995) Biotechnology 13: 563-564. Improved methods for cloning in vitro amplified nucleic acids are described in Wallace et al., U.S. Pat. No. 5,426,039. Improved methods for amplifying large nucleic acids by PCR are summarized in Cheng et al. (1994) Nature 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

Appropriate culture conditions are conditions of culture medium pH, ionic strength, nutritive content, etc.; temperature; oxygen/$CO_2$/nitrogen content; humidity; and other culture conditions that permit production of the compound by the host microorganism, i.e., by the metabolic action of the microorganism. Appropriate culture conditions are well known for microorganisms that can serve as host cells.

The disclosure is illustrated in the following examples, which are provided by way of illustration and are not intended to be limiting.

EXAMPLES

Figure 1C:
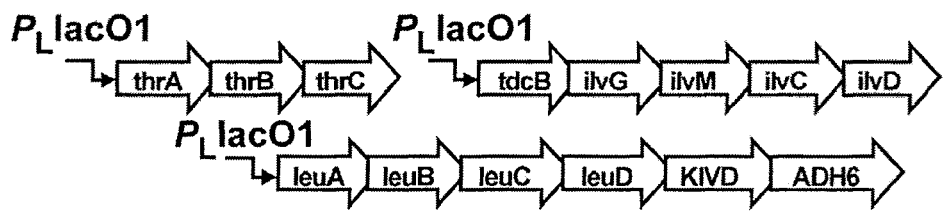
Figure 1D:
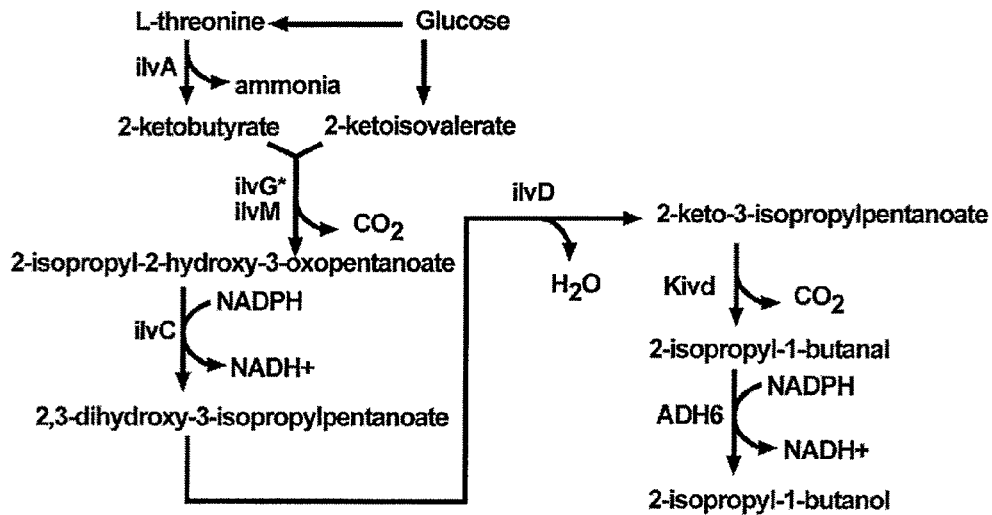
Figure 1E:
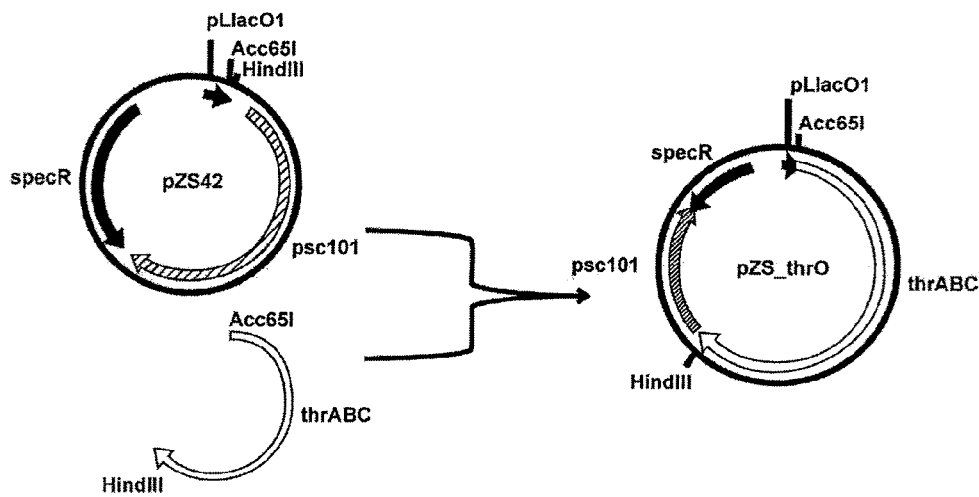
Figure 1E:
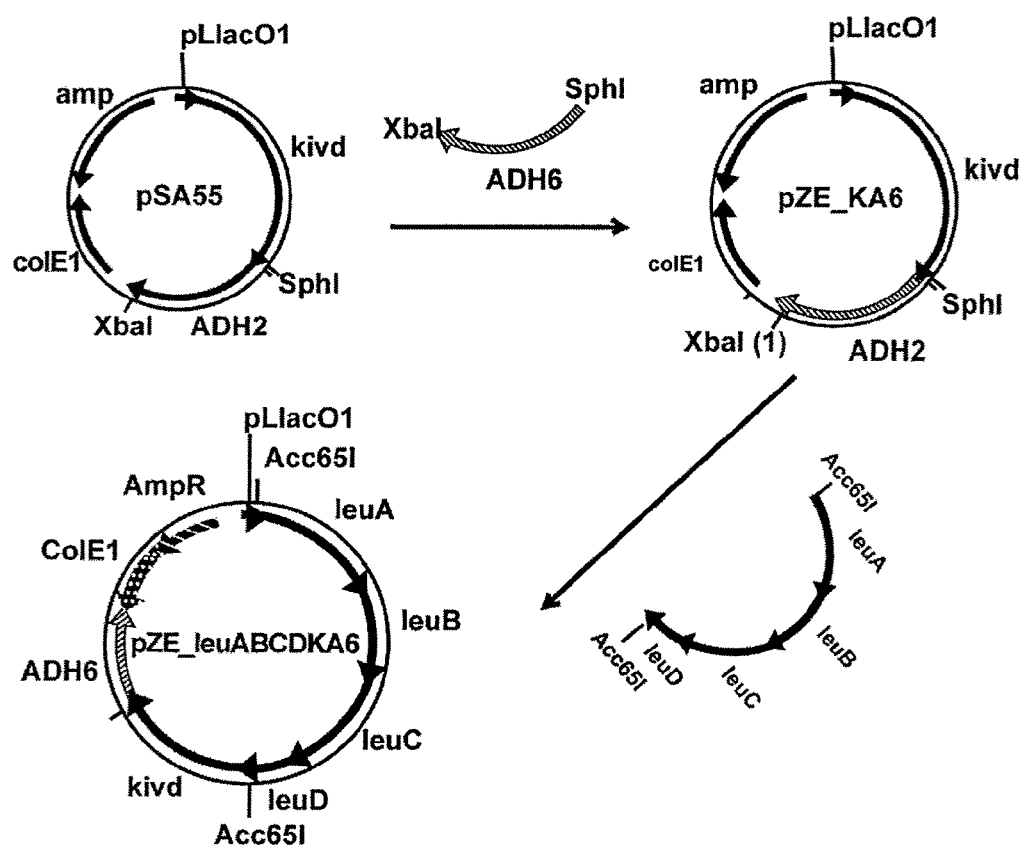
Figure 1E:
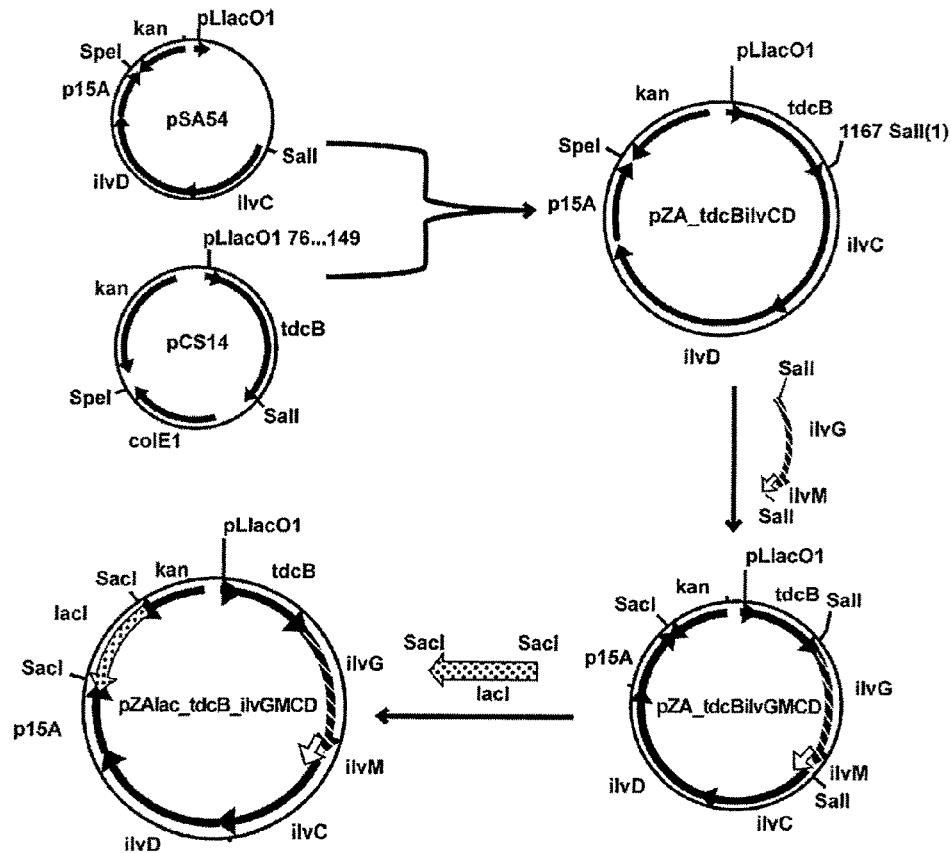

Vector Construction. All cloning procedures were carried out in the *E. coli* strain XL10-gold (Stratagene). Oligos were synthesized by Operon Biotechnologies. PCR reactions were performed with KOD polymerase (Novagen). The thrABC operon containing the feedback resistant mutant ThrA (G433R) was amplified from the genomic DNA of the threonine-overproducer ATCC 21277 using the primers thr_a-ccfwd and thr_hindrev. The PCR product was digested with Acc65I and HindIII, and cloned into pZS24 to yield pZS_thrO. Both pCS14 and pSA54 were digested with SpeI and SalI, and the resulting fragments containing either tdcB or ilvC-ilvD were joined to yield pZA_tdcBilvCD. The ilvG603 sequence containing a 2 base pair (TG) insertion before the stop codon TGA at position +982 was used to correct the ilvG frameshift mutation in wild type *E. coli*. To remove SalI restriction site from the ilvM gene, *E. coli* genomic DNA was amplified with primers SalI_remove, SalI_remove_rev, as well as the flanking oligos TGins_fwd_sap and ilvM_rev_SalI using overlap PCR. Another PCR reaction was performed with primers ilvG_fwd_SalI and TGins_rev_sap using *E. coli* genomic DNA as the template. Products from both PCR reactions were digested with SalI and SapI, and ligated into the SalI site of pZA_tdcBilvCD, creating plasmid pZA_tdcBilvGMCD. A gene fragment encoding lac repressor LadI was then inserted into the SacI site of pZA_tdcBilvGMCD to yield pZAlac_tdcBilvGMCD. The ADH6 gene fragment was amplified from yeast genomic DNA using primers adh6_sphfwd and adh6_xbarev. The PCR product was digested with SphI and XbaI, and ligated into pSA55 to yield pZE_KA6. Using E. coli genomic DNA as the template, the leuABCD operon was amplified with primers leu_accfwd and leu_accrev, and inserted into the Acc65I site of pZE_KA6 to create pZE_LeuABCDKA6. FIG. 1E shows the cloning strategy used. Site-specific mutagenesis on KIVD were performed with oligos V461A, M538A, M538L, F381A, or F381L and their corresponding reverse primers. Site-specific mutagenesis on LeuA was performed with oligos G462D, S139G, H97A, H97L, N167A, or N167L and their corresponding reverser primers.

Fermentation Procedure. The aminotransferase genes, ilvE, and tyrB, of a threonine-hyperproduction E. coli strain ATCC98082 were inactivated by P1 transduction. This modified strain was transformed with pZS_thrO, pZAlac_tdcBilvGMCD and pZE_LeuABCDKA6 for alcohol production. Overnight cultures incubated in LB medium were diluted 100 fold into 5 ml M9 medium supplemented with 1× trace metal mix A5, 0.5% yeast extract and 2% glucose in 125-ml conical flasks, Antibiotics were added appropriately (ampicillin 100 mg/L, spectinomycin 25 mg/L, kanamycin 25 mg/L). Cells were grown to an optical density at 600 nm of ~1.0 at 37° C., followed by adding 0.1 mM isopropyl-β-D-thiogalactoside (IPTG), Cultures were then transferred to a 30° C. shaker (250 rpm) and incubated for 40 hours.

GC-MS Analysis. The GC-MS system is composed of model 6890N network GC system (Agilent Technologies), a model 7883B injector and autosampler (Agilent Technologies) and a model 5973 network mass selective detector (Agilent Technologies). Samples were separated through a DB-5 ms capillary column (30 m, 0.25-mm internal diameter, 0.25-m film thickness; Agilent Technologies) with helium (1 ml min$^{-1}$) as the carrier gas. Alcohols extracted by 200 µl toluene from 1 ml fermentation medium were directly injected for mass analysis.

GC-FID Analysis. Alcohol compounds were quantified by a gas chromatograph equipped with flame ionization detector. The system is composed of a model 5890A gas chromatograph (Hewlett Packard) and a model 7673A automatic injector, sampler and controller (Hewlett Packard). Samples were separated through A DB-FFAP capillary column (30 m, 0.32-mm internal diameter, 0.25-µm film thickness; Agilent Technologies). GC oven temperature was initially placed at 40° C. for 2 min, increased with a gradient of 5° C. min$^{-1}$ until 45° C., and held for 4 min. And then it was increased with a gradient 15° C. min$^{-1}$ until 230° C. and held for 4 min. Helium was used as the carrier gas. The temperature of injector and detector was set at 225° C. Alcohol standards were purchased from either Sigma-Aldrich or TCI America.

For chiral GC analysis, samples were separated through a HP-CHIRAL 20B column (30 m, 0.32 mm internal diameter, 0.25 µm film thickness; Agilent Technologies). The racemic mixture of 3-methyl-1-pentanol could not be directly resolved. However, after reaction with N-Methyl-N-[tert-butyldimethyl-silyl]trifluoroacetimide (Pierce), the conjugated product could be resolved into 2 peaks. GC oven temperature was initially placed at 50° C. for 4 min, increased with a gradient of 10° C. min$^{-1}$ until 90° C., and held for 2 min. And then it was increased with a gradient 2° C. min$^{-1}$ until 130° C. and held for 2 min. Finally the temperature was increased with a gradient 35° C. min$^{-1}$ until 235° C. and held for 2 min. Helium was used as the carrier gas. The temperature of injector and detector was set at 225° C.

Protein Expression and Purification. Both gene fragments encoding wild type and F381L/V461A KIVD were amplified from plasmid pZE_LeuABCDKA6 using primers hiskivd_tevfwd and hiskivd_bamrev. After digestion with BamHI, the gene fragments were inserted into expression plasmid pQE9 (Qiagen) to yield pQE_hiskivd_wt and pQE_hiskivd_FL. The ADH6 gene fragment was amplified from yeast genomic DNA using primers hisadh_tevfwd and hisadh_bamrev, digested with BamHI and inserted into pQE9 to generate pQE_hisadh6. Similarly, genes encoding G462D and G462D/S139G LeuA were amplified from plasmid pZE_LeuABCDKA6 using primers hisleua_tevfwd and hisleua_bamrev. After digestion with BamHI, the PCR products were ligated into pQE9 to create pQE_hisleua_GD and pQE_hisleua_GS. The resulting expression plasmids pQE_hiskivd_wt, pQE_hiskivd_FL, pQE_hisadh6, pQE_hisleua_GD and pQE_hisleua_GS were transformed into E. coli strain BL21(DE3) harboring pREP4 (Qiagen). Cells were inoculated from an overnight pre-culture at 1/100 dilution and grown in 200 ml 2XYT rich medium containing 50 mg/L ampicillin and 25 mg/L kanamycin. At an OD$_{600}$ of 0.6, recombinant proteins were expressed by induction of the cell cultures with 0.1 mM IPTG, followed by incubation at 30° C. overnight. Cell pellets were lysed by sonication in a buffer containing 250 mM NaCl, 2 mM DTT, 5 mM imidazole, and 50 mM Tris pH 9.0. By applying a stepwise gradient of imidazole (up to 250 mM), enzymes were purified from crude cell lysates through Ni-NTA column chromatography. The fractions of highest purity were pooled and buffer-exchanged using Amicon Ultra centrifugal filters (Millipore). Storage buffer 1 (50 µM tris buffer, pH 8.0, 1 mM MgSO$_4$, and 20% glycerol) was used for LeuA and ADH6, and storage buffer 2 (50 µM tris buffer, pH 8.0, 1 mM MgSO$_4$, 0.2 mM ThDP, and 20% glycerol) was used for KIVD. The concentrated protein solutions were aliquoted (100 µl) into PCR tubes and flash frozen at −80° C. for long term storage.

Enzymatic Assay of KIVD. Substrate 2-ketoisovalerate (KIV) was purchased from Sigma-Aldrich, and (S)-2-keto-4-methylhexanoate (KHV) was custom synthesized by Asis-Chem. Inc. Protein concentration was determined by measuring UV absorbance at 280 nm. The decarboxylation activity of KIVD was measured at 30° C. using a coupled enzymatic assay method. Excess ADH6 was used to reduce aldehyde into alcohol, and concomitantly, cofactor NADPH was oxidized to NADP+. The assay mixture contained 0.2 mM NADPH, 0.1 µM ADH6 and 0.1-20 mM 2-keto acids in assay buffer (50 mM potassium phosphate buffer, pH 6.8, 1 mM MgSO$_4$, 0.5 mM ThDP) with a total volume of 0.2 mL. The reactions were started by adding 2 µl KIVD (final concentration: for KIV, 20 nM wt KIVD, 200 nM F381L/V461A KIVD; for KHV, 50 nM both), and the consumption of NADPH was monitored at 340 nm (extinction coefficient, 6.22 mM$^{-1}$ cm$^{-1}$). Kinetic parameters ($k_{cat}$ and $K_m$) were determined by fitting initial velocity data to the Michaelis-Menten equation using Origin.

Measurement of LeuA activity. The assay mixture contained 100 mM KCl, 2 mM MgCl$_2$, 1 mM acetyl-CoA, and 100 mM Tris pH 8.0 with a total volume of 100 µl. 100 nM G462D or G462D/S139G LeuA was reacted with 2-ketoisovalerate in a concentration range from 25 µM to 1 mM for 10 minutes at 30° C. While 4 µM G462D or 1.5 µM G462D/S139G LeuA was reacted with (S)-2-keto-3-methylvalerate in a concentration range from 50 µM to 2 mM for 30 minutes at 30° C. The reactions were stopped by adding 0.3 ml of ethanol. Then 0.2 ml of a fresh 1 mM solution of 5,5'-Dithio-Bis (2 Nitrobenzoic Acid) in 100 mM Tris buffer pH 8.0 was added, and the yellow color product was measured at 412 nm. The values obtained were corrected for unspecific hydrolysis by subtracting the absorbance of controlled samples without addition of 2-keto acids. A molar extinction coefficient of 13,600 $M^{-1}$ $cm^{-1}$ was used in the final calculations.

An exemplary list of oligonucleotides useful for PCR cloning and mutagenesis procedures are provided in Table 5. It is understood that the exemplary oligonucleotides can be modified according to the particular sequence targeted for PCR and/or cloning procedures.

TABLE 5

| Name | Sequence | |
|---|---|---|
| thr_accfwd | TCAGGTACCATGCGAGTGTTGAAGTTCGGCGGTACAT | (SEQ ID NO: 29) |
| thr_hindrev | TCAAAGCTTTTACTGATGATTCATCATCAATTTACGCAA | (SEQ ID NO: 30) |
| SalI_remove | CCAGCCCACGGTCGGTGGACTTACTGTTTAGTCAG | (SEQ ID NO: 31) |
| SalI_remove_rev | CTGACTAAACAGTAAGTCCACCGACCGTGGGCTGG | (SEQ ID NO: 32) |
| TGins_fwd_sap | GCATCGCTCTTCTGTGACTGGCAGCAACACTGC | (SEQ ID NO: 33) |
| TGins_rev_sap | GCATCGCTCTTCTCACATTGATTTAACGGCTGCTGTAATG | (SEQ ID NO: 34) |
| ilvG_fwd_SalI | CTAGCTGTCGACAGGAGAAAGGTACCATGAATGGCGCACAGTGGGTG | (SEQ ID NO: 35) |
| ilvM_rev_SalI | CTAGCTGTCGACTCAGGCGCGGATTTGTTGTGATG | (SEQ ID NO: 36) |
| adh6_sphfwd | CTAGCTGCATGCAGGAGATATACCATGTCTTATCCTGAGAAATTTGAAGGTATCG | (SEQ ID NO: 37) |
| adh6_xbarev | CTAGCTTCTAGACTAGTCTGAAAATTCTTTGTCGTAGCCGA | (SEQ ID NO: 38) |
| leu_accfwd | GCATC GGTACC ATGAGCCAGCAAGTCATTATTTTCGATACC | (SEQ ID NO: 39) |
| leu_accrev | GCATC GGTACCTTTCTCCTCTGCAGTTAATTCATAAACGCAGGTTGTTTTGCTTC | (SEQ ID NO: 40) |
| V461A | CAATAATGATGGTTATACAGCCGAAAGAGAAATTCATGG | (SEQ ID NO: 41) |
| V461A_rev | CCATGAATTTCTCTTTCGGCTGTATAACCATCATTATTG | (SEQ ID NO: 42) |
| M538A | GATGCACCAAAAGTACTGAAAAAAGCGGGCAAACTATTTGCTGAACAAAATAAATC | (SEQ ID NO: 43) |
| M538A_rev | GATTTATTTTGTTCAGCAAATAGTTTGCCCGCTTTTTTCAGTACTTTTGGTGCATC | (SEQ ID NO: 44) |
| M538L | GATGCACCAAAAGTACTGAAAAAACTGGGCAAACTATTTGCTGAACAAAATAAATC | (SEQ ID NO: 45) |
| M538L_rev | GATTTATTTTGTTCAGCAAATAGTTTGCCCAGTTTTTTCAGTACTTTTGGTGCATC | (SEQ ID NO: 46) |
| F381A | GTTGCTGAACAAGGGACATCAGCGTTTGGCGCTTCATCAATTTTCT | (SEQ ID NO: 47) |
| F381A_rev | AGAAAATTGATGAAGCGCCAAACGCTGATGTCCCTTGTTCAGCAAC | (SEQ ID NO: 48) |
| F381L | GTTGCTGAACAAGGGACATCACTGTTTGGCGCTTCATCAATTTTCT | (SEQ ID NO: 49) |
| F381L_rev | AGAAAATTGATGAAGCGCCAAACAGTGATGTCCCTTGTTCAGCAAC | (SEQ ID NO: 50) |
| G462D | CACGGTAAAGATGCGCTGGATCAGGTGGATATCGTCGCTAAC | (SEQ ID NO: 51) |
| G462D_rev | GTTAGCGACGATATCCACCTGATCCAGCGCATCTTTACCGTG | (SEQ ID NO: 52) |
| S139G | CCGATGATGTTGAATTTGGTTGCGAAGATGCCGGGCGTAC | (SEQ ID NO: 53) |
| S139G_rev | GTACGCCCGGCATCTTCGCAACCAAATTCAACATCATCGG | (SEQ ID NO: 54) |
| H97A | GTCGCCGAAGCCTTCCGTATTGCGACCTTTATTGCCACTTC | (SEQ ID NO: 55) |
| H97A_rev | GAAGTGGCAATAAAGGTCGCAATACGGAAGGCTTCGGCGAC | (SEQ ID NO: 56) |
| H97L | GTCGCCGAAGCCTTCCGTATTCTGACCTTTATTGCCACTTC | (SEQ ID NO: 57) |
| H97L_rev | GAAGTGGCAATAAAGGTCAGAATACGGAAGGCTTCGGCGAC | (SEQ ID NO: 58) |
| N167A | CCGGTGCCACCACCATCGCGATTCCGGACACCGTGG | (SEQ ID NO: 59) |
| N167A_rev | CCACGGTGTCCGGAATCGCGATGGTGGTGGCACCGG | (SEQ ID NO: 60) |
| N167L | CCGGTGCCACCACCATCCTGATTCCGGACACCGTGG | (SEQ ID NO: 61) |
| N167L_rev | CCACGGTGTCCGGAATCAGGATGGTGGTGGCACCGG | (SEQ ID NO: 62) |

TABLE 5-continued

| Name | Sequence | |
|---|---|---|
| hiskivd_tevfwd | CG GGATCCGAAAACCTGTATTTTCAGGGAATGTATACAGTAGGAGATTACCTAT | (SEQ ID NO: 63) |
| hiskivd_bamrev | CG GGATCCTTATGATTTATTTTGTTCAGCAAATAGTTTG | (SEQ ID NO: 64) |
| Hisadh_tevfwd | CGGGATCCGAAAACCTGTATTTTCAGGGAATGTCTTATCCTGAGAAATTTGAAG GTATCG | (SEQ ID NO: 65) |
| hisadh_bamrev | CG GGATCCCTAGTCTGAAAATTCTTTGTCGTAGC | (SEQ ID NO: 66) |
| hisleua_tevfwd | CG GGATCCGAAAACCTGTATTTTCAGGGAATGAGCCAGCAAGTCATTATTTTCG | (SEQ ID NO: 67) |
| hisleua_bamrev | CG GGATCCTCACACGGTTTCCTTGTTGTTTTC | (SEQ ID NO: 68) |

Construction of a Nonnatural Metabolic Pathway for Biosynthesis of (S)-3-methyl-1-pentanol. Three synthetic operons were constructed (FIG. 1C) under the control of the $P_L$lacO1 promoter: the first operon is composed of three genes on a low copy plasmid in the transcriptional order thrA-thrB-thrC; the second operon is composed of five genes on a medium copy plasmid in the transcriptional order tdcB-ilvG-ilvM-ilvC-ilvD; and the third operon is composed of six genes on a high copy plasmid in the transcriptional order leuA-leuB-leuC-leuD-KIVD-ADH6 (and a control operon without leuABCD). Except for KIVD, ADH6 and ThrA (G433R mutant insensitive to threonine feedback inhibition), all other genes encode wild-type E. coli enzymes. As a result of overexpressing these fourteen genes in a modified threonine-hyperproduction strain (ATCC98082, ΔilvE, ΔtyrB), 6.5 mg/L of 3-methyl-1-pentanol was produced from 20 g/L glucose (Table 1, column 4), while a leucine-feedback insensitive G462D mutant LeuA produced 40.8 mg/L of C6 alcohol (Table 1, column 5). In contrast, without overexpression of LeuABCD, no C6 alcohol production was detected (Table 1, column 3).

Structure-Based Redesign of KIVD. Since KIVD and ADH6 are promiscuous enzymes, they can also convert other intracellular 2-keto acids into alcohols (FIG. 1B, Table 1). In order to reduce the formation of byproducts and drive the carbon flux towards the target C6 alcohol, the effect of engineering KIVD with higher selectivity towards 2-keto-4-methylhexanoate was examined. The protein sequence alignment shows that KIVD has 40% and 31% sequence identities with Enterobacter cloacae indolepyruvate decarboxylase IPDC and Z. mobilis pyruvate decarboxylase ZmPDC, respectively. A homology model for the substrate-binding region of KIVD and IPDC was built based on the crystal structures of ZmPDC (PDB: 1ZPD). As can be seen from FIG. 2, four residues, Ser286, Phe381, Val461 and Met 538, in combination with cofactor ThDP, delineate the keto-acid binding pocket of KIVD. Noticeably, the corresponding residues of ZmPDC have bulkier side chains, Tyr290, Trp392, Ile472, and Trp551; and those of IPDC have smaller ones, Thr290, Ala387, Val467, and Leu542. These differences can explain the substrate spectrum of these 2-keto acid decarboxylases and suggests that substitution of related amino acids might be able to change substrate specificity. Previously a ZmPDC I472A variant has been shown to be more active on longer-chain keto acids other than pyruvate, the corresponding residue of KIVD, V461 was thus mutated to alanine. Compared to the wild type KIVD, the V461A mutant produced 3 times more 3-methyl-1-pentanol (Table 1, column 6). Further optimization was performed by mutating either F381 or M538 to smaller hydrophobic side chains such as leucine or alanine (Table 1). The F381L/V461A mutant was the best variant obtained and produced 384.3 mg/L of 3-methyl-1-pentanol.

Both wild type and F381L/V461A KIVD were added to an N-terminal 6×His-tag, overexpressed and purified through Ni-NTA columns. The kinetic parameters for activation of 2-ketoisovalerate (cognate substrate) and 2-keto-4-methylhexanoate (nonnatural substrate) were determined using a coupled enzymatic assay. Compared to the wild type KIVD, for the smaller substrate, 2-ketoisovalerate, F381L/V461A KIVD has a significantly lower $k_{cat}$ (2.7 s$^{-1}$ versus 38.3 s$^{-1}$) and higher $K_m$ (7.7 mM versus 2.2 mM); for 2-keto-4-methylhexanoate, F381L/V461A KIVD has a comparable $k_{cat}$ (3.0 s$^{-1}$ versus 10.8 s$^{-1}$) and a slightly higher $K_m$ (0.22 mM versus 0.14 mM). Thus the specificity constant $k_{cat}/K_m$ of F381L/V461A KIVD towards 2-keto-4-methylhexanoate is 40 fold higher than that towards 2-ketoisovalerate. In comparison, the specificity constant $k_{cat}/K_m$ of wild type KIVD towards 2-keto-4-methylhexanoate is only 4 fold higher than that towards 2-ketoisovalerate (Table 2). Such a change in KIVD specificity distinguishably affects the distribution profile of alcohol products (more long-chain alcohols and less short-chain alcohols).

Enlarging the Binding Pocket of LeuA. Besides KIVD, another key enzyme determining the carbon flux towards 3-methyl-1-pentanol production is LeuA. LeuA catalyzes the condensation of acetyl-CoA with 2-keto-3-methylvalerate, which is the first step of the expanded metabolic pathway (FIG. 1B). LeuA also competes with KIVD for substrate 2-keto-3-methylvalerate, and thus reduces the formation of side product 2-methyl-1-butanol. Engineering KIVD with higher activity towards 2-keto-3-methylvalerate should help increase 3-methyl-1-pentanol production. As inferred from the crystal structure of Mycobacterium tuberculosis LeuA, residues His167, Ser216, and Asn250 are within a radius of 4 Å of the γ-methyl group of bound 2-ketoisovalerate (FIG. 3A). Nonnatural substrate (S)-2-keto-3-methylvalerate contains one more methyl group that would cause steric hinderance with Ser216, which could be relieved by mutating serine to glycine. Multiple protein sequence alignment shows that E. coli LeuA shares 92% and only 21% sequence identity with Salmonella typhimurium LeuA and Mycobacterium tuberculosis LeuA respectively. Fortunately, the binding pocket is well conserved and the corresponding residues of E. coli LeuA are His97, Ser139 and Asn167 (FIG. 3B). The G462D/S139G mutant LeuA was cloned and produced 793.5 mg/L 3-methyl-1-pentanol (Table 3, column 3), twice the amount by G462D LeuA.

Enzymatic assay indicates that G462D LeuA has an extremely low $k_{cat}$ (0.018 s$^{-1}$) for (S)-2-keto-3-methylvalerate, which is 333 fold less than that for 2-ketoisovalerate (6.0 s$^{-1}$). Since G462D LeuA has a comparable $K_m$ for both substrates (55 μM versus 182 μm), the low $k_{cat}$ may be why a previous report showed that 2-keto-3-methylvalerate is a strong inhibitor of LeuA. On the other hand, the S139G mutation increases the $k_{cat}$ 7 fold for (S)-2-keto-3-methylvalerate to 0.12 s$^{-1}$ (Table 4).

The following table and the disclosure provides of mutant Kivd and LeuA polypeptides useful in the methods and compositions of the disclosure.

TABLE 1

| | | Alcohol titer (mg/L) | | | | | | | |
|---|---|---|---|---|---|---|---|---|---|
| Product | Structure | No plasmid-encoded LeuABCD KIVD: Wild Type | LeuA: Wild Type KIVD: Wild Type | LeuA: G462D KIVD: Wild Type | LeuA: G462D KIVD: V461A | LeuA: G462D KIVD: V461A/ M538A | LeuA: G462D KIVD: V461A/ M538L | LeuA: G462D KIVD: V461A/ F381A | LeuA: G462D KIVD: V461A/ F381L |
| 1-Propanol | ∕∕∕OH | 41.1 ± 4.1 | 94.6 ± 11.5 | 213.2 ± 12.3 | 132.7 ± 14.3 | 27.3 ± 5.1 | 100.7 ± 18.0 | 43.3 ± 12.9 | 83.3 ± 6.2 |
| Isobutanol | (CH3)2CHCH2OH | 1179.1 ± 76.5 | 936.2 ± 42.7 | 81.8 ± 19.1 | 49.6 ± 12.9 | 5.3 ± 2.9 | 37.3 ± 8.1 | 16.1 ± 3.3 | 8.0 ± 1.1 |
| 1-Butanol | ∕∕∕∕OH | ND | 17.8 ± 0.9 | 493.2 ± 31.5 | 371.4 ± 14.6 | 192.1 ± 7.7 | 432.1 ± 52.0 | 219.3 ± 51.7 | 381.7 ± 36.3 |
| (S)-2-Methyl-1-butanol | | 54.1 ± 5.5 | 63.4 ± 14.8 | 205.2 ± 9.4 | 264.5 ± 9.9 | 142.9 ± 10.5 | 246.2 ± 38.0 | 122.8 ± 33.6 | 68.0 ± 6.7 |
| 3-Methyl-1-butanol | | 131.6 ± 2.6 | 384.7 ± 91.3 | 726.4 ± 5.9 | 687.5 ± 16.9 | 898.7 ± 11.6 | 750.5 ± 149.4 | 826.8 ± 144.4 | 963.1 ± 48.3 |
| 1-Pentanol | ∕∕∕∕∕OH | ND | ND | 494.1 ± 22.9 | 503.9 ± 4.6 | 750.5 ± 52.9 | 556.6 ± 86.8 | 482.9 ± 111.9 | 444.6 ± 35.5 |
| 4-Methyl-1-pentanol | | ND | ND | ND | ND | ND | ND | ND | ND |
| (S)-3-Methyl-1-pentanol | | ND | 6.5 ± 1.1 | 40.8 ± 5.5 | 135.6 ± 7.8 | 299.2 ± 6.8 | 141.7 ± 11.7 | 264.5 ± 51.6 | 384.3 ± 30.3 |
| 1-Hexanol | ∕∕∕∕∕∕OH | ND | ND | ND | ND | 17.4 ± 0.3 | ND | 18.5 ± 0.9 | 7.3 ± 0.4 |

Production profile of alcohols from the designed pathway, with different KIVD mutants (Note that the V461A/F381L mutant gives the highest titer of 3-methyl-1-pentanol). *E. coli* cultures were grown in M9 medium with 20 g/L glucose plus 0.1 mM IPTG at 30 C. for 40 hours. These products were identified by GC-MS and quantified by GC-FID. ND, not detectable.

TABLE 2

Kinetic parameters of wild-type and mutant KIVD

| | | Wild type | | | V461A/F381L | | |
|---|---|---|---|---|---|---|---|
| Substrate | Structure | $K_m$ (mM) | $k_{cat}$ (s$^{-1}$) | $k_{cat}/K_m$ (mM$^{-1}$s$^{-1}$) | $K_m$ (mM) | $k_{cat}$ (s$^{-1}$) | $k_{cat}/K_m$ (mM$^{-1}$s$^{-1}$) |
| 2-Ketoisovalerate | (CH3)2CHCOCOOH | 2.2 ± 0.9 | 38.3 ± 9.8 | 17 | 7.7 ± 1.8 | 2.7 ± 0.6 | 0.35 |
| (S)-2-keto-4-methylhexanoate | | 0.14 ± 0.01 | 10.8 ± 0.3 | 77 | 0.22 ± 0.02 | 3.0 ± 0.1 | 14 |

TABLE 3

| Product | Structure | Alcohol titer (mg/L) | | | | | |
|---|---|---|---|---|---|---|---|
| | | LeuA: G462D/ S139G KIVD: V461A/ F381L | LeuA: G462D/ S139G/ H97A KIVD: V461A/ F381L | LeuA: G462D/ S139G/ H97L KIVD: V461A/ F381L | LeuA: G462D/ S139G/ N167A KIVD: V461A/ F381L | LeuA: G462D/ S139G/ N167L KIVD: V461A/ F381L | LeuA: G462D/ S139G/ H97A/N167A KIVD: V461A/ F381L |
| 1-Propanol | ⌒⌒OH | 117.2 ± 3.8 | 122.1 ± 7.2 | 51.1 ± 6.9 | 39.4 ± 1.3 | 33.2 ± 5.7 | 54.7 ± 7.4 |
| Isobutanol | ⌄OH | 49.6 ± 2.2 | 70.0 ± 9.0 | 155.2 ± 12.3 | 165.1 ± 18.6 | 208.1 ± 8.3 | 230.4 ± 39.1 |
| 1-Butanol | ⌒⌒⌒OH | 178.5 ± 5.5 | 174.1 ± 13.1 | 25.2 ± 4.2 | 30.6 ± 2.6 | 28.6 ± 2.4 | 17.9 ± 6.3 |
| (S)-2-Methyl-1-butanol | 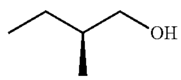 | 37.4 ± 2.3 | 69.4 ± 8.8 | 37.3 ± 7.9 | 16.4 ± 2.6 | 81.8 ± 2.6 | 12.2 ± 1.9 |
| 3-Methyl-1-butanol | 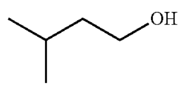 | 901.3 ± 28.6 | 867.2 ± 20.8 | 594.7 ± 40.2 | 661.3 ± 21.2 | 740.5 ± 28.2 | 613.5 ± 43.9 |
| 1-Pentanol | 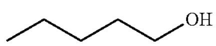 | 204.7 ± 16.5 | 169.8 ± 36.5 | 29.9 ± 4.4 | 17.3 ± 0.5 | 14.2 ± 1.3 | ND |
| 4-Methyl-1-pentanol | 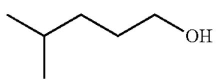 | 70.5 ± 4.6 | 48.5 ± 18.0 | 202.4 ± 1.1 | 123.2 ± 12.2 | ND | 80.1 ± 5.6 |
| (S)-3-Methyl-1-pentanol | 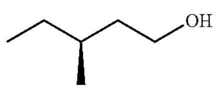 | 793.5 ± 46.5 | 685.7 ± 16.0 | 337.4 ± 41.0 | 288.1 ± 32.5 | 119.1 ± 6.0 | 290.6 ± 34.1 |
| 1-Hexanol | 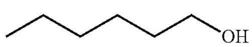 | 37.4 ± 2.8 | 38.4 ± 8.3 | 16.6 ± 0.9 | 16.5 ± 1.4 | ND | ND |
| (S)-4-Methyl-1-hexanol | 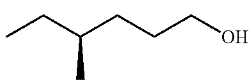 | ND | ND | ND | 51.9 ± 9.3 | ND | 57.3 ± 7.8 |
| (S)-5-Methyl-1-heptanol | 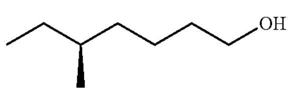 | ND | ND | ND | ND | ND | 22.0 ± 2.5 |

Alcohol production with different LeuA mutants (Note that the G462D/S139G mutant gives the highest titer of 3-methyl-1-pentanol). *E. coli* cultures were grown in M9 medium with 20 g/L glucose plus 0.1 mM IPTG at 30° C. for 40 hours. These products were identified by GC-MS and quantified by GC-FID. ND, not detectable.

TABLE 4

Kinetic parameters of wild type and mutant LeuA.

| | | G462D | | | G462D/S139G | | |
|---|---|---|---|---|---|---|---|
| Substrate | Structure | $K_m$ (μM) | $k_{cat}$ (s$^{-1}$) | $k_{cat}/K_m$ (mM$^{-1}$s$^{-1}$) | $K_m$ (μM) | $k_{cat}$ (s$^{-1}$) | $k_{cat}/K_m$ (mM$^{-1}$s$^{-1}$) |
| 2-Ketoisovalerate | | 182 ± 2 | 6.0 ± 0.3 | 33 | 104 ± 5 | 2.1 ± 0.1 | 20 |

TABLE 4-continued

Kinetic parameters of wild type and mutant LeuA.

| | | G462D | | | G462D/S139G | | |
|---|---|---|---|---|---|---|---|
| Substrate | Structure | $K_m$ (μM) | $k_{cat}$ (s$^{-1}$) | $k_{cat}/K_m$ (mM$^{-1}$s$^{-1}$) | $K_m$ (μM) | $k_{cat}$ (s$^{-1}$) | $k_{cat}/K_m$ (mM$^{-1}$s$^{-1}$) |
| (S)-2-keto-3-methylvalerate | 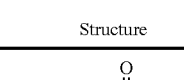 | 55 ± 6 | 0.018 ± 0.001 | 0.33 | 144 ± 13 | 0.12 ± 0.02 | 0.83 |

Additional mutations were then performed on His97 and Asn167. Interestingly, the G462D/S139G/N167A triple mutant produced 51.9 mg/L 4-methyl-1-hexanol (C7), and the G462D/S139G/H97A/N167A quadruple mutant produced 57.3 mg/L 4-methyl-1-hexanol (C7) and 22.0 mg/L 5-methyl-1-heptanol (C8).

Figure 4A:
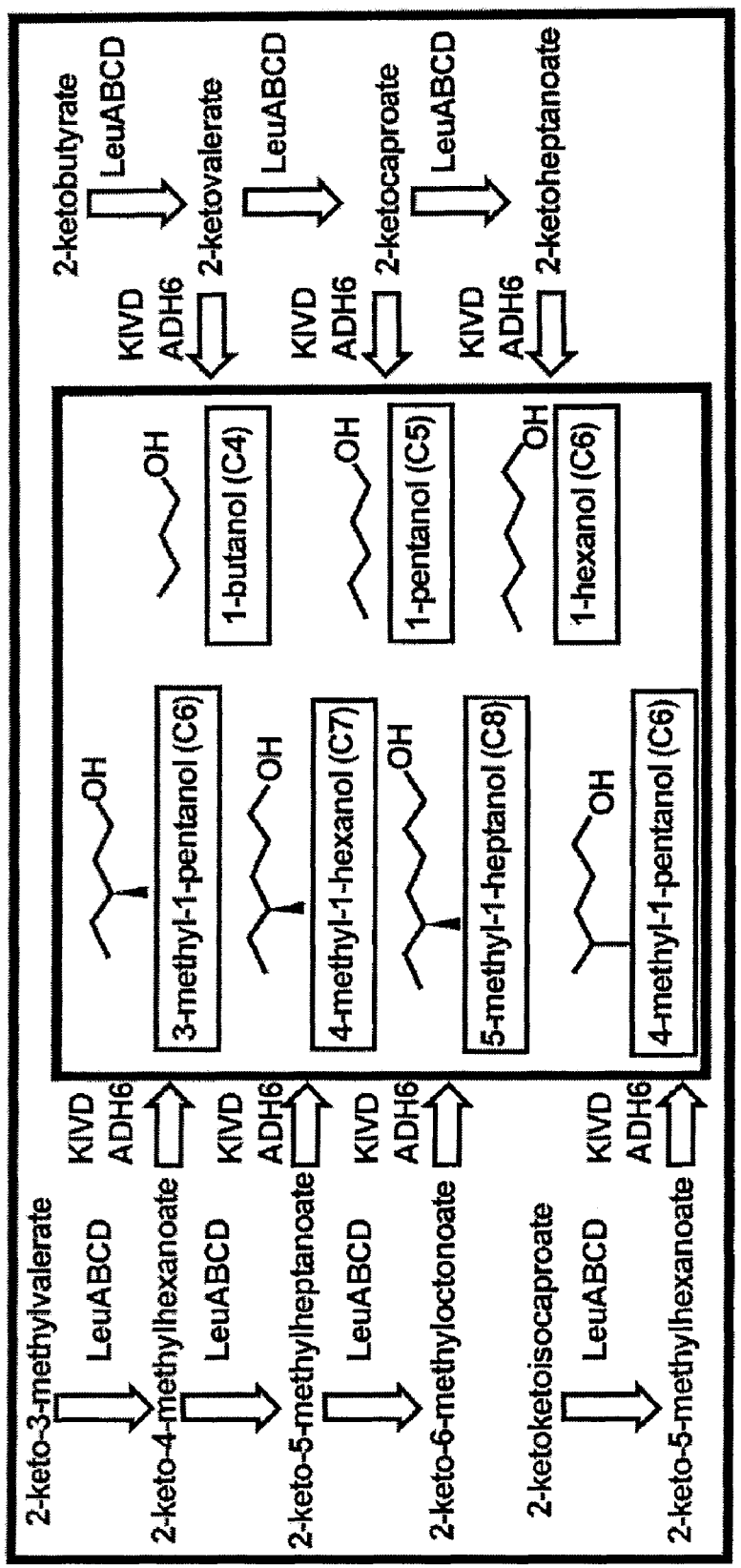
FIG. 4A-C shows a repertoire of nonnatural metabolites. (A) Nonnatural alcohols produced and their corresponding metabolic pathways. (B) Aminotransferase IlvE or TyrB can convert the keto-acid precursor of 3-methyl-1-pentanol to a nonnatural amino acid, S,S-2-amino-4-methylhexanoic acid. (C) It was detected by GC-MS after MTBSTFA (N-Methyl-N-[tert-butyldimethyl-silyl]trifluoroacetimide) derivatization (M+373).
Figure 4B:
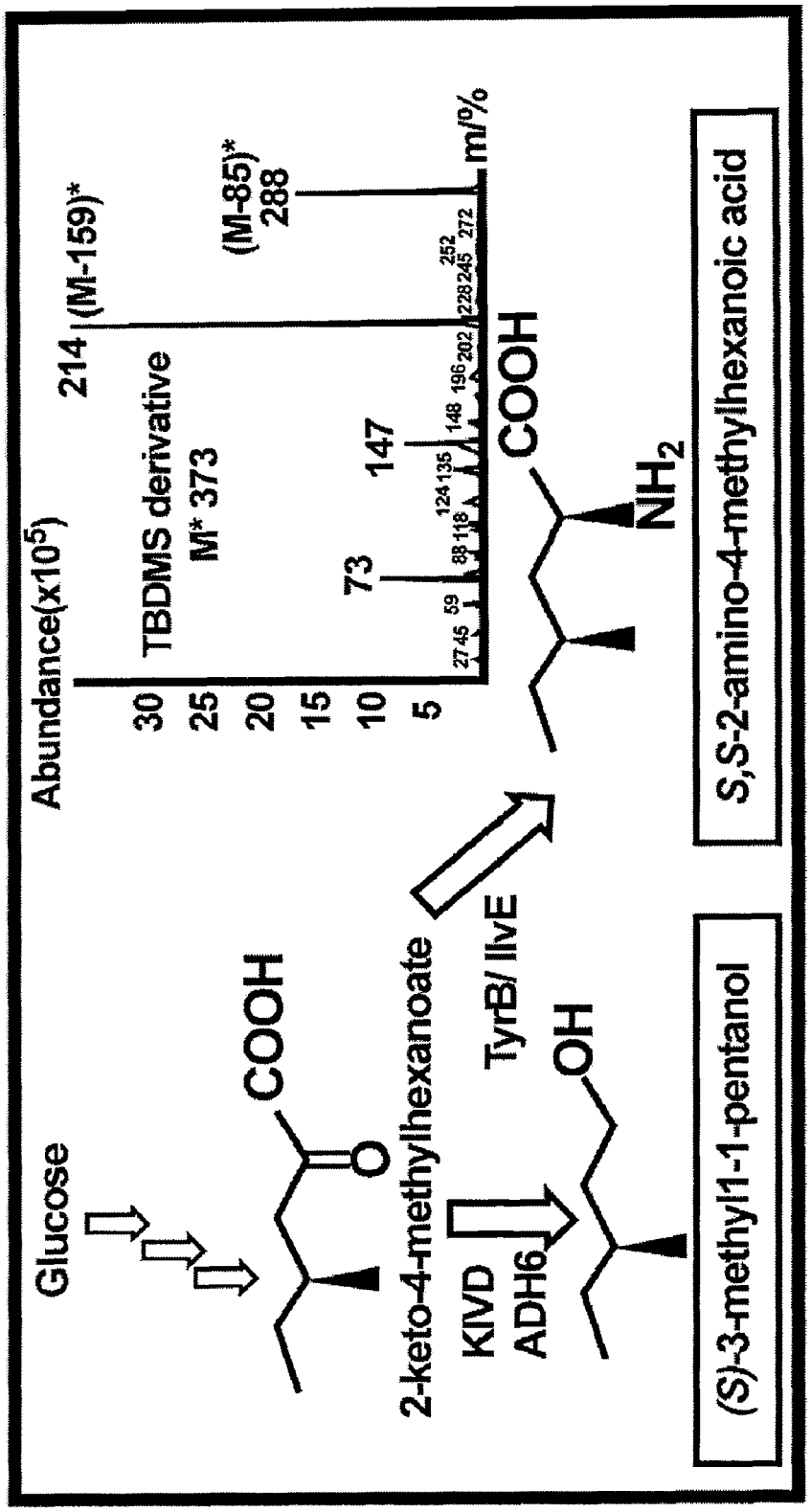
Figure 4C:
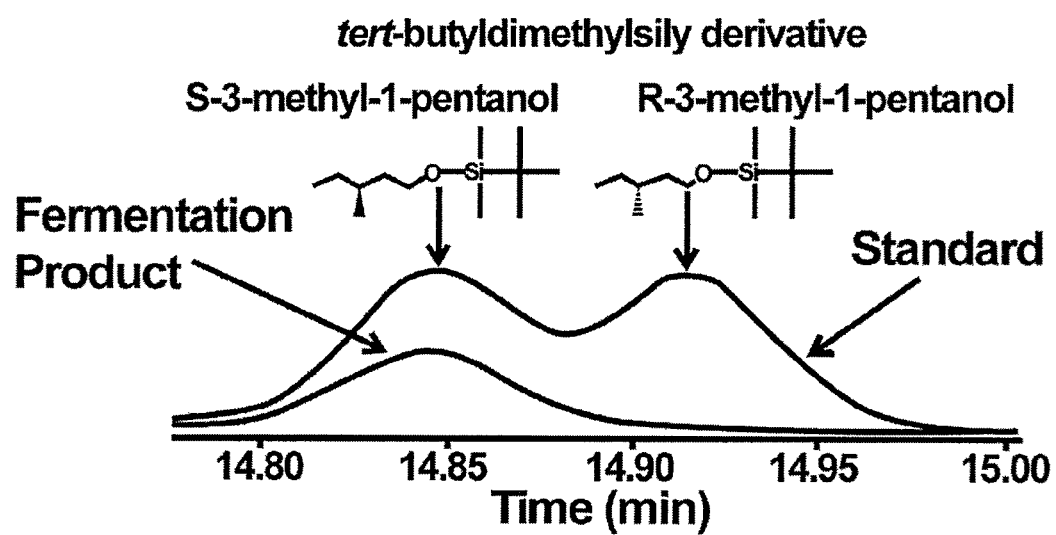

Biosynthesis of a Repertoire of Nonnatural Alcohols and Amino Acids. Since the engineered LeuA has larger binding pockets, the chain elongation activities may continue several more rounds by LeuA on the 2-keto acids produced from the LeuABCD or other pathways (FIG. 4A). For example, 2-ketobutyrate can be converted to 2-ketovalerate, then to 2-ketocaproate, and finally to 2-ketoheptanoate by LeuABCD. In parallel, 2-keto-3-methylvalerate can be converted to 2-keto-4-methylhexanoate, then to 2-keto-5-methylheptanoate and to 2-keto-6-methyloctanoate. All these keto acids are substrates of F381L/V461A KIVD. Upon decarboxylation, the corresponding aldehydes are reduced to the corresponding alcohols by ADH6. Indeed, accumulation of five other nonnatural alcohols: 1-pentanol, 1-hexanol, 4-methyl-1-pentanol, 4-methyl-1-hexanol, and 5-methyl-1-heptanol (Table 1 and 3) were observed. The anteiso-methyl-branched alcohols are all derived from the same chiral precursor, (S)-2-keto-3-methylvalerate. The S-configuration of the stereogenic center in these alcohols remains unchanged during biosynthesis as confirmed by chiral GC analysis of (S)-2-methyl-1-butanol and (S)-3-methyl-1-pentanol (FIG. 4B). These enantiomerically pure alcohols may be useful chiral synthons for chemical synthesis.

The examples set forth above are provided to give those of ordinary skill in the art a complete disclosure and description of how to make and use the embodiments of the devices, systems and methods of the disclosure, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

A number of embodiments of the invention have been described. Nevertheless, it will be understood that various modifications may be made without departing from the spirit and scope of the invention. Accordingly, other embodiments are within the scope of the following claims.

The embodiments of the invention in which an exclusive property or privilege is claimed are defined as follows:

1. A purified polypeptide consisting of SEQ ID NO:2, having a mutation in any of the following residues D430, A453, A460, or G462 to remove leucine feedback inhibition, and comprising an additional mutation consisting of S139G, wherein the polypeptide initiates the conversion of 2-keto-3-methylvalerate to a C6-C9 keto acid.

2. The purified polypeptide of claim 1, wherein the polypeptide comprises a sequence that is selected from the group consisting of SEQ ID NO:4, 6, 8, 10, 12, 14, and 16 that when expressed with a LeuB, LeuC, and LeuD converts 2-keto-3-methylvalerate to 2-keto-4-methylhexanoate.

* * * * *

SEQUENCE LISTING

```
<160> NUMBER OF SEQ ID NOS: 112

<210> SEQ ID NO 1
<211> LENGTH: 1572
<212> TYPE: DNA
<213> ORGANISM: Escherichia coli
<220> FEATURE:
<221> NAME/KEY: CDS
<222> LOCATION: (1)..(1572)

<400> SEQUENCE: 1 atg agc cag caa gtc att att ttc gat acc aca ttg cgc gac ggt gaa        48
Met Ser Gln Gln Val Ile Ile Phe Asp Thr Thr Leu Arg Asp Gly Glu
1               5                   10                  15 cag gcg tta cag gca agc ttg agt gtg aaa gaa aaa ctg caa att gcg        96
Gln Ala Leu Gln Ala Ser Leu Ser Val Lys Glu Lys Leu Gln Ile Ala
            20                  25                  30 ctg gcc ctt gag cgt atg ggt gtt gac gtg atg gaa gtc ggt ttc ccc       144
Leu Ala Leu Glu Arg Met Gly Val Asp Val Met Glu Val Gly Phe Pro
        35                  40                  45 gtc tct tcg ccg ggc gat ttt gaa tcg gtg caa acc atc gcc cgc cag       192
Val Ser Ser Pro Gly Asp Phe Glu Ser Val Gln Thr Ile Ala Arg Gln
    50                  55                  60
```

```
gtt aaa aac agc cgc gta tgt gcg tta gct cgc tgc gtg gaa aaa gat        240
Val Lys Asn Ser Arg Val Cys Ala Leu Ala Arg Cys Val Glu Lys Asp
 65              70                  75                  80 atc gac gtg gcg gcc gaa tcc ctg aaa gtc gcc gaa gcc ttc cgt att        288
Ile Asp Val Ala Ala Glu Ser Leu Lys Val Ala Glu Ala Phe Arg Ile
                 85                  90                  95 cat acc ttt att gcc act tcg cca atg cac atc gcc acc aag ctg cgc        336
His Thr Phe Ile Ala Thr Ser Pro Met His Ile Ala Thr Lys Leu Arg
            100                 105                 110 agc acg ctg gac gag gtg atc gaa cgc gct atc tat atg gtg aaa cgc        384
Ser Thr Leu Asp Glu Val Ile Glu Arg Ala Ile Tyr Met Val Lys Arg
        115                 120                 125 gcc cgt aat tac acc gat gat gtt gaa ttt tct tgc gaa gat gcc ggg        432
Ala Arg Asn Tyr Thr Asp Asp Val Glu Phe Ser Cys Glu Asp Ala Gly
130                 135                 140 cgt aca ccc att gcc gat ctg gcg cga gtg gtc gaa gcg gcg att aat        480
Arg Thr Pro Ile Ala Asp Leu Ala Arg Val Val Glu Ala Ala Ile Asn
145                 150                 155                 160 gcc ggt gcc acc acc atc aac att ccg gac acc gtg ggc tac acc atg        528
Ala Gly Ala Thr Thr Ile Asn Ile Pro Asp Thr Val Gly Tyr Thr Met
                165                 170                 175 ccg ttt gag ttc gcc gga atc atc agc ggc ctg tat gaa cgc gtg cct        576
Pro Phe Glu Phe Ala Gly Ile Ile Ser Gly Leu Tyr Glu Arg Val Pro
            180                 185                 190 aac atc gac aaa gcc att atc tcc gta cat acc cac gat ttg ggc            624
Asn Ile Asp Lys Ala Ile Ile Ser Val His Thr His Asp Leu Gly
        195                 200                 205 ctg gcg gtc gga aac tca ctg gcg gcg gta cat gcc ggt gca cgc cag        672
Leu Ala Val Gly Asn Ser Leu Ala Ala Val His Ala Gly Ala Arg Gln
210                 215                 220 gtg gaa ggc gca atg aac ggg atc ggc gag cgt gcc gga aac tgt tcc        720
Val Glu Gly Ala Met Asn Gly Ile Gly Glu Arg Ala Gly Asn Cys Ser
225                 230                 235                 240 ctg gaa gaa gtc atc atg gcg atc aaa gtt cgt aag gat att ctc aac        768
Leu Glu Glu Val Ile Met Ala Ile Lys Val Arg Lys Asp Ile Leu Asn
                245                 250                 255 gtc cac acc gcc att aat cac cag gag ata tgg cgc acc agc cag tta        816
Val His Thr Ala Ile Asn His Gln Glu Ile Trp Arg Thr Ser Gln Leu
            260                 265                 270 gtt agc cag att tgt aat atg ccg atc ccg gca aac aaa gcc att gtt        864
Val Ser Gln Ile Cys Asn Met Pro Ile Pro Ala Asn Lys Ala Ile Val
        275                 280                 285 ggc agc ggc gca ttc gca cac tcc tcc ggt ata cac cag gat ggc gtg        912
Gly Ser Gly Ala Phe Ala His Ser Ser Gly Ile His Gln Asp Gly Val
    290                 295                 300 ctg aaa aac cgc gaa aac tac gaa atc atg aca cca gaa tct att ggt        960
Leu Lys Asn Arg Glu Asn Tyr Glu Ile Met Thr Pro Glu Ser Ile Gly
305                 310                 315                 320 ctg aac caa atc cag ctg aat ctg acc tct cgt tcg ggg cgt gcg gcg       1008
Leu Asn Gln Ile Gln Leu Asn Leu Thr Ser Arg Ser Gly Arg Ala Ala
                325                 330                 335 gtg aaa cat cgc atg gat gag atg ggg tat aaa gaa agt gaa tat aat       1056
Val Lys His Arg Met Asp Glu Met Gly Tyr Lys Glu Ser Glu Tyr Asn
            340                 345                 350 tta gac aat ttg tac gat gct ttc ctg aag ctg gcg gac aaa aaa ggt       1104
Leu Asp Asn Leu Tyr Asp Ala Phe Leu Lys Leu Ala Asp Lys Lys Gly
        355                 360                 365 cag gtg ttt gat tac gat ctg gag gcg ctg gcc ttc atc ggt aag cag       1152
Gln Val Phe Asp Tyr Asp Leu Glu Ala Leu Ala Phe Ile Gly Lys Gln
    370                 375                 380
```

```
caa gaa gag ccg gag cat ttc cgt ctg gat tac ttc agc gtg cag tct    1200
Gln Glu Glu Pro Glu His Phe Arg Leu Asp Tyr Phe Ser Val Gln Ser
385                 390                 395                 400 ggc tct aac gat atc gcc acc gcc gcc gtc aaa ctg gcc tgt ggc gaa    1248
Gly Ser Asn Asp Ile Ala Thr Ala Ala Val Lys Leu Ala Cys Gly Glu
                405                 410                 415 gaa gtc aaa gca gaa gcc gcc aac ggt aac ggt ccg gtc gat gcc gtc    1296
Glu Val Lys Ala Glu Ala Ala Asn Gly Asn Gly Pro Val Asp Ala Val
            420                 425                 430 tat cag gca att aac cgc atc act gaa tat aac gtc gaa ctg gtg aaa    1344
Tyr Gln Ala Ile Asn Arg Ile Thr Glu Tyr Asn Val Glu Leu Val Lys
        435                 440                 445 tac agc ctg acc gcc aaa ggc cac ggt aaa gat gcg ctg ggt cag gtg    1392
Tyr Ser Leu Thr Ala Lys Gly His Gly Lys Asp Ala Leu Gly Gln Val
    450                 455                 460 gat atc gtc gct aac tac aac ggt cgc cgc ttc cac ggc gtc ggc ctg    1440
Asp Ile Val Ala Asn Tyr Asn Gly Arg Arg Phe His Gly Val Gly Leu
465                 470                 475                 480 gct acc gat att gtc gag tca tct gcc aaa gcc atg gtg cac gtt ctg    1488
Ala Thr Asp Ile Val Glu Ser Ser Ala Lys Ala Met Val His Val Leu
                485                 490                 495 aac aat atc tgg cgt gcc gca gaa gtc gaa aaa gag ttg caa cgc aaa    1536
Asn Asn Ile Trp Arg Ala Ala Glu Val Glu Lys Glu Leu Gln Arg Lys
            500                 505                 510 gct caa cac aac gaa aac aac aag gaa acc gtg tga                    1572
Ala Gln His Asn Glu Asn Asn Lys Glu Thr Val
        515                 520

<210> SEQ ID NO 2
<211> LENGTH: 523
<212> TYPE: PRT
<213> ORGANISM: Escherichia coli

<400> SEQUENCE: 2

Met Ser Gln Gln Val Ile Ile Phe Asp Thr Thr Leu Arg Asp Gly Glu
1               5                   10                  15

Gln Ala Leu Gln Ala Ser Leu Ser Val Lys Glu Lys Leu Gln Ile Ala
            20                  25                  30

Leu Ala Leu Glu Arg Met Gly Val Asp Val Met Glu Val Gly Phe Pro
        35                  40                  45

Val Ser Ser Pro Gly Asp Phe Glu Ser Val Gln Thr Ile Ala Arg Gln
    50                  55                  60

Val Lys Asn Ser Arg Val Cys Ala Leu Ala Arg Cys Val Glu Lys Asp
65                  70                  75                  80

Ile Asp Val Ala Ala Glu Ser Leu Lys Val Ala Glu Ala Phe Arg Ile
                85                  90                  95

His Thr Phe Ile Ala Thr Ser Pro Met His Ile Ala Thr Lys Leu Arg
            100                 105                 110

Ser Thr Leu Asp Glu Val Ile Glu Arg Ala Ile Tyr Met Val Lys Arg
        115                 120                 125

Ala Arg Asn Tyr Thr Asp Asp Val Glu Phe Ser Cys Glu Asp Ala Gly
    130                 135                 140

Arg Thr Pro Ile Ala Asp Leu Ala Arg Val Val Glu Ala Ala Ile Asn
145                 150                 155                 160

Ala Gly Ala Thr Thr Ile Asn Ile Pro Asp Thr Val Gly Tyr Thr Met
                165                 170                 175

Pro Phe Glu Phe Ala Gly Ile Ile Ser Gly Leu Tyr Glu Arg Val Pro
            180                 185                 190
```

```
Asn Ile Asp Lys Ala Ile Ile Ser Val His Thr His Asp Leu Gly
            195                 200                 205
Leu Ala Val Gly Asn Ser Leu Ala Ala Val His Ala Gly Ala Arg Gln
210                 215                 220
Val Glu Gly Ala Met Asn Gly Ile Gly Glu Arg Ala Gly Asn Cys Ser
225                 230                 235                 240
Leu Glu Glu Val Ile Met Ala Ile Lys Val Arg Lys Asp Ile Leu Asn
                245                 250                 255
Val His Thr Ala Ile Asn His Gln Glu Ile Trp Arg Thr Ser Gln Leu
            260                 265                 270
Val Ser Gln Ile Cys Asn Met Pro Ile Pro Ala Asn Lys Ala Ile Val
        275                 280                 285
Gly Ser Gly Ala Phe Ala His Ser Ser Gly Ile His Gln Asp Gly Val
    290                 295                 300
Leu Lys Asn Arg Glu Asn Tyr Glu Ile Met Thr Pro Glu Ser Ile Gly
305                 310                 315                 320
Leu Asn Gln Ile Gln Leu Asn Leu Thr Ser Arg Ser Gly Arg Ala Ala
                325                 330                 335
Val Lys His Arg Met Asp Glu Met Gly Tyr Lys Glu Ser Glu Tyr Asn
            340                 345                 350
Leu Asp Asn Leu Tyr Asp Ala Phe Leu Lys Leu Ala Asp Lys Lys Gly
        355                 360                 365
Gln Val Phe Asp Tyr Asp Leu Glu Ala Leu Ala Phe Ile Gly Lys Gln
    370                 375                 380
Gln Glu Glu Pro Glu His Phe Arg Leu Asp Tyr Phe Ser Val Gln Ser
385                 390                 395                 400
Gly Ser Asn Asp Ile Ala Thr Ala Ala Val Lys Leu Ala Cys Gly Glu
                405                 410                 415
Glu Val Lys Ala Glu Ala Ala Asn Gly Asn Gly Pro Val Asp Ala Val
            420                 425                 430
Tyr Gln Ala Ile Asn Arg Ile Thr Glu Tyr Asn Val Glu Leu Val Lys
        435                 440                 445
Tyr Ser Leu Thr Ala Lys Gly His Gly Lys Asp Ala Leu Gly Gln Val
    450                 455                 460
Asp Ile Val Ala Asn Tyr Asn Gly Arg Arg Phe His Gly Val Gly Leu
465                 470                 475                 480
Ala Thr Asp Ile Val Glu Ser Ser Ala Lys Ala Met Val His Val Leu
                485                 490                 495
Asn Asn Ile Trp Arg Ala Ala Glu Val Glu Lys Glu Leu Gln Arg Lys
            500                 505                 510
Ala Gln His Asn Glu Asn Asn Lys Glu Thr Val
        515                 520

<210> SEQ ID NO 3
<211> LENGTH: 1572
<212> TYPE: DNA
<213> ORGANISM: Artificial Sequence
<220> FEATURE:
<223> OTHER INFORMATION: Mutant LeuA (G462D)
<220> FEATURE:
<221> NAME/KEY: CDS
<222> LOCATION: (1)..(1572)

<400> SEQUENCE: 3 atg agc cag caa gtc att att ttc gat acc aca ttg cgc gac ggt gaa      48
Met Ser Gln Gln Val Ile Ile Phe Asp Thr Thr Leu Arg Asp Gly Glu
1               5                   10                  15
```

```
cag gcg tta cag gca agc ttg agt gtg aaa gaa aaa ctg caa att gcg      96
Gln Ala Leu Gln Ala Ser Leu Ser Val Lys Glu Lys Leu Gln Ile Ala
         20                  25                  30 ctg gcc ctt gag cgt atg ggt gtt gac gtg atg gaa gtc ggt ttc ccc     144
Leu Ala Leu Glu Arg Met Gly Val Asp Val Met Glu Val Gly Phe Pro
 35                  40                  45 gtc tct tcg ccg ggc gat ttt gaa tcg gtg caa acc atc gcc cgc cag     192
Val Ser Ser Pro Gly Asp Phe Glu Ser Val Gln Thr Ile Ala Arg Gln
     50                  55                  60 gtt aaa aac agc cgc gta tgt gcg tta gct cgc tgc gtg gaa aaa gat     240
Val Lys Asn Ser Arg Val Cys Ala Leu Ala Arg Cys Val Glu Lys Asp
 65                  70                  75                  80 atc gac gtg gcg gcc gaa tcc ctg aaa gtc gcc gaa gcc ttc cgt att     288
Ile Asp Val Ala Ala Glu Ser Leu Lys Val Ala Glu Ala Phe Arg Ile
                 85                  90                  95 cat acc ttt att gcc act tcg cca atg cac atc gcc acc aag ctg cgc     336
His Thr Phe Ile Ala Thr Ser Pro Met His Ile Ala Thr Lys Leu Arg
            100                 105                 110 agc acg ctg gac gag gtg atc gaa cgc gct atc tat atg gtg aaa cgc     384
Ser Thr Leu Asp Glu Val Ile Glu Arg Ala Ile Tyr Met Val Lys Arg
        115                 120                 125 gcc cgt aat tac acc gat gat gtt gaa ttt tct tgc gaa gat gcc ggg     432
Ala Arg Asn Tyr Thr Asp Asp Val Glu Phe Ser Cys Glu Asp Ala Gly
130                 135                 140 cgt aca ccc att gcc gat ctg gcg cga gtg gtc gaa gcg gcg att aat     480
Arg Thr Pro Ile Ala Asp Leu Ala Arg Val Val Glu Ala Ala Ile Asn
145                 150                 155                 160 gcc ggt gcc acc acc atc aac att ccg gac acc gtg ggc tac acc atg     528
Ala Gly Ala Thr Thr Ile Asn Ile Pro Asp Thr Val Gly Tyr Thr Met
                165                 170                 175 ccg ttt gag ttc gcc gga atc atc agc ggc ctg tat gaa cgc gtg cct     576
Pro Phe Glu Phe Ala Gly Ile Ile Ser Gly Leu Tyr Glu Arg Val Pro
            180                 185                 190 aac atc gac aaa gcc att atc tcc gta cat acc cac gac gat ttg ggc     624
Asn Ile Asp Lys Ala Ile Ile Ser Val His Thr His Asp Asp Leu Gly
        195                 200                 205 ctg gcg gtc gga aac tca ctg gcg gcg gta cat gcc ggt gca cgc cag     672
Leu Ala Val Gly Asn Ser Leu Ala Ala Val His Ala Gly Ala Arg Gln
210                 215                 220 gtg gaa ggc gca atg aac ggg atc ggc gag cgt gcc gga aac tgt tcc     720
Val Glu Gly Ala Met Asn Gly Ile Gly Glu Arg Ala Gly Asn Cys Ser
225                 230                 235                 240 ctg gaa gaa gtc atc atg gcg atc aaa gtt cgt aag gat att ctc aac     768
Leu Glu Glu Val Ile Met Ala Ile Lys Val Arg Lys Asp Ile Leu Asn
                245                 250                 255 gtc cac acc gcc att aat cac cag gag ata tgg cgc acc agc cag tta     816
Val His Thr Ala Ile Asn His Gln Glu Ile Trp Arg Thr Ser Gln Leu
            260                 265                 270 gtt agc cag att tgt aat atg ccg atc ccg gca aac aaa gcc att gtt     864
Val Ser Gln Ile Cys Asn Met Pro Ile Pro Ala Asn Lys Ala Ile Val
        275                 280                 285 ggc agc ggc gca ttc gca cac tcc tcc ggt ata cac cag gat ggc gtg     912
Gly Ser Gly Ala Phe Ala His Ser Ser Gly Ile His Gln Asp Gly Val
290                 295                 300 ctg aaa aac cgc gaa aac tac gaa atc atg aca cca gaa tct att ggt     960
Leu Lys Asn Arg Glu Asn Tyr Glu Ile Met Thr Pro Glu Ser Ile Gly
305                 310                 315                 320 ctg aac caa atc cag ctg aat ctg acc tct cgt tcg ggg cgt gcg gcg    1008
Leu Asn Gln Ile Gln Leu Asn Leu Thr Ser Arg Ser Gly Arg Ala Ala
                325                 330                 335
```

-continued

```
gtg aaa cat cgc atg gat gag atg ggg tat aaa gaa agt gaa tat aat      1056
Val Lys His Arg Met Asp Glu Met Gly Tyr Lys Glu Ser Glu Tyr Asn
            340                 345                 350 tta gac aat ttg tac gat gct ttc ctg aag ctg gcg gac aaa aaa ggt      1104
Leu Asp Asn Leu Tyr Asp Ala Phe Leu Lys Leu Ala Asp Lys Lys Gly
        355                 360                 365 cag gtg ttt gat tac gat ctg gag gcg ctg gcc ttc atc ggt aag cag      1152
Gln Val Phe Asp Tyr Asp Leu Glu Ala Leu Ala Phe Ile Gly Lys Gln
    370                 375                 380 caa gaa gag ccg gag cat ttc cgt ctg gat tac ttc agc gtg cag tct      1200
Gln Glu Glu Pro Glu His Phe Arg Leu Asp Tyr Phe Ser Val Gln Ser
385                 390                 395                 400 ggc tct aac gat atc gcc acc gcc gcc gtc aaa ctg gcc tgt ggc gaa      1248
Gly Ser Asn Asp Ile Ala Thr Ala Ala Val Lys Leu Ala Cys Gly Glu
                405                 410                 415 gaa gtc aaa gca gaa gcc gcc aac ggt aac ggt ccg gtc gat gcc gtc      1296
Glu Val Lys Ala Glu Ala Ala Asn Gly Asn Gly Pro Val Asp Ala Val
            420                 425                 430 tat cag gca att aac cgc atc act gaa tat aac gtc gaa ctg gtg aaa      1344
Tyr Gln Ala Ile Asn Arg Ile Thr Glu Tyr Asn Val Glu Leu Val Lys
        435                 440                 445 tac agc ctg acc gcc aaa ggc cac ggt aaa gat gcg ctg gat cag gtg      1392
Tyr Ser Leu Thr Ala Lys Gly His Gly Lys Asp Ala Leu Asp Gln Val
    450                 455                 460 gat atc gtc gct aac tac aac ggt cgc cgc ttc cac ggc gtc ggc ctg      1440
Asp Ile Val Ala Asn Tyr Asn Gly Arg Arg Phe His Gly Val Gly Leu
465                 470                 475                 480 gct acc gat att gtc gag tca tct gcc aaa gcc atg gtg cac gtt ctg      1488
Ala Thr Asp Ile Val Glu Ser Ser Ala Lys Ala Met Val His Val Leu
                485                 490                 495 aac aat atc tgg cgt gcc gca gaa gtc gaa aaa gag ttg caa cgc aaa      1536
Asn Asn Ile Trp Arg Ala Ala Glu Val Glu Lys Glu Leu Gln Arg Lys
            500                 505                 510 gct caa cac aac gaa aac aac aag gaa acc gtg tga                      1572
Ala Gln His Asn Glu Asn Asn Lys Glu Thr Val
        515                 520
```

<210> SEQ ID NO 4
<211> LENGTH: 523
<212> TYPE: PRT
<213> ORGANISM: Artificial Sequence
<220> FEATURE:
<223> OTHER INFORMATION: Synthetic Construct

<400> SEQUENCE: 4

```
Met Ser Gln Gln Val Ile Ile Phe Asp Thr Thr Leu Arg Asp Gly Glu
1               5                   10                  15

Gln Ala Leu Gln Ala Ser Leu Ser Val Lys Glu Lys Leu Gln Ile Ala
            20                  25                  30

Leu Ala Leu Glu Arg Met Gly Val Asp Val Met Glu Val Gly Phe Pro
        35                  40                  45

Val Ser Ser Pro Gly Asp Phe Glu Ser Val Gln Thr Ile Ala Arg Gln
    50                  55                  60

Val Lys Asn Ser Arg Val Cys Ala Leu Ala Arg Cys Val Glu Lys Asp
65                  70                  75                  80

Ile Asp Val Ala Ala Glu Ser Leu Lys Val Ala Glu Ala Phe Arg Ile
                85                  90                  95

His Thr Phe Ile Ala Thr Ser Pro Met His Ile Ala Thr Lys Leu Arg
            100                 105                 110

Ser Thr Leu Asp Glu Val Ile Glu Arg Ala Ile Tyr Met Val Lys Arg
```

```
                115                 120                 125
Ala Arg Asn Tyr Thr Asp Asp Val Glu Phe Ser Cys Glu Asp Ala Gly
        130                 135                 140

Arg Thr Pro Ile Ala Asp Leu Ala Arg Val Val Glu Ala Ala Ile Asn
145                 150                 155                 160

Ala Gly Ala Thr Thr Ile Asn Ile Pro Asp Thr Val Gly Tyr Thr Met
                165                 170                 175

Pro Phe Glu Phe Ala Gly Ile Ile Ser Gly Leu Tyr Glu Arg Val Pro
            180                 185                 190

Asn Ile Asp Lys Ala Ile Ile Ser Val His Thr His Asp Asp Leu Gly
            195                 200                 205

Leu Ala Val Gly Asn Ser Leu Ala Ala Val His Ala Gly Ala Arg Gln
        210                 215                 220

Val Glu Gly Ala Met Asn Gly Ile Gly Glu Arg Ala Gly Asn Cys Ser
225                 230                 235                 240

Leu Glu Glu Val Ile Met Ala Ile Lys Val Arg Lys Asp Ile Leu Asn
                245                 250                 255

Val His Thr Ala Ile Asn His Gln Glu Ile Trp Arg Thr Ser Gln Leu
            260                 265                 270

Val Ser Gln Ile Cys Asn Met Pro Ile Pro Ala Asn Lys Ala Ile Val
    275                 280                 285

Gly Ser Gly Ala Phe Ala His Ser Ser Gly Ile His Gln Asp Gly Val
290                 295                 300

Leu Lys Asn Arg Glu Asn Tyr Glu Ile Met Thr Pro Glu Ser Ile Gly
305                 310                 315                 320

Leu Asn Gln Ile Gln Leu Asn Leu Thr Ser Arg Ser Gly Arg Ala Ala
                325                 330                 335

Val Lys His Arg Met Asp Glu Met Gly Tyr Lys Glu Ser Glu Tyr Asn
            340                 345                 350

Leu Asp Asn Leu Tyr Asp Ala Phe Leu Lys Leu Ala Asp Lys Lys Gly
        355                 360                 365

Gln Val Phe Asp Tyr Asp Leu Glu Ala Leu Ala Phe Ile Gly Lys Gln
    370                 375                 380

Gln Glu Glu Pro Glu His Phe Arg Leu Asp Tyr Phe Ser Val Gln Ser
385                 390                 395                 400

Gly Ser Asn Asp Ile Ala Thr Ala Ala Val Lys Leu Ala Cys Gly Glu
                405                 410                 415

Glu Val Lys Ala Glu Ala Asn Gly Asn Gly Pro Val Asp Ala Val
            420                 425                 430

Tyr Gln Ala Ile Asn Arg Ile Thr Glu Tyr Asn Val Glu Leu Val Lys
        435                 440                 445

Tyr Ser Leu Thr Ala Lys Gly His Gly Lys Asp Ala Leu Asp Gln Val
    450                 455                 460

Asp Ile Val Ala Asn Tyr Asn Gly Arg Arg Phe His Gly Val Gly Leu
465                 470                 475                 480

Ala Thr Asp Ile Val Glu Ser Ser Ala Lys Ala Met Val His Val Leu
                485                 490                 495

Asn Asn Ile Trp Arg Ala Ala Glu Val Glu Lys Glu Leu Gln Arg Lys
            500                 505                 510

Ala Gln His Asn Glu Asn Asn Lys Glu Thr Val
        515                 520

<210> SEQ ID NO 5
<211> LENGTH: 1572
```

```
<212> TYPE: DNA
<213> ORGANISM: Artificial Sequence
<220> FEATURE:
<223> OTHER INFORMATION: Mutant LeuA (G462D/S139G)
<220> FEATURE:
<221> NAME/KEY: CDS
<222> LOCATION: (1)..(1572)

<400> SEQUENCE: 5 atg agc cag caa gtc att att ttc gat acc aca ttg cgc gac ggt gaa     48
Met Ser Gln Gln Val Ile Ile Phe Asp Thr Thr Leu Arg Asp Gly Glu
1               5                   10                  15 cag gcg tta cag gca agc ttg agt gtg aaa gaa aaa ctg caa att gcg     96
Gln Ala Leu Gln Ala Ser Leu Ser Val Lys Glu Lys Leu Gln Ile Ala
            20                  25                  30 ctg gcc ctt gag cgt atg ggt gtt gac gtg atg gaa gtc ggt ttc ccc    144
Leu Ala Leu Glu Arg Met Gly Val Asp Val Met Glu Val Gly Phe Pro
        35                  40                  45 gtc tct tcg ccg ggc gat ttt gaa tcg gtg caa acc atc gcc cgc cag    192
Val Ser Ser Pro Gly Asp Phe Glu Ser Val Gln Thr Ile Ala Arg Gln
    50                  55                  60 gtt aaa aac agc cgc gta tgt gcg tta gct cgc tgc gtg gaa aaa gat    240
Val Lys Asn Ser Arg Val Cys Ala Leu Ala Arg Cys Val Glu Lys Asp
65                  70                  75                  80 atc gac gtg gcg gcc gaa tcc ctg aaa gtc gcc gaa gcc ttc cgt att    288
Ile Asp Val Ala Ala Glu Ser Leu Lys Val Ala Glu Ala Phe Arg Ile
                85                  90                  95 cat acc ttt att gcc act tcg cca atg cac atc gcc acc aag ctg cgc    336
His Thr Phe Ile Ala Thr Ser Pro Met His Ile Ala Thr Lys Leu Arg
            100                 105                 110 agc acg ctg gac gag gtg atc gaa cgc gct atc tat atg gtg aaa cgc    384
Ser Thr Leu Asp Glu Val Ile Glu Arg Ala Ile Tyr Met Val Lys Arg
        115                 120                 125 gcc cgt aat tac acc gat gat gtt gaa ttt ggt tgc gaa gat gcc ggg    432
Ala Arg Asn Tyr Thr Asp Asp Val Glu Phe Gly Cys Glu Asp Ala Gly
    130                 135                 140 cgt aca ccc att gcc gat ctg gcg cga gtg gtc gaa gcg gcg att aat    480
Arg Thr Pro Ile Ala Asp Leu Ala Arg Val Val Glu Ala Ala Ile Asn
145                 150                 155                 160 gcc ggt gcc acc acc atc aac att ccg gac acc gtg ggc tac acc atg    528
Ala Gly Ala Thr Thr Ile Asn Ile Pro Asp Thr Val Gly Tyr Thr Met
                165                 170                 175 ccg ttt gag ttc gcc gga atc atc agc ggc ctg tat gaa cgc gtg cct    576
Pro Phe Glu Phe Ala Gly Ile Ile Ser Gly Leu Tyr Glu Arg Val Pro
            180                 185                 190 aac atc gac aaa gcc att atc tcc gta cat acc cac gat gat ttg ggc    624
Asn Ile Asp Lys Ala Ile Ile Ser Val His Thr His Asp Asp Leu Gly
        195                 200                 205 ctg gcg gtc gga aac tca ctg gcg gcg gta cat gcc ggt gca cgc cag    672
Leu Ala Val Gly Asn Ser Leu Ala Ala Val His Ala Gly Ala Arg Gln
    210                 215                 220 gtg gaa ggc gca atg aac ggg atc ggc gag cgt gcc gga aac tgt tcc    720
Val Glu Gly Ala Met Asn Gly Ile Gly Glu Arg Ala Gly Asn Cys Ser
225                 230                 235                 240 ctg gaa gaa gtc atc atg gcg atc aaa gtt cgt aag gat att ctc aac    768
Leu Glu Glu Val Ile Met Ala Ile Lys Val Arg Lys Asp Ile Leu Asn
                245                 250                 255 gtc cac acc gcc att aat cac cag gag ata tgg cgc acc agc cag tta    816
Val His Thr Ala Ile Asn His Gln Glu Ile Trp Arg Thr Ser Gln Leu
            260                 265                 270 gtt agc cag att tgt aat atg ccg atc ccg gca aac aaa gcc att gtt    864
Val Ser Gln Ile Cys Asn Met Pro Ile Pro Ala Asn Lys Ala Ile Val
```

```
                275                 280                 285
ggc agc ggc gca ttc gca cac tcc tcc ggt ata cac cag gat ggc gtg        912
Gly Ser Gly Ala Phe Ala His Ser Ser Gly Ile His Gln Asp Gly Val
        290                 295                 300 ctg aaa aac cgc gaa aac tac gaa atc atg aca cca gaa tct att ggt        960
Leu Lys Asn Arg Glu Asn Tyr Glu Ile Met Thr Pro Glu Ser Ile Gly
305                 310                 315                 320 ctg aac caa atc cag ctg aat ctg acc tct cgt tcg ggg cgt gcg gcg       1008
Leu Asn Gln Ile Gln Leu Asn Leu Thr Ser Arg Ser Gly Arg Ala Ala
                325                 330                 335 gtg aaa cat cgc atg gat gag atg ggg tat aaa gaa agt gaa tat aat       1056
Val Lys His Arg Met Asp Glu Met Gly Tyr Lys Glu Ser Glu Tyr Asn
            340                 345                 350 tta gac aat ttg tac gat gct ttc ctg aag ctg gcg gac aaa aaa ggt       1104
Leu Asp Asn Leu Tyr Asp Ala Phe Leu Lys Leu Ala Asp Lys Lys Gly
        355                 360                 365 cag gtg ttt gat tac gat ctg gag gcg ctg gcc ttc atc ggt aag cag       1152
Gln Val Phe Asp Tyr Asp Leu Glu Ala Leu Ala Phe Ile Gly Lys Gln
    370                 375                 380 caa gaa gag ccg gag cat ttc cgt ctg gat tac ttc agc gtg cag tct       1200
Gln Glu Glu Pro Glu His Phe Arg Leu Asp Tyr Phe Ser Val Gln Ser
385                 390                 395                 400 ggc tct aac gat atc gcc acc gcc gcc gtc aaa ctg gcc tgt ggc gaa       1248
Gly Ser Asn Asp Ile Ala Thr Ala Ala Val Lys Leu Ala Cys Gly Glu
                405                 410                 415 gaa gtc aaa gca gaa gcc gcc aac ggt aac ggt ccg gtc gat gcc gtc       1296
Glu Val Lys Ala Glu Ala Ala Asn Gly Asn Gly Pro Val Asp Ala Val
            420                 425                 430 tat cag gca att aac cgc atc act gaa tat aac gtc gaa ctg gtg aaa       1344
Tyr Gln Ala Ile Asn Arg Ile Thr Glu Tyr Asn Val Glu Leu Val Lys
        435                 440                 445 tac agc ctg acc gcc aaa ggc cac ggt aaa gat gcg ctg gat cag gtg       1392
Tyr Ser Leu Thr Ala Lys Gly His Gly Lys Asp Ala Leu Asp Gln Val
    450                 455                 460 gat atc gtc gct aac tac aac ggt cgc cgc ttc cac ggc gtc ggc ctg       1440
Asp Ile Val Ala Asn Tyr Asn Gly Arg Arg Phe His Gly Val Gly Leu
465                 470                 475                 480 gct acc gat att gtc gag tca tct gcc aaa gcc atg gtg cac gtt ctg       1488
Ala Thr Asp Ile Val Glu Ser Ser Ala Lys Ala Met Val His Val Leu
                485                 490                 495 aac aat atc tgg cgt gcc gca gaa gtc gaa aaa gag ttg caa cgc aaa       1536
Asn Asn Ile Trp Arg Ala Ala Glu Val Glu Lys Glu Leu Gln Arg Lys
            500                 505                 510 gct caa cac aac gaa aac aac aag gaa acc gtg tga                       1572
Ala Gln His Asn Glu Asn Asn Lys Glu Thr Val
        515                 520

<210> SEQ ID NO 6
<211> LENGTH: 523
<212> TYPE: PRT
<213> ORGANISM: Artificial Sequence
<220> FEATURE:
<223> OTHER INFORMATION: Synthetic Construct

<400> SEQUENCE: 6

Met Ser Gln Gln Val Ile Ile Phe Asp Thr Thr Leu Arg Asp Gly Glu
1               5                   10                  15

Gln Ala Leu Gln Ala Ser Leu Ser Val Lys Glu Lys Leu Gln Ile Ala
            20                  25                  30

Leu Ala Leu Glu Arg Met Gly Val Asp Val Met Glu Val Gly Phe Pro
        35                  40                  45
```

```
Val Ser Ser Pro Gly Asp Phe Glu Ser Val Gln Thr Ile Ala Arg Gln
 50                  55                  60

Val Lys Asn Ser Arg Val Cys Ala Leu Ala Arg Cys Val Glu Lys Asp
 65                  70                  75                  80

Ile Asp Val Ala Ala Glu Ser Leu Lys Val Ala Glu Ala Phe Arg Ile
                 85                  90                  95

His Thr Phe Ile Ala Thr Ser Pro Met His Ile Ala Thr Lys Leu Arg
                100                 105                 110

Ser Thr Leu Asp Glu Val Ile Glu Arg Ala Ile Tyr Met Val Lys Arg
            115                 120                 125

Ala Arg Asn Tyr Thr Asp Asp Val Glu Phe Gly Cys Glu Asp Ala Gly
        130                 135                 140

Arg Thr Pro Ile Ala Asp Leu Ala Arg Val Val Glu Ala Ala Ile Asn
145                 150                 155                 160

Ala Gly Ala Thr Thr Ile Asn Ile Pro Asp Thr Val Gly Tyr Thr Met
                165                 170                 175

Pro Phe Glu Phe Ala Gly Ile Ile Ser Gly Leu Tyr Glu Arg Val Pro
                180                 185                 190

Asn Ile Asp Lys Ala Ile Ile Ser Val His Thr His Asp Asp Leu Gly
            195                 200                 205

Leu Ala Val Gly Asn Ser Leu Ala Ala Val His Ala Gly Ala Arg Gln
210                 215                 220

Val Glu Gly Ala Met Asn Gly Ile Gly Glu Arg Ala Gly Asn Cys Ser
225                 230                 235                 240

Leu Glu Glu Val Ile Met Ala Ile Lys Val Arg Lys Asp Ile Leu Asn
                245                 250                 255

Val His Thr Ala Ile Asn His Gln Glu Ile Trp Arg Thr Ser Gln Leu
                260                 265                 270

Val Ser Gln Ile Cys Asn Met Pro Ile Pro Ala Asn Lys Ala Ile Val
            275                 280                 285

Gly Ser Gly Ala Phe Ala His Ser Ser Gly Ile His Gln Asp Gly Val
290                 295                 300

Leu Lys Asn Arg Glu Asn Tyr Glu Ile Met Thr Pro Glu Ser Ile Gly
305                 310                 315                 320

Leu Asn Gln Ile Gln Leu Asn Leu Thr Ser Arg Ser Gly Arg Ala Ala
                325                 330                 335

Val Lys His Arg Met Asp Glu Met Gly Tyr Lys Glu Ser Glu Tyr Asn
                340                 345                 350

Leu Asp Asn Leu Tyr Asp Ala Phe Leu Lys Leu Ala Asp Lys Lys Gly
            355                 360                 365

Gln Val Phe Asp Tyr Asp Leu Glu Ala Leu Ala Phe Ile Gly Lys Gln
        370                 375                 380

Gln Glu Glu Pro Glu His Phe Arg Leu Asp Tyr Phe Ser Val Gln Ser
385                 390                 395                 400

Gly Ser Asn Asp Ile Ala Thr Ala Ala Val Lys Leu Ala Cys Gly Glu
                405                 410                 415

Glu Val Lys Ala Glu Ala Ala Asn Gly Asn Gly Pro Val Asp Ala Val
            420                 425                 430

Tyr Gln Ala Ile Asn Arg Ile Thr Glu Tyr Asn Val Glu Leu Val Lys
        435                 440                 445

Tyr Ser Leu Thr Ala Lys Gly His Gly Lys Asp Ala Leu Asp Gln Val
450                 455                 460

Asp Ile Val Ala Asn Tyr Asn Gly Arg Arg Phe His Gly Val Gly Leu
```

```
                465                 470                 475                 480
Ala Thr Asp Ile Val Glu Ser Ser Ala Lys Ala Met Val His Val Leu
                        485                 490                 495

Asn Asn Ile Trp Arg Ala Ala Glu Val Glu Lys Glu Leu Gln Arg Lys
                500                 505                 510

Ala Gln His Asn Glu Asn Asn Lys Glu Thr Val
        515                 520

<210> SEQ ID NO 7
<211> LENGTH: 1572
<212> TYPE: DNA
<213> ORGANISM: Artificial Sequence
<220> FEATURE:
<223> OTHER INFORMATION: Mutant LeuA (G462D/S139G/H97A)
<220> FEATURE:
<221> NAME/KEY: CDS
<222> LOCATION: (1)..(1572)

<400> SEQUENCE: 7 atg agc cag caa gtc att att ttc gat acc aca ttg cgc gac ggt gaa      48
Met Ser Gln Gln Val Ile Ile Phe Asp Thr Thr Leu Arg Asp Gly Glu
1               5                   10                  15 cag gcg tta cag gca agc ttg agt gtg aaa gaa aaa ctg caa att gcg      96
Gln Ala Leu Gln Ala Ser Leu Ser Val Lys Glu Lys Leu Gln Ile Ala
            20                  25                  30 ctg gcc ctt gag cgt atg ggt gtt gac gtg atg gaa gtc ggt ttc ccc     144
Leu Ala Leu Glu Arg Met Gly Val Asp Val Met Glu Val Gly Phe Pro
        35                  40                  45 gtc tct tcg ccg ggc gat ttt gaa tcg gtg caa acc atc gcc cgc cag     192
Val Ser Ser Pro Gly Asp Phe Glu Ser Val Gln Thr Ile Ala Arg Gln
    50                  55                  60 gtt aaa aac agc cgc gta tgt gcg tta gct cgc tgc gtg gaa aaa gat     240
Val Lys Asn Ser Arg Val Cys Ala Leu Ala Arg Cys Val Glu Lys Asp
65                  70                  75                  80 atc gac gtg gcg gcc gaa tcc ctg aaa gtc gcc gaa gcc ttc cgt att     288
Ile Asp Val Ala Ala Glu Ser Leu Lys Val Ala Glu Ala Phe Arg Ile
                85                  90                  95 gcg acc ttt att gcc act tcg cca atg cac atc gcc acc aag ctg cgc     336
Ala Thr Phe Ile Ala Thr Ser Pro Met His Ile Ala Thr Lys Leu Arg
            100                 105                 110 agc acg ctg gac gag gtg atc gaa cgc gct atc tat atg gtg aaa cgc     384
Ser Thr Leu Asp Glu Val Ile Glu Arg Ala Ile Tyr Met Val Lys Arg
        115                 120                 125 gcc cgt aat tac acc gat gat gtt gaa ttt ggt tgc gaa gat gcc ggg     432
Ala Arg Asn Tyr Thr Asp Asp Val Glu Phe Gly Cys Glu Asp Ala Gly
    130                 135                 140 cgt aca ccc att gcc gat ctg gcg cga gtg gtc gaa gcg gcg att aat     480
Arg Thr Pro Ile Ala Asp Leu Ala Arg Val Val Glu Ala Ala Ile Asn
145                 150                 155                 160 gcc ggt gcc acc acc atc aac att ccg gac acc gtg ggc tac acc atg     528
Ala Gly Ala Thr Thr Ile Asn Ile Pro Asp Thr Val Gly Tyr Thr Met
                165                 170                 175 ccg ttt gag ttc gcc gga atc atc agc ggc ctg tat gaa cgc gtg cct     576
Pro Phe Glu Phe Ala Gly Ile Ile Ser Gly Leu Tyr Glu Arg Val Pro
            180                 185                 190 aac atc gac aaa gcc att atc tcc gta cat acc cac gat gat ttg ggc     624
Asn Ile Asp Lys Ala Ile Ile Ser Val His Thr His Asp Asp Leu Gly
        195                 200                 205 ctg gcg gtc gga aac tca ctg gcg gcg gta cat gcc ggt gca cgc cag     672
Leu Ala Val Gly Asn Ser Leu Ala Ala Val His Ala Gly Ala Arg Gln
    210                 215                 220
```

```
gtg gaa ggc gca atg aac ggg atc ggc gag cgt gcc gga aac tgt tcc      720
Val Glu Gly Ala Met Asn Gly Ile Gly Glu Arg Ala Gly Asn Cys Ser
225                 230                 235                 240 ctg gaa gaa gtc atc atg gcg atc aaa gtt cgt aag gat att ctc aac      768
Leu Glu Glu Val Ile Met Ala Ile Lys Val Arg Lys Asp Ile Leu Asn
            245                 250                 255 gtc cac acc gcc att aat cac cag gag ata tgg cgc acc agc cag tta      816
Val His Thr Ala Ile Asn His Gln Glu Ile Trp Arg Thr Ser Gln Leu
        260                 265                 270 gtt agc cag att tgt aat atg ccg atc ccg gca aac aaa gcc att gtt      864
Val Ser Gln Ile Cys Asn Met Pro Ile Pro Ala Asn Lys Ala Ile Val
    275                 280                 285 ggc agc ggc gca ttc gca cac tcc tcc ggt ata cac cag gat ggc gtg      912
Gly Ser Gly Ala Phe Ala His Ser Ser Gly Ile His Gln Asp Gly Val
290                 295                 300 ctg aaa aac cgc gaa aac tac gaa atc atg aca cca gaa tct att ggt      960
Leu Lys Asn Arg Glu Asn Tyr Glu Ile Met Thr Pro Glu Ser Ile Gly
305                 310                 315                 320 ctg aac caa atc cag ctg aat ctg acc tct cgt tcg ggg cgt gcg gcg     1008
Leu Asn Gln Ile Gln Leu Asn Leu Thr Ser Arg Ser Gly Arg Ala Ala
            325                 330                 335 gtg aaa cat cgc atg gat gag atg ggg tat aaa gaa agt gaa tat aat     1056
Val Lys His Arg Met Asp Glu Met Gly Tyr Lys Glu Ser Glu Tyr Asn
        340                 345                 350 tta gac aat ttg tac gat gct ttc ctg aag ctg gcg gac aaa aaa ggt     1104
Leu Asp Asn Leu Tyr Asp Ala Phe Leu Lys Leu Ala Asp Lys Lys Gly
    355                 360                 365 cag gtg ttt gat tac gat ctg gag gcg ctg gcc ttc atc ggt aag cag     1152
Gln Val Phe Asp Tyr Asp Leu Glu Ala Leu Ala Phe Ile Gly Lys Gln
370                 375                 380 caa gaa gag ccg gag cat ttc cgt ctg gat tac ttc agc gtg cag tct     1200
Gln Glu Glu Pro Glu His Phe Arg Leu Asp Tyr Phe Ser Val Gln Ser
385                 390                 395                 400 ggc tct aac gat atc gcc acc gcc gcc gtc aaa ctg gcc tgt ggc gaa     1248
Gly Ser Asn Asp Ile Ala Thr Ala Ala Val Lys Leu Ala Cys Gly Glu
            405                 410                 415 gaa gtc aaa gca gaa gcc gcc aac ggt aac ggt ccg gtc gat gcc gtc     1296
Glu Val Lys Ala Glu Ala Ala Asn Gly Asn Gly Pro Val Asp Ala Val
        420                 425                 430 tat cag gca att aac cgc atc act gaa tat aac gtc gaa ctg gtg aaa     1344
Tyr Gln Ala Ile Asn Arg Ile Thr Glu Tyr Asn Val Glu Leu Val Lys
    435                 440                 445 tac agc ctg acc gcc aaa ggc cac ggt aaa gat gcg ctg gat cag gtg     1392
Tyr Ser Leu Thr Ala Lys Gly His Gly Lys Asp Ala Leu Asp Gln Val
450                 455                 460 gat atc gtc gct aac tac aac ggt cgc cgc ttc cac ggc gtc ggc ctg     1440
Asp Ile Val Ala Asn Tyr Asn Gly Arg Arg Phe His Gly Val Gly Leu
465                 470                 475                 480 gct acc gat att gtc gag tca tct gcc aaa gcc atg gtg cac gtt ctg     1488
Ala Thr Asp Ile Val Glu Ser Ser Ala Lys Ala Met Val His Val Leu
            485                 490                 495 aac aat atc tgg cgt gcc gca gaa gtc gaa aaa gag ttg caa cgc aaa     1536
Asn Asn Ile Trp Arg Ala Ala Glu Val Glu Lys Glu Leu Gln Arg Lys
        500                 505                 510 gct caa cac aac gaa aac aac aag gaa acc gtg tga                     1572
Ala Gln His Asn Glu Asn Asn Lys Glu Thr Val
    515                 520

<210> SEQ ID NO 8
<211> LENGTH: 523
<212> TYPE: PRT
```

<213> ORGANISM: Artificial Sequence
<220> FEATURE:
<223> OTHER INFORMATION: Synthetic Construct

<400> SEQUENCE: 8

```
Met Ser Gln Gln Val Ile Ile Phe Asp Thr Thr Leu Arg Asp Gly Glu
1               5                   10                  15

Gln Ala Leu Gln Ala Ser Leu Ser Val Lys Glu Lys Leu Gln Ile Ala
            20                  25                  30

Leu Ala Leu Glu Arg Met Gly Val Asp Val Met Glu Val Gly Phe Pro
        35                  40                  45

Val Ser Ser Pro Gly Asp Phe Glu Ser Val Gln Thr Ile Ala Arg Gln
50                  55                  60

Val Lys Asn Ser Arg Val Cys Ala Leu Ala Arg Cys Val Glu Lys Asp
65                  70                  75                  80

Ile Asp Val Ala Ala Glu Ser Leu Lys Val Ala Glu Ala Phe Arg Ile
                85                  90                  95

Ala Thr Phe Ile Ala Thr Ser Pro Met His Ile Ala Thr Lys Leu Arg
            100                 105                 110

Ser Thr Leu Asp Glu Val Ile Glu Arg Ala Ile Tyr Met Val Lys Arg
        115                 120                 125

Ala Arg Asn Tyr Thr Asp Asp Val Glu Phe Gly Cys Glu Asp Ala Gly
    130                 135                 140

Arg Thr Pro Ile Ala Asp Leu Ala Arg Val Val Glu Ala Ala Ile Asn
145                 150                 155                 160

Ala Gly Ala Thr Thr Ile Asn Ile Pro Asp Thr Val Gly Tyr Thr Met
                165                 170                 175

Pro Phe Glu Phe Ala Gly Ile Ile Ser Gly Leu Tyr Glu Arg Val Pro
            180                 185                 190

Asn Ile Asp Lys Ala Ile Ile Ser Val His Thr His Asp Asp Leu Gly
        195                 200                 205

Leu Ala Val Gly Asn Ser Leu Ala Ala Val His Ala Gly Ala Arg Gln
    210                 215                 220

Val Glu Gly Ala Met Asn Gly Ile Gly Glu Arg Ala Gly Asn Cys Ser
225                 230                 235                 240

Leu Glu Glu Val Ile Met Ala Ile Lys Val Arg Lys Asp Ile Leu Asn
                245                 250                 255

Val His Thr Ala Ile Asn His Gln Glu Ile Trp Arg Thr Ser Gln Leu
            260                 265                 270

Val Ser Gln Ile Cys Asn Met Pro Ile Pro Ala Asn Lys Ala Ile Val
        275                 280                 285

Gly Ser Gly Ala Phe Ala His Ser Ser Gly Ile His Gln Asp Gly Val
    290                 295                 300

Leu Lys Asn Arg Glu Asn Tyr Glu Ile Met Thr Pro Glu Ser Ile Gly
305                 310                 315                 320

Leu Asn Gln Ile Gln Leu Asn Leu Thr Ser Arg Ser Gly Arg Ala Ala
                325                 330                 335

Val Lys His Arg Met Asp Glu Met Gly Tyr Lys Glu Ser Glu Tyr Asn
            340                 345                 350

Leu Asp Asn Leu Tyr Asp Ala Phe Leu Lys Leu Ala Asp Lys Lys Gly
        355                 360                 365

Gln Val Phe Asp Tyr Asp Leu Glu Ala Leu Ala Phe Ile Gly Lys Gln
    370                 375                 380

Gln Glu Glu Pro Glu His Phe Arg Leu Asp Tyr Phe Ser Val Gln Ser
385                 390                 395                 400
```

```
Gly Ser Asn Asp Ile Ala Thr Ala Ala Val Lys Leu Ala Cys Gly Glu
                405                 410                 415

Glu Val Lys Ala Glu Ala Ala Asn Gly Asn Gly Pro Val Asp Ala Val
            420                 425                 430

Tyr Gln Ala Ile Asn Arg Ile Thr Glu Tyr Asn Val Glu Leu Val Lys
                435                 440                 445

Tyr Ser Leu Thr Ala Lys Gly His Gly Lys Asp Ala Leu Asp Gln Val
450                 455                 460

Asp Ile Val Ala Asn Tyr Asn Gly Arg Arg Phe His Gly Val Gly Leu
465                 470                 475                 480

Ala Thr Asp Ile Val Glu Ser Ala Lys Ala Met Val His Val Leu
                485                 490                 495

Asn Asn Ile Trp Arg Ala Ala Glu Val Glu Lys Glu Leu Gln Arg Lys
                500                 505                 510

Ala Gln His Asn Glu Asn Asn Lys Glu Thr Val
                515                 520

<210> SEQ ID NO 9
<211> LENGTH: 1572
<212> TYPE: DNA
<213> ORGANISM: Artificial Sequence
<220> FEATURE:
<223> OTHER INFORMATION: Mutant LeuA (G462D/S139G/H97L)
<220> FEATURE:
<221> NAME/KEY: CDS
<222> LOCATION: (1)..(1572)

<400> SEQUENCE: 9 atg agc cag caa gtc att att ttc gat acc aca ttg cgc gac ggt gaa      48
Met Ser Gln Gln Val Ile Ile Phe Asp Thr Thr Leu Arg Asp Gly Glu
1               5                   10                  15 cag gcg tta cag gca agc ttg agt gtg aaa gaa aaa ctg caa att gcg      96
Gln Ala Leu Gln Ala Ser Leu Ser Val Lys Glu Lys Leu Gln Ile Ala
                20                  25                  30 ctg gcc ctt gag cgt atg ggt gtt gac gtg atg gaa gtc ggt ttc ccc     144
Leu Ala Leu Glu Arg Met Gly Val Asp Val Met Glu Val Gly Phe Pro
            35                  40                  45 gtc tct tcg ccg ggc gat ttt gaa tcg gtg caa acc atc gcc cgc cag     192
Val Ser Ser Pro Gly Asp Phe Glu Ser Val Gln Thr Ile Ala Arg Gln
        50                  55                  60 gtt aaa aac agc cgc gta tgt gcg tta gct cgc tgc gtg gaa aaa gat     240
Val Lys Asn Ser Arg Val Cys Ala Leu Ala Arg Cys Val Glu Lys Asp
65                  70                  75                  80 atc gac gtg gcg gcc gaa tcc ctg aaa gtc gcc gaa gcc ttc cgt att     288
Ile Asp Val Ala Ala Glu Ser Leu Lys Val Ala Glu Ala Phe Arg Ile
                85                  90                  95 ctg acc ttt att gcc act tcg cca atg cac atc gcc acc aag ctg cgc     336
Leu Thr Phe Ile Ala Thr Ser Pro Met His Ile Ala Thr Lys Leu Arg
            100                 105                 110 agc acg ctg gac gag gtg atc gaa cgc gct atc tat atg gtg aaa cgc     384
Ser Thr Leu Asp Glu Val Ile Glu Arg Ala Ile Tyr Met Val Lys Arg
        115                 120                 125 gcc cgt aat tac acc gat gat gtt gaa ttt ggt tgc gaa gat gcc ggg     432
Ala Arg Asn Tyr Thr Asp Asp Val Glu Phe Gly Cys Glu Asp Ala Gly
    130                 135                 140 cgt aca ccc att gcc gat ctg gcg cga gtg gtc gaa gcg gcg att aat     480
Arg Thr Pro Ile Ala Asp Leu Ala Arg Val Val Glu Ala Ala Ile Asn
145                 150                 155                 160 gcc ggt gcc acc acc atc aac att ccg gac acc gtg ggc tac acc atg     528
Ala Gly Ala Thr Thr Ile Asn Ile Pro Asp Thr Val Gly Tyr Thr Met
```

-continued

```
                165                 170                 175
ccg ttt gag ttc gcc gga atc atc agc ggc ctg tat gaa cgc gtg cct      576
Pro Phe Glu Phe Ala Gly Ile Ile Ser Gly Leu Tyr Glu Arg Val Pro
                    180                 185                 190 aac atc gac aaa gcc att atc tcc gta cat acc cac gac gat ttg ggc      624
Asn Ile Asp Lys Ala Ile Ile Ser Val His Thr His Asp Asp Leu Gly
            195                 200                 205 ctg gcg gtc gga aac tca ctg gcg gcg gta cat gcc ggt gca cgc cag      672
Leu Ala Val Gly Asn Ser Leu Ala Ala Val His Ala Gly Ala Arg Gln
        210                 215                 220 gtg gaa ggc gca atg aac ggg atc ggc gag cgt gcc gga aac tgt tcc      720
Val Glu Gly Ala Met Asn Gly Ile Gly Glu Arg Ala Gly Asn Cys Ser
225                 230                 235                 240 ctg gaa gaa gtc atc atg gcg atc aaa gtt cgt aag gat att ctc aac      768
Leu Glu Glu Val Ile Met Ala Ile Lys Val Arg Lys Asp Ile Leu Asn
                245                 250                 255 gtc cac acc gcc att aat cac cag gag ata tgg cgc acc agc cag tta      816
Val His Thr Ala Ile Asn His Gln Glu Ile Trp Arg Thr Ser Gln Leu
            260                 265                 270 gtt agc cag att tgt aat atg ccg atc ccg gca aac aaa gcc att gtt      864
Val Ser Gln Ile Cys Asn Met Pro Ile Pro Ala Asn Lys Ala Ile Val
        275                 280                 285 ggc agc ggc gca ttc gca cac tcc tcc ggt ata cac cag gat ggc gtg      912
Gly Ser Gly Ala Phe Ala His Ser Ser Gly Ile His Gln Asp Gly Val
    290                 295                 300 ctg aaa aac cgc gaa aac tac gaa atc atg aca cca gaa tct att ggt      960
Leu Lys Asn Arg Glu Asn Tyr Glu Ile Met Thr Pro Glu Ser Ile Gly
305                 310                 315                 320 ctg aac caa atc cag ctg aat ctg acc tct cgt tcg ggg cgt gcg gcg     1008
Leu Asn Gln Ile Gln Leu Asn Leu Thr Ser Arg Ser Gly Arg Ala Ala
                325                 330                 335 gtg aaa cat cgc atg gat gag atg ggg tat aaa gaa agt gaa tat aat     1056
Val Lys His Arg Met Asp Glu Met Gly Tyr Lys Glu Ser Glu Tyr Asn
            340                 345                 350 tta gac aat ttg tac gat gct ttc ctg aag ctg gcg gac aaa aaa ggt     1104
Leu Asp Asn Leu Tyr Asp Ala Phe Leu Lys Leu Ala Asp Lys Lys Gly
        355                 360                 365 cag gtg ttt gat tac gat ctg gag gcg ctg gcc ttc atc ggt aag cag     1152
Gln Val Phe Asp Tyr Asp Leu Glu Ala Leu Ala Phe Ile Gly Lys Gln
    370                 375                 380 caa gaa gag ccg gag cat ttc cgt ctg gat tac ttc agc gtg cag tct     1200
Gln Glu Glu Pro Glu His Phe Arg Leu Asp Tyr Phe Ser Val Gln Ser
385                 390                 395                 400 ggc tct aac gat atc gcc acc gcc gcc gtc aaa ctg gcc tgt ggc gaa     1248
Gly Ser Asn Asp Ile Ala Thr Ala Ala Val Lys Leu Ala Cys Gly Glu
                405                 410                 415 gaa gtc aaa gca gaa gcc gcc aac ggt aac ggt ccg gtc gat gcc gtc     1296
Glu Val Lys Ala Glu Ala Ala Asn Gly Asn Gly Pro Val Asp Ala Val
            420                 425                 430 tat cag gca att aac cgc atc act gaa tat aac gtc gaa ctg gtg aaa     1344
Tyr Gln Ala Ile Asn Arg Ile Thr Glu Tyr Asn Val Glu Leu Val Lys
        435                 440                 445 tac agc ctg acc gcc aaa ggc cac ggt aaa gat gcg ctg gat cag gtg     1392
Tyr Ser Leu Thr Ala Lys Gly His Gly Lys Asp Ala Leu Asp Gln Val
    450                 455                 460 gat atc gtc gct aac tac aac ggt cgc cgc ttc cac ggc gtc ggc ctg     1440
Asp Ile Val Ala Asn Tyr Asn Gly Arg Arg Phe His Gly Val Gly Leu
465                 470                 475                 480 gct acc gat att gtc gag tca tct gcc aaa gcc atg gtg cac gtt ctg     1488
Ala Thr Asp Ile Val Glu Ser Ser Ala Lys Ala Met Val His Val Leu
```

-continued

```
                    485                 490                 495
aac aat atc tgg cgt gcc gca gaa gtc gaa aaa gag ttg caa cgc aaa      1536
Asn Asn Ile Trp Arg Ala Ala Glu Val Glu Lys Glu Leu Gln Arg Lys
        500                 505                 510 gct caa cac aac gaa aac aac aag gaa acc gtg tga                     1572
Ala Gln His Asn Glu Asn Asn Lys Glu Thr Val
        515                 520

<210> SEQ ID NO 10
<211> LENGTH: 523
<212> TYPE: PRT
<213> ORGANISM: Artificial Sequence
<220> FEATURE:
<223> OTHER INFORMATION: Synthetic Construct

<400> SEQUENCE: 10

Met Ser Gln Gln Val Ile Ile Phe Asp Thr Thr Leu Arg Asp Gly Glu
1               5                   10                  15

Gln Ala Leu Gln Ala Ser Leu Ser Val Lys Glu Lys Leu Gln Ile Ala
            20                  25                  30

Leu Ala Leu Glu Arg Met Gly Val Asp Val Met Glu Val Gly Phe Pro
        35                  40                  45

Val Ser Ser Pro Gly Asp Phe Glu Ser Val Gln Thr Ile Ala Arg Gln
    50                  55                  60

Val Lys Asn Ser Arg Val Cys Ala Leu Ala Arg Cys Val Glu Lys Asp
65                  70                  75                  80

Ile Asp Val Ala Ala Glu Ser Leu Lys Val Ala Glu Ala Phe Arg Ile
                85                  90                  95

Leu Thr Phe Ile Ala Thr Ser Pro Met His Ile Ala Thr Lys Leu Arg
            100                 105                 110

Ser Thr Leu Asp Glu Val Ile Glu Arg Ala Ile Tyr Met Val Lys Arg
        115                 120                 125

Ala Arg Asn Tyr Thr Asp Asp Val Glu Phe Gly Cys Glu Asp Ala Gly
    130                 135                 140

Arg Thr Pro Ile Ala Asp Leu Ala Arg Val Val Glu Ala Ala Ile Asn
145                 150                 155                 160

Ala Gly Ala Thr Thr Ile Asn Ile Pro Asp Thr Val Gly Tyr Thr Met
                165                 170                 175

Pro Phe Glu Phe Ala Gly Ile Ile Ser Gly Leu Tyr Glu Arg Val Pro
            180                 185                 190

Asn Ile Asp Lys Ala Ile Ile Ser Val His Thr His Asp Asp Leu Gly
        195                 200                 205

Leu Ala Val Gly Asn Ser Leu Ala Ala Val His Ala Gly Ala Arg Gln
    210                 215                 220

Val Glu Gly Ala Met Asn Gly Ile Gly Glu Arg Ala Gly Asn Cys Ser
225                 230                 235                 240

Leu Glu Glu Val Ile Met Ala Ile Lys Val Arg Lys Asp Ile Leu Asn
                245                 250                 255

Val His Thr Ala Ile Asn His Gln Glu Ile Trp Arg Thr Ser Gln Leu
            260                 265                 270

Val Ser Gln Ile Cys Asn Met Pro Ile Pro Ala Asn Lys Ala Ile Val
        275                 280                 285

Gly Ser Gly Ala Phe Ala His Ser Ser Gly Ile His Gln Asp Gly Val
    290                 295                 300

Leu Lys Asn Arg Glu Asn Tyr Glu Ile Met Thr Pro Glu Ser Ile Gly
305                 310                 315                 320
```

```
Leu Asn Gln Ile Gln Leu Asn Leu Thr Ser Arg Ser Gly Arg Ala Ala
                325                 330                 335

Val Lys His Arg Met Asp Glu Met Gly Tyr Lys Glu Ser Glu Tyr Asn
            340                 345                 350

Leu Asp Asn Leu Tyr Asp Ala Phe Leu Lys Leu Ala Asp Lys Lys Gly
            355                 360                 365

Gln Val Phe Asp Tyr Asp Leu Glu Ala Leu Ala Phe Ile Gly Lys Gln
        370                 375                 380

Gln Glu Glu Pro Glu His Phe Arg Leu Asp Tyr Phe Ser Val Gln Ser
385                 390                 395                 400

Gly Ser Asn Asp Ile Ala Thr Ala Ala Val Lys Leu Ala Cys Gly Glu
                405                 410                 415

Glu Val Lys Ala Glu Ala Asn Gly Asn Gly Pro Val Asp Ala Val
            420                 425                 430

Tyr Gln Ala Ile Asn Arg Ile Thr Glu Tyr Asn Val Glu Leu Val Lys
                435                 440                 445

Tyr Ser Leu Thr Ala Lys Gly His Gly Lys Asp Ala Leu Asp Gln Val
        450                 455                 460

Asp Ile Val Ala Asn Tyr Asn Gly Arg Arg Phe His Gly Val Gly Leu
465                 470                 475                 480

Ala Thr Asp Ile Val Glu Ser Ser Ala Lys Ala Met Val His Val Leu
                485                 490                 495

Asn Asn Ile Trp Arg Ala Ala Glu Val Glu Lys Glu Leu Gln Arg Lys
                500                 505                 510

Ala Gln His Asn Glu Asn Asn Lys Glu Thr Val
        515                 520

<210> SEQ ID NO 11
<211> LENGTH: 1572
<212> TYPE: DNA
<213> ORGANISM: Artificial Sequence
<220> FEATURE:
<223> OTHER INFORMATION: Mutant LeuA (G462D/S139G/N167A)
<220> FEATURE:
<221> NAME/KEY: CDS
<222> LOCATION: (1)..(1572)

<400> SEQUENCE: 11 atg agc cag caa gtc att att ttc gat acc aca ttg cgc gac ggt gaa      48
Met Ser Gln Gln Val Ile Ile Phe Asp Thr Thr Leu Arg Asp Gly Glu
1               5                   10                  15 cag gcg tta cag gca agc ttg agt gtg aaa gaa aaa ctg caa att gcg     96
Gln Ala Leu Gln Ala Ser Leu Ser Val Lys Glu Lys Leu Gln Ile Ala
            20                  25                  30 ctg gcc ctt gag cgt atg ggt gtt gac gtg atg gaa gtc ggt ttc ccc    144
Leu Ala Leu Glu Arg Met Gly Val Asp Val Met Glu Val Gly Phe Pro
        35                  40                  45 gtc tct tcg ccg ggc gat ttt gaa tcg gtg caa acc atc gcc cgc cag    192
Val Ser Ser Pro Gly Asp Phe Glu Ser Val Gln Thr Ile Ala Arg Gln
    50                  55                  60 gtt aaa aac agc cgc gta tgt gcg tta gct cgc tgc gtg gaa aaa gat    240
Val Lys Asn Ser Arg Val Cys Ala Leu Ala Arg Cys Val Glu Lys Asp
65                  70                  75                  80 atc gac gtg gcg gcc gaa tcc ctg aaa gtc gcc gaa gcc ttc cgt att    288
Ile Asp Val Ala Ala Glu Ser Leu Lys Val Ala Glu Ala Phe Arg Ile
                85                  90                  95 cat acc ttt att gcc act tcg cca atg cac atc gcc acc aag ctg cgc    336
His Thr Phe Ile Ala Thr Ser Pro Met His Ile Ala Thr Lys Leu Arg
            100                 105                 110
```

```
agc acg ctg gac gag gtg atc gaa cgc gct atc tat atg gtg aaa cgc      384
Ser Thr Leu Asp Glu Val Ile Glu Arg Ala Ile Tyr Met Val Lys Arg
        115                 120                 125 gcc cgt aat tac acc gat gat gtt gaa ttt ggt tgc gaa gat gcc ggg      432
Ala Arg Asn Tyr Thr Asp Asp Val Glu Phe Gly Cys Glu Asp Ala Gly
130                 135                 140 cgt aca ccc att gcc gat ctg gcg cga gtg gtc gaa gcg gcg att aat      480
Arg Thr Pro Ile Ala Asp Leu Ala Arg Val Val Glu Ala Ala Ile Asn
145                 150                 155                 160 gcc ggt gcc acc acc atc gcg att ccg gac acc gtg ggc tac acc atg      528
Ala Gly Ala Thr Thr Ile Ala Ile Pro Asp Thr Val Gly Tyr Thr Met
                165                 170                 175 ccg ttt gag ttc gcc gga atc atc agc ggc ctg tat gaa cgc gtg cct      576
Pro Phe Glu Phe Ala Gly Ile Ile Ser Gly Leu Tyr Glu Arg Val Pro
            180                 185                 190 aac atc gac aaa gcc att atc tcc gta cat acc cac gac gat ttg ggc      624
Asn Ile Asp Lys Ala Ile Ile Ser Val His Thr His Asp Asp Leu Gly
        195                 200                 205 ctg gcg gtc gga aac tca ctg gcg gcg gta cat gcc ggt gca cgc cag      672
Leu Ala Val Gly Asn Ser Leu Ala Ala Val His Ala Gly Ala Arg Gln
210                 215                 220 gtg gaa ggc gca atg aac ggg atc ggc gag cgt gcc gga aac tgt tcc      720
Val Glu Gly Ala Met Asn Gly Ile Gly Glu Arg Ala Gly Asn Cys Ser
225                 230                 235                 240 ctg gaa gaa gtc atc atg gcg atc aaa gtt cgt aag gat att ctc aac      768
Leu Glu Glu Val Ile Met Ala Ile Lys Val Arg Lys Asp Ile Leu Asn
                245                 250                 255 gtc cac acc gcc att aat cac cag gag ata tgg cgc acc agc cag tta      816
Val His Thr Ala Ile Asn His Gln Glu Ile Trp Arg Thr Ser Gln Leu
            260                 265                 270 gtt agc cag att tgt aat atg ccg atc ccg gca aac aaa gcc att gtt      864
Val Ser Gln Ile Cys Asn Met Pro Ile Pro Ala Asn Lys Ala Ile Val
        275                 280                 285 ggc agc ggc gca ttc gca cac tcc tcc ggt ata cac cag gat ggc gtg      912
Gly Ser Gly Ala Phe Ala His Ser Ser Gly Ile His Gln Asp Gly Val
290                 295                 300 ctg aaa aac cgc gaa aac tac gaa atc atg aca cca gaa tct att ggt      960
Leu Lys Asn Arg Glu Asn Tyr Glu Ile Met Thr Pro Glu Ser Ile Gly
305                 310                 315                 320 ctg aac caa atc cag ctg aat ctg acc tct cgt tcg ggg cgt gcg gcg     1008
Leu Asn Gln Ile Gln Leu Asn Leu Thr Ser Arg Ser Gly Arg Ala Ala
                325                 330                 335 gtg aaa cat cgc atg gat gag atg ggg tat aaa gaa agt gaa tat aat     1056
Val Lys His Arg Met Asp Glu Met Gly Tyr Lys Glu Ser Glu Tyr Asn
            340                 345                 350 tta gac aat ttg tac gat gct ttc ctg aag ctg gcg gac aaa aaa ggt     1104
Leu Asp Asn Leu Tyr Asp Ala Phe Leu Lys Leu Ala Asp Lys Lys Gly
        355                 360                 365 cag gtg ttt gat tac gat ctg gag gcg ctg gcc ttc atc ggt aag cag     1152
Gln Val Phe Asp Tyr Asp Leu Glu Ala Leu Ala Phe Ile Gly Lys Gln
370                 375                 380 caa gaa gag ccg gag cat ttc cgt ctg gat tac ttc agc gtg cag tct     1200
Gln Glu Glu Pro Glu His Phe Arg Leu Asp Tyr Phe Ser Val Gln Ser
385                 390                 395                 400 ggc tct aac gat atc gcc acc gcc gcc gtc aaa ctg gcc tgt ggc gaa     1248
Gly Ser Asn Asp Ile Ala Thr Ala Ala Val Lys Leu Ala Cys Gly Glu
                405                 410                 415 gaa gtc aaa gca gaa gcc gcc aac ggt aac ggt ccg gtc gat gcc gtc     1296
Glu Val Lys Ala Glu Ala Ala Asn Gly Asn Gly Pro Val Asp Ala Val
            420                 425                 430
```

```
tat cag gca att aac cgc atc act gaa tat aac gtc gaa ctg gtg aaa    1344
Tyr Gln Ala Ile Asn Arg Ile Thr Glu Tyr Asn Val Glu Leu Val Lys
        435                 440                 445 tac agc ctg acc gcc aaa ggc cac ggt aaa gat gcg ctg gat cag gtg    1392
Tyr Ser Leu Thr Ala Lys Gly His Gly Lys Asp Ala Leu Asp Gln Val
    450                 455                 460 gat atc gtc gct aac tac aac ggt cgc cgc ttc cac ggc gtc ggc ctg    1440
Asp Ile Val Ala Asn Tyr Asn Gly Arg Arg Phe His Gly Val Gly Leu
465                 470                 475                 480 gct acc gat att gtc gag tca tct gcc aaa gcc atg gtg cac gtt ctg    1488
Ala Thr Asp Ile Val Glu Ser Ser Ala Lys Ala Met Val His Val Leu
                485                 490                 495 aac aat atc tgg cgt gcc gca gaa gtc gaa aaa gag ttg caa cgc aaa    1536
Asn Asn Ile Trp Arg Ala Ala Glu Val Glu Lys Glu Leu Gln Arg Lys
            500                 505                 510 gct caa cac aac gaa aac aac aag gaa acc gtg tga                    1572
Ala Gln His Asn Glu Asn Asn Lys Glu Thr Val
            515                 520
```

<210> SEQ ID NO 12
<211> LENGTH: 523
<212> TYPE: PRT
<213> ORGANISM: Artificial Sequence
<220> FEATURE:
<223> OTHER INFORMATION: Synthetic Construct

<400> SEQUENCE: 12

```
Met Ser Gln Gln Val Ile Ile Phe Asp Thr Thr Leu Arg Asp Gly Glu
1               5                   10                  15

Gln Ala Leu Gln Ala Ser Leu Ser Val Lys Glu Lys Leu Gln Ile Ala
            20                  25                  30

Leu Ala Leu Glu Arg Met Gly Val Asp Val Met Glu Val Gly Phe Pro
        35                  40                  45

Val Ser Ser Pro Gly Asp Phe Glu Ser Val Gln Thr Ile Ala Arg Gln
    50                  55                  60

Val Lys Asn Ser Arg Val Cys Ala Leu Ala Arg Cys Val Glu Lys Asp
65                  70                  75                  80

Ile Asp Val Ala Ala Glu Ser Leu Lys Val Ala Glu Ala Phe Arg Ile
                85                  90                  95

His Thr Phe Ile Ala Thr Ser Pro Met His Ile Ala Thr Lys Leu Arg
            100                 105                 110

Ser Thr Leu Asp Glu Val Ile Glu Arg Ala Ile Tyr Met Val Lys Arg
        115                 120                 125

Ala Arg Asn Tyr Thr Asp Asp Val Glu Phe Gly Cys Glu Asp Ala Gly
    130                 135                 140

Arg Thr Pro Ile Ala Asp Leu Ala Arg Val Val Glu Ala Ala Ile Asn
145                 150                 155                 160

Ala Gly Ala Thr Thr Ile Ala Ile Pro Asp Thr Val Gly Tyr Thr Met
                165                 170                 175

Pro Phe Glu Phe Ala Gly Ile Ile Ser Gly Leu Tyr Glu Arg Val Pro
            180                 185                 190

Asn Ile Asp Lys Ala Ile Ile Ser Val His Thr His Asp Asp Leu Gly
        195                 200                 205

Leu Ala Val Gly Asn Ser Leu Ala Ala Val His Ala Gly Ala Arg Gln
    210                 215                 220

Val Glu Gly Ala Met Asn Gly Ile Gly Glu Arg Ala Gly Asn Cys Ser
225                 230                 235                 240

Leu Glu Glu Val Ile Met Ala Ile Lys Val Arg Lys Asp Ile Leu Asn
```

```
                   245                 250                 255
Val His Thr Ala Ile Asn His Gln Glu Ile Trp Arg Thr Ser Gln Leu
        260                 265                 270

Val Ser Gln Ile Cys Asn Met Pro Ile Pro Ala Asn Lys Ala Ile Val
    275                 280                 285

Gly Ser Gly Ala Phe Ala His Ser Ser Gly Ile His Gln Asp Gly Val
290                 295                 300

Leu Lys Asn Arg Glu Asn Tyr Glu Ile Met Thr Pro Glu Ser Ile Gly
305                 310                 315                 320

Leu Asn Gln Ile Gln Leu Asn Leu Thr Ser Arg Ser Gly Arg Ala Ala
                325                 330                 335

Val Lys His Arg Met Asp Glu Met Gly Tyr Lys Glu Ser Glu Tyr Asn
            340                 345                 350

Leu Asp Asn Leu Tyr Asp Ala Phe Leu Lys Leu Ala Asp Lys Lys Gly
        355                 360                 365

Gln Val Phe Asp Tyr Asp Leu Glu Ala Leu Ala Phe Ile Gly Lys Gln
    370                 375                 380

Gln Glu Glu Pro Glu His Phe Arg Leu Asp Tyr Phe Ser Val Gln Ser
385                 390                 395                 400

Gly Ser Asn Asp Ile Ala Thr Ala Ala Val Lys Leu Ala Cys Gly Glu
                405                 410                 415

Glu Val Lys Glu Ala Ala Asn Gly Asn Gly Pro Val Asp Ala Val
            420                 425                 430

Tyr Gln Ala Ile Asn Arg Ile Thr Glu Tyr Asn Val Glu Leu Val Lys
        435                 440                 445

Tyr Ser Leu Thr Ala Lys Gly His Gly Lys Asp Ala Leu Asp Gln Val
    450                 455                 460

Asp Ile Val Ala Asn Tyr Asn Gly Arg Arg Phe His Gly Val Gly Leu
465                 470                 475                 480

Ala Thr Asp Ile Val Glu Ser Ser Ala Lys Ala Met Val His Val Leu
                485                 490                 495

Asn Asn Ile Trp Arg Ala Ala Glu Val Glu Lys Glu Leu Gln Arg Lys
            500                 505                 510

Ala Gln His Asn Glu Asn Asn Lys Glu Thr Val
        515                 520

<210> SEQ ID NO 13
<211> LENGTH: 1572
<212> TYPE: DNA
<213> ORGANISM: Artificial Sequence
<220> FEATURE:
<223> OTHER INFORMATION: Mutant LeuA (G462D/S139G/N167L)
<220> FEATURE:
<221> NAME/KEY: CDS
<222> LOCATION: (1)..(1572)

<400> SEQUENCE: 13 atg agc cag caa gtc att att ttc gat acc aca ttg cgc gac ggt gaa    48
Met Ser Gln Gln Val Ile Ile Phe Asp Thr Thr Leu Arg Asp Gly Glu
1               5                  10                  15 cag gcg tta cag gca agc ttg agt gtg aaa gaa aaa ctg caa att gcg    96
Gln Ala Leu Gln Ala Ser Leu Ser Val Lys Glu Lys Leu Gln Ile Ala
            20                  25                  30 ctg gcc ctt gag cgt atg ggt gtt gac gtg atg gaa gtc ggt ttc ccc   144
Leu Ala Leu Glu Arg Met Gly Val Asp Val Met Glu Val Gly Phe Pro
        35                  40                  45 gtc tct tcg ccg ggc gat ttt gaa tcg gtg caa acc atc gcc cgc cag   192
Val Ser Ser Pro Gly Asp Phe Glu Ser Val Gln Thr Ile Ala Arg Gln
```

-continued

```
            50                  55                  60
gtt aaa aac agc cgc gta tgt gcg tta gct cgc tgc gtg gaa aaa gat    240
Val Lys Asn Ser Arg Val Cys Ala Leu Ala Arg Cys Val Glu Lys Asp
 65                  70                  75                  80 atc gac gtg gcg gcc gaa tcc ctg aaa gtc gcc gaa gcc ttc cgt att    288
Ile Asp Val Ala Ala Glu Ser Leu Lys Val Ala Glu Ala Phe Arg Ile
                     85                  90                  95 cat acc ttt att gcc act tcg cca atg cac atc gcc acc aag ctg cgc    336
His Thr Phe Ile Ala Thr Ser Pro Met His Ile Ala Thr Lys Leu Arg
            100                 105                 110 agc acg ctg gac gag gtg atc gaa cgc gct atc tat atg gtg aaa cgc    384
Ser Thr Leu Asp Glu Val Ile Glu Arg Ala Ile Tyr Met Val Lys Arg
            115                 120                 125 gcc cgt aat tac acc gat gat gtt gaa ttt ggt tgc gaa gat gcc ggg    432
Ala Arg Asn Tyr Thr Asp Asp Val Glu Phe Gly Cys Glu Asp Ala Gly
130                 135                 140 cgt aca ccc att gcc gat ctg gcg cga gtg gtc gaa gcg gcg att aat    480
Arg Thr Pro Ile Ala Asp Leu Ala Arg Val Val Glu Ala Ala Ile Asn
145                 150                 155                 160 gcc ggt gcc acc acc atc ctg att ccg gac acc gtg ggc tac acc atg    528
Ala Gly Ala Thr Thr Ile Leu Ile Pro Asp Thr Val Gly Tyr Thr Met
                    165                 170                 175 ccg ttt gag ttc gcc gga atc atc agc ggc ctg tat gaa cgc gtg cct    576
Pro Phe Glu Phe Ala Gly Ile Ile Ser Gly Leu Tyr Glu Arg Val Pro
                180                 185                 190 aac atc gac aaa gcc att atc tcc gta cat acc cac gat gat ttg ggc    624
Asn Ile Asp Lys Ala Ile Ile Ser Val His Thr His Asp Asp Leu Gly
            195                 200                 205 ctg gcg gtc gga aac tca ctg gcg gcg gta cat gcc ggt gca cgc cag    672
Leu Ala Val Gly Asn Ser Leu Ala Ala Val His Ala Gly Ala Arg Gln
            210                 215                 220 gtg gaa ggc gca atg aac ggg atc ggc gag cgt gcc gga aac tgt tcc    720
Val Glu Gly Ala Met Asn Gly Ile Gly Glu Arg Ala Gly Asn Cys Ser
225                 230                 235                 240 ctg gaa gaa gtc atc atg gcg atc aaa gtt cgt aag gat att ctc aac    768
Leu Glu Glu Val Ile Met Ala Ile Lys Val Arg Lys Asp Ile Leu Asn
                    245                 250                 255 gtc cac acc gcc att aat cac cag gag ata tgg cgc acc agc cag tta    816
Val His Thr Ala Ile Asn His Gln Glu Ile Trp Arg Thr Ser Gln Leu
                260                 265                 270 gtt agc cag att tgt aat atg ccg atc ccg gca aac aaa gcc att gtt    864
Val Ser Gln Ile Cys Asn Met Pro Ile Pro Ala Asn Lys Ala Ile Val
                275                 280                 285 ggc agc ggc gca ttc gca cac tcc tcc ggt ata cac cag gat ggc gtg    912
Gly Ser Gly Ala Phe Ala His Ser Ser Gly Ile His Gln Asp Gly Val
            290                 295                 300 ctg aaa aac cgc gaa aac tac gaa atc atg aca cca gaa tct att ggt    960
Leu Lys Asn Arg Glu Asn Tyr Glu Ile Met Thr Pro Glu Ser Ile Gly
305                 310                 315                 320 ctg aac caa atc cag ctg aat ctg acc tct cgt tcg ggg cgt gcg gcg    1008
Leu Asn Gln Ile Gln Leu Asn Leu Thr Ser Arg Ser Gly Arg Ala Ala
                    325                 330                 335 gtg aaa cat cgc atg gat gag atg ggg tat aaa gaa agt gaa tat aat    1056
Val Lys His Arg Met Asp Glu Met Gly Tyr Lys Glu Ser Glu Tyr Asn
                340                 345                 350 tta gac aat ttg tac gat gct ttc ctg aag ctg gcg gac aaa aaa ggt    1104
Leu Asp Asn Leu Tyr Asp Ala Phe Leu Lys Leu Ala Asp Lys Lys Gly
                355                 360                 365 cag gtg ttt gat tac gat ctg gag gcg ctg gcc ttc atc ggt aag cag    1152
Gln Val Phe Asp Tyr Asp Leu Glu Ala Leu Ala Phe Ile Gly Lys Gln
```

```
                     370                375                380
caa gaa gag ccg gag cat ttc cgt ctg gat tac ttc agc gtg cag tct       1200
Gln Glu Glu Pro Glu His Phe Arg Leu Asp Tyr Phe Ser Val Gln Ser
385                 390                395                400 ggc tct aac gat atc gcc acc gcc gcc gtc aaa ctg gcc tgt ggc gaa       1248
Gly Ser Asn Asp Ile Ala Thr Ala Ala Val Lys Leu Ala Cys Gly Glu
                405                410                415 gaa gtc aaa gca gaa gcc gcc aac ggt aac ggt ccg gtc gat gcc gtc       1296
Glu Val Lys Ala Glu Ala Ala Asn Gly Asn Gly Pro Val Asp Ala Val
            420                425                430 tat cag gca att aac cgc atc act gaa tat aac gtc gaa ctg gtg aaa       1344
Tyr Gln Ala Ile Asn Arg Ile Thr Glu Tyr Asn Val Glu Leu Val Lys
        435                440                445 tac agc ctg acc gcc aaa ggc cac ggt aaa gat gcg ctg gat cag gtg       1392
Tyr Ser Leu Thr Ala Lys Gly His Gly Lys Asp Ala Leu Asp Gln Val
450                455                460 gat atc gtc gct aac tac aac ggt cgc cgc ttc cac ggc gtc ggc ctg       1440
Asp Ile Val Ala Asn Tyr Asn Gly Arg Arg Phe His Gly Val Gly Leu
465                 470                475                480 gct acc gat att gtc gag tca tct gcc aaa gcc atg gtg cac gtt ctg       1488
Ala Thr Asp Ile Val Glu Ser Ser Ala Lys Ala Met Val His Val Leu
                485                490                495 aac aat atc tgg cgt gcc gca gaa gtc gaa aaa gag ttg caa cgc aaa       1536
Asn Asn Ile Trp Arg Ala Ala Glu Val Glu Lys Glu Leu Gln Arg Lys
            500                505                510 gct caa cac aac gaa aac aac aag gaa acc gtg tga                       1572
Ala Gln His Asn Glu Asn Asn Lys Glu Thr Val
        515                520

<210> SEQ ID NO 14
<211> LENGTH: 523
<212> TYPE: PRT
<213> ORGANISM: Artificial Sequence
<220> FEATURE:
<223> OTHER INFORMATION: Synthetic Construct

<400> SEQUENCE: 14

Met Ser Gln Gln Val Ile Ile Phe Asp Thr Thr Leu Arg Asp Gly Glu
1               5                   10                  15

Gln Ala Leu Gln Ala Ser Leu Ser Val Lys Glu Lys Leu Gln Ile Ala
            20                  25                  30

Leu Ala Leu Glu Arg Met Gly Val Asp Val Met Glu Val Gly Phe Pro
        35                  40                  45

Val Ser Ser Pro Gly Asp Phe Glu Ser Val Gln Thr Ile Ala Arg Gln
    50                  55                  60

Val Lys Asn Ser Arg Val Cys Ala Leu Ala Arg Cys Val Glu Lys Asp
65                  70                  75                  80

Ile Asp Val Ala Ala Glu Ser Leu Lys Val Ala Glu Ala Phe Arg Ile
                85                  90                  95

His Thr Phe Ile Ala Thr Ser Pro Met His Ile Ala Thr Lys Leu Arg
            100                 105                 110

Ser Thr Leu Asp Glu Val Ile Glu Arg Ala Ile Tyr Met Val Lys Arg
        115                 120                 125

Ala Arg Asn Tyr Thr Asp Asp Val Glu Phe Gly Cys Glu Asp Ala Gly
    130                 135                 140

Arg Thr Pro Ile Ala Asp Leu Ala Arg Val Val Glu Ala Ala Ile Asn
145                 150                 155                 160

Ala Gly Ala Thr Thr Ile Leu Ile Pro Asp Thr Val Gly Tyr Thr Met
                165                 170                 175
```

```
Pro Phe Glu Phe Ala Gly Ile Ile Ser Gly Leu Tyr Glu Arg Val Pro
            180                 185                 190

Asn Ile Asp Lys Ala Ile Ile Ser Val His Thr His Asp Asp Leu Gly
        195                 200                 205

Leu Ala Val Gly Asn Ser Leu Ala Ala Val His Gly Ala Arg Gln
    210                 215                 220

Val Glu Gly Ala Met Asn Gly Ile Gly Glu Arg Ala Gly Asn Cys Ser
225                 230                 235                 240

Leu Glu Glu Val Ile Met Ala Ile Lys Val Arg Lys Asp Ile Leu Asn
                245                 250                 255

Val His Thr Ala Ile Asn His Gln Glu Ile Trp Arg Thr Ser Gln Leu
            260                 265                 270

Val Ser Gln Ile Cys Asn Met Pro Ile Pro Ala Asn Lys Ala Ile Val
        275                 280                 285

Gly Ser Gly Ala Phe Ala His Ser Ser Gly Ile His Gln Asp Gly Val
    290                 295                 300

Leu Lys Asn Arg Glu Asn Tyr Glu Ile Met Thr Pro Glu Ser Ile Gly
305                 310                 315                 320

Leu Asn Gln Ile Gln Leu Asn Leu Thr Ser Arg Ser Gly Arg Ala Ala
                325                 330                 335

Val Lys His Arg Met Asp Glu Met Gly Tyr Lys Glu Ser Glu Tyr Asn
            340                 345                 350

Leu Asp Asn Leu Tyr Asp Ala Phe Leu Lys Leu Ala Asp Lys Lys Gly
        355                 360                 365

Gln Val Phe Asp Tyr Asp Leu Glu Ala Leu Ala Phe Ile Gly Lys Gln
    370                 375                 380

Gln Glu Glu Pro Glu His Phe Arg Leu Asp Tyr Phe Ser Val Gln Ser
385                 390                 395                 400

Gly Ser Asn Asp Ile Ala Thr Ala Ala Val Lys Leu Ala Cys Gly Glu
                405                 410                 415

Glu Val Lys Ala Glu Ala Ala Asn Gly Asn Gly Pro Val Asp Ala Val
            420                 425                 430

Tyr Gln Ala Ile Asn Arg Ile Thr Glu Tyr Asn Val Glu Leu Val Lys
        435                 440                 445

Tyr Ser Leu Thr Ala Lys Gly His Gly Lys Asp Ala Leu Asp Gln Val
    450                 455                 460

Asp Ile Val Ala Asn Tyr Asn Gly Arg Arg Phe His Gly Val Gly Leu
465                 470                 475                 480

Ala Thr Asp Ile Val Glu Ser Ser Ala Lys Ala Met Val His Val Leu
                485                 490                 495

Asn Asn Ile Trp Arg Ala Ala Glu Val Glu Lys Glu Leu Gln Arg Lys
            500                 505                 510

Ala Gln His Asn Glu Asn Asn Lys Glu Thr Val
        515                 520
```

<210> SEQ ID NO 15
<211> LENGTH: 1572
<212> TYPE: DNA
<213> ORGANISM: Artificial Sequence
<220> FEATURE:
<223> OTHER INFORMATION: Mutant LeuA (G462D/S139G/H97A/N167A)
<220> FEATURE:
<221> NAME/KEY: CDS
<222> LOCATION: (1)..(1572)

<400> SEQUENCE: 15

```
atg agc cag caa gtc att att ttc gat acc aca ttg cgc gac ggt gaa      48
Met Ser Gln Gln Val Ile Ile Phe Asp Thr Thr Leu Arg Asp Gly Glu
1               5                   10                  15 cag gcg tta cag gca agc ttg agt gtg aaa gaa aaa ctg caa att gcg      96
Gln Ala Leu Gln Ala Ser Leu Ser Val Lys Glu Lys Leu Gln Ile Ala
            20                  25                  30 ctg gcc ctt gag cgt atg ggt gtt gac gtg atg gaa gtc ggt ttc ccc     144
Leu Ala Leu Glu Arg Met Gly Val Asp Val Met Glu Val Gly Phe Pro
        35                  40                  45 gtc tct tcg ccg ggc gat ttt gaa tcg gtg caa acc atc gcc cgc cag     192
Val Ser Ser Pro Gly Asp Phe Glu Ser Val Gln Thr Ile Ala Arg Gln
    50                  55                  60 gtt aaa aac agc cgc gta tgt gcg tta gct cgc tgc gtg gaa aaa gat     240
Val Lys Asn Ser Arg Val Cys Ala Leu Ala Arg Cys Val Glu Lys Asp
65                  70                  75                  80 atc gac gtg gcg gcc gaa tcc ctg aaa gtc gcc gaa gcc ttc cgt att     288
Ile Asp Val Ala Ala Glu Ser Leu Lys Val Ala Glu Ala Phe Arg Ile
                85                  90                  95 gcg acc ttt att gcc act tcg cca atg cac atc gcc acc aag ctg cgc     336
Ala Thr Phe Ile Ala Thr Ser Pro Met His Ile Ala Thr Lys Leu Arg
            100                 105                 110 agc acg ctg gac gag gtg atc gaa cgc gct atc tat atg gtg aaa cgc     384
Ser Thr Leu Asp Glu Val Ile Glu Arg Ala Ile Tyr Met Val Lys Arg
        115                 120                 125 gcc cgt aat tac acc gat gat gtt gaa ttt ggt tgc gaa gat gcc ggg     432
Ala Arg Asn Tyr Thr Asp Asp Val Glu Phe Gly Cys Glu Asp Ala Gly
    130                 135                 140 cgt aca ccc att gcc gat ctg gcg cga gtg gtc gaa gcg gcg att aat     480
Arg Thr Pro Ile Ala Asp Leu Ala Arg Val Val Glu Ala Ala Ile Asn
145                 150                 155                 160 gcc ggt gcc acc acc atc gcg att ccg gac acc gtg ggc tac acc atg     528
Ala Gly Ala Thr Thr Ile Ala Ile Pro Asp Thr Val Gly Tyr Thr Met
                165                 170                 175 ccg ttt gag ttc gcc gga atc atc agc ggc ctg tat gaa cgc gtg cct     576
Pro Phe Glu Phe Ala Gly Ile Ile Ser Gly Leu Tyr Glu Arg Val Pro
            180                 185                 190 aac atc gac aaa gcc att atc tcc gta cat acc cac gac gat ttg ggc     624
Asn Ile Asp Lys Ala Ile Ile Ser Val His Thr His Asp Asp Leu Gly
        195                 200                 205 ctg gcg gtc gga aac tca ctg gcg gcg gta cat gcc ggt gca cgc cag     672
Leu Ala Val Gly Asn Ser Leu Ala Ala Val His Ala Gly Ala Arg Gln
    210                 215                 220 gtg gaa ggc gca atg aac ggg atc ggc gag cgt gcc gga aac tgt tcc     720
Val Glu Gly Ala Met Asn Gly Ile Gly Glu Arg Ala Gly Asn Cys Ser
225                 230                 235                 240 ctg gaa gaa gtc atc atg gcg atc aaa gtt cgt aag gat att ctc aac     768
Leu Glu Glu Val Ile Met Ala Ile Lys Val Arg Lys Asp Ile Leu Asn
                245                 250                 255 gtc cac acc gcc att aat cac cag gag ata tgg cgc acc agc cag tta     816
Val His Thr Ala Ile Asn His Gln Glu Ile Trp Arg Thr Ser Gln Leu
            260                 265                 270 gtt agc cag att tgt aat atg ccg atc ccg gca aac aaa gcc att gtt     864
Val Ser Gln Ile Cys Asn Met Pro Ile Pro Ala Asn Lys Ala Ile Val
        275                 280                 285 ggc agc ggc gca ttc gca cac tcc tcc ggt ata cac cag gat ggc gtg     912
Gly Ser Gly Ala Phe Ala His Ser Ser Gly Ile His Gln Asp Gly Val
    290                 295                 300 ctg aaa aac cgc gaa aac tac gaa atc atg aca cca gaa tct att ggt     960
Leu Lys Asn Arg Glu Asn Tyr Glu Ile Met Thr Pro Glu Ser Ile Gly
305                 310                 315                 320
```

```
ctg aac caa atc cag ctg aat ctg acc tct cgt tcg ggg cgt gcg gcg    1008
Leu Asn Gln Ile Gln Leu Asn Leu Thr Ser Arg Ser Gly Arg Ala Ala
            325                 330                 335 gtg aaa cat cgc atg gat gag atg ggg tat aaa gaa agt gaa tat aat    1056
Val Lys His Arg Met Asp Glu Met Gly Tyr Lys Glu Ser Glu Tyr Asn
        340                 345                 350 tta gac aat ttg tac gat gct ttc ctg aag ctg gcg gac aaa aaa ggt    1104
Leu Asp Asn Leu Tyr Asp Ala Phe Leu Lys Leu Ala Asp Lys Lys Gly
    355                 360                 365 cag gtg ttt gat tac gat ctg gag gcg ctg gcc ttc atc ggt aag cag    1152
Gln Val Phe Asp Tyr Asp Leu Glu Ala Leu Ala Phe Ile Gly Lys Gln
370                 375                 380 caa gaa gag ccg gag cat ttc cgt ctg gat tac ttc agc gtg cag tct    1200
Gln Glu Glu Pro Glu His Phe Arg Leu Asp Tyr Phe Ser Val Gln Ser
385                 390                 395                 400 ggc tct aac gat atc gcc acc gcc gcc gtc aaa ctg gcc tgt ggc gaa    1248
Gly Ser Asn Asp Ile Ala Thr Ala Ala Val Lys Leu Ala Cys Gly Glu
            405                 410                 415 gaa gtc aaa gca gaa gcc gcc aac ggt aac ggt ccg gtc gat gcc gtc    1296
Glu Val Lys Ala Glu Ala Ala Asn Gly Asn Gly Pro Val Asp Ala Val
        420                 425                 430 tat cag gca att aac cgc atc act gaa tat aac gtc gaa ctg gtg aaa    1344
Tyr Gln Ala Ile Asn Arg Ile Thr Glu Tyr Asn Val Glu Leu Val Lys
    435                 440                 445 tac agc ctg acc gcc aaa ggc cac ggt aaa gat gcg ctg gat cag gtg    1392
Tyr Ser Leu Thr Ala Lys Gly His Gly Lys Asp Ala Leu Asp Gln Val
450                 455                 460 gat atc gtc gct aac tac aac ggt cgc cgc ttc cac ggc gtc ggc ctg    1440
Asp Ile Val Ala Asn Tyr Asn Gly Arg Arg Phe His Gly Val Gly Leu
465                 470                 475                 480 gct acc gat att gtc gag tca tct gcc aaa gcc atg gtg cac gtt ctg    1488
Ala Thr Asp Ile Val Glu Ser Ser Ala Lys Ala Met Val His Val Leu
            485                 490                 495 aac aat atc tgg cgt gcc gca gaa gtc gaa aaa gag ttg caa cgc aaa    1536
Asn Asn Ile Trp Arg Ala Ala Glu Val Glu Lys Glu Leu Gln Arg Lys
        500                 505                 510 gct caa cac aac gaa aac aac aag gaa acc gtg tga                    1572
Ala Gln His Asn Glu Asn Asn Lys Glu Thr Val
    515                 520
```

<210> SEQ ID NO 16
<211> LENGTH: 523
<212> TYPE: PRT
<213> ORGANISM: Artificial Sequence
<220> FEATURE:
<223> OTHER INFORMATION: Synthetic Construct

<400> SEQUENCE: 16

```
Met Ser Gln Gln Val Ile Ile Phe Asp Thr Thr Leu Arg Asp Gly Glu
1               5                   10                  15

Gln Ala Leu Gln Ala Ser Leu Ser Val Lys Glu Lys Leu Gln Ile Ala
            20                  25                  30

Leu Ala Leu Glu Arg Met Gly Val Asp Val Met Glu Val Gly Phe Pro
        35                  40                  45

Val Ser Ser Pro Gly Asp Phe Glu Ser Val Gln Thr Ile Ala Arg Gln
    50                  55                  60

Val Lys Asn Ser Arg Val Cys Ala Leu Ala Arg Cys Val Glu Lys Asp
65                  70                  75                  80

Ile Asp Val Ala Ala Glu Ser Leu Lys Val Ala Glu Ala Phe Arg Ile
            85                  90                  95
```

```
Ala Thr Phe Ile Ala Thr Ser Pro Met His Ile Ala Thr Lys Leu Arg
                100                 105                 110

Ser Thr Leu Asp Glu Val Ile Glu Arg Ala Ile Tyr Met Val Lys Arg
            115                 120                 125

Ala Arg Asn Tyr Thr Asp Asp Val Glu Phe Gly Cys Glu Asp Ala Gly
        130                 135                 140

Arg Thr Pro Ile Ala Asp Leu Ala Arg Val Val Glu Ala Ala Ile Asn
145                 150                 155                 160

Ala Gly Ala Thr Thr Ile Ala Ile Pro Asp Thr Val Gly Tyr Thr Met
                165                 170                 175

Pro Phe Glu Phe Ala Gly Ile Ile Ser Gly Leu Tyr Glu Arg Val Pro
            180                 185                 190

Asn Ile Asp Lys Ala Ile Ile Ser Val His Thr His Asp Asp Leu Gly
        195                 200                 205

Leu Ala Val Gly Asn Ser Leu Ala Ala Val His Ala Gly Ala Arg Gln
210                 215                 220

Val Glu Gly Ala Met Asn Gly Ile Gly Glu Arg Ala Gly Asn Cys Ser
225                 230                 235                 240

Leu Glu Glu Val Ile Met Ala Ile Lys Val Arg Lys Asp Ile Leu Asn
                245                 250                 255

Val His Thr Ala Ile Asn His Gln Glu Ile Trp Arg Thr Ser Gln Leu
        260                 265                 270

Val Ser Gln Ile Cys Asn Met Pro Ile Pro Ala Asn Lys Ala Ile Val
    275                 280                 285

Gly Ser Gly Ala Phe Ala His Ser Ser Gly Ile His Gln Asp Gly Val
290                 295                 300

Leu Lys Asn Arg Glu Asn Tyr Glu Ile Met Thr Pro Glu Ser Ile Gly
305                 310                 315                 320

Leu Asn Gln Ile Gln Leu Asn Leu Thr Ser Arg Ser Gly Arg Ala Ala
                325                 330                 335

Val Lys His Arg Met Asp Glu Met Gly Tyr Lys Glu Ser Glu Tyr Asn
            340                 345                 350

Leu Asp Asn Leu Tyr Asp Ala Phe Leu Lys Leu Ala Asp Lys Lys Gly
        355                 360                 365

Gln Val Phe Asp Tyr Asp Leu Glu Ala Leu Ala Phe Ile Gly Lys Gln
370                 375                 380

Gln Glu Glu Pro Glu His Phe Arg Leu Asp Tyr Phe Ser Val Gln Ser
385                 390                 395                 400

Gly Ser Asn Asp Ile Ala Thr Ala Val Lys Leu Ala Cys Gly Glu
                405                 410                 415

Glu Val Lys Ala Glu Ala Asn Gly Asn Gly Pro Val Asp Ala Val
            420                 425                 430

Tyr Gln Ala Ile Asn Arg Ile Thr Glu Tyr Asn Val Glu Leu Val Lys
        435                 440                 445

Tyr Ser Leu Thr Ala Lys Gly His Gly Lys Asp Ala Leu Asp Gln Val
    450                 455                 460

Asp Ile Val Ala Asn Tyr Asn Gly Arg Arg Phe His Gly Val Gly Leu
465                 470                 475                 480

Ala Thr Asp Ile Val Glu Ser Ser Ala Lys Ala Met Val His Val Leu
                485                 490                 495

Asn Asn Ile Trp Arg Ala Ala Glu Val Glu Lys Glu Leu Gln Arg Lys
            500                 505                 510

Ala Gln His Asn Glu Asn Asn Lys Glu Thr Val
        515                 520
```

<210> SEQ ID NO 17
<211> LENGTH: 1647
<212> TYPE: DNA
<213> ORGANISM: Lactococcus lactis
<220> FEATURE:
<221> NAME/KEY: CDS
<222> LOCATION: (1)..(1647)

<400> SEQUENCE: 17

| | | | | | | | | | | | | | | | | |
|---|---|---|---|---|---|---|---|---|---|---|---|---|---|---|---|---|
| atg | tat | aca | gta | gga | gat | tac | cta | tta | gac | cga | tta | cac | gag | tta | gga | 48 |
| Met | Tyr | Thr | Val | Gly | Asp | Tyr | Leu | Leu | Asp | Arg | Leu | His | Glu | Leu | Gly | |
| 1 | | | | 5 | | | | | 10 | | | | | 15 | | |
| att | gaa | gaa | att | ttt | gga | gtc | cct | gga | gac | tat | aac | tta | caa | ttt | tta | 96 |
| Ile | Glu | Glu | Ile | Phe | Gly | Val | Pro | Gly | Asp | Tyr | Asn | Leu | Gln | Phe | Leu | |
| | | | 20 | | | | | 25 | | | | | 30 | | | |
| gat | caa | att | att | tcc | cgc | aag | gat | atg | aaa | tgg | gtc | gga | aat | gct | aat | 144 |
| Asp | Gln | Ile | Ile | Ser | Arg | Lys | Asp | Met | Lys | Trp | Val | Gly | Asn | Ala | Asn | |
| | | 35 | | | | | 40 | | | | | 45 | | | | |
| gaa | tta | aat | gct | tca | tat | atg | gct | gat | ggc | tat | gct | cgt | act | aaa | aaa | 192 |
| Glu | Leu | Asn | Ala | Ser | Tyr | Met | Ala | Asp | Gly | Tyr | Ala | Arg | Thr | Lys | Lys | |
| | 50 | | | | | 55 | | | | | 60 | | | | | |
| gct | gcc | gca | ttt | ctt | aca | acc | ttt | gga | gta | ggt | gaa | ttg | agt | gca | gtt | 240 |
| Ala | Ala | Ala | Phe | Leu | Thr | Thr | Phe | Gly | Val | Gly | Glu | Leu | Ser | Ala | Val | |
| 65 | | | | | 70 | | | | | 75 | | | | | 80 | |
| aat | gga | tta | gca | gga | agt | tac | gcc | gaa | aat | tta | cca | gta | gta | gaa | ata | 288 |
| Asn | Gly | Leu | Ala | Gly | Ser | Tyr | Ala | Glu | Asn | Leu | Pro | Val | Val | Glu | Ile | |
| | | | | 85 | | | | | 90 | | | | | 95 | | |
| gtg | gga | tca | cct | aca | tca | aaa | gtt | caa | aat | gaa | gga | aaa | ttt | gtt | cat | 336 |
| Val | Gly | Ser | Pro | Thr | Ser | Lys | Val | Gln | Asn | Glu | Gly | Lys | Phe | Val | His | |
| | | | 100 | | | | | 105 | | | | | 110 | | | |
| cat | acg | ctg | gct | gac | ggt | gat | ttt | aaa | cac | ttt | atg | aaa | atg | cac | gaa | 384 |
| His | Thr | Leu | Ala | Asp | Gly | Asp | Phe | Lys | His | Phe | Met | Lys | Met | His | Glu | |
| | | 115 | | | | | 120 | | | | | 125 | | | | |
| cct | gtt | aca | gca | gct | cga | act | tta | ctg | aca | gca | gaa | aat | gca | acc | gtt | 432 |
| Pro | Val | Thr | Ala | Ala | Arg | Thr | Leu | Leu | Thr | Ala | Glu | Asn | Ala | Thr | Val | |
| | 130 | | | | | 135 | | | | | 140 | | | | | |
| gaa | att | gac | cga | gta | ctt | tct | gca | cta | tta | aaa | gaa | aga | aaa | cct | gtc | 480 |
| Glu | Ile | Asp | Arg | Val | Leu | Ser | Ala | Leu | Leu | Lys | Glu | Arg | Lys | Pro | Val | |
| 145 | | | | | 150 | | | | | 155 | | | | | 160 | |
| tat | atc | aac | tta | cca | gtt | gat | gtt | gct | gct | gca | aaa | gca | gag | aaa | ccc | 528 |
| Tyr | Ile | Asn | Leu | Pro | Val | Asp | Val | Ala | Ala | Ala | Lys | Ala | Glu | Lys | Pro | |
| | | | | 165 | | | | | 170 | | | | | 175 | | |
| tca | ctc | cct | ttg | aaa | aaa | gaa | aac | tca | act | tca | aat | aca | agt | gac | caa | 576 |
| Ser | Leu | Pro | Leu | Lys | Lys | Glu | Asn | Ser | Thr | Ser | Asn | Thr | Ser | Asp | Gln | |
| | | | 180 | | | | | 185 | | | | | 190 | | | |
| gag | atc | ttg | aac | aaa | att | caa | gaa | agc | ttg | aaa | aat | gcc | aaa | aaa | cca | 624 |
| Glu | Ile | Leu | Asn | Lys | Ile | Gln | Glu | Ser | Leu | Lys | Asn | Ala | Lys | Lys | Pro | |
| | | 195 | | | | | 200 | | | | | 205 | | | | |
| atc | gtg | att | aca | gga | cat | gaa | ata | att | agt | ttt | ggc | tta | gaa | aaa | aca | 672 |
| Ile | Val | Ile | Thr | Gly | His | Glu | Ile | Ile | Ser | Phe | Gly | Leu | Glu | Lys | Thr | |
| | 210 | | | | | 215 | | | | | 220 | | | | | |
| gtc | tct | caa | ttt | att | tca | aag | aca | aaa | cta | cct | att | acg | aca | tta | aac | 720 |
| Val | Ser | Gln | Phe | Ile | Ser | Lys | Thr | Lys | Leu | Pro | Ile | Thr | Thr | Leu | Asn | |
| 225 | | | | | 230 | | | | | 235 | | | | | 240 | |
| ttt | gga | aaa | agt | tca | gtt | gat | gaa | gct | ctc | cct | tca | ttt | tta | gga | atc | 768 |
| Phe | Gly | Lys | Ser | Ser | Val | Asp | Glu | Ala | Leu | Pro | Ser | Phe | Leu | Gly | Ile | |
| | | | | 245 | | | | | 250 | | | | | 255 | | |
| tat | aat | ggt | aaa | ctc | tca | gag | cct | aat | ctt | aaa | gaa | ttc | gtg | gaa | tca | 816 |
| Tyr | Asn | Gly | Lys | Leu | Ser | Glu | Pro | Asn | Leu | Lys | Glu | Phe | Val | Glu | Ser | |
| | | | 260 | | | | | 265 | | | | | 270 | | | |

| | | |
|---|---|---|
| gcc gac ttc atc ctg atg ctt gga gtt aaa ctc aca gac tct tca aca<br>Ala Asp Phe Ile Leu Met Leu Gly Val Lys Leu Thr Asp Ser Ser Thr<br>275 280 285 | | 864 |
| gga gcc ttc act cat cat tta aat gaa aat aaa atg att tca ctg aat<br>Gly Ala Phe Thr His His Leu Asn Glu Asn Lys Met Ile Ser Leu Asn<br>290 295 300 | | 912 |
| ata gat gaa gga aaa ata ttt aac gaa agc atc caa aat ttt gat ttt<br>Ile Asp Glu Gly Lys Ile Phe Asn Glu Ser Ile Gln Asn Phe Asp Phe<br>305 310 315 320 | | 960 |
| gaa tcc ctc atc tcc tct ctc tta gac cta agc gaa ata gaa tac aaa<br>Glu Ser Leu Ile Ser Ser Leu Leu Asp Leu Ser Glu Ile Glu Tyr Lys<br>325 330 335 | | 1008 |
| gga aaa tat atc gat aaa aag caa gaa gac ttt gtt cca tca aat gcg<br>Gly Lys Tyr Ile Asp Lys Lys Gln Glu Asp Phe Val Pro Ser Asn Ala<br>340 345 350 | | 1056 |
| ctt tta tca caa gac cgc cta tgg caa gca gtt gaa aac cta act caa<br>Leu Leu Ser Gln Asp Arg Leu Trp Gln Ala Val Glu Asn Leu Thr Gln<br>355 360 365 | | 1104 |
| agc aat gaa aca atc gtt gct gaa caa ggg aca tca ttc ttt ggc gct<br>Ser Asn Glu Thr Ile Val Ala Glu Gln Gly Thr Ser Phe Phe Gly Ala<br>370 375 380 | | 1152 |
| tca tca att ttc tta aaa cca aag agt cat ttt att ggt caa ccc tta<br>Ser Ser Ile Phe Leu Lys Pro Lys Ser His Phe Ile Gly Gln Pro Leu<br>385 390 395 400 | | 1200 |
| tgg gga tca att gga tat aca ttc cca gca gca tta gga agc caa att<br>Trp Gly Ser Ile Gly Tyr Thr Phe Pro Ala Ala Leu Gly Ser Gln Ile<br>405 410 415 | | 1248 |
| gca gat aaa gaa agc aga cac ctt tta ttt att ggt gat ggt tca ctt<br>Ala Asp Lys Glu Ser Arg His Leu Leu Phe Ile Gly Asp Gly Ser Leu<br>420 425 430 | | 1296 |
| caa ctt acg gtg caa gaa tta gga tta gca atc aga gaa aaa att aat<br>Gln Leu Thr Val Gln Glu Leu Gly Leu Ala Ile Arg Glu Lys Ile Asn<br>435 440 445 | | 1344 |
| cca att tgc ttt att atc aat aat gat ggt tat aca gtc gaa aga gaa<br>Pro Ile Cys Phe Ile Ile Asn Asn Asp Gly Tyr Thr Val Glu Arg Glu<br>450 455 460 | | 1392 |
| att cat gga cca aat caa agc tac aat gat att cca atg tgg aat tac<br>Ile His Gly Pro Asn Gln Ser Tyr Asn Asp Ile Pro Met Trp Asn Tyr<br>465 470 475 480 | | 1440 |
| tca aaa tta cca gaa tca ttt gga gca aca gaa gaa cga gta gtc tcg<br>Ser Lys Leu Pro Glu Ser Phe Gly Ala Thr Glu Glu Arg Val Val Ser<br>485 490 495 | | 1488 |
| aaa atc gtt aga act gaa aat gaa ttt gtg tct gtc atg aaa gaa gct<br>Lys Ile Val Arg Thr Glu Asn Glu Phe Val Ser Val Met Lys Glu Ala<br>500 505 510 | | 1536 |
| caa gca gat cca aat aga atg tac tgg att gag tta att ttg gca aaa<br>Gln Ala Asp Pro Asn Arg Met Tyr Trp Ile Glu Leu Ile Leu Ala Lys<br>515 520 525 | | 1584 |
| gaa gat gca cca aaa gta ctg aaa aaa atg ggc aaa cta ttt gct gaa<br>Glu Asp Ala Pro Lys Val Leu Lys Lys Met Gly Lys Leu Phe Ala Glu<br>530 535 540 | | 1632 |
| caa aat aaa tca taa<br>Gln Asn Lys Ser<br>545 | | 1647 |

<210> SEQ ID NO 18
<211> LENGTH: 548
<212> TYPE: PRT
<213> ORGANISM: Lactococcus lactis

<400> SEQUENCE: 18

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
            35                  40                  45

Glu Leu Asn Ala Ser Tyr Met Ala Asp Gly Tyr Ala Arg Thr Lys Lys
        50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
            115                 120                 125

Pro Val Thr Ala Ala Arg Thr Leu Leu Thr Ala Glu Asn Ala Thr Val
            130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
            195                 200                 205

Ile Val Ile Thr Gly His Glu Ile Ile Ser Phe Gly Leu Glu Lys Thr
210                 215                 220

Val Ser Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
            245                 250                 255

Tyr Asn Gly Lys Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
            275                 280                 285

Gly Ala Phe Thr His His Leu Asn Glu Asn Lys Met Ile Ser Leu Asn
            290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Glu Ile Glu Tyr Lys
            325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
            355                 360                 365

Ser Asn Glu Thr Ile Val Ala Glu Gln Gly Thr Ser Phe Phe Gly Ala
            370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430
```

```
Gln Leu Thr Val Gln Glu Leu Gly Leu Ala Ile Arg Glu Lys Ile Asn
         435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Glu Arg Val Val Ser
                485                 490                 495

Lys Ile Val Arg Thr Glu Asn Glu Phe Val Ser Val Met Lys Glu Ala
                500                 505                 510

Gln Ala Asp Pro Asn Arg Met Tyr Trp Ile Glu Leu Ile Leu Ala Lys
            515                 520                 525

Glu Asp Ala Pro Lys Val Leu Lys Lys Met Gly Lys Leu Phe Ala Glu
        530                 535                 540

Gln Asn Lys Ser
545

<210> SEQ ID NO 19
<211> LENGTH: 1647
<212> TYPE: DNA
<213> ORGANISM: Artificial Sequence
<220> FEATURE:
<223> OTHER INFORMATION: Mutant Kivd (V461A)
<220> FEATURE:
<221> NAME/KEY: CDS
<222> LOCATION: (1)..(1647)

<400> SEQUENCE: 19 atg tat aca gta gga gat tac cta tta gac cga tta cac gag tta gga      48
Met Tyr Thr Val Gly Asp Tyr Leu Leu Asp Arg Leu His Glu Leu Gly
1               5                   10                  15 att gaa gaa att ttt gga gtc cct gga gac tat aac tta caa ttt tta      96
Ile Glu Glu Ile Phe Gly Val Pro Gly Asp Tyr Asn Leu Gln Phe Leu
            20                  25                  30 gat caa att att tcc cgc aag gat atg aaa tgg gtc gga aat gct aat     144
Asp Gln Ile Ile Ser Arg Lys Asp Met Lys Trp Val Gly Asn Ala Asn
        35                  40                  45 gaa tta aat gct tca tat atg gct gat ggc tat gct cgt act aaa aaa     192
Glu Leu Asn Ala Ser Tyr Met Ala Asp Gly Tyr Ala Arg Thr Lys Lys
    50                  55                  60 gct gcc gca ttt ctt aca acc ttt gga gta ggt gaa ttg agt gca gtt     240
Ala Ala Ala Phe Leu Thr Thr Phe Gly Val Gly Glu Leu Ser Ala Val
65                  70                  75                  80 aat gga tta gca gga agt tac gcc gaa aat tta cca gta gta gaa ata     288
Asn Gly Leu Ala Gly Ser Tyr Ala Glu Asn Leu Pro Val Val Glu Ile
                85                  90                  95 gtg gga tca cct aca tca aaa gtt caa aat gaa gga aaa ttt gtt cat     336
Val Gly Ser Pro Thr Ser Lys Val Gln Asn Glu Gly Lys Phe Val His
            100                 105                 110 cat acg ctg gct gac ggt gat ttt aaa cac ttt atg aaa atg cac gaa     384
His Thr Leu Ala Asp Gly Asp Phe Lys His Phe Met Lys Met His Glu
        115                 120                 125 cct gtt aca gca gct cga act tta ctg aca gca gaa aat gca acc gtt     432
Pro Val Thr Ala Ala Arg Thr Leu Leu Thr Ala Glu Asn Ala Thr Val
    130                 135                 140 gaa att gac cga gta ctt tct gca cta tta aaa gaa aga aaa cct gtc     480
Glu Ile Asp Arg Val Leu Ser Ala Leu Leu Lys Glu Arg Lys Pro Val
145                 150                 155                 160 tat atc aac tta cca gtt gat gtt gct gct gca aaa gca gag aaa ccc     528
Tyr Ile Asn Leu Pro Val Asp Val Ala Ala Ala Lys Ala Glu Lys Pro
```

-continued

|     |     |     |     | 165 |     |     |     | 170 |     |     |     | 175 |     |     |     |      |
|-----|-----|-----|-----|-----|-----|-----|-----|-----|-----|-----|-----|-----|-----|-----|-----|------|
| tca | ctc | cct | ttg | aaa | aaa | gaa | aac | tca | act | tca | aat | aca | agt | gac | caa | 576  |
| Ser | Leu | Pro | Leu | Lys | Lys | Glu | Asn | Ser | Thr | Ser | Asn | Thr | Ser | Asp | Gln |      |
|     |     | 180 |     |     |     |     | 185 |     |     |     |     | 190 |     |     |     |      |

| gag | atc | ttg | aac | aaa | att | caa | gaa | agc | ttg | aaa | aat | gcc | aaa | aaa | cca | 624  |
| Glu | Ile | Leu | Asn | Lys | Ile | Gln | Glu | Ser | Leu | Lys | Asn | Ala | Lys | Lys | Pro |      |
| 195 |     |     |     |     | 200 |     |     |     |     | 205 |     |     |     |     |     |      |

| atc | gtg | att | aca | gga | cat | gaa | ata | att | agt | ttt | ggc | tta | gaa | aaa | aca | 672  |
| Ile | Val | Ile | Thr | Gly | His | Glu | Ile | Ile | Ser | Phe | Gly | Leu | Glu | Lys | Thr |      |
|     | 210 |     |     |     |     | 215 |     |     |     |     | 220 |     |     |     |     |      |

| gtc | tct | caa | ttt | att | tca | aag | aca | aaa | cta | cct | att | acg | aca | tta | aac | 720  |
| Val | Ser | Gln | Phe | Ile | Ser | Lys | Thr | Lys | Leu | Pro | Ile | Thr | Thr | Leu | Asn |      |
| 225 |     |     |     |     | 230 |     |     |     |     | 235 |     |     |     |     | 240 |      |

| ttt | gga | aaa | agt | tca | gtt | gat | gaa | gct | ctc | cct | tca | ttt | tta | gga | atc | 768  |
| Phe | Gly | Lys | Ser | Ser | Val | Asp | Glu | Ala | Leu | Pro | Ser | Phe | Leu | Gly | Ile |      |
|     |     |     |     | 245 |     |     |     |     | 250 |     |     |     |     | 255 |     |      |

| tat | aat | ggt | aaa | ctc | tca | gag | cct | aat | ctt | aaa | gaa | ttc | gtg | gaa | tca | 816  |
| Tyr | Asn | Gly | Lys | Leu | Ser | Glu | Pro | Asn | Leu | Lys | Glu | Phe | Val | Glu | Ser |      |
|     |     |     | 260 |     |     |     |     | 265 |     |     |     |     | 270 |     |     |      |

| gcc | gac | ttc | atc | ctg | atg | ctt | gga | gtt | aaa | ctc | aca | gac | tct | tca | aca | 864  |
| Ala | Asp | Phe | Ile | Leu | Met | Leu | Gly | Val | Lys | Leu | Thr | Asp | Ser | Ser | Thr |      |
|     |     | 275 |     |     |     |     | 280 |     |     |     |     | 285 |     |     |     |      |

| gga | gcc | ttc | act | cat | cat | tta | aat | gaa | aat | aaa | atg | att | tca | ctg | aat | 912  |
| Gly | Ala | Phe | Thr | His | His | Leu | Asn | Glu | Asn | Lys | Met | Ile | Ser | Leu | Asn |      |
| 290 |     |     |     |     |     | 295 |     |     |     |     | 300 |     |     |     |     |      |

| ata | gat | gaa | gga | aaa | ata | ttt | aac | gaa | agc | atc | caa | aat | ttt | gat | ttt | 960  |
| Ile | Asp | Glu | Gly | Lys | Ile | Phe | Asn | Glu | Ser | Ile | Gln | Asn | Phe | Asp | Phe |      |
| 305 |     |     |     |     | 310 |     |     |     |     | 315 |     |     |     |     | 320 |      |

| gaa | tcc | ctc | atc | tcc | tct | ctc | tta | gac | cta | agc | gaa | ata | gaa | tac | aaa | 1008 |
| Glu | Ser | Leu | Ile | Ser | Ser | Leu | Leu | Asp | Leu | Ser | Glu | Ile | Glu | Tyr | Lys |      |
|     |     |     |     | 325 |     |     |     |     | 330 |     |     |     |     | 335 |     |      |

| gga | aaa | tat | atc | gat | aaa | aag | caa | gaa | gac | ttt | gtt | cca | tca | aat | gcg | 1056 |
| Gly | Lys | Tyr | Ile | Asp | Lys | Lys | Gln | Glu | Asp | Phe | Val | Pro | Ser | Asn | Ala |      |
|     |     |     | 340 |     |     |     |     | 345 |     |     |     |     | 350 |     |     |      |

| ctt | tta | tca | caa | gac | cgc | cta | tgg | caa | gca | gtt | gaa | aac | cta | act | caa | 1104 |
| Leu | Leu | Ser | Gln | Asp | Arg | Leu | Trp | Gln | Ala | Val | Glu | Asn | Leu | Thr | Gln |      |
|     |     | 355 |     |     |     |     | 360 |     |     |     |     | 365 |     |     |     |      |

| agc | aat | gaa | aca | atc | gtt | gct | gaa | caa | ggg | aca | tca | ttc | ttt | ggc | gct | 1152 |
| Ser | Asn | Glu | Thr | Ile | Val | Ala | Glu | Gln | Gly | Thr | Ser | Phe | Phe | Gly | Ala |      |
| 370 |     |     |     |     | 375 |     |     |     |     | 380 |     |     |     |     |     |      |

| tca | tca | att | ttc | tta | aaa | cca | aag | agt | cat | ttt | att | ggt | caa | ccc | tta | 1200 |
| Ser | Ser | Ile | Phe | Leu | Lys | Pro | Lys | Ser | His | Phe | Ile | Gly | Gln | Pro | Leu |      |
| 385 |     |     |     |     | 390 |     |     |     |     | 395 |     |     |     |     | 400 |      |

| tgg | gga | tca | att | gga | tat | aca | ttc | cca | gca | gca | tta | gga | agc | caa | att | 1248 |
| Trp | Gly | Ser | Ile | Gly | Tyr | Thr | Phe | Pro | Ala | Ala | Leu | Gly | Ser | Gln | Ile |      |
|     |     |     |     | 405 |     |     |     |     | 410 |     |     |     |     | 415 |     |      |

| gca | gat | aaa | gaa | agc | aga | cac | ctt | tta | ttt | att | ggt | gat | ggt | tca | ctt | 1296 |
| Ala | Asp | Lys | Glu | Ser | Arg | His | Leu | Leu | Phe | Ile | Gly | Asp | Gly | Ser | Leu |      |
|     |     |     | 420 |     |     |     |     | 425 |     |     |     |     | 430 |     |     |      |

| caa | ctt | acg | gtg | caa | gaa | tta | gga | tta | gca | atc | aga | gaa | aaa | att | aat | 1344 |
| Gln | Leu | Thr | Val | Gln | Glu | Leu | Gly | Leu | Ala | Ile | Arg | Glu | Lys | Ile | Asn |      |
|     |     | 435 |     |     |     |     | 440 |     |     |     |     | 445 |     |     |     |      |

| cca | att | tgc | ttt | att | atc | aat | aat | gat | ggt | tat | aca | gcc | gaa | aga | gaa | 1392 |
| Pro | Ile | Cys | Phe | Ile | Ile | Asn | Asn | Asp | Gly | Tyr | Thr | Ala | Glu | Arg | Glu |      |
| 450 |     |     |     |     | 455 |     |     |     |     | 460 |     |     |     |     |     |      |

| att | cat | gga | cca | aat | caa | agc | tac | aat | gat | att | cca | atg | tgg | aat | tac | 1440 |
| Ile | His | Gly | Pro | Asn | Gln | Ser | Tyr | Asn | Asp | Ile | Pro | Met | Trp | Asn | Tyr |      |
| 465 |     |     |     |     | 470 |     |     |     |     | 475 |     |     |     |     | 480 |      |

| tca | aaa | tta | cca | gaa | tca | ttt | gga | gca | aca | gaa | gaa | cga | gta | gtc | tcg | 1488 |
| Ser | Lys | Leu | Pro | Glu | Ser | Phe | Gly | Ala | Thr | Glu | Glu | Arg | Val | Val | Ser |      |

```
                    485                 490                 495
aaa atc gtt aga act gaa aat gaa ttt gtg tct gtc atg aaa gaa gct      1536
Lys Ile Val Arg Thr Glu Asn Glu Phe Val Ser Val Met Lys Glu Ala
            500                 505                 510 caa gca gat cca aat aga atg tac tgg att gag tta att ttg gca aaa      1584
Gln Ala Asp Pro Asn Arg Met Tyr Trp Ile Glu Leu Ile Leu Ala Lys
        515                 520                 525 gaa gat gca cca aaa gta ctg aaa aaa atg ggc aaa cta ttt gct gaa      1632
Glu Asp Ala Pro Lys Val Leu Lys Lys Met Gly Lys Leu Phe Ala Glu
    530                 535                 540 caa aat aaa tca taa                                                   1647
Gln Asn Lys Ser
545

<210> SEQ ID NO 20
<211> LENGTH: 548
<212> TYPE: PRT
<213> ORGANISM: Artificial Sequence
<220> FEATURE:
<223> OTHER INFORMATION: Synthetic Construct

<400> SEQUENCE: 20

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Ser Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Lys Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
```

```
                275                 280                 285
Gly Ala Phe Thr His His Leu Asn Glu Asn Lys Met Ile Ser Leu Asn
            290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
            355                 360                 365

Ser Asn Glu Thr Ile Val Ala Glu Gln Gly Thr Ser Phe Phe Gly Ala
        370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Ala Glu Arg Glu
        450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Glu Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
            515                 520                 525

Glu Asp Ala Pro Lys Val Leu Lys Lys Met Gly Lys Leu Phe Ala Glu
        530                 535                 540

Gln Asn Lys Ser
545

<210> SEQ ID NO 21
<211> LENGTH: 1647
<212> TYPE: DNA
<213> ORGANISM: Artificial Sequence
<220> FEATURE:
<223> OTHER INFORMATION: Mutant Kivd (V461A/M538A)
<220> FEATURE:
<221> NAME/KEY: CDS
<222> LOCATION: (1)..(1647)

<400> SEQUENCE: 21 atg tat aca gta gga gat tac cta tta gac cga tta cac gag tta gga        48
Met Tyr Thr Val Gly Asp Tyr Leu Leu Asp Arg Leu His Glu Leu Gly
1               5                   10                  15 att gaa gaa att ttt gga gtc cct gga gac tat aac tta caa ttt tta        96
Ile Glu Glu Ile Phe Gly Val Pro Gly Asp Tyr Asn Leu Gln Phe Leu
                20                  25                  30 gat caa att att tcc cgc aag gat atg aaa tgg gtc gga aat gct aat       144
Asp Gln Ile Ile Ser Arg Lys Asp Met Lys Trp Val Gly Asn Ala Asn
            35                  40                  45 gaa tta aat gct tca tat atg gct gat ggc tat gct cgt act aaa aaa       192
Glu Leu Asn Ala Ser Tyr Met Ala Asp Gly Tyr Ala Arg Thr Lys Lys
```

```
                50                    55                    60
gct gcc gca ttt ctt aca acc ttt gga gta ggt gaa ttg agt gca gtt      240
Ala Ala Ala Phe Leu Thr Thr Phe Gly Val Gly Glu Leu Ser Ala Val
 65                  70                  75                  80 aat gga tta gca gga agt tac gcc gaa aat tta cca gta gta gaa ata      288
Asn Gly Leu Ala Gly Ser Tyr Ala Glu Asn Leu Pro Val Val Glu Ile
                 85                  90                  95 gtg gga tca cct aca tca aaa gtt caa aat gaa gga aaa ttt gtt cat      336
Val Gly Ser Pro Thr Ser Lys Val Gln Asn Glu Gly Lys Phe Val His
            100                 105                 110 cat acg ctg gct gac ggt gat ttt aaa cac ttt atg aaa atg cac gaa      384
His Thr Leu Ala Asp Gly Asp Phe Lys His Phe Met Lys Met His Glu
        115                 120                 125 cct gtt aca gca gct cga act tta ctg aca gca gaa aat gca acc gtt      432
Pro Val Thr Ala Ala Arg Thr Leu Leu Thr Ala Glu Asn Ala Thr Val
    130                 135                 140 gaa att gac cga gta ctt tct gca cta tta aaa gaa aga aaa cct gtc      480
Glu Ile Asp Arg Val Leu Ser Ala Leu Leu Lys Glu Arg Lys Pro Val
145                 150                 155                 160 tat atc aac tta cca gtt gat gtt gct gct gca aaa gca gag aaa ccc      528
Tyr Ile Asn Leu Pro Val Asp Val Ala Ala Ala Lys Ala Glu Lys Pro
                165                 170                 175 tca ctc cct ttg aaa aaa gaa aac tca act tca aat aca agt gac caa      576
Ser Leu Pro Leu Lys Lys Glu Asn Ser Thr Ser Asn Thr Ser Asp Gln
            180                 185                 190 gag atc ttg aac aaa att caa gaa agc ttg aaa aat gcc aaa aaa cca      624
Glu Ile Leu Asn Lys Ile Gln Glu Ser Leu Lys Asn Ala Lys Lys Pro
        195                 200                 205 atc gtg att aca gga cat gaa ata att agt ttt ggc tta gaa aaa aca      672
Ile Val Ile Thr Gly His Glu Ile Ile Ser Phe Gly Leu Glu Lys Thr
    210                 215                 220 gtc tct caa ttt att tca aag aca aaa cta cct att acg aca tta aac      720
Val Ser Gln Phe Ile Ser Lys Thr Lys Leu Pro Ile Thr Thr Leu Asn
225                 230                 235                 240 ttt gga aaa agt tca gtt gat gaa gct ctc cct tca ttt tta gga atc      768
Phe Gly Lys Ser Ser Val Asp Glu Ala Leu Pro Ser Phe Leu Gly Ile
                245                 250                 255 tat aat ggt aaa ctc tca gag cct aat ctt aaa gaa ttc gtg gaa tca      816
Tyr Asn Gly Lys Leu Ser Glu Pro Asn Leu Lys Glu Phe Val Glu Ser
            260                 265                 270 gcc gac ttc atc ctg atg ctt gga gtt aaa ctc aca gac tct tca aca      864
Ala Asp Phe Ile Leu Met Leu Gly Val Lys Leu Thr Asp Ser Ser Thr
        275                 280                 285 gga gcc ttc act cat cat tta aat gaa aat aaa atg att tca ctg aat      912
Gly Ala Phe Thr His His Leu Asn Glu Asn Lys Met Ile Ser Leu Asn
    290                 295                 300 ata gat gaa gga aaa ata ttt aac gaa agc atc caa aat ttt gat ttt      960
Ile Asp Glu Gly Lys Ile Phe Asn Glu Ser Ile Gln Asn Phe Asp Phe
305                 310                 315                 320 gaa tcc ctc atc tcc tct ctc tta gac cta agc gaa ata gaa tac aaa     1008
Glu Ser Leu Ile Ser Ser Leu Leu Asp Leu Ser Glu Ile Glu Tyr Lys
                325                 330                 335 gga aaa tat atc gat aaa aag caa gaa gac ttt gtt cca tca aat gcg     1056
Gly Lys Tyr Ile Asp Lys Lys Gln Glu Asp Phe Val Pro Ser Asn Ala
            340                 345                 350 ctt tta tca caa gac cgc cta tgg caa gca gtt gaa aac cta act caa     1104
Leu Leu Ser Gln Asp Arg Leu Trp Gln Ala Val Glu Asn Leu Thr Gln
        355                 360                 365 agc aat gaa aca atc gtt gct gaa caa ggg aca tca ttc ttt ggc gct     1152
Ser Asn Glu Thr Ile Val Ala Glu Gln Gly Thr Ser Phe Phe Gly Ala
```

```
                370             375             380
tca tca att ttc tta aaa cca aag agt cat ttt att ggt caa ccc tta     1200
Ser Ser Ile Phe Leu Lys Pro Lys Ser His Phe Ile Gly Gln Pro Leu
385                 390                 395                 400 tgg gga tca att gga tat aca ttc cca gca gca tta gga agc caa att     1248
Trp Gly Ser Ile Gly Tyr Thr Phe Pro Ala Ala Leu Gly Ser Gln Ile
                405                 410                 415 gca gat aaa gaa agc aga cac ctt tta ttt att ggt gat ggt tca ctt     1296
Ala Asp Lys Glu Ser Arg His Leu Leu Phe Ile Gly Asp Gly Ser Leu
            420                 425                 430 caa ctt acg gtg caa gaa tta gga tta gca atc aga gaa aaa att aat     1344
Gln Leu Thr Val Gln Glu Leu Gly Leu Ala Ile Arg Glu Lys Ile Asn
        435                 440                 445 cca att tgc ttt att atc aat aat gat ggt tat aca gcc gaa aga gaa     1392
Pro Ile Cys Phe Ile Ile Asn Asn Asp Gly Tyr Thr Ala Glu Arg Glu
    450                 455                 460 att cat gga cca aat caa agc tac aat gat att cca atg tgg aat tac     1440
Ile His Gly Pro Asn Gln Ser Tyr Asn Asp Ile Pro Met Trp Asn Tyr
465                 470                 475                 480 tca aaa tta cca gaa tca ttt gga gca aca gaa gaa cga gta gtc tcg     1488
Ser Lys Leu Pro Glu Ser Phe Gly Ala Thr Glu Glu Arg Val Val Ser
                485                 490                 495 aaa atc gtt aga act gaa aat gaa ttt gtg tct gtc atg aaa gaa gct     1536
Lys Ile Val Arg Thr Glu Asn Glu Phe Val Ser Val Met Lys Glu Ala
            500                 505                 510 caa gca gat cca aat aga atg tac tgg att gag tta att ttg gca aaa     1584
Gln Ala Asp Pro Asn Arg Met Tyr Trp Ile Glu Leu Ile Leu Ala Lys
        515                 520                 525 gaa gat gca cca aaa gta ctg aaa aaa gcg ggc aaa cta ttt gct gaa     1632
Glu Asp Ala Pro Lys Val Leu Lys Lys Ala Gly Lys Leu Phe Ala Glu
    530                 535                 540 caa aat aaa tca taa                                                  1647
Gln Asn Lys Ser
545

<210> SEQ ID NO 22
<211> LENGTH: 548
<212> TYPE: PRT
<213> ORGANISM: Artificial Sequence
<220> FEATURE:
<223> OTHER INFORMATION: Synthetic Construct

<400> SEQUENCE: 22

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125
```

```
Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
210                 215                 220

Val Ser Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Lys Leu Ser Glu Pro Asn Leu Lys Glu Phe Val Glu Ser
                260                 265                 270

Ala Asp Phe Ile Leu Met Leu Gly Val Lys Leu Thr Asp Ser Ser Thr
            275                 280                 285

Gly Ala Phe Thr His His Leu Asn Glu Asn Lys Met Ile Ser Leu Asn
        290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
                340                 345                 350

Leu Leu Ser Gln Asp Arg Leu Trp Gln Ala Val Glu Asn Leu Thr Gln
            355                 360                 365

Ser Asn Glu Thr Ile Val Ala Glu Gln Gly Thr Ser Phe Phe Gly Ala
        370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
                420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Ala Glu Arg Glu
        450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Arg Val Val Ser
                485                 490                 495

Lys Ile Val Arg Thr Glu Asn Glu Phe Val Ser Val Met Lys Glu Ala
                500                 505                 510

Gln Ala Asp Pro Asn Arg Met Tyr Trp Ile Glu Leu Ile Leu Ala Lys
            515                 520                 525

Glu Asp Ala Pro Lys Val Leu Lys Lys Ala Gly Lys Leu Phe Ala Glu
        530                 535                 540

Gln Asn Lys Ser
545
```

<210> SEQ ID NO 23
<211> LENGTH: 1647
<212> TYPE: DNA
<213> ORGANISM: Artificial Sequence
<220> FEATURE:
<223> OTHER INFORMATION: Mutant Kivd (V461A/M538L)
<220> FEATURE:
<221> NAME/KEY: CDS
<222> LOCATION: (1)..(1647)

<400> SEQUENCE: 23

```
atg tat aca gta gga gat tac cta tta gac cga tta cac gag tta gga      48
Met Tyr Thr Val Gly Asp Tyr Leu Leu Asp Arg Leu His Glu Leu Gly
1               5                   10                  15 att gaa gaa att ttt gga gtc cct gga gac tat aac tta caa ttt tta      96
Ile Glu Glu Ile Phe Gly Val Pro Gly Asp Tyr Asn Leu Gln Phe Leu
                20                  25                  30 gat caa att att tcc cgc aag gat atg aaa tgg gtc gga aat gct aat     144
Asp Gln Ile Ile Ser Arg Lys Asp Met Lys Trp Val Gly Asn Ala Asn
            35                  40                  45 gaa tta aat gct tca tat atg gct gat ggc tat gct cgt act aaa aaa     192
Glu Leu Asn Ala Ser Tyr Met Ala Asp Gly Tyr Ala Arg Thr Lys Lys
        50                  55                  60 gct gcc gca ttt ctt aca acc ttt gga gta ggt gaa ttg agt gca gtt     240
Ala Ala Ala Phe Leu Thr Thr Phe Gly Val Gly Glu Leu Ser Ala Val
65                  70                  75                  80 aat gga tta gca gga agt tac gcc gaa aat tta cca gta gta gaa ata     288
Asn Gly Leu Ala Gly Ser Tyr Ala Glu Asn Leu Pro Val Val Glu Ile
                85                  90                  95 gtg gga tca cct aca tca aaa gtt caa aat gaa gga aaa ttt gtt cat     336
Val Gly Ser Pro Thr Ser Lys Val Gln Asn Glu Gly Lys Phe Val His
                100                 105                 110 cat acg ctg gct gac ggt gat ttt aaa cac ttt atg aaa atg cac gaa     384
His Thr Leu Ala Asp Gly Asp Phe Lys His Phe Met Lys Met His Glu
            115                 120                 125 cct gtt aca gca gct cga act tta ctg aca gca gaa aat gca acc gtt     432
Pro Val Thr Ala Ala Arg Thr Leu Leu Thr Ala Glu Asn Ala Thr Val
        130                 135                 140 gaa att gac cga gta ctt tct gca cta tta aaa gaa aga aaa cct gtc     480
Glu Ile Asp Arg Val Leu Ser Ala Leu Leu Lys Glu Arg Lys Pro Val
145                 150                 155                 160 tat atc aac tta cca gtt gat gtt gct gct gca aaa gca gag aaa ccc     528
Tyr Ile Asn Leu Pro Val Asp Val Ala Ala Ala Lys Ala Glu Lys Pro
                165                 170                 175 tca ctc cct ttg aaa aaa gaa aac tca act tca aat aca agt gac caa     576
Ser Leu Pro Leu Lys Lys Glu Asn Ser Thr Ser Asn Thr Ser Asp Gln
            180                 185                 190 gag atc ttg aac aaa att caa gaa agc ttg aaa aat gcc aaa aaa cca     624
Glu Ile Leu Asn Lys Ile Gln Glu Ser Leu Lys Asn Ala Lys Lys Pro
        195                 200                 205 atc gtg att aca gga cat gaa ata att agt ttt ggc tta gaa aaa aca     672
Ile Val Ile Thr Gly His Glu Ile Ile Ser Phe Gly Leu Glu Lys Thr
    210                 215                 220 gtc tct caa ttt att tca aag aca aaa cta cct att acg aca tta aac     720
Val Ser Gln Phe Ile Ser Lys Thr Lys Leu Pro Ile Thr Thr Leu Asn
225                 230                 235                 240 ttt gga aaa agt tca gtt gat gaa gct ctc cct tca ttt tta gga atc     768
Phe Gly Lys Ser Ser Val Asp Glu Ala Leu Pro Ser Phe Leu Gly Ile
                245                 250                 255 tat aat ggt aaa ctc tca gag cct aat ctt aaa gaa ttc gtg gaa tca     816
Tyr Asn Gly Lys Leu Ser Glu Pro Asn Leu Lys Glu Phe Val Glu Ser
```

```
                        260                 265                 270
gcc gac ttc atc ctg atg ctt gga gtt aaa ctc aca gac tct tca aca      864
Ala Asp Phe Ile Leu Met Leu Gly Val Lys Leu Thr Asp Ser Ser Thr
        275                 280                 285 gga gcc ttc act cat cat tta aat gaa aat aaa atg att tca ctg aat      912
Gly Ala Phe Thr His His Leu Asn Glu Asn Lys Met Ile Ser Leu Asn
    290                 295                 300 ata gat gaa gga aaa ata ttt aac gaa agc atc caa aat ttt gat ttt      960
Ile Asp Glu Gly Lys Ile Phe Asn Glu Ser Ile Gln Asn Phe Asp Phe
305                 310                 315                 320 gaa tcc ctc atc tcc tct ctc tta gac cta agc gaa ata gaa tac aaa     1008
Glu Ser Leu Ile Ser Ser Leu Leu Asp Leu Ser Glu Ile Glu Tyr Lys
                325                 330                 335 gga aaa tat atc gat aaa aag caa gaa gac ttt gtt cca tca aat gcg     1056
Gly Lys Tyr Ile Asp Lys Lys Gln Glu Asp Phe Val Pro Ser Asn Ala
            340                 345                 350 ctt tta tca caa gac cgc cta tgg caa gca gtt gaa aac cta act caa     1104
Leu Leu Ser Gln Asp Arg Leu Trp Gln Ala Val Glu Asn Leu Thr Gln
        355                 360                 365 agc aat gaa aca atc gtt gct gaa caa ggg aca tca ttc ttt ggc gct     1152
Ser Asn Glu Thr Ile Val Ala Glu Gln Gly Thr Ser Phe Phe Gly Ala
    370                 375                 380 tca tca att ttc tta aaa cca aag agt cat ttt att ggt caa ccc tta     1200
Ser Ser Ile Phe Leu Lys Pro Lys Ser His Phe Ile Gly Gln Pro Leu
385                 390                 395                 400 tgg gga tca att gga tat aca ttc cca gca gca tta gga agc caa att     1248
Trp Gly Ser Ile Gly Tyr Thr Phe Pro Ala Ala Leu Gly Ser Gln Ile
                405                 410                 415 gca gat aaa gaa agc aga cac ctt tta ttt att ggt gat ggt tca ctt     1296
Ala Asp Lys Glu Ser Arg His Leu Leu Phe Ile Gly Asp Gly Ser Leu
            420                 425                 430 caa ctt acg gtg caa gaa tta gga tta gca atc aga gaa aaa att aat     1344
Gln Leu Thr Val Gln Glu Leu Gly Leu Ala Ile Arg Glu Lys Ile Asn
        435                 440                 445 cca att tgc ttt att atc aat aat gat ggt tat aca gcc gaa aga gaa     1392
Pro Ile Cys Phe Ile Ile Asn Asn Asp Gly Tyr Thr Ala Glu Arg Glu
    450                 455                 460 att cat gga cca aat caa agc tac aat gat att cca atg tgg aat tac     1440
Ile His Gly Pro Asn Gln Ser Tyr Asn Asp Ile Pro Met Trp Asn Tyr
465                 470                 475                 480 tca aaa tta cca gaa tca ttt gga gca aca gaa gaa cga gta gtc tcg     1488
Ser Lys Leu Pro Glu Ser Phe Gly Ala Thr Glu Glu Arg Val Val Ser
                485                 490                 495 aaa atc gtt aga act gaa aat gaa ttt gtg tct gtc atg aaa gaa gct     1536
Lys Ile Val Arg Thr Glu Asn Glu Phe Val Ser Val Met Lys Glu Ala
            500                 505                 510 caa gca gat cca aat aga atg tac tgg att gag tta att ttg gca aaa     1584
Gln Ala Asp Pro Asn Arg Met Tyr Trp Ile Glu Leu Ile Leu Ala Lys
        515                 520                 525 gaa gat gca cca aaa gta ctg aaa aaa ctg ggc aaa cta ttt gct gaa     1632
Glu Asp Ala Pro Lys Val Leu Lys Lys Leu Gly Lys Leu Phe Ala Glu
    530                 535                 540 caa aat aaa tca taa                                                 1647
Gln Asn Lys Ser
545

<210> SEQ ID NO 24
<211> LENGTH: 548
<212> TYPE: PRT
<213> ORGANISM: Artificial Sequence
<220> FEATURE:
```

<223> OTHER INFORMATION: Synthetic Construct

<400> SEQUENCE: 24

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Ser Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Lys Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile
```

```
                        405                 410                 415
Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Ala Glu Arg Glu
            450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Glu Arg Val Val Ser
                    485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
            515                 520                 525

Glu Asp Ala Pro Lys Val Leu Lys Lys Leu Gly Lys Leu Phe Ala Glu
            530                 535                 540

Gln Asn Lys Ser
545

<210> SEQ ID NO 25
<211> LENGTH: 1647
<212> TYPE: DNA
<213> ORGANISM: Artificial Sequence
<220> FEATURE:
<223> OTHER INFORMATION: Mutant Kivd (V461A/F381A)
<220> FEATURE:
<221> NAME/KEY: CDS
<222> LOCATION: (1)..(1647)

<400> SEQUENCE: 25 atg tat aca gta gga gat tac cta tta gac cga tta cac gag tta gga      48
Met Tyr Thr Val Gly Asp Tyr Leu Leu Asp Arg Leu His Glu Leu Gly
1               5                  10                  15 att gaa gaa att ttt gga gtc cct gga gac tat aac tta caa ttt tta      96
Ile Glu Glu Ile Phe Gly Val Pro Gly Asp Tyr Asn Leu Gln Phe Leu
                20                  25                  30 gat caa att att tcc cgc aag gat atg aaa tgg gtc gga aat gct aat     144
Asp Gln Ile Ile Ser Arg Lys Asp Met Lys Trp Val Gly Asn Ala Asn
            35                  40                  45 gaa tta aat gct tca tat atg gct gat ggc tat gct cgt act aaa aaa    192
Glu Leu Asn Ala Ser Tyr Met Ala Asp Gly Tyr Ala Arg Thr Lys Lys
        50                  55                  60 gct gcc gca ttt ctt aca acc ttt gga gta ggt gaa ttg agt gca gtt    240
Ala Ala Ala Phe Leu Thr Thr Phe Gly Val Gly Glu Leu Ser Ala Val
65                  70                  75                  80 aat gga tta gca gga agt tac gcc gaa aat tta cca gta gta gaa ata    288
Asn Gly Leu Ala Gly Ser Tyr Ala Glu Asn Leu Pro Val Val Glu Ile
                85                  90                  95 gtg gga tca cct aca tca aaa gtt caa aat gaa gga aaa ttt gtt cat    336
Val Gly Ser Pro Thr Ser Lys Val Gln Asn Glu Gly Lys Phe Val His
            100                 105                 110 cat acg ctg gct gac ggt gat ttt aaa cac ttt atg aaa atg cac gaa    384
His Thr Leu Ala Asp Gly Asp Phe Lys His Phe Met Lys Met His Glu
        115                 120                 125 cct gtt aca gca gct cga act tta ctg aca gca gaa aat gca acc gtt    432
Pro Val Thr Ala Ala Arg Thr Leu Leu Thr Ala Glu Asn Ala Thr Val
        130                 135                 140 gaa att gac cga gta ctt tct gca cta tta aaa gaa aga aaa cct gtc    480
Glu Ile Asp Arg Val Leu Ser Ala Leu Leu Lys Glu Arg Lys Pro Val
```

-continued

```
              145                 150                 155                 160
tat atc aac tta cca gtt gat gtt gct gct gca aaa gca gag aaa ccc         528
Tyr Ile Asn Leu Pro Val Asp Val Ala Ala Ala Lys Ala Glu Lys Pro
                165                 170                 175 tca ctc cct ttg aaa aaa gaa aac tca act tca aat aca agt gac caa         576
Ser Leu Pro Leu Lys Lys Glu Asn Ser Thr Ser Asn Thr Ser Asp Gln
            180                 185                 190 gag atc ttg aac aaa att caa gaa agc ttg aaa aat gcc aaa aaa cca         624
Glu Ile Leu Asn Lys Ile Gln Glu Ser Leu Lys Asn Ala Lys Lys Pro
                195                 200                 205 atc gtg att aca gga cat gaa ata att agt ttt ggc tta gaa aaa aca         672
Ile Val Ile Thr Gly His Glu Ile Ile Ser Phe Gly Leu Glu Lys Thr
    210                 215                 220 gtc tct caa ttt att tca aag aca aaa cta cct att acg aca tta aac         720
Val Ser Gln Phe Ile Ser Lys Thr Lys Leu Pro Ile Thr Thr Leu Asn
225                 230                 235                 240 ttt gga aaa agt tca gtt gat gaa gct ctc cct tca ttt tta gga atc         768
Phe Gly Lys Ser Ser Val Asp Glu Ala Leu Pro Ser Phe Leu Gly Ile
                245                 250                 255 tat aat ggt aaa ctc tca gag cct aat ctt aaa gaa ttc gtg gaa tca         816
Tyr Asn Gly Lys Leu Ser Glu Pro Asn Leu Lys Glu Phe Val Glu Ser
            260                 265                 270 gcc gac ttc atc ctg atg ctt gga gtt aaa ctc aca gac tct tca aca         864
Ala Asp Phe Ile Leu Met Leu Gly Val Lys Leu Thr Asp Ser Ser Thr
                275                 280                 285 gga gcc ttc act cat cat tta aat gaa aat aaa atg att tca ctg aat         912
Gly Ala Phe Thr His His Leu Asn Glu Asn Lys Met Ile Ser Leu Asn
    290                 295                 300 ata gat gaa gga aaa ata ttt aac gaa agc atc caa aat ttt gat ttt         960
Ile Asp Glu Gly Lys Ile Phe Asn Glu Ser Ile Gln Asn Phe Asp Phe
305                 310                 315                 320 gaa tcc ctc atc tcc tct ctc tta gac cta agc gaa ata gaa tac aaa        1008
Glu Ser Leu Ile Ser Ser Leu Leu Asp Leu Ser Glu Ile Glu Tyr Lys
                325                 330                 335 gga aaa tat atc gat aaa aag caa gaa gac ttt gtt cca tca aat gcg        1056
Gly Lys Tyr Ile Asp Lys Lys Gln Glu Asp Phe Val Pro Ser Asn Ala
            340                 345                 350 ctt tta tca caa gac cgc cta tgg caa gca gtt gaa aac cta act caa        1104
Leu Leu Ser Gln Asp Arg Leu Trp Gln Ala Val Glu Asn Leu Thr Gln
                355                 360                 365 agc aat gaa aca atc gtt gct gaa caa ggg aca tca ttc gcg ggc gct        1152
Ser Asn Glu Thr Ile Val Ala Glu Gln Gly Thr Ser Phe Ala Gly Ala
    370                 375                 380 tca tca att ttc tta aaa cca aag agt cat ttt att ggt caa ccc tta        1200
Ser Ser Ile Phe Leu Lys Pro Lys Ser His Phe Ile Gly Gln Pro Leu
385                 390                 395                 400 tgg gga tca att gga tat aca ttc cca gca gca tta gga agc caa att        1248
Trp Gly Ser Ile Gly Tyr Thr Phe Pro Ala Ala Leu Gly Ser Gln Ile
                405                 410                 415 gca gat aaa gaa agc aga cac ctt tta ttt att ggt gat ggt tca ctt        1296
Ala Asp Lys Glu Ser Arg His Leu Leu Phe Ile Gly Asp Gly Ser Leu
            420                 425                 430 caa ctt acg gtg caa gaa tta gga tta gca atc aga gaa aaa att aat        1344
Gln Leu Thr Val Gln Glu Leu Gly Leu Ala Ile Arg Glu Lys Ile Asn
                435                 440                 445 cca att tgc ttt att atc aat aat gat ggt tat aca gcc gaa aga gaa        1392
Pro Ile Cys Phe Ile Ile Asn Asn Asp Gly Tyr Thr Ala Glu Arg Glu
    450                 455                 460 att cat gga cca aat caa agc tac aat gat att cca atg tgg aat tac        1440
Ile His Gly Pro Asn Gln Ser Tyr Asn Asp Ile Pro Met Trp Asn Tyr
```

```
                465                 470                 475                 480
tca aaa tta cca gaa tca ttt gga gca aca gaa gaa cga gta gtc tcg           1488
Ser Lys Leu Pro Glu Ser Phe Gly Ala Thr Glu Glu Arg Val Val Ser
            485                 490                 495 aaa atc gtt aga act gaa aat gaa ttt gtg tct gtc atg aaa gaa gct           1536
Lys Ile Val Arg Thr Glu Asn Glu Phe Val Ser Val Met Lys Glu Ala
        500                 505                 510 caa gca gat cca aat aga atg tac tgg att gag tta att ttg gca aaa           1584
Gln Ala Asp Pro Asn Arg Met Tyr Trp Ile Glu Leu Ile Leu Ala Lys
    515                 520                 525 gaa gat gca cca aaa gta ctg aaa aaa atg ggc aaa cta ttt gct gaa           1632
Glu Asp Ala Pro Lys Val Leu Lys Lys Met Gly Lys Leu Phe Ala Glu
530                 535                 540 caa aat aaa tca taa                                                       1647
Gln Asn Lys Ser
545

<210> SEQ ID NO 26
<211> LENGTH: 548
<212> TYPE: PRT
<213> ORGANISM: Artificial Sequence
<220> FEATURE:
<223> OTHER INFORMATION: Synthetic Construct

<400> SEQUENCE: 26

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Ser Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255
```

```
Tyr Asn Gly Lys Leu Ser Glu Pro Asn Leu Lys Glu Phe Val Glu Ser
                260                 265                 270

Ala Asp Phe Ile Leu Met Leu Gly Val Lys Leu Thr Asp Ser Ser Thr
            275                 280                 285

Gly Ala Phe Thr His His Leu Asn Glu Asn Lys Met Ile Ser Leu Asn
    290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Asp Leu Ser Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
    355                 360                 365

Ser Asn Glu Thr Ile Val Ala Glu Gln Gly Thr Ser Phe Ala Gly Ala
370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
    435                 440                 445

Pro Ile Cys Phe Ile Ile Asn Asn Asp Gly Tyr Thr Ala Glu Arg Glu
450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
    515                 520                 525

Glu Asp Ala Pro Lys Val Leu Lys Lys Met Gly Lys Leu Phe Ala Glu
530                 535                 540

Gln Asn Lys Ser
545

<210> SEQ ID NO 27
<211> LENGTH: 1647
<212> TYPE: DNA
<213> ORGANISM: Artificial Sequence
<220> FEATURE:
<223> OTHER INFORMATION: Mutant Kivd (V461A/F381L)
<220> FEATURE:
<221> NAME/KEY: CDS
<222> LOCATION: (1)..(1647)

<400> SEQUENCE: 27 atg tat aca gta gga gat tac cta tta gac cga tta cac gag tta gga      48
Met Tyr Thr Val Gly Asp Tyr Leu Leu Asp Arg Leu His Glu Leu Gly
1               5                   10                  15 att gaa gaa att ttt gga gtc cct gga gac tat aac tta caa ttt tta      96
Ile Glu Glu Ile Phe Gly Val Pro Gly Asp Tyr Asn Leu Gln Phe Leu
            20                  25                  30 gat caa att att tcc cgc aag gat atg aaa tgg gtc gga aat gct aat     144
Asp Gln Ile Ile Ser Arg Lys Asp Met Lys Trp Val Gly Asn Ala Asn
```

```
                35                   40                   45
gaa tta aat gct tca tat atg gct gat ggc tat gct cgt act aaa aaa     192
Glu Leu Asn Ala Ser Tyr Met Ala Asp Gly Tyr Ala Arg Thr Lys Lys
 50                  55                   60 gct gcc gca ttt ctt aca acc ttt gga gta ggt gaa ttg agt gca gtt     240
Ala Ala Ala Phe Leu Thr Thr Phe Gly Val Gly Glu Leu Ser Ala Val
 65                  70                   75                   80 aat gga tta gca gga agt tac gcc gaa aat tta cca gta gta gaa ata     288
Asn Gly Leu Ala Gly Ser Tyr Ala Glu Asn Leu Pro Val Val Glu Ile
                 85                   90                   95 gtg gga tca cct aca tca aaa gtt caa aat gaa gga aaa ttt gtt cat     336
Val Gly Ser Pro Thr Ser Lys Val Gln Asn Glu Gly Lys Phe Val His
            100                  105                  110 cat acg ctg gct gac ggt gat ttt aaa cac ttt atg aaa atg cac gaa     384
His Thr Leu Ala Asp Gly Asp Phe Lys His Phe Met Lys Met His Glu
            115                  120                  125 cct gtt aca gca gct cga act tta ctg aca gca gaa aat gca acc gtt     432
Pro Val Thr Ala Ala Arg Thr Leu Leu Thr Ala Glu Asn Ala Thr Val
        130                  135                  140 gaa att gac cga gta ctt tct gca cta tta aaa gaa aga aaa cct gtc     480
Glu Ile Asp Arg Val Leu Ser Ala Leu Leu Lys Glu Arg Lys Pro Val
145                  150                  155                  160 tat atc aac tta cca gtt gat gtt gct gct gca aaa gca gag aaa ccc     528
Tyr Ile Asn Leu Pro Val Asp Val Ala Ala Ala Lys Ala Glu Lys Pro
                165                  170                  175 tca ctc cct ttg aaa aaa gaa aac tca act tca aat aca agt gac caa     576
Ser Leu Pro Leu Lys Lys Glu Asn Ser Thr Ser Asn Thr Ser Asp Gln
            180                  185                  190 gag atc ttg aac aaa att caa gaa agc ttg aaa aat gcc aaa aaa cca     624
Glu Ile Leu Asn Lys Ile Gln Glu Ser Leu Lys Asn Ala Lys Lys Pro
        195                  200                  205 atc gtg att aca gga cat gaa ata att agt ttt ggc tta gaa aaa aca     672
Ile Val Ile Thr Gly His Glu Ile Ile Ser Phe Gly Leu Glu Lys Thr
        210                  215                  220 gtc tct caa ttt att tca aag aca aaa cta cct att acg aca tta aac     720
Val Ser Gln Phe Ile Ser Lys Thr Lys Leu Pro Ile Thr Thr Leu Asn
225                  230                  235                  240 ttt gga aaa agt tca gtt gat gaa gct ctc cct tca ttt tta gga atc     768
Phe Gly Lys Ser Ser Val Asp Glu Ala Leu Pro Ser Phe Leu Gly Ile
                245                  250                  255 tat aat ggt aaa ctc tca gag cct aat ctt aaa gaa ttc gtg gaa tca     816
Tyr Asn Gly Lys Leu Ser Glu Pro Asn Leu Lys Glu Phe Val Glu Ser
            260                  265                  270 gcc gac ttc atc ctg atg ctt gga gtt aaa ctc aca gac tct tca aca     864
Ala Asp Phe Ile Leu Met Leu Gly Val Lys Leu Thr Asp Ser Ser Thr
        275                  280                  285 gga gcc ttc act cat cat tta aat gaa aat aaa atg att tca ctg aat     912
Gly Ala Phe Thr His His Leu Asn Glu Asn Lys Met Ile Ser Leu Asn
        290                  295                  300 ata gat gaa gga aaa ata ttt aac gaa agc atc caa aat ttt gat ttt     960
Ile Asp Glu Gly Lys Ile Phe Asn Glu Ser Ile Gln Asn Phe Asp Phe
305                  310                  315                  320 gaa tcc ctc atc tcc tct ctc tta gac cta agc gaa ata gaa tac aaa    1008
Glu Ser Leu Ile Ser Ser Leu Leu Asp Leu Ser Glu Ile Glu Tyr Lys
                325                  330                  335 gga aaa tat atc gat aaa aag caa gaa gac ttt gtt cca tca aat gcg    1056
Gly Lys Tyr Ile Asp Lys Lys Gln Glu Asp Phe Val Pro Ser Asn Ala
            340                  345                  350 ctt tta tca caa gac cgc cta tgg caa gca gtt gaa aac cta act caa    1104
Leu Leu Ser Gln Asp Arg Leu Trp Gln Ala Val Glu Asn Leu Thr Gln
```

```
                355                 360                 365
agc aat gaa aca atc gtt gct gaa caa ggg aca tca ttc ctg ggc gct       1152
Ser Asn Glu Thr Ile Val Ala Glu Gln Gly Thr Ser Phe Leu Gly Ala
370                 375                 380 tca tca att ttc tta aaa cca aag agt cat ttt att ggt caa ccc tta       1200
Ser Ser Ile Phe Leu Lys Pro Lys Ser His Phe Ile Gly Gln Pro Leu
385                 390                 395                 400 tgg gga tca att gga tat aca ttc cca gca gca tta gga agc caa att       1248
Trp Gly Ser Ile Gly Tyr Thr Phe Pro Ala Ala Leu Gly Ser Gln Ile
            405                 410                 415 gca gat aaa gaa agc aga cac ctt tta ttt att ggt gat ggt tca ctt       1296
Ala Asp Lys Glu Ser Arg His Leu Leu Phe Ile Gly Asp Gly Ser Leu
420                 425                 430 caa ctt acg gtg caa gaa tta gga tta gca atc aga gaa aaa att aat       1344
Gln Leu Thr Val Gln Glu Leu Gly Leu Ala Ile Arg Glu Lys Ile Asn
            435                 440                 445 cca att tgc ttt att atc aat aat gat ggt tat aca gcc gaa aga gaa       1392
Pro Ile Cys Phe Ile Ile Asn Asn Asp Gly Tyr Thr Ala Glu Arg Glu
450                 455                 460 att cat gga cca aat caa agc tac aat gat att cca atg tgg aat tac       1440
Ile His Gly Pro Asn Gln Ser Tyr Asn Asp Ile Pro Met Trp Asn Tyr
465                 470                 475                 480 tca aaa tta cca gaa tca ttt gga gca aca gaa gaa cga gta gtc tcg       1488
Ser Lys Leu Pro Glu Ser Phe Gly Ala Thr Glu Glu Arg Val Val Ser
            485                 490                 495 aaa atc gtt aga act gaa aat gaa ttt gtg tct gtc atg aaa gaa gct       1536
Lys Ile Val Arg Thr Glu Asn Glu Phe Val Ser Val Met Lys Glu Ala
                500                 505                 510 caa gca gat cca aat aga atg tac tgg att gag tta att ttg gca aaa       1584
Gln Ala Asp Pro Asn Arg Met Tyr Trp Ile Glu Leu Ile Leu Ala Lys
            515                 520                 525 gaa gat gca cca aaa gta ctg aaa aaa atg ggc aaa cta ttt gct gaa       1632
Glu Asp Ala Pro Lys Val Leu Lys Lys Met Gly Lys Leu Phe Ala Glu
530                 535                 540 caa aat aaa tca taa                                                   1647
Gln Asn Lys Ser
545

<210> SEQ ID NO 28
<211> LENGTH: 548
<212> TYPE: PRT
<213> ORGANISM: Artificial Sequence
<220> FEATURE:
<223> OTHER INFORMATION: Synthetic Construct

<400> SEQUENCE: 28

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110
```

```
His Thr Leu Ala Asp Gly Asp Phe Lys His Phe Met Lys Met His Glu
            115                 120                 125

Pro Val Thr Ala Ala Arg Thr Leu Leu Thr Ala Glu Asn Ala Thr Val
        130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Lys Ala Glu Lys Pro
                165                 170                 175

Ser Leu Pro Leu Lys Lys Glu Asn Ser Thr Ser Asn Thr Ser Asp Gln
                180                 185                 190

Glu Ile Leu Asn Lys Ile Gln Glu Ser Leu Lys Asn Ala Lys Lys Pro
                195                 200                 205

Ile Val Ile Thr Gly His Glu Ile Ile Ser Phe Gly Leu Glu Lys Thr
        210                 215                 220

Val Ser Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Lys Leu Ser Glu Pro Asn Leu Lys Glu Phe Val Glu Ser
                260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
        290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
                340                 345                 350

Leu Leu Ser Gln Asp Arg Leu Trp Gln Ala Val Glu Asn Leu Thr Gln
                355                 360                 365

Ser Asn Glu Thr Ile Val Ala Glu Gln Gly Thr Ser Phe Leu Gly Ala
        370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
                420                 425                 430

Gln Leu Thr Val Gln Glu Leu Gly Leu Ala Ile Arg Glu Lys Ile Asn
                435                 440                 445

Pro Ile Cys Phe Ile Ile Asn Asn Asp Gly Tyr Thr Ala Glu Arg Glu
        450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Arg Val Val Ser
                485                 490                 495

Lys Ile Val Arg Thr Glu Asn Glu Phe Val Ser Val Met Lys Glu Ala
                500                 505                 510

Gln Ala Asp Pro Asn Arg Met Tyr Trp Ile Glu Leu Ile Leu Ala Lys
                515                 520                 525

Glu Asp Ala Pro Lys Val Leu Lys Lys Met Gly Lys Leu Phe Ala Glu
```

Gln Asn Lys Ser
545

<210> SEQ ID NO 29
<211> LENGTH: 37
<212> TYPE: DNA
<213> ORGANISM: Artificial Sequence
<220> FEATURE:
<223> OTHER INFORMATION: Oligonucleotide primer (thr_accfwd)

<400> SEQUENCE: 29
tcaggtacca tgcgagtgtt gaagttcggc ggtacat                      37

<210> SEQ ID NO 30
<211> LENGTH: 39
<212> TYPE: DNA
<213> ORGANISM: Artificial Sequence
<220> FEATURE:
<223> OTHER INFORMATION: Oligonucleotide Primer (thr_hindrev)

<400> SEQUENCE: 30
tcaaagcttt tactgatgat tcatcatcaa tttacgcaa                    39

<210> SEQ ID NO 31
<211> LENGTH: 35
<212> TYPE: DNA
<213> ORGANISM: Artificial Sequence
<220> FEATURE:
<223> OTHER INFORMATION: Oligonucleotide Primer (SalI_remove)

<400> SEQUENCE: 31
ccagcccacg gtcggtggac ttactgttta gtcag                        35

<210> SEQ ID NO 32
<211> LENGTH: 35
<212> TYPE: DNA
<213> ORGANISM: Artificial Sequence
<220> FEATURE:
<223> OTHER INFORMATION: Oligonucleotide Primer (SalI_remove_rev)

<400> SEQUENCE: 32
ctgactaaac agtaagtcca ccgaccgtgg gctgg                        35

<210> SEQ ID NO 33
<211> LENGTH: 33
<212> TYPE: DNA
<213> ORGANISM: Artificial Sequence
<220> FEATURE:
<223> OTHER INFORMATION: Oligonucleotide Primer (TGins_fwd_sap)

<400> SEQUENCE: 33
gcatcgctct tctgtgactg gcagcaacac tgc                          33

<210> SEQ ID NO 34
<211> LENGTH: 40
<212> TYPE: DNA
<213> ORGANISM: Artificial Sequence
<220> FEATURE:
<223> OTHER INFORMATION: Oligonucleotide Primer (TGins_rev_sap)

<400> SEQUENCE: 34
gcatcgctct tctcacattg atttaacggc tgctgtaatg                   40

<210> SEQ ID NO 35
<211> LENGTH: 47

```
<212> TYPE: DNA
<213> ORGANISM: Artificial Sequence
<220> FEATURE:
<223> OTHER INFORMATION: Oligonucleotide Primer (ilvG_fwd_SalI)

<400> SEQUENCE: 35
ctagctgtcg acaggagaaa ggtaccatga atggcgcaca gtgggtg                    47

<210> SEQ ID NO 36
<211> LENGTH: 35
<212> TYPE: DNA
<213> ORGANISM: Artificial Sequence
<220> FEATURE:
<223> OTHER INFORMATION: Oligonucleotide Primer (IlvM_rev_SalI)

<400> SEQUENCE: 36
ctagctgtcg actcaggcgc ggatttgttg tgatg                                 35

<210> SEQ ID NO 37
<211> LENGTH: 55
<212> TYPE: DNA
<213> ORGANISM: Artificial Sequence
<220> FEATURE:
<223> OTHER INFORMATION: Oligonucleotide Primer (adh6_sphfwd)

<400> SEQUENCE: 37
ctagctgcat gcaggagata taccatgtct tatcctgaga aatttgaagg tatcg           55

<210> SEQ ID NO 38
<211> LENGTH: 41
<212> TYPE: DNA
<213> ORGANISM: Artificial Sequence
<220> FEATURE:
<223> OTHER INFORMATION: Oligonucleotide Primer (adh6_xbarev)

<400> SEQUENCE: 38
ctagcttcta gactagtctg aaaattcttt gtcgtagccg a                          41

<210> SEQ ID NO 39
<211> LENGTH: 41
<212> TYPE: DNA
<213> ORGANISM: Artificial Sequence
<220> FEATURE:
<223> OTHER INFORMATION: Oligonucleotide Primer (leu_accfwd)

<400> SEQUENCE: 39
gcatcggtac catgagccag caagtcatta ttttcgatac c                          41

<210> SEQ ID NO 40
<211> LENGTH: 55
<212> TYPE: DNA
<213> ORGANISM: Artificial Sequence
<220> FEATURE:
<223> OTHER INFORMATION: Oligonucleotide Primer (leu_accrev)

<400> SEQUENCE: 40
gcatcggtac ctttctcctc tgcagttaat tcataaacgc aggttgtttt gcttc           55

<210> SEQ ID NO 41
<211> LENGTH: 39
<212> TYPE: DNA
<213> ORGANISM: Artificial Sequence
<220> FEATURE:
<223> OTHER INFORMATION: Oligonucleotide Primer (V461A)

<400> SEQUENCE: 41
caataatgat ggttatacag ccgaaagaga aattcatgg                             39
```

<210> SEQ ID NO 42
<211> LENGTH: 39
<212> TYPE: DNA
<213> ORGANISM: Artificial Sequence
<220> FEATURE:
<223> OTHER INFORMATION: Oligonucleotide Primer (V461A_rev)

<400> SEQUENCE: 42
ccatgaattt ctctttcggc tgtataacca tcattattg                                    39

<210> SEQ ID NO 43
<211> LENGTH: 56
<212> TYPE: DNA
<213> ORGANISM: Artificial Sequence
<220> FEATURE:
<223> OTHER INFORMATION: Olignucleotide Primer (M538A)

<400> SEQUENCE: 43
gatgcaccaa aagtactgaa aaaagcgggc aaactatttg ctgaacaaaa taaatc                  56

<210> SEQ ID NO 44
<211> LENGTH: 56
<212> TYPE: DNA
<213> ORGANISM: Artificial Sequence
<220> FEATURE:
<223> OTHER INFORMATION: Oligonucleotide Primer (M538A_rev)

<400> SEQUENCE: 44
gatttatttt gttcagcaaa tagtttgccc gcttttttca gtactttggt gcatc                   56

<210> SEQ ID NO 45
<211> LENGTH: 56
<212> TYPE: DNA
<213> ORGANISM: Artificial Sequence
<220> FEATURE:
<223> OTHER INFORMATION: Oligonucleotide Primer (M538L)

<400> SEQUENCE: 45
gatgcaccaa aagtactgaa aaaactgggc aaactatttg ctgaacaaaa taaatc                  56

<210> SEQ ID NO 46
<211> LENGTH: 56
<212> TYPE: DNA
<213> ORGANISM: Artificial Sequence
<220> FEATURE:
<223> OTHER INFORMATION: Oligonucleotide Primer (M538L_rev)

<400> SEQUENCE: 46
gatttatttt gttcagcaaa tagtttgccc agttttttca gtactttggt gcatc                   56

<210> SEQ ID NO 47
<211> LENGTH: 46
<212> TYPE: DNA
<213> ORGANISM: Artificial Sequence
<220> FEATURE:
<223> OTHER INFORMATION: Oligonucleotide Primer (F381A)

<400> SEQUENCE: 47
gttgctgaac aagggacatc agcgtttggc gcttcatcaa ttttct                             46

<210> SEQ ID NO 48
<211> LENGTH: 46
<212> TYPE: DNA
<213> ORGANISM: Artificial Sequence
<220> FEATURE:
<223> OTHER INFORMATION: Oligonucleotide Primer (F381A_rev)

<400> SEQUENCE: 48
agaaaattga tgaagcgcca aacgctgatg tcccttgttc agcaac　　　　　　　46

<210> SEQ ID NO 49
<211> LENGTH: 46
<212> TYPE: DNA
<213> ORGANISM: Artificial Sequence
<220> FEATURE:
<223> OTHER INFORMATION: Oligonucleotide Primer (F381L)

<400> SEQUENCE: 49
gttgctgaac aagggacatc actgtttggc gcttcatcaa ttttct　　　　　　　46

<210> SEQ ID NO 50
<211> LENGTH: 46
<212> TYPE: DNA
<213> ORGANISM: Artificial Sequence
<220> FEATURE:
<223> OTHER INFORMATION: Oligonucleotide Primer (F381L_rev)

<400> SEQUENCE: 50
agaaaattga tgaagcgcca aacagtgatg tcccttgttc agcaac　　　　　　　46

<210> SEQ ID NO 51
<211> LENGTH: 42
<212> TYPE: DNA
<213> ORGANISM: Artificial Sequence
<220> FEATURE:
<223> OTHER INFORMATION: Oligonucleotide Primer (G462D)

<400> SEQUENCE: 51
cacggtaaag atgcgctgga tcaggtggat atcgtcgcta ac　　　　　　　　　42

<210> SEQ ID NO 52
<211> LENGTH: 42
<212> TYPE: DNA
<213> ORGANISM: Artificial Sequence
<220> FEATURE:
<223> OTHER INFORMATION: Oligonucleotide Primer (G462D_rev)

<400> SEQUENCE: 52
gttagcgacg atatccacct gatccagcgc atctttaccg tg　　　　　　　　　42

<210> SEQ ID NO 53
<211> LENGTH: 40
<212> TYPE: DNA
<213> ORGANISM: Artificial Sequence
<220> FEATURE:
<223> OTHER INFORMATION: Oligonucleotide Primer (S139G)

<400> SEQUENCE: 53
ccgatgatgt tgaatttggt tgcgaagatg ccgggcgtac　　　　　　　　　　40

<210> SEQ ID NO 54
<211> LENGTH: 40
<212> TYPE: DNA
<213> ORGANISM: Artificial Sequence
<220> FEATURE:
<223> OTHER INFORMATION: Oligonucleotide Primer (S139G_rev)

<400> SEQUENCE: 54
gtacgcccgg catcttcgca accaaattca acatcatcgg　　　　　　　　　　40

<210> SEQ ID NO 55
<211> LENGTH: 41

```
<212> TYPE: DNA
<213> ORGANISM: Artificial Sequence
<220> FEATURE:
<223> OTHER INFORMATION: Oligonucleotide Primer

<400> SEQUENCE: 55
gtcgccgaag ccttccgtat tgcgaccttt attgccactt c                    41

<210> SEQ ID NO 56
<211> LENGTH: 41
<212> TYPE: DNA
<213> ORGANISM: Artificial Sequence
<220> FEATURE:
<223> OTHER INFORMATION: Oligonucleotide Primer (H97A_rev)

<400> SEQUENCE: 56
gaagtggcaa taaaggtcgc aatacggaag gcttcggcga c                    41

<210> SEQ ID NO 57
<211> LENGTH: 41
<212> TYPE: DNA
<213> ORGANISM: Artificial Sequence
<220> FEATURE:
<223> OTHER INFORMATION: Oligonucleotide Primer (H97L)

<400> SEQUENCE: 57
gtcgccgaag ccttccgtat tctgaccttt attgccactt c                    41

<210> SEQ ID NO 58
<211> LENGTH: 41
<212> TYPE: DNA
<213> ORGANISM: Artificial Sequence
<220> FEATURE:
<223> OTHER INFORMATION: Oligonucleotide Primer (H97L_rev)

<400> SEQUENCE: 58
gaagtggcaa taaaggtcag aatacggaag gcttcggcga c                    41

<210> SEQ ID NO 59
<211> LENGTH: 36
<212> TYPE: DNA
<213> ORGANISM: Artificial Sequence
<220> FEATURE:
<223> OTHER INFORMATION: Oligonucleotide Primer (N167A)

<400> SEQUENCE: 59
ccggtgccac caccatcgcg attccggaca ccgtgg                          36

<210> SEQ ID NO 60
<211> LENGTH: 36
<212> TYPE: DNA
<213> ORGANISM: Artificial Sequence
<220> FEATURE:
<223> OTHER INFORMATION: Oligonucleotide Primer (N167A_rev)

<400> SEQUENCE: 60
ccacggtgtc cggaatcgcg atggtggtgg caccgg                          36

<210> SEQ ID NO 61
<211> LENGTH: 36
<212> TYPE: DNA
<213> ORGANISM: Artificial Sequence
<220> FEATURE:
<223> OTHER INFORMATION: Oligonucleotide Primer (N167L)

<400> SEQUENCE: 61
ccggtgccac caccatcctg attccggaca ccgtgg                          36
```

<210> SEQ ID NO 62
<211> LENGTH: 36
<212> TYPE: DNA
<213> ORGANISM: Artificial Sequence
<220> FEATURE:
<223> OTHER INFORMATION: Oligonucleotide Primer (N167L_rev)

<400> SEQUENCE: 62
ccacggtgtc cggaatcagg atggtggtgg caccgg                               36

<210> SEQ ID NO 63
<211> LENGTH: 54
<212> TYPE: DNA
<213> ORGANISM: Artificial Sequence
<220> FEATURE:
<223> OTHER INFORMATION: Oligonucleotide Primer (hiskivd_tevfwd)

<400> SEQUENCE: 63
cgggatccga aaacctgtat tttcagggaa tgtatacagt aggagattac ctat           54

<210> SEQ ID NO 64
<211> LENGTH: 39
<212> TYPE: DNA
<213> ORGANISM: Artificial Sequence
<220> FEATURE:
<223> OTHER INFORMATION: Oligonucleotide Primer (hiskivd_bamrev)

<400> SEQUENCE: 64
cgggatcctt atgatttatt ttgttcagca aatagtttg                            39

<210> SEQ ID NO 65
<211> LENGTH: 60
<212> TYPE: DNA
<213> ORGANISM: Artificial Sequence
<220> FEATURE:
<223> OTHER INFORMATION: Oligonucleotide Primer (hisadh_tevfwd)

<400> SEQUENCE: 65
cgggatccga aaacctgtat tttcagggaa tgtcttatcc tgagaaattt gaaggtatcg     60

<210> SEQ ID NO 66
<211> LENGTH: 34
<212> TYPE: DNA
<213> ORGANISM: Artificial Sequence
<220> FEATURE:
<223> OTHER INFORMATION: Oligonucleotide Primer (hisadh_bamrev)

<400> SEQUENCE: 66
cgggatccct agtctgaaaa ttctttgtcg tagc                                 34

<210> SEQ ID NO 67
<211> LENGTH: 54
<212> TYPE: DNA
<213> ORGANISM: Artificial Sequence
<220> FEATURE:
<223> OTHER INFORMATION: Oligonucleotide Primer (hisleua_tevfwd)

<400> SEQUENCE: 67
cgggatccga aaacctgtat tttcagggaa tgagccagca agtcattatt ttcg           54

<210> SEQ ID NO 68
<211> LENGTH: 32
<212> TYPE: DNA
<213> ORGANISM: Artificial Sequence
<220> FEATURE:
<223> OTHER INFORMATION: Oligonucleotide Primer (hisleua_bamrev)

<400> SEQUENCE: 68

```
cgggatcctc acacggtttc cttgttgttt tc                                32
```

<210> SEQ ID NO 69
<211> LENGTH: 1692
<212> TYPE: DNA
<213> ORGANISM: Saccharomyces cerevisiae
<220> FEATURE:
<221> NAME/KEY: CDS
<222> LOCATION: (1)..(1692)

<400> SEQUENCE: 69

| | | | | | | | | | | | | | | | | |
|---|---|---|---|---|---|---|---|---|---|---|---|---|---|---|---|---|
| atg | tct | gaa | att | act | ctt | gga | aaa | tac | tta | ttt | gaa | aga | ttg | aag | caa | 48 |
| Met | Ser | Glu | Ile | Thr | Leu | Gly | Lys | Tyr | Leu | Phe | Glu | Arg | Leu | Lys | Gln | |
| 1 | | | | 5 | | | | | 10 | | | | | 15 | | |

| gtt | aat | gtt | aac | acc | att | ttt | ggg | cta | cca | ggc | gac | ttc | aac | ttg | tcc | 96 |
|---|---|---|---|---|---|---|---|---|---|---|---|---|---|---|---|---|
| Val | Asn | Val | Asn | Thr | Ile | Phe | Gly | Leu | Pro | Gly | Asp | Phe | Asn | Leu | Ser | |
| | | | 20 | | | | | 25 | | | | | 30 | | | |

| cta | ttg | gac | aag | att | tac | gag | gta | gat | gga | ttg | aga | tgg | gct | ggt | aat | 144 |
|---|---|---|---|---|---|---|---|---|---|---|---|---|---|---|---|---|
| Leu | Leu | Asp | Lys | Ile | Tyr | Glu | Val | Asp | Gly | Leu | Arg | Trp | Ala | Gly | Asn | |
| | | 35 | | | | | 40 | | | | | 45 | | | | |

| gca | aat | gag | ctg | aac | gcc | gcc | tat | gcc | gcc | gat | ggt | tac | gca | cgc | atc | 192 |
|---|---|---|---|---|---|---|---|---|---|---|---|---|---|---|---|---|
| Ala | Asn | Glu | Leu | Asn | Ala | Ala | Tyr | Ala | Ala | Asp | Gly | Tyr | Ala | Arg | Ile | |
| 50 | | | | | 55 | | | | | 60 | | | | | | |

| aag | ggt | tta | tct | gtg | ctg | gta | act | act | ttt | ggc | gta | ggt | gaa | tta | tcc | 240 |
|---|---|---|---|---|---|---|---|---|---|---|---|---|---|---|---|---|
| Lys | Gly | Leu | Ser | Val | Leu | Val | Thr | Thr | Phe | Gly | Val | Gly | Glu | Leu | Ser | |
| 65 | | | | | 70 | | | | | 75 | | | | | 80 | |

| gcc | ttg | aat | ggt | att | gca | gga | tcg | tat | gca | gaa | cac | gtc | ggt | gta | ctg | 288 |
|---|---|---|---|---|---|---|---|---|---|---|---|---|---|---|---|---|
| Ala | Leu | Asn | Gly | Ile | Ala | Gly | Ser | Tyr | Ala | Glu | His | Val | Gly | Val | Leu | |
| | | | | 85 | | | | | 90 | | | | | 95 | | |

| cat | gtt | gtt | ggt | gtc | ccc | tct | atc | tcc | gct | cag | gct | aag | caa | ttg | ttg | 336 |
|---|---|---|---|---|---|---|---|---|---|---|---|---|---|---|---|---|
| His | Val | Val | Gly | Val | Pro | Ser | Ile | Ser | Ala | Gln | Ala | Lys | Gln | Leu | Leu | |
| | | | 100 | | | | | 105 | | | | | 110 | | | |

| ttg | cat | cat | acc | ttg | ggt | aac | ggt | gat | ttt | acc | gtt | ttt | cac | aga | atg | 384 |
|---|---|---|---|---|---|---|---|---|---|---|---|---|---|---|---|---|
| Leu | His | His | Thr | Leu | Gly | Asn | Gly | Asp | Phe | Thr | Val | Phe | His | Arg | Met | |
| | | 115 | | | | | 120 | | | | | 125 | | | | |

| tcc | gcc | aat | atc | tca | gaa | act | aca | tca | atg | att | aca | gac | att | gct | aca | 432 |
|---|---|---|---|---|---|---|---|---|---|---|---|---|---|---|---|---|
| Ser | Ala | Asn | Ile | Ser | Glu | Thr | Thr | Ser | Met | Ile | Thr | Asp | Ile | Ala | Thr | |
| 130 | | | | | 135 | | | | | 140 | | | | | | |

| gcc | cct | tca | gaa | atc | gat | agg | ttg | atc | agg | aca | aca | ttt | ata | aca | caa | 480 |
|---|---|---|---|---|---|---|---|---|---|---|---|---|---|---|---|---|
| Ala | Pro | Ser | Glu | Ile | Asp | Arg | Leu | Ile | Arg | Thr | Thr | Phe | Ile | Thr | Gln | |
| 145 | | | | | 150 | | | | | 155 | | | | | 160 | |

| agg | cct | agc | tac | ttg | ggg | ttg | cca | gcg | aat | ttg | gta | gat | cta | aag | gtt | 528 |
|---|---|---|---|---|---|---|---|---|---|---|---|---|---|---|---|---|
| Arg | Pro | Ser | Tyr | Leu | Gly | Leu | Pro | Ala | Asn | Leu | Val | Asp | Leu | Lys | Val | |
| | | | | 165 | | | | | 170 | | | | | 175 | | |

| cct | ggt | tct | ctt | ttg | gaa | aaa | ccg | att | gat | cta | tca | tta | aaa | cct | aac | 576 |
|---|---|---|---|---|---|---|---|---|---|---|---|---|---|---|---|---|
| Pro | Gly | Ser | Leu | Leu | Glu | Lys | Pro | Ile | Asp | Leu | Ser | Leu | Lys | Pro | Asn | |
| | | | 180 | | | | | 185 | | | | | 190 | | | |

| gat | ccc | gaa | gct | gaa | aag | gaa | gtt | att | gat | acc | gta | cta | gaa | ttg | atc | 624 |
|---|---|---|---|---|---|---|---|---|---|---|---|---|---|---|---|---|
| Asp | Pro | Glu | Ala | Glu | Lys | Glu | Val | Ile | Asp | Thr | Val | Leu | Glu | Leu | Ile | |
| | | 195 | | | | | 200 | | | | | 205 | | | | |

| cag | aat | tcg | aaa | aac | cct | gtt | ata | cta | tcg | gat | gcc | tgt | gct | tct | agg | 672 |
|---|---|---|---|---|---|---|---|---|---|---|---|---|---|---|---|---|
| Gln | Asn | Ser | Lys | Asn | Pro | Val | Ile | Leu | Ser | Asp | Ala | Cys | Ala | Ser | Arg | |
| 210 | | | | | 215 | | | | | 220 | | | | | | |

| cac | aac | gtt | aaa | aaa | gaa | acc | cag | aag | tta | att | gat | ttg | acg | caa | ttc | 720 |
|---|---|---|---|---|---|---|---|---|---|---|---|---|---|---|---|---|
| His | Asn | Val | Lys | Lys | Glu | Thr | Gln | Lys | Leu | Ile | Asp | Leu | Thr | Gln | Phe | |
| 225 | | | | | 230 | | | | | 235 | | | | | 240 | |

| cca | gct | ttt | gtg | aca | cct | cta | ggt | aaa | ggg | tca | ata | gat | gaa | cag | cat | 768 |
|---|---|---|---|---|---|---|---|---|---|---|---|---|---|---|---|---|
| Pro | Ala | Phe | Val | Thr | Pro | Leu | Gly | Lys | Gly | Ser | Ile | Asp | Glu | Gln | His | |
| | | | | 245 | | | | | 250 | | | | | 255 | | |

```
ccc aga tat ggc ggt gtt tat gtg gga acg ctg tcc aaa caa gac gtg      816
Pro Arg Tyr Gly Gly Val Tyr Val Gly Thr Leu Ser Lys Gln Asp Val
            260                 265                 270 aaa cag gcc gtt gag tcg gct gat ttg atc ctt tcg gtc ggt gct ttg      864
Lys Gln Ala Val Glu Ser Ala Asp Leu Ile Leu Ser Val Gly Ala Leu
        275                 280                 285 ctc tct gat ttt aac aca ggt tcg ttt tcc tac tcc tac aag act aaa      912
Leu Ser Asp Phe Asn Thr Gly Ser Phe Ser Tyr Ser Tyr Lys Thr Lys
    290                 295                 300 aat gta gtg gag ttt cat tcc gat tac gta aag gtg aag aac gct acg      960
Asn Val Val Glu Phe His Ser Asp Tyr Val Lys Val Lys Asn Ala Thr
305                 310                 315                 320 ttc ctc ggt gta caa atg aaa ttt gca cta caa aac tta ctg aag gtt     1008
Phe Leu Gly Val Gln Met Lys Phe Ala Leu Gln Asn Leu Leu Lys Val
                325                 330                 335 att ccc gat gtt gtt aag ggc tac aag agc gtt ccc gta cca acc aaa     1056
Ile Pro Asp Val Val Lys Gly Tyr Lys Ser Val Pro Val Pro Thr Lys
            340                 345                 350 act ccc gca aac aaa ggt gta cct gct agc acg ccc ttg aaa caa gag     1104
Thr Pro Ala Asn Lys Gly Val Pro Ala Ser Thr Pro Leu Lys Gln Glu
        355                 360                 365 tgg ttg tgg aac gaa ttg tcc aaa ttc ttg caa gaa ggt gat gtt atc     1152
Trp Leu Trp Asn Glu Leu Ser Lys Phe Leu Gln Glu Gly Asp Val Ile
    370                 375                 380 att tcc gag acc ggc acg tct gcc ttc ggt atc aat caa act atc ttt     1200
Ile Ser Glu Thr Gly Thr Ser Ala Phe Gly Ile Asn Gln Thr Ile Phe
385                 390                 395                 400 cct aag gac gcc tac ggt atc tcg cag gtg ttg tgg ggg tcc atc ggt     1248
Pro Lys Asp Ala Tyr Gly Ile Ser Gln Val Leu Trp Gly Ser Ile Gly
                405                 410                 415 ttt aca aca gga gca act tta ggt gct gcc ttt gcc gct gag gag att     1296
Phe Thr Thr Gly Ala Thr Leu Gly Ala Ala Phe Ala Ala Glu Glu Ile
            420                 425                 430 gac ccc aac aag aga gtc atc tta ttc ata ggt gac ggg tct ttg cag     1344
Asp Pro Asn Lys Arg Val Ile Leu Phe Ile Gly Asp Gly Ser Leu Gln
        435                 440                 445 tta acc gtc caa gaa atc tcc acc atg atc aga tgg ggg tta aag ccg     1392
Leu Thr Val Gln Glu Ile Ser Thr Met Ile Arg Trp Gly Leu Lys Pro
    450                 455                 460 tat ctt ttt gtc ctt aac aac gac ggc tac act atc gaa aag ctg att     1440
Tyr Leu Phe Val Leu Asn Asn Asp Gly Tyr Thr Ile Glu Lys Leu Ile
465                 470                 475                 480 cat ggg cct cac gca gag tac aac gaa atc cag acc tgg gat cac ctc     1488
His Gly Pro His Ala Glu Tyr Asn Glu Ile Gln Thr Trp Asp His Leu
                485                 490                 495 gcc ctg ttg ccc gca ttt ggt gcg aaa aag tac gaa aat cac aag atc     1536
Ala Leu Leu Pro Ala Phe Gly Ala Lys Lys Tyr Glu Asn His Lys Ile
            500                 505                 510 gcc act acg ggt gag tgg gat gcc tta acc act gat tca gag ttc cag     1584
Ala Thr Thr Gly Glu Trp Asp Ala Leu Thr Thr Asp Ser Glu Phe Gln
        515                 520                 525 aaa aac tcg gtg atc aga cta att gaa ctg aaa ctg ccc gtc ttt gat     1632
Lys Asn Ser Val Ile Arg Leu Ile Glu Leu Lys Leu Pro Val Phe Asp
    530                 535                 540 gct ccg gaa agt ttg atc aaa caa gcg caa ttg act gcc gct aca aat     1680
Ala Pro Glu Ser Leu Ile Lys Gln Ala Gln Leu Thr Ala Ala Thr Asn
545                 550                 555                 560 gcc aaa caa taa                                                     1692
Ala Lys Gln
```

<210> SEQ ID NO 70
<211> LENGTH: 563
<212> TYPE: PRT
<213> ORGANISM: Saccharomyces cerevisiae

<400> SEQUENCE: 70

```
Met Ser Glu Ile Thr Leu Gly Lys Tyr Leu Phe Glu Arg Leu Lys Gln
1               5                   10                  15

Val Asn Val Asn Thr Ile Phe Gly Leu Pro Gly Asp Phe Asn Leu Ser
            20                  25                  30

Leu Leu Asp Lys Ile Tyr Glu Val Asp Gly Leu Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Leu Ser Val Leu Val Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ser Met Ile Thr Asp Ile Ala Thr
    130                 135                 140

Ala Pro Ser Glu Ile Asp Arg Leu Ile Arg Thr Thr Phe Ile Thr Gln
145                 150                 155                 160

Arg Pro Ser Tyr Leu Gly Leu Pro Ala Asn Leu Val Asp Leu Lys Val
                165                 170                 175

Pro Gly Ser Leu Leu Glu Lys Pro Ile Asp Leu Ser Leu Lys Pro Asn
            180                 185                 190

Asp Pro Glu Ala Glu Lys Glu Val Ile Asp Thr Val Leu Glu Leu Ile
        195                 200                 205

Gln Asn Ser Lys Asn Pro Val Ile Leu Ser Asp Ala Cys Ala Ser Arg
    210                 215                 220

His Asn Val Lys Lys Glu Thr Gln Lys Leu Ile Asp Leu Thr Gln Phe
225                 230                 235                 240

Pro Ala Phe Val Thr Pro Leu Gly Lys Gly Ser Ile Asp Glu Gln His
                245                 250                 255

Pro Arg Tyr Gly Gly Val Tyr Val Gly Thr Leu Ser Lys Gln Asp Val
            260                 265                 270

Lys Gln Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Val Val Glu Phe His Ser Asp Tyr Val Lys Val Lys Asn Ala Thr
305                 310                 315                 320

Phe Leu Gly Val Gln Met Lys Phe Ala Leu Gln Asn Leu Leu Lys Val
                325                 330                 335

Ile Pro Asp Val Val Lys Gly Tyr Lys Ser Val Pro Val Pro Thr Lys
            340                 345                 350

Thr Pro Ala Asn Lys Gly Val Pro Ala Ser Thr Pro Leu Lys Gln Glu
        355                 360                 365

Trp Leu Trp Asn Glu Leu Ser Lys Phe Leu Gln Glu Gly Asp Val Ile
    370                 375                 380

Ile Ser Glu Thr Gly Thr Ser Ala Phe Gly Ile Asn Gln Thr Ile Phe
```

```
                385                 390                 395                 400
Pro Lys Asp Ala Tyr Gly Ile Ser Gln Val Leu Trp Gly Ser Ile Gly
                    405                 410                 415

Phe Thr Thr Gly Ala Thr Leu Gly Ala Ala Phe Ala Ala Glu Glu Ile
                420                 425                 430

Asp Pro Asn Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
        450                 455                 460

Tyr Leu Phe Val Leu Asn Asn Asp Gly Tyr Thr Ile Glu Lys Leu Ile
465                 470                 475                 480

His Gly Pro His Ala Glu Tyr Asn Glu Ile Gln Thr Trp Asp His Leu
                485                 490                 495

Ala Leu Leu Pro Ala Phe Gly Ala Lys Lys Tyr Glu Asn His Lys Ile
            500                 505                 510

Ala Thr Thr Gly Glu Trp Asp Ala Leu Thr Thr Asp Ser Glu Phe Gln
        515                 520                 525

Lys Asn Ser Val Ile Arg Leu Ile Glu Leu Lys Leu Pro Val Phe Asp
    530                 535                 540

Ala Pro Glu Ser Leu Ile Lys Gln Ala Gln Leu Thr Ala Ala Thr Asn
545                 550                 555                 560

Ala Lys Gln

<210> SEQ ID NO 71
<211> LENGTH: 1908
<212> TYPE: DNA
<213> ORGANISM: Saccharomyces cerevisiae
<220> FEATURE:
<221> NAME/KEY: CDS
<222> LOCATION: (1)..(1908)

<400> SEQUENCE: 71 atg gca cct gtt aca att gaa aag ttc gta aat caa gaa gaa cga cac      48
Met Ala Pro Val Thr Ile Glu Lys Phe Val Asn Gln Glu Glu Arg His
1               5                   10                  15 ctt gtt tcc aac cga tca gca aca att ccg ttt ggt gaa tac ata ttt      96
Leu Val Ser Asn Arg Ser Ala Thr Ile Pro Phe Gly Glu Tyr Ile Phe
            20                  25                  30 aaa aga ttg ttg tcc atc gat acg aaa tca gtt ttc ggt gtt cct ggt      144
Lys Arg Leu Leu Ser Ile Asp Thr Lys Ser Val Phe Gly Val Pro Gly
        35                  40                  45 gac ttc aac tta tct cta tta gaa tat ctc tat tca cct agt gtt gaa      192
Asp Phe Asn Leu Ser Leu Leu Glu Tyr Leu Tyr Ser Pro Ser Val Glu
    50                  55                  60 tca gct ggc cta aga tgg gtc ggc acg tgt aat gaa ctg aac gcc gct      240
Ser Ala Gly Leu Arg Trp Val Gly Thr Cys Asn Glu Leu Asn Ala Ala
65                  70                  75                  80 tat gcg gcc gac gga tat tcc cgt tac tct aat aag att ggc tgt tta      288
Tyr Ala Ala Asp Gly Tyr Ser Arg Tyr Ser Asn Lys Ile Gly Cys Leu
                85                  90                  95 ata acc acg tat ggc gtt ggt gaa tta agc gcc ttg aac ggt ata gcc      336
Ile Thr Thr Tyr Gly Val Gly Glu Leu Ser Ala Leu Asn Gly Ile Ala
            100                 105                 110 ggt tcg ttc gct gaa aat gtc aaa gtt ttg cac att gtt ggt gtg gcc      384
Gly Ser Phe Ala Glu Asn Val Lys Val Leu His Ile Val Gly Val Ala
        115                 120                 125 aag tcc ata gat tcg cgt tca agt aac ttt agt gat cgg aac cta cat      432
Lys Ser Ile Asp Ser Arg Ser Ser Asn Phe Ser Asp Arg Asn Leu His
    130                 135                 140
```

```
cat ttg gtc cca cag cta cat gat tca aat ttt aaa ggg cca aat cat    480
His Leu Val Pro Gln Leu His Asp Ser Asn Phe Lys Gly Pro Asn His
145                 150                 155                 160 aaa gta tat cat gat atg gta aaa gat aga gtc gct tgc tcg gta gcc    528
Lys Val Tyr His Asp Met Val Lys Asp Arg Val Ala Cys Ser Val Ala
                165                 170                 175 tac ttg gag gat att gaa act gca tgt gac caa gtc gat aat gtt atc    576
Tyr Leu Glu Asp Ile Glu Thr Ala Cys Asp Gln Val Asp Asn Val Ile
            180                 185                 190 cgc gat att tac aag tat tct aaa cct ggt tat att ttt gtt cct gca    624
Arg Asp Ile Tyr Lys Tyr Ser Lys Pro Gly Tyr Ile Phe Val Pro Ala
        195                 200                 205 gat ttt gcg gat atg tct gtt aca tgt gat aat ttg gtt aat gtt cca    672
Asp Phe Ala Asp Met Ser Val Thr Cys Asp Asn Leu Val Asn Val Pro
    210                 215                 220 cgt ata tct caa caa gat tgt ata gta tac cct tct gaa aac caa ttg    720
Arg Ile Ser Gln Gln Asp Cys Ile Val Tyr Pro Ser Glu Asn Gln Leu
225                 230                 235                 240 tct gac ata atc aac aag att act agt tgg ata tat tcc agt aaa aca    768
Ser Asp Ile Ile Asn Lys Ile Thr Ser Trp Ile Tyr Ser Ser Lys Thr
                245                 250                 255 cct gcg atc ctt gga gac gta ctg act gat agg tat ggt gtg agt aac    816
Pro Ala Ile Leu Gly Asp Val Leu Thr Asp Arg Tyr Gly Val Ser Asn
            260                 265                 270 ttt ttg aac aag ctt atc tgc aaa act ggg att tgg aat ttt tcc act    864
Phe Leu Asn Lys Leu Ile Cys Lys Thr Gly Ile Trp Asn Phe Ser Thr
        275                 280                 285 gtt atg gga aaa tct gta att gat gag tca aac cca act tat atg ggt    912
Val Met Gly Lys Ser Val Ile Asp Glu Ser Asn Pro Thr Tyr Met Gly
    290                 295                 300 caa tat aat ggt aaa gaa ggt tta aaa caa gtc tat gaa cat ttt gaa    960
Gln Tyr Asn Gly Lys Glu Gly Leu Lys Gln Val Tyr Glu His Phe Glu
305                 310                 315                 320 ctg tgc gac ttg gtc ttg cat ttt gga gtc gac atc aat gaa att aat   1008
Leu Cys Asp Leu Val Leu His Phe Gly Val Asp Ile Asn Glu Ile Asn
                325                 330                 335 aat ggg cat tat act ttt act tat aaa cca aat gct aaa atc att caa   1056
Asn Gly His Tyr Thr Phe Thr Tyr Lys Pro Asn Ala Lys Ile Ile Gln
            340                 345                 350 ttt cat ccg aat tat att cgc ctt gtg gac act agg cag ggc aat gag   1104
Phe His Pro Asn Tyr Ile Arg Leu Val Asp Thr Arg Gln Gly Asn Glu
        355                 360                 365 caa atg ttc aaa gga atc aat ttt gcc cct att tta aaa gaa cta tac   1152
Gln Met Phe Lys Gly Ile Asn Phe Ala Pro Ile Leu Lys Glu Leu Tyr
    370                 375                 380 aag cgc att gac gtt tct aaa ctt tct ttg caa tat gat tca aat gta   1200
Lys Arg Ile Asp Val Ser Lys Leu Ser Leu Gln Tyr Asp Ser Asn Val
385                 390                 395                 400 act caa tat acg aac gaa aca atg cgg tta gaa gat cct acc aat gga   1248
Thr Gln Tyr Thr Asn Glu Thr Met Arg Leu Glu Asp Pro Thr Asn Gly
                405                 410                 415 caa tca agc att att aca caa gtt cac tta caa aag acg atg cct aaa   1296
Gln Ser Ser Ile Ile Thr Gln Val His Leu Gln Lys Thr Met Pro Lys
            420                 425                 430 ttt ttg aac cct ggt gat gtt gtc gtt tgt gaa aca ggc tct ttt caa   1344
Phe Leu Asn Pro Gly Asp Val Val Val Cys Glu Thr Gly Ser Phe Gln
        435                 440                 445 ttc tct gtt cgt gat ttc gcg ttt cct tcg caa tta aaa tat ata tcg   1392
Phe Ser Val Arg Asp Phe Ala Phe Pro Ser Gln Leu Lys Tyr Ile Ser
    450                 455                 460
```

```
caa gga ttt ttc ctt tcc att ggc atg gcc ctt cct gcc gcc cta ggt    1440
Gln Gly Phe Phe Leu Ser Ile Gly Met Ala Leu Pro Ala Ala Leu Gly
465                 470                 475                 480 gtt gga att gcc atg caa gac cac tca aac gct cac atc aat ggt ggc    1488
Val Gly Ile Ala Met Gln Asp His Ser Asn Ala His Ile Asn Gly Gly
                485                 490                 495 aac gta aaa gag gac tat aag cca aga tta att ttg ttt gaa ggt gac    1536
Asn Val Lys Glu Asp Tyr Lys Pro Arg Leu Ile Leu Phe Glu Gly Asp
            500                 505                 510 ggt gca gca cag atg aca atc caa gaa ctg agc acc att ctg aag tgc    1584
Gly Ala Ala Gln Met Thr Ile Gln Glu Leu Ser Thr Ile Leu Lys Cys
        515                 520                 525 aat att cca cta gaa gtt atc att tgg aac aat aac ggc tac act att    1632
Asn Ile Pro Leu Glu Val Ile Ile Trp Asn Asn Asn Gly Tyr Thr Ile
    530                 535                 540 gaa aga gcc atc atg ggc cct acc agg tcg tat aac gac gtt atg tct    1680
Glu Arg Ala Ile Met Gly Pro Thr Arg Ser Tyr Asn Asp Val Met Ser
545                 550                 555                 560 tgg aaa tgg acc aaa cta ttt gaa gca ttc gga gac ttc gac gga aag    1728
Trp Lys Trp Thr Lys Leu Phe Glu Ala Phe Gly Asp Phe Asp Gly Lys
                565                 570                 575 tat act aat agc act ctc att caa tgt ccc tct aaa tta gca ctg aaa    1776
Tyr Thr Asn Ser Thr Leu Ile Gln Cys Pro Ser Lys Leu Ala Leu Lys
            580                 585                 590 ttg gag gag ctt aag aat tca aac aaa aga agc ggg ata gaa ctt tta    1824
Leu Glu Glu Leu Lys Asn Ser Asn Lys Arg Ser Gly Ile Glu Leu Leu
        595                 600                 605 gaa gtc aaa tta ggc gaa ttg gat ttc ccc gaa cag cta aag tgc atg    1872
Glu Val Lys Leu Gly Glu Leu Asp Phe Pro Glu Gln Leu Lys Cys Met
    610                 615                 620 gtt gaa gca gcg gca ctt aaa aga aat aaa aaa tag                    1908
Val Glu Ala Ala Ala Leu Lys Arg Asn Lys Lys
625                 630                 635

<210> SEQ ID NO 72
<211> LENGTH: 635
<212> TYPE: PRT
<213> ORGANISM: Saccharomyces cerevisiae

<400> SEQUENCE: 72

Met Ala Pro Val Thr Ile Glu Lys Phe Val Asn Gln Glu Glu Arg His
1               5                   10                  15

Leu Val Ser Asn Arg Ser Ala Thr Ile Pro Phe Gly Tyr Ile Phe
            20                  25                  30

Lys Arg Leu Leu Ser Ile Asp Thr Lys Ser Val Phe Gly Val Pro Gly
        35                  40                  45

Asp Phe Asn Leu Ser Leu Leu Glu Tyr Leu Tyr Ser Pro Ser Val Glu
    50                  55                  60

Ser Ala Gly Leu Arg Trp Val Gly Thr Cys Asn Glu Leu Asn Ala Ala
65                  70                  75                  80

Tyr Ala Ala Asp Gly Tyr Ser Arg Tyr Ser Asn Lys Ile Gly Cys Leu
                85                  90                  95

Ile Thr Thr Tyr Gly Val Gly Glu Leu Ser Ala Leu Asn Gly Ile Ala
            100                 105                 110

Gly Ser Phe Ala Glu Asn Val Lys Val Leu His Ile Val Gly Val Ala
        115                 120                 125

Lys Ser Ile Asp Ser Arg Ser Ser Asn Phe Ser Asp Arg Asn Leu His
    130                 135                 140
```

-continued

His Leu Val Pro Gln Leu His Asp Ser Asn Phe Lys Gly Pro Asn His
145                 150                 155                 160

Lys Val Tyr His Asp Met Val Lys Asp Arg Val Ala Cys Ser Val Ala
            165                 170                 175

Tyr Leu Glu Asp Ile Glu Thr Ala Cys Asp Gln Val Asp Asn Val Ile
            180                 185                 190

Arg Asp Ile Tyr Lys Tyr Ser Lys Pro Gly Tyr Ile Phe Val Pro Ala
            195                 200                 205

Asp Phe Ala Asp Met Ser Val Thr Cys Asp Asn Leu Val Asn Val Pro
            210                 215                 220

Arg Ile Ser Gln Gln Asp Cys Ile Val Tyr Pro Ser Glu Asn Gln Leu
225                 230                 235                 240

Ser Asp Ile Ile Asn Lys Ile Thr Ser Trp Ile Tyr Ser Ser Lys Thr
            245                 250                 255

Pro Ala Ile Leu Gly Asp Val Leu Thr Asp Arg Tyr Gly Val Ser Asn
            260                 265                 270

Phe Leu Asn Lys Leu Ile Cys Lys Thr Gly Ile Trp Asn Phe Ser Thr
            275                 280                 285

Val Met Gly Lys Ser Val Ile Asp Glu Ser Asn Pro Thr Tyr Met Gly
            290                 295                 300

Gln Tyr Asn Gly Lys Glu Gly Leu Lys Gln Val Tyr Glu His Phe Glu
305                 310                 315                 320

Leu Cys Asp Leu Val Leu His Phe Gly Val Asp Ile Asn Glu Ile Asn
            325                 330                 335

Asn Gly His Tyr Thr Phe Thr Tyr Lys Pro Asn Ala Lys Ile Ile Gln
            340                 345                 350

Phe His Pro Asn Tyr Ile Arg Leu Val Asp Thr Arg Gln Gly Asn Glu
            355                 360                 365

Gln Met Phe Lys Gly Ile Asn Phe Ala Pro Ile Leu Lys Glu Leu Tyr
            370                 375                 380

Lys Arg Ile Asp Val Ser Lys Leu Ser Leu Gln Tyr Asp Ser Asn Val
385                 390                 395                 400

Thr Gln Tyr Thr Asn Glu Thr Met Arg Leu Glu Asp Pro Thr Asn Gly
            405                 410                 415

Gln Ser Ser Ile Ile Thr Gln Val His Leu Gln Lys Thr Met Pro Lys
            420                 425                 430

Phe Leu Asn Pro Gly Asp Val Val Cys Glu Thr Gly Ser Phe Gln
            435                 440                 445

Phe Ser Val Arg Asp Phe Ala Phe Pro Ser Gln Leu Lys Tyr Ile Ser
            450                 455                 460

Gln Gly Phe Phe Leu Ser Ile Gly Met Ala Leu Pro Ala Ala Leu Gly
465                 470                 475                 480

Val Gly Ile Ala Met Gln Asp His Ser Asn Ala His Ile Asn Gly Gly
            485                 490                 495

Asn Val Lys Glu Asp Tyr Lys Pro Arg Leu Ile Leu Phe Glu Gly Asp
            500                 505                 510

Gly Ala Ala Gln Met Thr Ile Gln Glu Leu Ser Thr Ile Leu Lys Cys
            515                 520                 525

Asn Ile Pro Leu Glu Val Ile Ile Trp Asn Asn Gly Tyr Thr Ile
            530                 535                 540

Glu Arg Ala Ile Met Gly Pro Thr Arg Ser Tyr Asn Asp Val Met Ser
545                 550                 555                 560

Trp Lys Trp Thr Lys Leu Phe Glu Ala Phe Gly Asp Phe Asp Gly Lys
            565                 570                 575

```
Tyr Thr Asn Ser Thr Leu Ile Gln Cys Pro Ser Lys Leu Ala Leu Lys
            580                 585                 590
Leu Glu Glu Leu Lys Asn Ser Asn Lys Arg Ser Gly Ile Glu Leu Leu
        595                 600                 605
Glu Val Lys Leu Gly Glu Leu Asp Phe Pro Gln Leu Lys Cys Met
610                 615                 620
Val Glu Ala Ala Ala Leu Lys Arg Asn Lys Lys
625                 630                 635

<210> SEQ ID NO 73
<211> LENGTH: 1830
<212> TYPE: DNA
<213> ORGANISM: Saccharomyces cerevisiae
<220> FEATURE:
<221> NAME/KEY: CDS
<222> LOCATION: (1)..(1830)

<400> SEQUENCE: 73
```

| Codons | AA | # |
|---|---|---|
| atg aat tct agc tat aca cag aga tat gca ctg ccg aag tgt ata gca | Met Asn Ser Ser Tyr Thr Gln Arg Tyr Ala Leu Pro Lys Cys Ile Ala | 48 |
| | 1           5                  10                  15 | |
| ata tca gat tat ctt ttc cat cgg ctc aac cag ctg aac ata cat acc | Ile Ser Asp Tyr Leu Phe His Arg Leu Asn Gln Leu Asn Ile His Thr | 96 |
| | 20                  25                  30 | |
| ata ttt gga ctc tcc gga gaa ttt agc atg ccg ttg ctg gat aaa cta | Ile Phe Gly Leu Ser Gly Glu Phe Ser Met Pro Leu Leu Asp Lys Leu | 144 |
| | 35                  40                  45 | |
| tac aac att ccg aac tta cga tgg gcc ggt aat tct aat gag tta aat | Tyr Asn Ile Pro Asn Leu Arg Trp Ala Gly Asn Ser Asn Glu Leu Asn | 192 |
| | 50                  55                  60 | |
| gct gcc tac gca gca gat gga tac tca cga cta aaa ggc ttg gga tgt | Ala Ala Tyr Ala Ala Asp Gly Tyr Ser Arg Leu Lys Gly Leu Gly Cys | 240 |
| | 65                  70                  75                  80 | |
| ctc ata aca acc ttt ggt gta ggc gaa tta tcg gca atc aat ggc gtg | Leu Ile Thr Thr Phe Gly Val Gly Glu Leu Ser Ala Ile Asn Gly Val | 288 |
| | 85                  90                  95 | |
| gcc gga tct tac gct gaa cat gta gga ata ctt cac ata gtg ggt atg | Ala Gly Ser Tyr Ala Glu His Val Gly Ile Leu His Ile Val Gly Met | 336 |
| | 100                 105                 110 | |
| ccg cca aca agt gca caa acg aaa caa cta cta ctg cat cat act ctg | Pro Pro Thr Ser Ala Gln Thr Lys Gln Leu Leu Leu His His Thr Leu | 384 |
| | 115                 120                 125 | |
| ggc aat ggt gat ttc acg gta ttt cat aga ata gcc agt gat gta gca | Gly Asn Gly Asp Phe Thr Val Phe His Arg Ile Ala Ser Asp Val Ala | 432 |
| | 130                 135                 140 | |
| tgc tat aca aca ttg att att gac tct gaa tta tgt gcc gac gaa gtc | Cys Tyr Thr Thr Leu Ile Ile Asp Ser Glu Leu Cys Ala Asp Glu Val | 480 |
| 145                 150                 155                 160 | | |
| gat aag tgc atc aaa aag gct tgg ata gaa cag agg cca gta tac atg | Asp Lys Cys Ile Lys Lys Ala Trp Ile Glu Gln Arg Pro Val Tyr Met | 528 |
| | 165                 170                 175 | |
| ggc atg cct gtc aac cag gta aat ctc ccg att gaa tca gca agg ctt | Gly Met Pro Val Asn Gln Val Asn Leu Pro Ile Glu Ser Ala Arg Leu | 576 |
| | 180                 185                 190 | |
| aat aca cct ctg gat tta caa ttg cat aaa aac gac cca gac gta gag | Asn Thr Pro Leu Asp Leu Gln Leu His Lys Asn Asp Pro Asp Val Glu | 624 |
| | 195                 200                 205 | |
| aaa gaa gtt att tct cga ata ttg agt ttt ata tac aaa agc cag aat | Lys Glu Val Ile Ser Arg Ile Leu Ser Phe Ile Tyr Lys Ser Gln Asn | 672 |
| | 210                 215                 220 | |

```
ccg gca atc atc gta gat gca tgt act agt cga cag aat tta atc gag    720
Pro Ala Ile Ile Val Asp Ala Cys Thr Ser Arg Gln Asn Leu Ile Glu
225             230                 235                 240 gag act aaa gag ctt tgt aat agg ctt aaa ttt cca gtt ttt gtt aca    768
Glu Thr Lys Glu Leu Cys Asn Arg Leu Lys Phe Pro Val Phe Val Thr
            245                 250                 255 cct atg ggt aag ggt aca gta aac gaa aca gac ccg caa ttt ggg ggc    816
Pro Met Gly Lys Gly Thr Val Asn Glu Thr Asp Pro Gln Phe Gly Gly
        260                 265                 270 gta ttc acg ggc tcg ata tca gcc cca gaa gta aga gaa gta gtt gat    864
Val Phe Thr Gly Ser Ile Ser Ala Pro Glu Val Arg Glu Val Val Asp
    275                 280                 285 ttt gcc gat ttt atc atc gtc att ggt tgc atg ctc tcc gaa ttc agc    912
Phe Ala Asp Phe Ile Ile Val Ile Gly Cys Met Leu Ser Glu Phe Ser
290                 295                 300 acg tca act ttc cac ttc caa tat aaa act aag aat tgt gcg cta cta    960
Thr Ser Thr Phe His Phe Gln Tyr Lys Thr Lys Asn Cys Ala Leu Leu
305                 310                 315                 320 tat tct aca tct gtg aaa ttg aaa aat gcc aca tat cct gac ttg agc   1008
Tyr Ser Thr Ser Val Lys Leu Lys Asn Ala Thr Tyr Pro Asp Leu Ser
                325                 330                 335 att aaa tta cta cta cag aaa ata tta gca aat ctt gat gaa tct aaa   1056
Ile Lys Leu Leu Leu Gln Lys Ile Leu Ala Asn Leu Asp Glu Ser Lys
            340                 345                 350 ctg tct tac caa cca agc gaa caa ccc agt atg atg gtt cca aga cct   1104
Leu Ser Tyr Gln Pro Ser Glu Gln Pro Ser Met Met Val Pro Arg Pro
        355                 360                 365 tac cca gca gga aat gtc ctc ttg aga caa gaa tgg gtc tgg aat gaa   1152
Tyr Pro Ala Gly Asn Val Leu Leu Arg Gln Glu Trp Val Trp Asn Glu
    370                 375                 380 ata tcc cat tgg ttc caa cca ggt gac ata atc ata aca gaa act ggt   1200
Ile Ser His Trp Phe Gln Pro Gly Asp Ile Ile Ile Thr Glu Thr Gly
385                 390                 395                 400 gct tct gca ttt gga gtt aac cag acc aga ttt ccg gta aat aca cta   1248
Ala Ser Ala Phe Gly Val Asn Gln Thr Arg Phe Pro Val Asn Thr Leu
                405                 410                 415 ggt att tcg caa gct ctt tgg gga tct gtc gga tat aca atg ggg gcg   1296
Gly Ile Ser Gln Ala Leu Trp Gly Ser Val Gly Tyr Thr Met Gly Ala
            420                 425                 430 tgt ctt ggg gca gaa ttt gct gtt caa gag ata aac aag gat aaa ttc   1344
Cys Leu Gly Ala Glu Phe Ala Val Gln Glu Ile Asn Lys Asp Lys Phe
        435                 440                 445 ccc gca act aaa cat aga gtt att ctg ttt atg ggt gac ggt gct ttc   1392
Pro Ala Thr Lys His Arg Val Ile Leu Phe Met Gly Asp Gly Ala Phe
    450                 455                 460 caa ttg aca gtt caa gaa tta tcc aca att gtt aag tgg gga ttg aca   1440
Gln Leu Thr Val Gln Glu Leu Ser Thr Ile Val Lys Trp Gly Leu Thr
465                 470                 475                 480 cct tat att ttt gtg atg aat aac caa ggt tac tct gtg gac agg ttt   1488
Pro Tyr Ile Phe Val Met Asn Asn Gln Gly Tyr Ser Val Asp Arg Phe
                485                 490                 495 ttg cat cac agg tca gat gct agt tat tac gat atc caa cct tgg aac   1536
Leu His His Arg Ser Asp Ala Ser Tyr Tyr Asp Ile Gln Pro Trp Asn
            500                 505                 510 tac ttg gga tta ttg cga gta ttt ggt tgc acg aac tac gaa acg aaa   1584
Tyr Leu Gly Leu Leu Arg Val Phe Gly Cys Thr Asn Tyr Glu Thr Lys
        515                 520                 525 aaa att att act gtt gga gaa ttc aga tcc atg atc agt gac cca aac   1632
Lys Ile Ile Thr Val Gly Glu Phe Arg Ser Met Ile Ser Asp Pro Asn
    530                 535                 540
```

```
ttt gcg acc aat gac aaa att cgg atg ata gag att atg cta cca cca    1680
Phe Ala Thr Asn Asp Lys Ile Arg Met Ile Glu Ile Met Leu Pro Pro
545                 550                 555                 560 agg gat gtt cca cag gct ctg ctt gac agg tgg gtg gta gaa aaa gaa    1728
Arg Asp Val Pro Gln Ala Leu Leu Asp Arg Trp Val Val Glu Lys Glu
                565                 570                 575 cag agc aaa caa gtg caa gag gag aac gaa aat tct agc gca gta aat    1776
Gln Ser Lys Gln Val Gln Glu Glu Asn Glu Asn Ser Ser Ala Val Asn
            580                 585                 590 acg cca act cca gaa ttc caa cca ctt cta aaa aaa aat caa gtt gga    1824
Thr Pro Thr Pro Glu Phe Gln Pro Leu Leu Lys Lys Asn Gln Val Gly
        595                 600                 605 tac tga                                                            1830
Tyr

<210> SEQ ID NO 74
<211> LENGTH: 609
<212> TYPE: PRT
<213> ORGANISM: Saccharomyces cerevisiae

<400> SEQUENCE: 74

Met Asn Ser Ser Tyr Thr Gln Arg Tyr Ala Leu Pro Lys Cys Ile Ala
1               5                   10                  15

Ile Ser Asp Tyr Leu Phe His Arg Leu Asn Gln Leu Asn Ile His Thr
            20                  25                  30

Ile Phe Gly Leu Ser Gly Glu Phe Ser Met Pro Leu Leu Asp Lys Leu
        35                  40                  45

Tyr Asn Ile Pro Asn Leu Arg Trp Ala Gly Asn Ser Asn Glu Leu Asn
    50                  55                  60

Ala Ala Tyr Ala Ala Asp Gly Tyr Ser Arg Leu Lys Gly Leu Gly Cys
65                  70                  75                  80

Leu Ile Thr Thr Phe Gly Val Gly Glu Leu Ser Ala Ile Asn Gly Val
                85                  90                  95

Ala Gly Ser Tyr Ala Glu His Val Gly Ile Leu His Ile Val Gly Met
            100                 105                 110

Pro Pro Thr Ser Ala Gln Thr Lys Gln Leu Leu Leu His His Thr Leu
        115                 120                 125

Gly Asn Gly Asp Phe Thr Val Phe His Arg Ile Ala Ser Asp Val Ala
    130                 135                 140

Cys Tyr Thr Thr Leu Ile Ile Asp Ser Glu Leu Cys Ala Asp Glu Val
145                 150                 155                 160

Asp Lys Cys Ile Lys Lys Ala Trp Ile Glu Gln Arg Pro Val Tyr Met
                165                 170                 175

Gly Met Pro Val Asn Gln Val Asn Leu Pro Ile Glu Ser Ala Arg Leu
            180                 185                 190

Asn Thr Pro Leu Asp Leu Gln Leu His Lys Asn Asp Pro Asp Val Glu
        195                 200                 205

Lys Glu Val Ile Ser Arg Ile Leu Ser Phe Ile Tyr Lys Ser Gln Asn
    210                 215                 220

Pro Ala Ile Ile Val Asp Ala Cys Thr Ser Arg Gln Asn Leu Ile Glu
225                 230                 235                 240

Glu Thr Lys Glu Leu Cys Asn Arg Leu Lys Phe Pro Val Phe Val Thr
                245                 250                 255

Pro Met Gly Lys Gly Thr Val Asn Glu Thr Asp Pro Gln Phe Gly Gly
            260                 265                 270

Val Phe Thr Gly Ser Ile Ser Ala Pro Glu Val Arg Glu Val Val Asp
        275                 280                 285
```

```
Phe Ala Asp Phe Ile Ile Val Ile Gly Cys Met Leu Ser Glu Phe Ser
    290                 295                 300
Thr Ser Thr Phe His Phe Gln Tyr Lys Thr Lys Asn Cys Ala Leu Leu
305                 310                 315                 320
Tyr Ser Thr Ser Val Lys Leu Lys Asn Ala Thr Tyr Pro Asp Leu Ser
                325                 330                 335
Ile Lys Leu Leu Leu Gln Lys Ile Leu Ala Asn Leu Asp Glu Ser Lys
            340                 345                 350
Leu Ser Tyr Gln Pro Ser Glu Gln Pro Ser Met Met Val Pro Arg Pro
        355                 360                 365
Tyr Pro Ala Gly Asn Val Leu Leu Arg Gln Glu Trp Val Trp Asn Glu
    370                 375                 380
Ile Ser His Trp Phe Gln Pro Gly Asp Ile Ile Thr Glu Thr Gly
385                 390                 395                 400
Ala Ser Ala Phe Gly Val Asn Gln Thr Arg Phe Pro Val Asn Thr Leu
                405                 410                 415
Gly Ile Ser Gln Ala Leu Trp Gly Ser Val Gly Tyr Thr Met Gly Ala
            420                 425                 430
Cys Leu Gly Ala Glu Phe Ala Val Gln Glu Ile Asn Lys Asp Lys Phe
        435                 440                 445
Pro Ala Thr Lys His Arg Val Ile Leu Phe Met Gly Asp Gly Ala Phe
    450                 455                 460
Gln Leu Thr Val Gln Glu Leu Ser Thr Ile Val Lys Trp Gly Leu Thr
465                 470                 475                 480
Pro Tyr Ile Phe Val Met Asn Asn Gln Gly Tyr Ser Val Asp Arg Phe
                485                 490                 495
Leu His His Arg Ser Asp Ala Ser Tyr Tyr Asp Ile Gln Pro Trp Asn
            500                 505                 510
Tyr Leu Gly Leu Leu Arg Val Phe Gly Cys Thr Asn Tyr Glu Thr Lys
        515                 520                 525
Lys Ile Ile Thr Val Gly Glu Phe Arg Ser Met Ile Ser Asp Pro Asn
    530                 535                 540
Phe Ala Thr Asn Asp Lys Ile Arg Met Ile Glu Ile Met Leu Pro Pro
545                 550                 555                 560
Arg Asp Val Pro Gln Ala Leu Leu Asp Arg Trp Val Val Glu Lys Glu
                565                 570                 575
Gln Ser Lys Gln Val Gln Glu Glu Asn Glu Asn Ser Ser Ala Val Asn
            580                 585                 590
Thr Pro Thr Pro Glu Phe Gln Pro Leu Leu Lys Lys Asn Gln Val Gly
        595                 600                 605
Tyr

<210> SEQ ID NO 75
<211> LENGTH: 1665
<212> TYPE: DNA
<213> ORGANISM: Clostridium acetobutylicum
<220> FEATURE:
<221> NAME/KEY: CDS
<222> LOCATION: (1)..(1665)

<400> SEQUENCE: 75 ttg aag agt gaa tac aca att gga aga tat ttg tta gac cgt tta tca      48
Leu Lys Ser Glu Tyr Thr Ile Gly Arg Tyr Leu Leu Asp Arg Leu Ser
1               5                   10                  15 gag ttg ggt att cgg cat atc ttt ggt gta cct gga gat tac aat cta      96
Glu Leu Gly Ile Arg His Ile Phe Gly Val Pro Gly Asp Tyr Asn Leu
```

```
                    20                  25                  30
tcc ttt tta gac tat ata atg gag tac aaa ggg ata gat tgg gtt gga      144
Ser Phe Leu Asp Tyr Ile Met Glu Tyr Lys Gly Ile Asp Trp Val Gly
         35                  40                  45 aat tgc aat gaa ttg aat gct ggg tat gct gct gat gga tat gca aga      192
Asn Cys Asn Glu Leu Asn Ala Gly Tyr Ala Ala Asp Gly Tyr Ala Arg
 50                  55                  60 ata aat gga att gga gcc ata ctt aca aca ttt ggt gtt gga gaa tta      240
Ile Asn Gly Ile Gly Ala Ile Leu Thr Thr Phe Gly Val Gly Glu Leu
 65                  70                  75                  80 agt gcc att aac gca att gct ggg gca tac gct gag caa gtt cca gtt      288
Ser Ala Ile Asn Ala Ile Ala Gly Ala Tyr Ala Glu Gln Val Pro Val
                 85                  90                  95 gtt aaa att aca ggt atc ccc aca gca aaa gtt agg gac aat gga tta      336
Val Lys Ile Thr Gly Ile Pro Thr Ala Lys Val Arg Asp Asn Gly Leu
            100                 105                 110 tat gta cac cac aca tta ggt gac gga agg ttt gat cac ttt ttt gaa      384
Tyr Val His His Thr Leu Gly Asp Gly Arg Phe Asp His Phe Phe Glu
            115                 120                 125 atg ttt aga gaa gta aca gtt gct gag gca tta cta agc gaa gaa aat      432
Met Phe Arg Glu Val Thr Val Ala Glu Ala Leu Leu Ser Glu Glu Asn
130                 135                 140 gca gca caa gaa att gat cgt gtt ctt att tca tgc tgg aga caa aaa      480
Ala Ala Gln Glu Ile Asp Arg Val Leu Ile Ser Cys Trp Arg Gln Lys
145                 150                 155                 160 cgt cct gtt ctt ata aat tta ccg att gat gta tat gat aaa cca att      528
Arg Pro Val Leu Ile Asn Leu Pro Ile Asp Val Tyr Asp Lys Pro Ile
                165                 170                 175 aac aaa cca tta aag cca tta ctc gat tat act att tca agt aac aaa      576
Asn Lys Pro Leu Lys Pro Leu Leu Asp Tyr Thr Ile Ser Ser Asn Lys
            180                 185                 190 gag gct gca tgt gaa ttt gtt aca gaa ata gta cct ata ata aat agg      624
Glu Ala Ala Cys Glu Phe Val Thr Glu Ile Val Pro Ile Ile Asn Arg
            195                 200                 205 gca aaa aag cct gtt att ctt gca gat tat gga gta tat cgt tac caa      672
Ala Lys Lys Pro Val Ile Leu Ala Asp Tyr Gly Val Tyr Arg Tyr Gln
        210                 215                 220 gtt caa cat gtg ctt aaa aac ttg gcc gaa aaa acc gga ttt cct gtg      720
Val Gln His Val Leu Lys Asn Leu Ala Glu Lys Thr Gly Phe Pro Val
225                 230                 235                 240 gct aca cta agt atg gga aaa ggt gtt ttc aat gaa gca cac cct caa      768
Ala Thr Leu Ser Met Gly Lys Gly Val Phe Asn Glu Ala His Pro Gln
                245                 250                 255 ttt att ggt gtt tat aat gga gat gta agt tct cct tat tta agg cag      816
Phe Ile Gly Val Tyr Asn Gly Asp Val Ser Ser Pro Tyr Leu Arg Gln
            260                 265                 270 cga gtt gat gaa gca gac tgc att att agc gtt ggt gta aaa ttg acg      864
Arg Val Asp Glu Ala Asp Cys Ile Ile Ser Val Gly Val Lys Leu Thr
            275                 280                 285 gat tca acc aca ggg gga ttt tct cat gga ttt tct aaa agg aat gta      912
Asp Ser Thr Thr Gly Gly Phe Ser His Gly Phe Ser Lys Arg Asn Val
        290                 295                 300 att cac att gat cct ttt tca ata aag gca aaa ggt aaa aaa tat gca      960
Ile His Ile Asp Pro Phe Ser Ile Lys Ala Lys Gly Lys Lys Tyr Ala
305                 310                 315                 320 cct att acg atg aaa gat gct tta aca gaa tta aca agt aaa att gag     1008
Pro Ile Thr Met Lys Asp Ala Leu Thr Glu Leu Thr Ser Lys Ile Glu
                325                 330                 335 cat aga aac ttt gag gat tta gat ata aag cct tac aaa tca gat aat     1056
His Arg Asn Phe Glu Asp Leu Asp Ile Lys Pro Tyr Lys Ser Asp Asn
```

-continued

```
                340                 345                 350
caa aag tat ttt gca aaa gag aag cca att aca caa aaa cgt ttt ttt   1104
Gln Lys Tyr Phe Ala Lys Glu Lys Pro Ile Thr Gln Lys Arg Phe Phe
        355                 360                 365 gag cgt att gct cac ttt ata aaa gaa aaa gat gta tta tta gca gaa   1152
Glu Arg Ile Ala His Phe Ile Lys Glu Lys Asp Val Leu Leu Ala Glu
370                 375                 380 cag ggt aca tgc ttt ttt ggt gcg tca acc ata caa cta ccc aaa gat   1200
Gln Gly Thr Cys Phe Phe Gly Ala Ser Thr Ile Gln Leu Pro Lys Asp
385                 390                 395                 400 gca act ttt att ggt caa cct tta tgg gga tct att gga tac aca ctt   1248
Ala Thr Phe Ile Gly Gln Pro Leu Trp Gly Ser Ile Gly Tyr Thr Leu
                405                 410                 415 cct gct tta tta ggt tca caa tta gct gat caa aaa agg cgt aat att   1296
Pro Ala Leu Leu Gly Ser Gln Leu Ala Asp Gln Lys Arg Arg Asn Ile
            420                 425                 430 ctt tta att ggg gat ggt gca ttt caa atg aca gca caa gaa att tca   1344
Leu Leu Ile Gly Asp Gly Ala Phe Gln Met Thr Ala Gln Glu Ile Ser
        435                 440                 445 aca atg ctt cgt tta caa atc aaa cct att att ttt tta att aat aac   1392
Thr Met Leu Arg Leu Gln Ile Lys Pro Ile Ile Phe Leu Ile Asn Asn
450                 455                 460 gat ggt tat aca att gaa cgt gct att cat ggt aga gaa caa gta tat   1440
Asp Gly Tyr Thr Ile Glu Arg Ala Ile His Gly Arg Glu Gln Val Tyr
465                 470                 475                 480 aac aat att caa atg tgg cga tat cat aat gtt cca aag gtt tta ggt   1488
Asn Asn Ile Gln Met Trp Arg Tyr His Asn Val Pro Lys Val Leu Gly
                485                 490                 495 cct aaa gaa tgc agc tta acc ttt aaa gta caa agt gaa act gaa ctt   1536
Pro Lys Glu Cys Ser Leu Thr Phe Lys Val Gln Ser Glu Thr Glu Leu
            500                 505                 510 gaa aag gct ctt tta gtg gca gat aag gat tgt gaa cat ttg att ttt   1584
Glu Lys Ala Leu Leu Val Ala Asp Lys Asp Cys Glu His Leu Ile Phe
        515                 520                 525 ata gaa gtt gtt atg gat cgt tat gat aaa ccc gag cct tta gaa cgt   1632
Ile Glu Val Val Met Asp Arg Tyr Asp Lys Pro Glu Pro Leu Glu Arg
530                 535                 540 ctt tcg aaa cgt ttt gca aat caa aat aat tag                       1665
Leu Ser Lys Arg Phe Ala Asn Gln Asn Asn
545                 550

<210> SEQ ID NO 76
<211> LENGTH: 554
<212> TYPE: PRT
<213> ORGANISM: Clostridium acetobutylicum

<400> SEQUENCE: 76

Leu Lys Ser Glu Tyr Thr Ile Gly Arg Tyr Leu Leu Asp Arg Leu Ser
1               5                   10                  15

Glu Leu Gly Ile Arg His Ile Phe Gly Val Pro Gly Asp Tyr Asn Leu
            20                  25                  30

Ser Phe Leu Asp Tyr Ile Met Glu Tyr Lys Gly Ile Asp Trp Val Gly
        35                  40                  45

Asn Cys Asn Glu Leu Asn Ala Gly Tyr Ala Ala Asp Gly Tyr Ala Arg
    50                  55                  60

Ile Asn Gly Ile Gly Ala Ile Leu Thr Thr Phe Gly Val Gly Glu Leu
65                  70                  75                  80

Ser Ala Ile Asn Ala Ile Ala Gly Ala Tyr Ala Glu Gln Val Pro Val
                85                  90                  95
```

```
Val Lys Ile Thr Gly Ile Pro Thr Ala Lys Val Arg Asp Asn Gly Leu
            100                 105                 110

Tyr Val His His Thr Leu Gly Asp Gly Arg Phe Asp His Phe Phe Glu
            115                 120                 125

Met Phe Arg Glu Val Thr Val Ala Glu Ala Leu Leu Ser Glu Glu Asn
130                 135                 140

Ala Ala Gln Glu Ile Asp Arg Val Leu Ile Ser Cys Trp Arg Gln Lys
145                 150                 155                 160

Arg Pro Val Leu Ile Asn Leu Pro Ile Asp Val Tyr Asp Lys Pro Ile
                165                 170                 175

Asn Lys Pro Leu Lys Pro Leu Leu Asp Tyr Thr Ile Ser Ser Asn Lys
            180                 185                 190

Glu Ala Ala Cys Glu Phe Val Thr Glu Ile Val Pro Ile Ile Asn Arg
            195                 200                 205

Ala Lys Lys Pro Val Ile Leu Ala Asp Tyr Gly Val Tyr Arg Tyr Gln
210                 215                 220

Val Gln His Val Leu Lys Asn Leu Ala Glu Lys Thr Gly Phe Pro Val
225                 230                 235                 240

Ala Thr Leu Ser Met Gly Lys Gly Val Phe Asn Glu Ala His Pro Gln
                245                 250                 255

Phe Ile Gly Val Tyr Asn Gly Asp Val Ser Ser Pro Tyr Leu Arg Gln
            260                 265                 270

Arg Val Asp Glu Ala Asp Cys Ile Ile Ser Val Gly Val Lys Leu Thr
            275                 280                 285

Asp Ser Thr Thr Gly Gly Phe Ser His Gly Phe Ser Lys Arg Asn Val
290                 295                 300

Ile His Ile Asp Pro Phe Ser Ile Lys Ala Lys Gly Lys Lys Tyr Ala
305                 310                 315                 320

Pro Ile Thr Met Lys Asp Ala Leu Thr Glu Leu Thr Ser Lys Ile Glu
                325                 330                 335

His Arg Asn Phe Glu Asp Leu Asp Ile Lys Pro Tyr Lys Ser Asp Asn
            340                 345                 350

Gln Lys Tyr Phe Ala Lys Glu Lys Pro Ile Thr Gln Lys Arg Phe Phe
            355                 360                 365

Glu Arg Ile Ala His Phe Ile Lys Glu Lys Asp Val Leu Leu Ala Glu
370                 375                 380

Gln Gly Thr Cys Phe Phe Gly Ala Ser Thr Ile Gln Leu Pro Lys Asp
385                 390                 395                 400

Ala Thr Phe Ile Gly Gln Pro Leu Trp Gly Ser Ile Gly Tyr Thr Leu
                405                 410                 415

Pro Ala Leu Leu Gly Ser Gln Leu Ala Asp Gln Lys Arg Arg Asn Ile
            420                 425                 430

Leu Leu Ile Gly Asp Gly Ala Phe Gln Met Thr Ala Gln Glu Ile Ser
            435                 440                 445

Thr Met Leu Arg Leu Gln Ile Lys Pro Ile Ile Phe Leu Ile Asn Asn
450                 455                 460

Asp Gly Tyr Thr Ile Glu Arg Ala Ile His Gly Arg Glu Gln Val Tyr
465                 470                 475                 480

Asn Asn Ile Gln Met Trp Arg Tyr His Asn Val Pro Lys Val Leu Gly
                485                 490                 495

Pro Lys Glu Cys Ser Leu Thr Phe Lys Val Gln Ser Glu Thr Glu Leu
            500                 505                 510

Glu Lys Ala Leu Leu Val Ala Asp Lys Asp Cys Glu His Leu Ile Phe
            515                 520                 525
```

```
Ile Glu Val Val Met Asp Arg Tyr Asp Lys Pro Glu Pro Leu Glu Arg
            530                 535                 540

Leu Ser Lys Arg Phe Ala Asn Gln Asn Asn
545                 550

<210> SEQ ID NO 77
<211> LENGTH: 1056
<212> TYPE: DNA
<213> ORGANISM: Saccharomyces cerevisiae
<220> FEATURE:
<221> NAME/KEY: CDS
<222> LOCATION: (1)..(1056)

<400> SEQUENCE: 77 atg cct tcg caa gtc att cct gaa aaa caa aag gct att gtc ttt tat      48
Met Pro Ser Gln Val Ile Pro Glu Lys Gln Lys Ala Ile Val Phe Tyr
1               5                  10                  15 gag aca gat gga aaa ttg gaa tat aaa gac gtc aca gtt ccg gaa cct      96
Glu Thr Asp Gly Lys Leu Glu Tyr Lys Asp Val Thr Val Pro Glu Pro
            20                  25                  30 aag cct aac gaa att tta gtc cac gtt aaa tat tct ggt gtt tgt cat     144
Lys Pro Asn Glu Ile Leu Val His Val Lys Tyr Ser Gly Val Cys His
        35                  40                  45 agt gac ttg cac gcg tgg cac ggt gat tgg cca ttt caa ttg aaa ttt     192
Ser Asp Leu His Ala Trp His Gly Asp Trp Pro Phe Gln Leu Lys Phe
    50                  55                  60 cca tta atc ggt ggt cac gaa ggt gct ggt gtt gtt aag ttg gga         240
Pro Leu Ile Gly Gly His Glu Gly Ala Gly Val Val Val Lys Leu Gly
65                  70                  75                  80 tct aac gtt aag ggc tgg aaa gtc ggt gat ttt gca ggt ata aaa tgg     288
Ser Asn Val Lys Gly Trp Lys Val Gly Asp Phe Ala Gly Ile Lys Trp
                85                  90                  95 ttg aat ggg act tgc atg tcc tgt gaa tat tgt gaa gta ggt aat gaa     336
Leu Asn Gly Thr Cys Met Ser Cys Glu Tyr Cys Glu Val Gly Asn Glu
            100                 105                 110 tct caa tgt cct tat ttg gat ggt act ggc ttc aca cat gat ggt act     384
Ser Gln Cys Pro Tyr Leu Asp Gly Thr Gly Phe Thr His Asp Gly Thr
        115                 120                 125 ttt caa gaa tac gca act gcc gat gcc gtt caa gct gcc cat att cca     432
Phe Gln Glu Tyr Ala Thr Ala Asp Ala Val Gln Ala Ala His Ile Pro
    130                 135                 140 cca aac gtc aat ctt gct gaa gtt gcc cca atc ttg tgt gca ggt atc     480
Pro Asn Val Asn Leu Ala Glu Val Ala Pro Ile Leu Cys Ala Gly Ile
145                 150                 155                 160 act gtt tat aag gcg ttg aaa aga gcc aat gtg ata cca ggc caa tgg     528
Thr Val Tyr Lys Ala Leu Lys Arg Ala Asn Val Ile Pro Gly Gln Trp
                165                 170                 175 gtc act ata tcc ggt gca tgc ggt ggc ttg ggt tct ctg gca atc caa     576
Val Thr Ile Ser Gly Ala Cys Gly Gly Leu Gly Ser Leu Ala Ile Gln
            180                 185                 190 tac gcc ctt gct atg ggt tac agg gtc att ggt atc gat ggt ggt aat     624
Tyr Ala Leu Ala Met Gly Tyr Arg Val Ile Gly Ile Asp Gly Gly Asn
        195                 200                 205 gcc aag cga aag tta ttt gaa caa tta ggc gga gaa ata ttc atc gat     672
Ala Lys Arg Lys Leu Phe Glu Gln Leu Gly Gly Glu Ile Phe Ile Asp
    210                 215                 220 ttc acg gaa gaa aaa gac att gtt ggt gct ata ata aag gcc act aat     720
Phe Thr Glu Glu Lys Asp Ile Val Gly Ala Ile Ile Lys Ala Thr Asn
225                 230                 235                 240 ggc ggt tct cat gga gtt att aat gtg tct gtt tct gaa gca gct atc     768
Gly Gly Ser His Gly Val Ile Asn Val Ser Val Ser Glu Ala Ala Ile
```

```
                 245                 250                 255
gag gct tct acg agg tat tgt agg ccc aat ggt act gtc gtc ctg gtt    816
Glu Ala Ser Thr Arg Tyr Cys Arg Pro Asn Gly Thr Val Val Leu Val
        260                 265                 270 ggt atg cca gct cat gct tac tgc aat tcc gat gtt ttc aat caa gtt    864
Gly Met Pro Ala His Ala Tyr Cys Asn Ser Asp Val Phe Asn Gln Val
    275                 280                 285 gta aaa tca atc tcc atc gtt gga tct tgt gtt gga aat aga gct gat    912
Val Lys Ser Ile Ser Ile Val Gly Ser Cys Val Gly Asn Arg Ala Asp
290                 295                 300 aca agg gag gct tta gat ttc ttc gcc aga ggt ttg atc aaa tct ccg    960
Thr Arg Glu Ala Leu Asp Phe Phe Ala Arg Gly Leu Ile Lys Ser Pro
305                 310                 315                 320 atc cac tta gct ggc cta tcg gat gtt cct gaa att ttt gca aag atg   1008
Ile His Leu Ala Gly Leu Ser Asp Val Pro Glu Ile Phe Ala Lys Met
            325                 330                 335 gag aag ggt gaa att gtt ggt aga tat gtt gtt gag act tct aaa tga   1056
Glu Lys Gly Glu Ile Val Gly Arg Tyr Val Val Glu Thr Ser Lys
        340                 345                 350

<210> SEQ ID NO 78
<211> LENGTH: 351
<212> TYPE: PRT
<213> ORGANISM: Saccharomyces cerevisiae

<400> SEQUENCE: 78

Met Pro Ser Gln Val Ile Pro Glu Lys Gln Lys Ala Ile Val Phe Tyr
1               5                   10                  15

Glu Thr Asp Gly Lys Leu Glu Tyr Lys Asp Val Thr Val Pro Glu Pro
            20                  25                  30

Lys Pro Asn Glu Ile Leu Val His Val Lys Tyr Ser Gly Val Cys His
        35                  40                  45

Ser Asp Leu His Ala Trp His Gly Asp Trp Pro Phe Gln Leu Lys Phe
    50                  55                  60

Pro Leu Ile Gly Gly His Glu Gly Ala Gly Val Val Lys Leu Gly
65                  70                  75                  80

Ser Asn Val Lys Gly Trp Lys Val Gly Asp Phe Ala Gly Ile Lys Trp
                85                  90                  95

Leu Asn Gly Thr Cys Met Ser Cys Glu Tyr Cys Glu Val Gly Asn Glu
            100                 105                 110

Ser Gln Cys Pro Tyr Leu Asp Gly Thr Gly Phe Thr His Asp Gly Thr
        115                 120                 125

Phe Gln Glu Tyr Ala Thr Ala Asp Ala Val Gln Ala Ala His Ile Pro
    130                 135                 140

Pro Asn Val Asn Leu Ala Glu Val Ala Pro Ile Leu Cys Ala Gly Ile
145                 150                 155                 160

Thr Val Tyr Lys Ala Leu Lys Arg Ala Asn Val Ile Pro Gly Gln Trp
                165                 170                 175

Val Thr Ile Ser Gly Ala Cys Gly Gly Leu Gly Ser Leu Ala Ile Gln
            180                 185                 190

Tyr Ala Leu Ala Met Gly Tyr Arg Val Ile Gly Ile Asp Gly Gly Asn
        195                 200                 205

Ala Lys Arg Lys Leu Phe Glu Gln Leu Gly Gly Glu Ile Phe Ile Asp
    210                 215                 220

Phe Thr Glu Glu Lys Asp Ile Val Gly Ala Ile Ile Lys Ala Thr Asn
225                 230                 235                 240

Gly Gly Ser His Gly Val Ile Asn Val Ser Val Ser Glu Ala Ala Ile
```

|  |  |  |  |  |  |  |  |  |  |  |  |
|---|---|---|---|---|---|---|---|---|---|---|---|
|  |  |  | 245 |  |  |  | 250 |  |  |  | 255 |
| Glu | Ala | Ser | Thr | Arg | Tyr | Cys | Arg | Pro | Asn | Gly | Thr | Val | Val | Leu | Val |
|  |  |  | 260 |  |  |  | 265 |  |  |  | 270 |
| Gly | Met | Pro | Ala | His | Ala | Tyr | Cys | Asn | Ser | Asp | Val | Phe | Asn | Gln | Val |
|  |  | 275 |  |  |  |  | 280 |  |  |  |  | 285 |
| Val | Lys | Ser | Ile | Ser | Ile | Val | Gly | Ser | Cys | Val | Gly | Asn | Arg | Ala | Asp |
|  | 290 |  |  |  |  | 295 |  |  |  |  | 300 |
| Thr | Arg | Glu | Ala | Leu | Asp | Phe | Phe | Ala | Arg | Gly | Leu | Ile | Lys | Ser | Pro |
| 305 |  |  |  |  | 310 |  |  |  |  | 315 |  |  |  |  | 320 |
| Ile | His | Leu | Ala | Gly | Leu | Ser | Asp | Val | Pro | Glu | Ile | Phe | Ala | Lys | Met |
|  |  |  |  | 325 |  |  |  |  | 330 |  |  |  |  | 335 |
| Glu | Lys | Gly | Glu | Ile | Val | Gly | Arg | Tyr | Val | Val | Glu | Thr | Ser | Lys |
|  |  |  | 340 |  |  |  |  | 345 |  |  |  |  | 350 |

<210> SEQ ID NO 79
<211> LENGTH: 1725
<212> TYPE: DNA
<213> ORGANISM: Escherichia coli
<220> FEATURE:
<221> NAME/KEY: CDS
<222> LOCATION: (1)..(1725)

<400> SEQUENCE: 79

```
atg gag atg ttg tct gga gcc gag atg gtc gtc cga tcg ctt atc gat      48
Met Glu Met Leu Ser Gly Ala Glu Met Val Val Arg Ser Leu Ile Asp
1               5                   10                  15 cag ggc gtt aaa caa gta ttc ggt tat ccc gga ggc gca gtc ctt gat      96
Gln Gly Val Lys Gln Val Phe Gly Tyr Pro Gly Gly Ala Val Leu Asp
            20                  25                  30 att tat gat gca ttg cat acc gtg ggt ggt att gat cat gta tta gtt     144
Ile Tyr Asp Ala Leu His Thr Val Gly Gly Ile Asp His Val Leu Val
        35                  40                  45 cgt cat gag cag gcg gcg gtg cat atg gcc gat ggc ctg gcg cgc gcg     192
Arg His Glu Gln Ala Ala Val His Met Ala Asp Gly Leu Ala Arg Ala
    50                  55                  60 acc ggg gaa gtc ggc gtc gtg ctg gta acg tcg ggt cca ggg gcg acc     240
Thr Gly Glu Val Gly Val Val Leu Val Thr Ser Gly Pro Gly Ala Thr
65                  70                  75                  80 aat gcg att act ggc atc gcc acc gct tat atg gat tcc att cca tta     288
Asn Ala Ile Thr Gly Ile Ala Thr Ala Tyr Met Asp Ser Ile Pro Leu
                85                  90                  95 gtt gtc ctt tcc ggg cag gta gcg acc tcg ttg ata ggt tac gat gcc     336
Val Val Leu Ser Gly Gln Val Ala Thr Ser Leu Ile Gly Tyr Asp Ala
            100                 105                 110 ttt cag gag tgc gac atg gtg ggg att tcg cga ccg gtg gtt aaa cac     384
Phe Gln Glu Cys Asp Met Val Gly Ile Ser Arg Pro Val Val Lys His
        115                 120                 125 agt ttt ctg gtt aag caa acg gaa gac att ccg cag gtg ctg aaa aag     432
Ser Phe Leu Val Lys Gln Thr Glu Asp Ile Pro Gln Val Leu Lys Lys
    130                 135                 140 gct ttc tgg ctg gcg gca agt ggt cgc cca gga cca gta gtc gtt gat     480
Ala Phe Trp Leu Ala Ala Ser Gly Arg Pro Gly Pro Val Val Val Asp
145                 150                 155                 160 tta ccg aaa gat att ctt aat ccg gcg aac aaa tta ccc tat gtc tgg     528
Leu Pro Lys Asp Ile Leu Asn Pro Ala Asn Lys Leu Pro Tyr Val Trp
                165                 170                 175 ccg gag tcg gtc agt atg cgt tct tac aat ccc act act acc gga cat     576
Pro Glu Ser Val Ser Met Arg Ser Tyr Asn Pro Thr Thr Thr Gly His
            180                 185                 190 aaa ggg caa att aag cgt gct ctg caa acg ctg gta gcg gca aaa aaa     624
```

-continued

| | | | | | | | | | | | | | | | |
|---|---|---|---|---|---|---|---|---|---|---|---|---|---|---|---|
| Lys | Gly | Gln | Ile | Lys | Arg | Ala | Leu | Gln | Thr | Leu | Val | Ala | Ala | Lys | Lys |
| | | 195 | | | | 200 | | | | 205 | | | | | |

```
ccg gtt gtc tac gta ggc ggt ggg gca atc acg gcg ggc tgc cat cag      672
Pro Val Val Tyr Val Gly Gly Gly Ala Ile Thr Ala Gly Cys His Gln
    210             215                 220 cag ttg aaa gaa acg gtg gag gcg ttg aat ctg ccc gtt gtt tgc tca      720
Gln Leu Lys Glu Thr Val Glu Ala Leu Asn Leu Pro Val Val Cys Ser
225             230                 235                 240 ttg atg ggg ctg ggg gcg ttt ccg gca acg cat cgt cag gca ctg ggc      768
Leu Met Gly Leu Gly Ala Phe Pro Ala Thr His Arg Gln Ala Leu Gly
            245                 250                 255 atg ctg gga atg cac ggt acc tac gaa gcc aat atg acg atg cat aac      816
Met Leu Gly Met His Gly Thr Tyr Glu Ala Asn Met Thr Met His Asn
260                 265                 270 gcg gat gtg att ttc gcc gtc ggg gta cga ttt gat gac cga acg acg      864
Ala Asp Val Ile Phe Ala Val Gly Val Arg Phe Asp Asp Arg Thr Thr
        275                 280                 285 aac aat ctg gca aag tac tgc cca aat gcc act gtt ctg cat atc gat      912
Asn Asn Leu Ala Lys Tyr Cys Pro Asn Ala Thr Val Leu His Ile Asp
            290                 295                 300 att gat cct act tcc att tct aaa acc gtg act gcg gat atc ccg att      960
Ile Asp Pro Thr Ser Ile Ser Lys Thr Val Thr Ala Asp Ile Pro Ile
305                 310                 315                 320 gtg ggg gat gct cgc cag gtc ctc gaa caa atg ctt gaa ctc ttg tcg     1008
Val Gly Asp Ala Arg Gln Val Leu Glu Gln Met Leu Glu Leu Leu Ser
                325                 330                 335 caa gaa tcc gcc cat caa cca ctg gat gag atc cgc gac tgg tgg cag     1056
Gln Glu Ser Ala His Gln Pro Leu Asp Glu Ile Arg Asp Trp Trp Gln
            340                 345                 350 caa att gaa cag tgg cgc gct cgt cag tgc ctg aaa tat gac act cac     1104
Gln Ile Glu Gln Trp Arg Ala Arg Gln Cys Leu Lys Tyr Asp Thr His
        355                 360                 365 agt gaa aag att aaa ccg cag gcg gtg atc gag act ctt tgg cgg ttg     1152
Ser Glu Lys Ile Lys Pro Gln Ala Val Ile Glu Thr Leu Trp Arg Leu
370                 375                 380 acg aag gga gac gct tac gtg acg tcc gat gtc ggg cag cac cag atg     1200
Thr Lys Gly Asp Ala Tyr Val Thr Ser Asp Val Gly Gln His Gln Met
385                 390                 395                 400 ttt gct gca ctt tat tat cca ttc gac aaa ccg cgt cgc tgg atc aat     1248
Phe Ala Ala Leu Tyr Tyr Pro Phe Asp Lys Pro Arg Arg Trp Ile Asn
                405                 410                 415 tcc ggt ggc ctc ggc acg atg ggt ttt ggt tta cct gcg gca ctg ggc     1296
Ser Gly Gly Leu Gly Thr Met Gly Phe Gly Leu Pro Ala Ala Leu Gly
            420                 425                 430 gtc aaa atg gcg ttg cca gaa gaa acc gtg gtt tgc gtc act ggc gac     1344
Val Lys Met Ala Leu Pro Glu Glu Thr Val Val Cys Val Thr Gly Asp
        435                 440                 445 ggc agt att cag atg aac atc cag gaa ctg tct acc gcg ttg caa tac     1392
Gly Ser Ile Gln Met Asn Ile Gln Glu Leu Ser Thr Ala Leu Gln Tyr
450                 455                 460 gag ttg ccc gta ctg gtg gtg aat ctc aat aac cgc tat ctg ggg atg     1440
Glu Leu Pro Val Leu Val Val Asn Leu Asn Asn Arg Tyr Leu Gly Met
465                 470                 475                 480 gtg aag cag tgg cag gac atg atc tat tcc ggc cgt cat tca caa tct     1488
Val Lys Gln Trp Gln Asp Met Ile Tyr Ser Gly Arg His Ser Gln Ser
                485                 490                 495 tat atg caa tcg cta ccc gat ttc gtc cgt ctg gcg gaa gcc tat ggg     1536
Tyr Met Gln Ser Leu Pro Asp Phe Val Arg Leu Ala Glu Ala Tyr Gly
            500                 505                 510 cat gtc ggg atc cag att tct cat ccg cat gag ctg gaa agc aaa ctt     1584
```

```
His Val Gly Ile Gln Ile Ser His Pro His Glu Leu Glu Ser Lys Leu
        515                 520                 525 agc gag gcg ctg gaa cag gtg cgc aat aat cgc ctg gtt ttt gtt gat    1632
Ser Glu Ala Leu Glu Gln Val Arg Asn Asn Arg Leu Val Phe Val Asp
530                 535                 540 gtt acc gtc gat ggc agc gag cac gtc tac ccg atg cag att cgc ggg    1680
Val Thr Val Asp Gly Ser Glu His Val Tyr Pro Met Gln Ile Arg Gly
545                 550                 555                 560 ggc gga atg gat gaa atg tgg tta agc aaa acg gag aga acc tga       1725
Gly Gly Met Asp Glu Met Trp Leu Ser Lys Thr Glu Arg Thr
                565                 570

<210> SEQ ID NO 80
<211> LENGTH: 574
<212> TYPE: PRT
<213> ORGANISM: Escherichia coli

<400> SEQUENCE: 80

Met Glu Met Leu Ser Gly Ala Glu Met Val Val Arg Ser Leu Ile Asp
1               5                   10                  15

Gln Gly Val Lys Gln Val Phe Gly Tyr Pro Gly Gly Ala Val Leu Asp
            20                  25                  30

Ile Tyr Asp Ala Leu His Thr Val Gly Gly Ile Asp His Val Leu Val
        35                  40                  45

Arg His Glu Gln Ala Ala Val His Met Ala Asp Gly Leu Ala Arg Ala
    50                  55                  60

Thr Gly Glu Val Gly Val Val Leu Val Thr Ser Gly Pro Gly Ala Thr
65                  70                  75                  80

Asn Ala Ile Thr Gly Ile Ala Thr Ala Tyr Met Asp Ser Ile Pro Leu
                85                  90                  95

Val Val Leu Ser Gly Gln Val Ala Thr Ser Leu Ile Gly Tyr Asp Ala
            100                 105                 110

Phe Gln Glu Cys Asp Met Val Gly Ile Ser Arg Pro Val Val Lys His
        115                 120                 125

Ser Phe Leu Val Lys Gln Thr Glu Asp Ile Pro Gln Val Leu Lys Lys
    130                 135                 140

Ala Phe Trp Leu Ala Ala Ser Gly Arg Pro Gly Pro Val Val Val Asp
145                 150                 155                 160

Leu Pro Lys Asp Ile Leu Asn Pro Ala Asn Lys Leu Pro Tyr Val Trp
                165                 170                 175

Pro Glu Ser Val Ser Met Arg Ser Tyr Asn Pro Thr Thr Thr Gly His
            180                 185                 190

Lys Gly Gln Ile Lys Arg Ala Leu Gln Thr Leu Val Ala Ala Lys Lys
        195                 200                 205

Pro Val Val Tyr Val Gly Gly Gly Ala Ile Thr Ala Gly Cys His Gln
    210                 215                 220

Gln Leu Lys Glu Thr Val Glu Ala Leu Asn Leu Pro Val Val Cys Ser
225                 230                 235                 240

Leu Met Gly Leu Gly Ala Phe Pro Ala Thr His Arg Gln Ala Leu Gly
                245                 250                 255

Met Leu Gly Met His Gly Thr Tyr Glu Ala Asn Met Thr Met His Asn
            260                 265                 270

Ala Asp Val Ile Phe Ala Val Gly Val Arg Phe Asp Asp Arg Thr Thr
        275                 280                 285

Asn Asn Leu Ala Lys Tyr Cys Pro Asn Ala Thr Val Leu His Ile Asp
    290                 295                 300
```

```
Ile Asp Pro Thr Ser Ile Ser Lys Thr Val Thr Ala Asp Ile Pro Ile
305                 310                 315                 320

Val Gly Asp Ala Arg Gln Val Leu Glu Gln Met Leu Glu Leu Leu Ser
            325                 330                 335

Gln Glu Ser Ala His Gln Pro Leu Asp Glu Ile Arg Asp Trp Trp Gln
        340                 345                 350

Gln Ile Glu Gln Trp Arg Ala Arg Gln Cys Leu Lys Tyr Asp Thr His
        355                 360                 365

Ser Glu Lys Ile Lys Pro Gln Ala Val Ile Glu Thr Leu Trp Arg Leu
370                 375                 380

Thr Lys Gly Asp Ala Tyr Val Thr Ser Asp Val Gly Gln His Gln Met
385                 390                 395                 400

Phe Ala Ala Leu Tyr Tyr Pro Phe Asp Lys Pro Arg Arg Trp Ile Asn
            405                 410                 415

Ser Gly Gly Leu Gly Thr Met Gly Phe Gly Leu Pro Ala Ala Leu Gly
        420                 425                 430

Val Lys Met Ala Leu Pro Glu Glu Thr Val Val Cys Val Thr Gly Asp
    435                 440                 445

Gly Ser Ile Gln Met Asn Ile Gln Glu Leu Ser Thr Ala Leu Gln Tyr
450                 455                 460

Glu Leu Pro Val Leu Val Val Asn Leu Asn Asn Arg Tyr Leu Gly Met
465                 470                 475                 480

Val Lys Gln Trp Gln Asp Met Ile Tyr Ser Gly Arg His Ser Gln Ser
            485                 490                 495

Tyr Met Gln Ser Leu Pro Asp Phe Val Arg Leu Ala Glu Ala Tyr Gly
        500                 505                 510

His Val Gly Ile Gln Ile Ser His Pro His Glu Leu Glu Ser Lys Leu
    515                 520                 525

Ser Glu Ala Leu Glu Gln Val Arg Asn Asn Arg Leu Val Phe Val Asp
530                 535                 540

Val Thr Val Asp Gly Ser Glu His Val Tyr Pro Met Gln Ile Arg Gly
545                 550                 555                 560

Gly Gly Met Asp Glu Met Trp Leu Ser Lys Thr Glu Arg Thr
            565                 570

<210> SEQ ID NO 81
<211> LENGTH: 492
<212> TYPE: DNA
<213> ORGANISM: Escherichia coli
<220> FEATURE:
<221> NAME/KEY: CDS
<222> LOCATION: (1)..(492)

<400> SEQUENCE: 81 atg cgc cgg ata tta tca gtc tta ctc gaa aat gaa tca ggc gcg tta     48
Met Arg Arg Ile Leu Ser Val Leu Leu Glu Asn Glu Ser Gly Ala Leu
1               5                   10                  15 tcc cgc gtg att ggc ctt ttt tcc cag cgt ggc tac aac att gaa agc     96
Ser Arg Val Ile Gly Leu Phe Ser Gln Arg Gly Tyr Asn Ile Glu Ser
                20                  25                  30 ctg acc gtt gcg cca acc gac gat ccg aca tta tcg cgt atg acc atc    144
Leu Thr Val Ala Pro Thr Asp Asp Pro Thr Leu Ser Arg Met Thr Ile
            35                  40                  45 cag acc gtg ggc gat gaa aaa gta ctt gag cag atc gaa aag caa tta    192
Gln Thr Val Gly Asp Glu Lys Val Leu Glu Gln Ile Glu Lys Gln Leu
        50                  55                  60 cac aaa ctg gtc gat gtc ttg cgc gtg agt gag ttg ggg cag ggc gcg    240
His Lys Leu Val Asp Val Leu Arg Val Ser Glu Leu Gly Gln Gly Ala
```

```
                65                  70                  75                  80
cat gtt gag cgg gaa atc atg ctg gtg aaa att cag gcc agc ggt tac        288
His Val Glu Arg Glu Ile Met Leu Val Lys Ile Gln Ala Ser Gly Tyr
                    85                  90                  95 ggg cgt gac gaa gtg aaa cgt aat acg gaa ata ttc cgt ggg caa att        336
Gly Arg Asp Glu Val Lys Arg Asn Thr Glu Ile Phe Arg Gly Gln Ile
                100                 105                 110 atc gat gtc aca ccc tcg ctt tat acc gtt caa tta gca ggc acc agc        384
Ile Asp Val Thr Pro Ser Leu Tyr Thr Val Gln Leu Ala Gly Thr Ser
                115                 120                 125 ggt aag ctt gat gca ttt tta gca tcg att cgc gat gtg gcg aaa att        432
Gly Lys Leu Asp Ala Phe Leu Ala Ser Ile Arg Asp Val Ala Lys Ile
            130                 135                 140 gtg gag gtt gct cgc tct ggt gtc gga ctt tcg cgc ggc gat aaa        480
Val Glu Val Ala Arg Ser Gly Val Val Gly Leu Ser Arg Gly Asp Lys
145                 150                 155                 160 ata atg cgt tga                                                        492
Ile Met Arg <210> SEQ ID NO 82
<211> LENGTH: 163
<212> TYPE: PRT
<213> ORGANISM: Escherichia coli

<400> SEQUENCE: 82

Met Arg Arg Ile Leu Ser Val Leu Leu Glu Asn Glu Ser Gly Ala Leu
1               5                   10                  15

Ser Arg Val Ile Gly Leu Phe Ser Gln Arg Gly Tyr Asn Ile Glu Ser
            20                  25                  30

Leu Thr Val Ala Pro Thr Asp Asp Pro Thr Leu Ser Arg Met Thr Ile
        35                  40                  45

Gln Thr Val Gly Asp Glu Lys Val Leu Glu Gln Ile Glu Lys Gln Leu
    50                  55                  60

His Lys Leu Val Asp Val Leu Arg Val Ser Glu Leu Gly Gln Gly Ala
65                  70                  75                  80

His Val Glu Arg Glu Ile Met Leu Val Lys Ile Gln Ala Ser Gly Tyr
                85                  90                  95

Gly Arg Asp Glu Val Lys Arg Asn Thr Glu Ile Phe Arg Gly Gln Ile
            100                 105                 110

Ile Asp Val Thr Pro Ser Leu Tyr Thr Val Gln Leu Ala Gly Thr Ser
        115                 120                 125

Gly Lys Leu Asp Ala Phe Leu Ala Ser Ile Arg Asp Val Ala Lys Ile
    130                 135                 140

Val Glu Val Ala Arg Ser Gly Val Val Gly Leu Ser Arg Gly Asp Lys
145                 150                 155                 160

Ile Met Arg

<210> SEQ ID NO 83
<211> LENGTH: 1476
<212> TYPE: DNA
<213> ORGANISM: Escherichia coli
<220> FEATURE:
<221> NAME/KEY: CDS
<222> LOCATION: (1)..(1476)

<400> SEQUENCE: 83 atg gct aac tac ttc aat aca ctg aat ctg cgc cag cag ctg gca cag        48
Met Ala Asn Tyr Phe Asn Thr Leu Asn Leu Arg Gln Gln Leu Ala Gln
1               5                   10                  15
```

```
ctg ggc aaa tgt cgc ttt atg ggc cgc gat gaa ttc gcc gat ggc gcg     96
Leu Gly Lys Cys Arg Phe Met Gly Arg Asp Glu Phe Ala Asp Gly Ala
         20                  25                  30 agc tac ctt cag ggt aaa aaa gta gtc atc gtc ggc tgt ggc gca cag    144
Ser Tyr Leu Gln Gly Lys Lys Val Val Ile Val Gly Cys Gly Ala Gln
     35                  40                  45 ggt ctg aac cag ggc ctg aac atg cgt gat tct ggt ctc gat atc tcc    192
Gly Leu Asn Gln Gly Leu Asn Met Arg Asp Ser Gly Leu Asp Ile Ser
 50                  55                  60 tac gct ctg cgt aaa gaa gcg att gcc gag aag cgc gcg tcc tgg cgt    240
Tyr Ala Leu Arg Lys Glu Ala Ile Ala Glu Lys Arg Ala Ser Trp Arg
 65                  70                  75                  80 aaa gcg acc gaa aat ggt ttt aaa gtg ggt act tac gaa gaa ctg atc    288
Lys Ala Thr Glu Asn Gly Phe Lys Val Gly Thr Tyr Glu Glu Leu Ile
                 85                  90                  95 cca cag gcg gat ctg gtg att aac ctg acg ccg gac aag cag cac tct    336
Pro Gln Ala Asp Leu Val Ile Asn Leu Thr Pro Asp Lys Gln His Ser
             100                 105                 110 gat gta gtg cgc acc gta cag cca ctg atg aaa gac ggc gcg gcg ctg    384
Asp Val Val Arg Thr Val Gln Pro Leu Met Lys Asp Gly Ala Ala Leu
                 115                 120                 125 ggc tac tcg cac ggt ttc aac atc gtc gaa gtg ggc gag cag atc cgt    432
Gly Tyr Ser His Gly Phe Asn Ile Val Glu Val Gly Glu Gln Ile Arg
             130                 135                 140 aaa gat atc acc gta gtg atg gtt gcg ccg aaa tgc cca ggc acc gaa    480
Lys Asp Ile Thr Val Val Met Val Ala Pro Lys Cys Pro Gly Thr Glu
145                 150                 155                 160 gtg cgt gaa gag tac aaa cgt ggg ttc ggc gta ccg acg ctg att gcc    528
Val Arg Glu Glu Tyr Lys Arg Gly Phe Gly Val Pro Thr Leu Ile Ala
                 165                 170                 175 gtt cac ccg gaa aac gat ccg aaa ggc gaa ggc atg gcg att gcc aaa    576
Val His Pro Glu Asn Asp Pro Lys Gly Glu Gly Met Ala Ile Ala Lys
             180                 185                 190 gcc tgg gcg gct gca acc ggt ggt cac cgt gcg ggt gtg ctg gaa tcg    624
Ala Trp Ala Ala Ala Thr Gly Gly His Arg Ala Gly Val Leu Glu Ser
         195                 200                 205 tcc ttc gtt gcg gaa gtg aaa tct gac ctg atg ggc gag caa acc atc    672
Ser Phe Val Ala Glu Val Lys Ser Asp Leu Met Gly Glu Gln Thr Ile
 210                 215                 220 ctg tgc ggt atg ttg cag gct ggc tct ctg ctg tgc ttc gac aag ctg    720
Leu Cys Gly Met Leu Gln Ala Gly Ser Leu Leu Cys Phe Asp Lys Leu
225                 230                 235                 240 gtg gaa gaa ggt acc gat cca gca tac gca gaa aaa ctg att cag ttc    768
Val Glu Glu Gly Thr Asp Pro Ala Tyr Ala Glu Lys Leu Ile Gln Phe
                 245                 250                 255 ggt tgg gaa acc atc acc gaa gca ctg aaa cag ggc ggc atc acc ctg    816
Gly Trp Glu Thr Ile Thr Glu Ala Leu Lys Gln Gly Gly Ile Thr Leu
             260                 265                 270 atg atg gac cgt ctc tct aac ccg gcg aaa ctg cgt gct tat gcg ctt    864
Met Met Asp Arg Leu Ser Asn Pro Ala Lys Leu Arg Ala Tyr Ala Leu
         275                 280                 285 tct gaa cag ctg aaa gag atc atg gca ccc ctg ttc cag aaa cat atg    912
Ser Glu Gln Leu Lys Glu Ile Met Ala Pro Leu Phe Gln Lys His Met
 290                 295                 300 gac gac atc atc tcc ggc gaa ttc tct tcc ggt atg atg gcg gac tgg    960
Asp Asp Ile Ile Ser Gly Glu Phe Ser Ser Gly Met Met Ala Asp Trp
305                 310                 315                 320 gcc aac gat gat aag aaa ctg ctg acc tgg cgt gaa gag acc ggc aaa   1008
Ala Asn Asp Asp Lys Lys Leu Leu Thr Trp Arg Glu Glu Thr Gly Lys
                 325                 330                 335
```

```
acc gcg ttt gaa acc gcg ccg cag tat gaa ggc aaa atc ggc gag cag       1056
Thr Ala Phe Glu Thr Ala Pro Gln Tyr Glu Gly Lys Ile Gly Glu Gln
            340                 345                 350 gag tac ttc gat aaa ggc gta ctg atg att gcg atg gtg aaa gcg ggc       1104
Glu Tyr Phe Asp Lys Gly Val Leu Met Ile Ala Met Val Lys Ala Gly
        355                 360                 365 gtt gaa ctg gcg ttc gaa acc atg gtc gat tcc ggc atc att gaa gag       1152
Val Glu Leu Ala Phe Glu Thr Met Val Asp Ser Gly Ile Ile Glu Glu
    370                 375                 380 tct gca tat tat gaa tca ctg cac gag ctg ccg ctg att gcc aac acc       1200
Ser Ala Tyr Tyr Glu Ser Leu His Glu Leu Pro Leu Ile Ala Asn Thr
385                 390                 395                 400 atc gcc cgt aag cgt ctg tac gaa atg aac gtg gtt atc tct gat acc       1248
Ile Ala Arg Lys Arg Leu Tyr Glu Met Asn Val Val Ile Ser Asp Thr
                405                 410                 415 gct gag tac ggt aac tat ctg ttc tct tac gct tgt gtg ccg ttg ctg       1296
Ala Glu Tyr Gly Asn Tyr Leu Phe Ser Tyr Ala Cys Val Pro Leu Leu
            420                 425                 430 aaa ccg ttt atg gca gag ctg caa ccg ggc gac ctg ggt aaa gct att       1344
Lys Pro Phe Met Ala Glu Leu Gln Pro Gly Asp Leu Gly Lys Ala Ile
        435                 440                 445 ccg gaa ggc gcg gta gat aac ggg caa ctg cgt gat gtg aac gaa gcg       1392
Pro Glu Gly Ala Val Asp Asn Gly Gln Leu Arg Asp Val Asn Glu Ala
    450                 455                 460 att cgc agc cat gcg att gag cag gta ggt aag aaa ctg cgc ggc tat       1440
Ile Arg Ser His Ala Ile Glu Gln Val Gly Lys Lys Leu Arg Gly Tyr
465                 470                 475                 480 atg aca gat atg aaa cgt att gct gtt gcg ggt taa                       1476
Met Thr Asp Met Lys Arg Ile Ala Val Ala Gly
                485                 490

<210> SEQ ID NO 84
<211> LENGTH: 491
<212> TYPE: PRT
<213> ORGANISM: Escherichia coli

<400> SEQUENCE: 84

Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175
```

```
Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490

<210> SEQ ID NO 85
<211> LENGTH: 1851
<212> TYPE: DNA
<213> ORGANISM: Escherichia coli
<220> FEATURE:
<221> NAME/KEY: CDS
<222> LOCATION: (1)..(1851)

<400> SEQUENCE: 85 atg cct aag tac cgt tcc gcc acc acc act cat ggt cgt aat atg gcg      48
Met Pro Lys Tyr Arg Ser Ala Thr Thr Thr His Gly Arg Asn Met Ala
1               5                   10                  15 ggt gct cgt gcg ctg tgg cgc gcc acc gga atg acc gac gcc gat ttc      96
Gly Ala Arg Ala Leu Trp Arg Ala Thr Gly Met Thr Asp Ala Asp Phe
            20                  25                  30
```

```
ggt aag ccg att atc gcg gtt gtg aac tcg ttc acc caa ttt gta ccg      144
Gly Lys Pro Ile Ile Ala Val Val Asn Ser Phe Thr Gln Phe Val Pro
        35              40                  45 ggt cac gtc cat ctg cgc gat ctc ggt aaa ctg gtc gcc gaa caa att      192
Gly His Val His Leu Arg Asp Leu Gly Lys Leu Val Ala Glu Gln Ile
 50              55                  60 gaa gcg gct ggc ggc gtt gcc aaa gag ttc aac acc att gcg gtg gat      240
Glu Ala Ala Gly Gly Val Ala Lys Glu Phe Asn Thr Ile Ala Val Asp
65              70                  75                  80 gat ggg att gcc atg ggc cac ggg ggg atg ctt tat tca ctg cca tct      288
Asp Gly Ile Ala Met Gly His Gly Gly Met Leu Tyr Ser Leu Pro Ser
                85                  90                  95 cgc gaa ctg atc gct gat tcc gtt gag tat atg gtc aac gcc cac tgc      336
Arg Glu Leu Ile Ala Asp Ser Val Glu Tyr Met Val Asn Ala His Cys
            100                 105                 110 gcc gac gcc atg gtc tgc atc tct aac tgc gac aaa atc acc ccg ggg      384
Ala Asp Ala Met Val Cys Ile Ser Asn Cys Asp Lys Ile Thr Pro Gly
            115                 120                 125 atg ctg atg gct tcc ctg cgc ctg aat att ccg gtg atc ttt gtt tcc      432
Met Leu Met Ala Ser Leu Arg Leu Asn Ile Pro Val Ile Phe Val Ser
130                 135                 140 ggc ggc ccg atg gag gcc ggg aaa acc aaa ctt tcc gat cag atc atc      480
Gly Gly Pro Met Glu Ala Gly Lys Thr Lys Leu Ser Asp Gln Ile Ile
145                 150                 155                 160 aag ctc gat ctg gtt gat gcg atg atc cag ggc gca gac ccg aaa gta      528
Lys Leu Asp Leu Val Asp Ala Met Ile Gln Gly Ala Asp Pro Lys Val
                165                 170                 175 tct gac tcc cag agc gat cag gtt gaa cgt tcc gcg tgt ccg acc tgc      576
Ser Asp Ser Gln Ser Asp Gln Val Glu Arg Ser Ala Cys Pro Thr Cys
            180                 185                 190 ggt tcc tgc tcc ggg atg ttt acc gct aac tca atg aac tgc ctg acc      624
Gly Ser Cys Ser Gly Met Phe Thr Ala Asn Ser Met Asn Cys Leu Thr
            195                 200                 205 gaa gcg ctg ggc ctg tcg cag ccg ggc aac ggc tcg ctg ctg gca acc      672
Glu Ala Leu Gly Leu Ser Gln Pro Gly Asn Gly Ser Leu Leu Ala Thr
210                 215                 220 cac gcc gac cgt aag cag ctg ttc ctt aat gct ggt aaa cgc att gtt      720
His Ala Asp Arg Lys Gln Leu Phe Leu Asn Ala Gly Lys Arg Ile Val
225                 230                 235                 240 gaa ttg acc aaa cgt tat tac gag caa aac gac gaa agt gca ctg ccg      768
Glu Leu Thr Lys Arg Tyr Tyr Glu Gln Asn Asp Glu Ser Ala Leu Pro
                245                 250                 255 cgt aat atc gcc agt aag gcg gcg ttt gaa aac gcc atg acg ctg gat      816
Arg Asn Ile Ala Ser Lys Ala Ala Phe Glu Asn Ala Met Thr Leu Asp
            260                 265                 270 atc gcg atg ggt gga tcg act aac acc gta ctt cac ctg ctg gcg gcg      864
Ile Ala Met Gly Gly Ser Thr Asn Thr Val Leu His Leu Leu Ala Ala
            275                 280                 285 gcg cag gaa gcg gaa atc gac ttc acc atg agt gat atc gat aag ctt      912
Ala Gln Glu Ala Glu Ile Asp Phe Thr Met Ser Asp Ile Asp Lys Leu
290                 295                 300 tcc cgc aag gtt cca cag ctg tgt aaa gtt gcg ccg agc acc cag aaa      960
Ser Arg Lys Val Pro Gln Leu Cys Lys Val Ala Pro Ser Thr Gln Lys
305                 310                 315                 320 tac cat atg gaa gat gtt cac cgt gct ggt ggt gtt atc ggt att ctc     1008
Tyr His Met Glu Asp Val His Arg Ala Gly Gly Val Ile Gly Ile Leu
                325                 330                 335 ggc gaa ctg gat cgc gcg ggg tta ctg aac cgt gat gtg aaa aac gta     1056
Gly Glu Leu Asp Arg Ala Gly Leu Leu Asn Arg Asp Val Lys Asn Val
                340                 345                 350
```

```
ctt ggc ctg acg ttg ccg caa acg ctg gaa caa tac gac gtt atg ctg      1104
Leu Gly Leu Thr Leu Pro Gln Thr Leu Glu Gln Tyr Asp Val Met Leu
        355                 360                 365 acc cag gat gac gcg gta aaa aat atg ttc cgc gca ggt cct gca ggc      1152
Thr Gln Asp Asp Ala Val Lys Asn Met Phe Arg Ala Gly Pro Ala Gly
    370                 375                 380 att cgt acc aca cag gca ttc tcg caa gat tgc cgt tgg gat acg ctg      1200
Ile Arg Thr Thr Gln Ala Phe Ser Gln Asp Cys Arg Trp Asp Thr Leu
385                 390                 395                 400 gac gac gat cgc gcc aat ggc tgt atc cgc tcg ctg gaa cac gcc tac      1248
Asp Asp Asp Arg Ala Asn Gly Cys Ile Arg Ser Leu Glu His Ala Tyr
                405                 410                 415 agc aaa gac ggc ggc ctg gcg gtg ctc tac ggt aac ttt gcg gaa aac      1296
Ser Lys Asp Gly Gly Leu Ala Val Leu Tyr Gly Asn Phe Ala Glu Asn
            420                 425                 430 ggc tgc atc gtg aaa acg gca ggc gtc gat gac agc atc ctc aaa ttc      1344
Gly Cys Ile Val Lys Thr Ala Gly Val Asp Asp Ser Ile Leu Lys Phe
        435                 440                 445 acc ggc ccg gcg aaa gtg tac gaa agc cag gac gat gcg gta gaa gcg      1392
Thr Gly Pro Ala Lys Val Tyr Glu Ser Gln Asp Asp Ala Val Glu Ala
    450                 455                 460 att ctc ggc ggt aaa gtt gtc gcc gga gat gtg gta gta att cgc tat      1440
Ile Leu Gly Gly Lys Val Val Ala Gly Asp Val Val Val Ile Arg Tyr
465                 470                 475                 480 gaa ggc ccg aaa ggc ggt ccg ggg atg cag gaa atg ctc tac cca acc      1488
Glu Gly Pro Lys Gly Gly Pro Gly Met Gln Glu Met Leu Tyr Pro Thr
                485                 490                 495 agc ttc ctg aaa tca atg ggt ctc ggc aaa gcc tgt gcg ctg atc acc      1536
Ser Phe Leu Lys Ser Met Gly Leu Gly Lys Ala Cys Ala Leu Ile Thr
            500                 505                 510 gac ggt cgt ttc tct ggt ggc acc tct ggt ctt tcc atc ggc cac gtc      1584
Asp Gly Arg Phe Ser Gly Gly Thr Ser Gly Leu Ser Ile Gly His Val
        515                 520                 525 tca ccg gaa gcg gca agc ggc ggc agc att ggc ctg att gaa gat ggt      1632
Ser Pro Glu Ala Ala Ser Gly Gly Ser Ile Gly Leu Ile Glu Asp Gly
    530                 535                 540 gac ctg atc gct atc gac atc ccg aac cgt ggc att cag tta cag gta      1680
Asp Leu Ile Ala Ile Asp Ile Pro Asn Arg Gly Ile Gln Leu Gln Val
545                 550                 555                 560 agc gat gcc gaa ctg gcg gcg cgt cgt gaa gcg cag gac gct cga ggt      1728
Ser Asp Ala Glu Leu Ala Ala Arg Arg Glu Ala Gln Asp Ala Arg Gly
                565                 570                 575 gac aaa gcc tgg acg ccg aaa aat cgt gaa cgt cag gtc tcc ttt gcc      1776
Asp Lys Ala Trp Thr Pro Lys Asn Arg Glu Arg Gln Val Ser Phe Ala
            580                 585                 590 ctg cgt gct tat gcc agc ctg gca acc agc gcc gac aaa ggc gcg gtg      1824
Leu Arg Ala Tyr Ala Ser Leu Ala Thr Ser Ala Asp Lys Gly Ala Val
        595                 600                 605 cgc gat aaa tcg aaa ctg ggg ggt taa                                  1851
Arg Asp Lys Ser Lys Leu Gly Gly
    610                 615

<210> SEQ ID NO 86
<211> LENGTH: 616
<212> TYPE: PRT
<213> ORGANISM: Escherichia coli

<400> SEQUENCE: 86

Met Pro Lys Tyr Arg Ser Ala Thr Thr Thr His Gly Arg Asn Met Ala
1               5                   10                  15

Gly Ala Arg Ala Leu Trp Arg Ala Thr Gly Met Thr Asp Ala Asp Phe
```

```
                   20                  25                  30
Gly Lys Pro Ile Ile Ala Val Val Asn Ser Phe Thr Gln Phe Val Pro
            35                  40                  45
Gly His Val His Leu Arg Asp Leu Gly Lys Leu Val Ala Glu Gln Ile
        50                  55                  60
Glu Ala Ala Gly Gly Val Ala Lys Glu Phe Asn Thr Ile Ala Val Asp
65                  70                  75                  80
Asp Gly Ile Ala Met Gly His Gly Gly Met Leu Tyr Ser Leu Pro Ser
                85                  90                  95
Arg Glu Leu Ile Ala Asp Ser Val Glu Tyr Met Val Asn Ala His Cys
            100                 105                 110
Ala Asp Ala Met Val Cys Ile Ser Asn Cys Asp Lys Ile Thr Pro Gly
        115                 120                 125
Met Leu Met Ala Ser Leu Arg Leu Asn Ile Pro Val Ile Phe Val Ser
    130                 135                 140
Gly Gly Pro Met Glu Ala Gly Lys Thr Lys Leu Ser Asp Gln Ile Ile
145                 150                 155                 160
Lys Leu Asp Leu Val Asp Ala Met Ile Gln Gly Ala Asp Pro Lys Val
                165                 170                 175
Ser Asp Ser Gln Ser Asp Gln Val Glu Arg Ser Ala Cys Pro Thr Cys
            180                 185                 190
Gly Ser Cys Ser Gly Met Phe Thr Ala Asn Ser Met Asn Cys Leu Thr
        195                 200                 205
Glu Ala Leu Gly Leu Ser Gln Pro Gly Asn Gly Ser Leu Leu Ala Thr
    210                 215                 220
His Ala Asp Arg Lys Gln Leu Phe Leu Asn Ala Gly Lys Arg Ile Val
225                 230                 235                 240
Glu Leu Thr Lys Arg Tyr Tyr Glu Gln Asn Asp Glu Ser Ala Leu Pro
                245                 250                 255
Arg Asn Ile Ala Ser Lys Ala Ala Phe Glu Asn Ala Met Thr Leu Asp
            260                 265                 270
Ile Ala Met Gly Gly Ser Thr Asn Thr Val Leu His Leu Leu Ala Ala
        275                 280                 285
Ala Gln Glu Ala Glu Ile Asp Phe Thr Met Ser Asp Ile Asp Lys Leu
    290                 295                 300
Ser Arg Lys Val Pro Gln Leu Cys Lys Val Ala Pro Ser Thr Gln Lys
305                 310                 315                 320
Tyr His Met Glu Asp Val His Arg Ala Gly Gly Val Ile Gly Ile Leu
                325                 330                 335
Gly Glu Leu Asp Arg Ala Gly Leu Leu Asn Arg Asp Val Lys Asn Val
            340                 345                 350
Leu Gly Leu Thr Leu Pro Gln Thr Leu Glu Gln Tyr Asp Val Met Leu
        355                 360                 365
Thr Gln Asp Asp Ala Val Lys Asn Met Phe Arg Ala Gly Pro Ala Gly
    370                 375                 380
Ile Arg Thr Thr Gln Ala Phe Ser Gln Asp Cys Arg Trp Asp Thr Leu
385                 390                 395                 400
Asp Asp Asp Arg Ala Asn Gly Cys Ile Arg Ser Leu Glu His Ala Tyr
                405                 410                 415
Ser Lys Asp Gly Gly Leu Ala Val Leu Tyr Gly Asn Phe Ala Glu Asn
            420                 425                 430
Gly Cys Ile Val Lys Thr Ala Gly Val Asp Asp Ser Ile Leu Lys Phe
        435                 440                 445
```

```
Thr Gly Pro Ala Lys Val Tyr Glu Ser Gln Asp Asp Ala Val Glu Ala
    450                 455                 460

Ile Leu Gly Gly Lys Val Val Ala Gly Asp Val Val Ile Arg Tyr
465                 470                 475                 480

Glu Gly Pro Lys Gly Gly Pro Gly Met Gln Glu Met Leu Tyr Pro Thr
                    485                 490                 495

Ser Phe Leu Lys Ser Met Gly Leu Gly Lys Ala Cys Ala Leu Ile Thr
                500                 505                 510

Asp Gly Arg Phe Ser Gly Gly Thr Ser Gly Leu Ser Ile Gly His Val
                515                 520                 525

Ser Pro Glu Ala Ala Ser Gly Gly Ser Ile Gly Leu Ile Glu Asp Gly
    530                 535                 540

Asp Leu Ile Ala Ile Asp Ile Pro Asn Arg Gly Ile Gln Leu Gln Val
545                 550                 555                 560

Ser Asp Ala Glu Leu Ala Ala Arg Arg Glu Ala Gln Asp Ala Arg Gly
                565                 570                 575

Asp Lys Ala Trp Thr Pro Lys Asn Arg Glu Arg Gln Val Ser Phe Ala
                580                 585                 590

Leu Arg Ala Tyr Ala Ser Leu Ala Thr Ser Ala Asp Lys Gly Ala Val
                595                 600                 605

Arg Asp Lys Ser Lys Leu Gly Gly
    610                 615

<210> SEQ ID NO 87
<211> LENGTH: 1545
<212> TYPE: DNA
<213> ORGANISM: Escherichia coli
<220> FEATURE:
<221> NAME/KEY: CDS
<222> LOCATION: (1)..(1545)

<400> SEQUENCE: 87 atg gct gac tcg caa ccc ctg tcc ggt gct ccg gaa ggt gcc gaa tat    48
Met Ala Asp Ser Gln Pro Leu Ser Gly Ala Pro Glu Gly Ala Glu Tyr
1               5                   10                  15 tta aga gca gtg ctg cgc gcg ccg gtt tac gag gcg gcg cag gtt acg    96
Leu Arg Ala Val Leu Arg Ala Pro Val Tyr Glu Ala Ala Gln Val Thr
                20                  25                  30 ccg cta caa aaa atg gaa aaa ctg tcg tcg cgt ctt gat aac gtc att   144
Pro Leu Gln Lys Met Glu Lys Leu Ser Ser Arg Leu Asp Asn Val Ile
            35                  40                  45 ctg gtg aag cgc gaa gat cgc cag cca gtg cac agc ttt aag ctg cgc   192
Leu Val Lys Arg Glu Asp Arg Gln Pro Val His Ser Phe Lys Leu Arg
        50                  55                  60 ggc gca tac gcc atg atg gcg ggc ctg acg gaa gaa cag aaa gcg cac   240
Gly Ala Tyr Ala Met Met Ala Gly Leu Thr Glu Glu Gln Lys Ala His
65                  70                  75                  80 ggc gtg atc act gct tct gcg ggt aac cac gcg cag ggc gtc gcg ttt   288
Gly Val Ile Thr Ala Ser Ala Gly Asn His Ala Gln Gly Val Ala Phe
                85                  90                  95 tct tct gcg cgg tta ggc gtg aag gcc ctg atc gtt atg cca acc gcc   336
Ser Ser Ala Arg Leu Gly Val Lys Ala Leu Ile Val Met Pro Thr Ala
            100                 105                 110 acc gcc gac atc aaa gtc gac gcg gtg cgc ggc ttc ggc ggc gaa gtg   384
Thr Ala Asp Ile Lys Val Asp Ala Val Arg Gly Phe Gly Gly Glu Val
        115                 120                 125 ctg ctc cac ggc gcg aac ttt gat gaa gcg aaa gcc aaa gcg atc gaa   432
Leu Leu His Gly Ala Asn Phe Asp Glu Ala Lys Ala Lys Ala Ile Glu
130                 135                 140
```

-continued

| | |
|---|---|
| ctg tca cag cag cag ggg ttc acc tgg gtg ccg ccg ttc gac cat ccg<br>Leu Ser Gln Gln Gln Gly Phe Thr Trp Val Pro Pro Phe Asp His Pro<br>145                  150                    155                   160 | 480 |
| atg gtg att gcc ggg caa ggc acg ctg gcg ctg gaa ctg ctc cag cag<br>Met Val Ile Ala Gly Gln Gly Thr Leu Ala Leu Glu Leu Leu Gln Gln<br>                 165                   170                   175 | 528 |
| gac gcc cat ctc gac cgc gta ttt gtg cca gtc ggc ggc ggt ctg<br>Asp Ala His Leu Asp Arg Val Phe Val Pro Val Gly Gly Gly Leu<br>              180                   185                 190 | 576 |
| gct gct ggc gtg gcg gtg ctg atc aaa caa ctg atg ccg caa atc aaa<br>Ala Ala Gly Val Ala Val Leu Ile Lys Gln Leu Met Pro Gln Ile Lys<br>      195                   200                   205 | 624 |
| gtg atc gcc gta gaa gcg gaa gac tcc gcc tgc ctg aaa gca gcg ctg<br>Val Ile Ala Val Glu Ala Glu Asp Ser Ala Cys Leu Lys Ala Ala Leu<br>210                  215                    220 | 672 |
| gat gcg ggt cat ccg gtt gat ctg ccg cgc gta ggg cta ttt gct gaa<br>Asp Ala Gly His Pro Val Asp Leu Pro Arg Val Gly Leu Phe Ala Glu<br>225                  230                   235                   240 | 720 |
| ggc gta gcg gta aaa cgc atc ggt gac gaa acc ttc cgt tta tgc cag<br>Gly Val Ala Val Lys Arg Ile Gly Asp Glu Thr Phe Arg Leu Cys Gln<br>                 245                   250                   255 | 768 |
| gag tat ctc gac gac atc atc acc gtc gat agc gat gcg atc tgt gcg<br>Glu Tyr Leu Asp Asp Ile Ile Thr Val Asp Ser Asp Ala Ile Cys Ala<br>              260                   265                   270 | 816 |
| gcg atg aag gat tta ttc gaa gat gtg cgc gcg gtg gcg gaa ccc tct<br>Ala Met Lys Asp Leu Phe Glu Asp Val Arg Ala Val Ala Glu Pro Ser<br>275                  280                   285 | 864 |
| ggc gcg ctg gcg ctg gcg gga atg aaa aaa tat atc gcc ctg cac aac<br>Gly Ala Leu Ala Leu Ala Gly Met Lys Lys Tyr Ile Ala Leu His Asn<br>          290                   295                   300 | 912 |
| att cgc ggc gaa cgg ctg gcg cat att ctt tcc ggt gcc aac gtg aac<br>Ile Arg Gly Glu Arg Leu Ala His Ile Leu Ser Gly Ala Asn Val Asn<br>305                  310                   315                   320 | 960 |
| ttc cac ggc ctg cgc tac gtc tca gaa cgc tgc gaa ctg ggc gaa cag<br>Phe His Gly Leu Arg Tyr Val Ser Glu Arg Cys Glu Leu Gly Glu Gln<br>                 325                   330                   335 | 1008 |
| cgt gaa gcg ttg ttg gcg gtg acc att ccg gaa gaa aaa ggc agc ttc<br>Arg Glu Ala Leu Leu Ala Val Thr Ile Pro Glu Glu Lys Gly Ser Phe<br>              340                   345                   350 | 1056 |
| ctc aaa ttc tgc caa ctg ctt ggc ggg cgt tcg gtc acc gag ttc aac<br>Leu Lys Phe Cys Gln Leu Leu Gly Gly Arg Ser Val Thr Glu Phe Asn<br>355                  360                   365 | 1104 |
| tac cgt ttt gcc gat gcc aaa aac gcc tgc atc ttt gtc ggt gtg cgc<br>Tyr Arg Phe Ala Asp Ala Lys Asn Ala Cys Ile Phe Val Gly Val Arg<br>          370                   375                   380 | 1152 |
| ctg agc cgc ggc ctc gaa gag cgc aaa gaa att ttg cag atg ctc aac<br>Leu Ser Arg Gly Leu Glu Glu Arg Lys Glu Ile Leu Gln Met Leu Asn<br>385                  390                   395                   400 | 1200 |
| gac ggc ggc tac agc gtg gtt gat ctc tcc gac gac gaa atg gcg aag<br>Asp Gly Gly Tyr Ser Val Val Asp Leu Ser Asp Asp Glu Met Ala Lys<br>                 405                   410                   415 | 1248 |
| cta cac gtg cgc tat atg gtc ggc gga cgt cca tcg cat ccg ttg cag<br>Leu His Val Arg Tyr Met Val Gly Gly Arg Pro Ser His Pro Leu Gln<br>              420                   425                   430 | 1296 |
| gaa cgc ctc tac agc ttc gaa ttc ccg gaa tca ccg ggc gcg ctg ctg<br>Glu Arg Leu Tyr Ser Phe Glu Phe Pro Glu Ser Pro Gly Ala Leu Leu<br>          435                   440                   445 | 1344 |
| cgc ttc ctc aac acg ctg ggt acg tac tgg aac att tct ttg ttc cac<br>Arg Phe Leu Asn Thr Leu Gly Thr Tyr Trp Asn Ile Ser Leu Phe His<br>450                  455                    460 | 1392 |

```
tat cgc agc cat ggc acc gac tac ggg cgc gta ctg gcg gcg ttc gaa      1440
Tyr Arg Ser His Gly Thr Asp Tyr Gly Arg Val Leu Ala Ala Phe Glu
465                 470                 475                 480 ctt ggc gac cat gaa ccg gat ttc gaa acc cgg ctg aat gag ctg ggc      1488
Leu Gly Asp His Glu Pro Asp Phe Glu Thr Arg Leu Asn Glu Leu Gly
                485                 490                 495 tac gat tgc cac gac gaa acc aat aac ccg gcg ttc agg ttc ttt ttg      1536
Tyr Asp Cys His Asp Glu Thr Asn Asn Pro Ala Phe Arg Phe Phe Leu
                500                 505                 510 gcg ggt tag                                                          1545
Ala Gly <210> SEQ ID NO 88
<211> LENGTH: 514
<212> TYPE: PRT
<213> ORGANISM: Escherichia coli

<400> SEQUENCE: 88

Met Ala Asp Ser Gln Pro Leu Ser Gly Ala Pro Glu Gly Ala Glu Tyr
1               5                   10                  15

Leu Arg Ala Val Leu Arg Ala Pro Val Tyr Glu Ala Ala Gln Val Thr
            20                  25                  30

Pro Leu Gln Lys Met Glu Lys Leu Ser Ser Arg Leu Asp Asn Val Ile
        35                  40                  45

Leu Val Lys Arg Glu Asp Arg Gln Pro Val His Ser Phe Lys Leu Arg
    50                  55                  60

Gly Ala Tyr Ala Met Met Ala Gly Leu Thr Glu Glu Gln Lys Ala His
65                  70                  75                  80

Gly Val Ile Thr Ala Ser Ala Gly Asn His Ala Gln Gly Val Ala Phe
                85                  90                  95

Ser Ser Ala Arg Leu Gly Val Lys Ala Leu Ile Val Met Pro Thr Ala
            100                 105                 110

Thr Ala Asp Ile Lys Val Asp Ala Val Arg Gly Phe Gly Gly Glu Val
        115                 120                 125

Leu Leu His Gly Ala Asn Phe Asp Glu Ala Lys Ala Lys Ala Ile Glu
    130                 135                 140

Leu Ser Gln Gln Gln Gly Phe Thr Trp Val Pro Pro Phe Asp His Pro
145                 150                 155                 160

Met Val Ile Ala Gly Gln Gly Thr Leu Ala Leu Glu Leu Leu Gln Gln
                165                 170                 175

Asp Ala His Leu Asp Arg Val Phe Val Pro Val Gly Gly Gly Gly Leu
            180                 185                 190

Ala Ala Gly Val Ala Val Leu Ile Lys Gln Leu Met Pro Gln Ile Lys
        195                 200                 205

Val Ile Ala Val Glu Ala Glu Asp Ser Ala Cys Leu Lys Ala Ala Leu
    210                 215                 220

Asp Ala Gly His Pro Val Asp Leu Pro Arg Val Gly Leu Phe Ala Glu
225                 230                 235                 240

Gly Val Ala Val Lys Arg Ile Gly Asp Glu Thr Phe Arg Leu Cys Gln
                245                 250                 255

Glu Tyr Leu Asp Asp Ile Ile Thr Val Asp Ser Asp Ala Ile Cys Ala
            260                 265                 270

Ala Met Lys Asp Leu Phe Glu Asp Val Arg Ala Val Ala Glu Pro Ser
        275                 280                 285

Gly Ala Leu Ala Leu Ala Gly Met Lys Lys Tyr Ile Ala Leu His Asn
    290                 295                 300
```

```
Ile Arg Gly Glu Arg Leu Ala His Ile Leu Ser Gly Ala Asn Val Asn
305                 310                 315                 320

Phe His Gly Leu Arg Tyr Val Ser Glu Arg Cys Glu Leu Gly Glu Gln
            325                 330                 335

Arg Glu Ala Leu Leu Ala Val Thr Ile Pro Glu Glu Lys Gly Ser Phe
        340                 345                 350

Leu Lys Phe Cys Gln Leu Leu Gly Gly Arg Ser Val Thr Glu Phe Asn
    355                 360                 365

Tyr Arg Phe Ala Asp Ala Lys Asn Ala Cys Ile Phe Val Gly Val Arg
370                 375                 380

Leu Ser Arg Gly Leu Glu Glu Arg Lys Glu Ile Leu Gln Met Leu Asn
385                 390                 395                 400

Asp Gly Gly Tyr Ser Val Val Asp Leu Ser Asp Glu Met Ala Lys
            405                 410                 415

Leu His Val Arg Tyr Met Val Gly Gly Arg Pro Ser His Pro Leu Gln
            420                 425                 430

Glu Arg Leu Tyr Ser Phe Glu Phe Pro Glu Ser Pro Gly Ala Leu Leu
        435                 440                 445

Arg Phe Leu Asn Thr Leu Gly Thr Tyr Trp Asn Ile Ser Leu Phe His
450                 455                 460

Tyr Arg Ser His Gly Thr Asp Tyr Gly Arg Val Leu Ala Ala Phe Glu
465                 470                 475                 480

Leu Gly Asp His Glu Pro Asp Phe Glu Thr Arg Leu Asn Glu Leu Gly
            485                 490                 495

Tyr Asp Cys His Asp Glu Thr Asn Asn Pro Ala Phe Arg Phe Phe Leu
        500                 505                 510

Ala Gly

<210> SEQ ID NO 89
<211> LENGTH: 1095
<212> TYPE: DNA
<213> ORGANISM: Escherichia coli
<220> FEATURE:
<221> NAME/KEY: CDS
<222> LOCATION: (1)..(1095)

<400> SEQUENCE: 89 gtg atg tcg aag aat tac cat att gcc gta ttg ccg ggg gac ggt att      48
Val Met Ser Lys Asn Tyr His Ile Ala Val Leu Pro Gly Asp Gly Ile
1               5                   10                  15 ggt ccg gaa gtg atg acc cag gcg ctg aaa gtg ctg gat gcc gtg cgc      96
Gly Pro Glu Val Met Thr Gln Ala Leu Lys Val Leu Asp Ala Val Arg
            20                  25                  30 aac cgc ttt gcg atg cgc atc acc acc agc cat tac gat gta ggc ggc     144
Asn Arg Phe Ala Met Arg Ile Thr Thr Ser His Tyr Asp Val Gly Gly
        35                  40                  45 gca gcc att gat aac cac ggg caa cca ctg ccg cct gcg acg gtt gaa     192
Ala Ala Ile Asp Asn His Gly Gln Pro Leu Pro Pro Ala Thr Val Glu
    50                  55                  60 ggt tgt gag caa gcc gat gcc gtg ctg ttt ggc tcg gta ggc ggc ccg     240
Gly Cys Glu Gln Ala Asp Ala Val Leu Phe Gly Ser Val Gly Gly Pro
65                  70                  75                  80 aag tgg gaa cat tta cca cca gac cag caa cca gaa cgc ggc gcg ctg     288
Lys Trp Glu His Leu Pro Pro Asp Gln Gln Pro Glu Arg Gly Ala Leu
                85                  90                  95 ctg cct ctg cgt aag cac ttc aaa tta ttc agc aac ctg cgc ccg gca     336
Leu Pro Leu Arg Lys His Phe Lys Leu Phe Ser Asn Leu Arg Pro Ala
            100                 105                 110
```

| | | | | | | | | | | | | | | | |
|---|---|---|---|---|---|---|---|---|---|---|---|---|---|---|---|
| aaa | ctg | tat | cag | ggg | ctg | gaa | gca | ttc | tgt | ccg | ctg | cgt | gca | gac | att | 384 |
| Lys | Leu | Tyr | Gln | Gly | Leu | Glu | Ala | Phe | Cys | Pro | Leu | Arg | Ala | Asp | Ile | |
| | | 115 | | | | 120 | | | | | 125 | | | | | |

| gcc | gca | aac | ggc | ttc | gac | atc | ctg | tgt | gtg | cgc | gaa | ctg | acc | ggc | ggc | 432 |
| Ala | Ala | Asn | Gly | Phe | Asp | Ile | Leu | Cys | Val | Arg | Glu | Leu | Thr | Gly | Gly | |
| 130 | | | | | 135 | | | | | 140 | | | | | | |

| atc | tat | ttc | ggt | cag | cca | aaa | ggc | cgc | gaa | ggt | agc | gga | caa | tat | gaa | 480 |
| Ile | Tyr | Phe | Gly | Gln | Pro | Lys | Gly | Arg | Glu | Gly | Ser | Gly | Gln | Tyr | Glu | |
| 145 | | | | | 150 | | | | | 155 | | | | | 160 | |

| aaa | gcc | ttt | gat | acc | gag | gtg | tat | cac | cgt | ttt | gag | atc | gaa | cgt | atc | 528 |
| Lys | Ala | Phe | Asp | Thr | Glu | Val | Tyr | His | Arg | Phe | Glu | Ile | Glu | Arg | Ile | |
| | | | | 165 | | | | | 170 | | | | | 175 | | |

| gcc | cgc | atc | gcg | ttt | gaa | tct | gct | cgc | aag | cgt | cgc | cac | aaa | gtg | acg | 576 |
| Ala | Arg | Ile | Ala | Phe | Glu | Ser | Ala | Arg | Lys | Arg | Arg | His | Lys | Val | Thr | |
| | | 180 | | | | 185 | | | | | 190 | | | | | |

| tcg | atc | gat | aaa | gcc | aac | gtg | ctg | caa | tcc | tct | att | tta | tgg | cgg | gag | 624 |
| Ser | Ile | Asp | Lys | Ala | Asn | Val | Leu | Gln | Ser | Ser | Ile | Leu | Trp | Arg | Glu | |
| | 195 | | | | | 200 | | | | | 205 | | | | | |

| atc | gtt | aac | gag | atc | gcc | acg | gaa | tac | ccg | gat | gtc | gaa | ctg | gcg | cat | 672 |
| Ile | Val | Asn | Glu | Ile | Ala | Thr | Glu | Tyr | Pro | Asp | Val | Glu | Leu | Ala | His | |
| | 210 | | | | | 215 | | | | | 220 | | | | | |

| atg | tac | atc | gac | aac | gcc | acc | atg | cag | ctg | att | aaa | gat | cca | tca | cag | 720 |
| Met | Tyr | Ile | Asp | Asn | Ala | Thr | Met | Gln | Leu | Ile | Lys | Asp | Pro | Ser | Gln | |
| 225 | | | | | 230 | | | | | 235 | | | | | 240 | |

| ttt | gac | gtt | ctg | ctg | tgc | tcc | aac | ctg | ttt | ggc | gac | att | ctg | tct | gac | 768 |
| Phe | Asp | Val | Leu | Leu | Cys | Ser | Asn | Leu | Phe | Gly | Asp | Ile | Leu | Ser | Asp | |
| | | | | 245 | | | | | 250 | | | | | 255 | | |

| gag | tgc | gca | atg | atc | act | ggc | tcg | atg | ggg | atg | ttg | cct | tcc | gcc | agc | 816 |
| Glu | Cys | Ala | Met | Ile | Thr | Gly | Ser | Met | Gly | Met | Leu | Pro | Ser | Ala | Ser | |
| | | | 260 | | | | | 265 | | | | | 270 | | | |

| ctg | aac | gag | caa | ggt | ttt | gga | ctg | tat | gaa | ccg | gcg | ggc | ggc | tcg | gca | 864 |
| Leu | Asn | Glu | Gln | Gly | Phe | Gly | Leu | Tyr | Glu | Pro | Ala | Gly | Gly | Ser | Ala | |
| | | | 275 | | | | | 280 | | | | | 285 | | | |

| cca | gat | atc | gca | ggc | aaa | aac | atc | gcc | aac | ccg | att | gca | caa | atc | ctt | 912 |
| Pro | Asp | Ile | Ala | Gly | Lys | Asn | Ile | Ala | Asn | Pro | Ile | Ala | Gln | Ile | Leu | |
| | 290 | | | | | 295 | | | | | 300 | | | | | |

| tcg | ctg | gca | ctg | ctg | ctg | cgt | tac | agc | ctg | gat | gcc | gat | gat | gcg | gct | 960 |
| Ser | Leu | Ala | Leu | Leu | Leu | Arg | Tyr | Ser | Leu | Asp | Ala | Asp | Asp | Ala | Ala | |
| 305 | | | | | 310 | | | | | 315 | | | | | 320 | |

| tgc | gcc | att | gaa | cgc | gcc | att | aac | cgc | gca | tta | gaa | gaa | ggc | att | cgc | 1008 |
| Cys | Ala | Ile | Glu | Arg | Ala | Ile | Asn | Arg | Ala | Leu | Glu | Glu | Gly | Ile | Arg | |
| | | | | 325 | | | | | 330 | | | | | 335 | | |

| acc | ggg | gat | tta | gcc | cgt | ggc | gct | gcc | gcc | gtt | agt | acc | gat | gaa | atg | 1056 |
| Thr | Gly | Asp | Leu | Ala | Arg | Gly | Ala | Ala | Ala | Val | Ser | Thr | Asp | Glu | Met | |
| | | | 340 | | | | | 345 | | | | | 350 | | | |

| ggc | gat | atc | att | gcc | cgc | tat | gta | gca | gaa | ggg | gtg | taa | | | | 1095 |
| Gly | Asp | Ile | Ile | Ala | Arg | Tyr | Val | Ala | Glu | Gly | Val | | | | | |
| | | | 355 | | | | | 360 | | | | | | | | |

<210> SEQ ID NO 90
<211> LENGTH: 364
<212> TYPE: PRT
<213> ORGANISM: Escherichia coli

<400> SEQUENCE: 90

| Val | Met | Ser | Lys | Asn | Tyr | His | Ile | Ala | Val | Leu | Pro | Gly | Asp | Gly | Ile |
|---|---|---|---|---|---|---|---|---|---|---|---|---|---|---|---|
| 1 | | | | 5 | | | | | 10 | | | | | 15 | |

| Gly | Pro | Glu | Val | Met | Thr | Gln | Ala | Leu | Lys | Val | Leu | Asp | Ala | Val | Arg |
|---|---|---|---|---|---|---|---|---|---|---|---|---|---|---|---|
| | | | 20 | | | | | 25 | | | | | 30 | | |

| Asn | Arg | Phe | Ala | Met | Arg | Ile | Thr | Thr | Ser | His | Tyr | Asp | Val | Gly | Gly |
|---|---|---|---|---|---|---|---|---|---|---|---|---|---|---|---|
| | | 35 | | | | | 40 | | | | | 45 | | | |

```
Ala Ala Ile Asp Asn His Gly Gln Pro Leu Pro Pro Ala Thr Val Glu
         50                  55                  60

Gly Cys Glu Gln Ala Asp Ala Val Leu Phe Gly Ser Val Gly Gly Pro
 65                  70                  75                  80

Lys Trp Glu His Leu Pro Pro Asp Gln Gln Pro Glu Arg Gly Ala Leu
                 85                  90                  95

Leu Pro Leu Arg Lys His Phe Lys Leu Phe Ser Asn Leu Arg Pro Ala
            100                 105                 110

Lys Leu Tyr Gln Gly Leu Glu Ala Phe Cys Pro Leu Arg Ala Asp Ile
        115                 120                 125

Ala Ala Asn Gly Phe Asp Ile Leu Cys Val Arg Glu Leu Thr Gly Gly
    130                 135                 140

Ile Tyr Phe Gly Gln Pro Lys Gly Arg Glu Gly Ser Gly Gln Tyr Glu
145                 150                 155                 160

Lys Ala Phe Asp Thr Glu Val Tyr His Arg Phe Glu Ile Glu Arg Ile
                165                 170                 175

Ala Arg Ile Ala Phe Glu Ser Ala Arg Lys Arg Arg His Lys Val Thr
            180                 185                 190

Ser Ile Asp Lys Ala Asn Val Leu Gln Ser Ser Ile Leu Trp Arg Glu
        195                 200                 205

Ile Val Asn Glu Ile Ala Thr Glu Tyr Pro Asp Val Glu Leu Ala His
    210                 215                 220

Met Tyr Ile Asp Asn Ala Thr Met Gln Leu Ile Lys Asp Pro Ser Gln
225                 230                 235                 240

Phe Asp Val Leu Leu Cys Ser Asn Leu Phe Gly Asp Ile Leu Ser Asp
                245                 250                 255

Glu Cys Ala Met Ile Thr Gly Ser Met Gly Met Leu Pro Ser Ala Ser
            260                 265                 270

Leu Asn Glu Gln Gly Phe Gly Leu Tyr Glu Pro Ala Gly Gly Ser Ala
        275                 280                 285

Pro Asp Ile Ala Gly Lys Asn Ile Ala Asn Pro Ile Ala Gln Ile Leu
    290                 295                 300

Ser Leu Ala Leu Leu Leu Arg Tyr Ser Leu Asp Ala Asp Asp Ala Ala
305                 310                 315                 320

Cys Ala Ile Glu Arg Ala Ile Asn Arg Ala Leu Glu Glu Gly Ile Arg
                325                 330                 335

Thr Gly Asp Leu Ala Arg Gly Ala Ala Val Ser Thr Asp Glu Met
            340                 345                 350

Gly Asp Ile Ile Ala Arg Tyr Val Ala Glu Gly Val
        355                 360
```

<210> SEQ ID NO 91
<211> LENGTH: 1401
<212> TYPE: DNA
<213> ORGANISM: Escherichia coli
<220> FEATURE:
<221> NAME/KEY: CDS
<222> LOCATION: (1)..(1401)

<400> SEQUENCE: 91

```
atg gct aag acg tta tac gaa aaa ttg ttc gac gct cac gtt gtg tac      48
Met Ala Lys Thr Leu Tyr Glu Lys Leu Phe Asp Ala His Val Val Tyr
 1               5                  10                  15 gaa gcc gaa aac gaa acc cca ctg tta tat atc gac cgc cac ctg gtg      96
Glu Ala Glu Asn Glu Thr Pro Leu Leu Tyr Ile Asp Arg His Leu Val
                20                  25                  30
```

```
cat gaa gtg acc tca ccg cag gcg ttc gat ggt ctg cgc gcc cac ggt      144
His Glu Val Thr Ser Pro Gln Ala Phe Asp Gly Leu Arg Ala His Gly
         35                  40                  45 cgc ccg gta cgt cag ccg ggc aaa acc ttc gct acc atg gat cac aac      192
Arg Pro Val Arg Gln Pro Gly Lys Thr Phe Ala Thr Met Asp His Asn
 50                  55                  60 gtc tct acc cag acc aaa gac att aat gcc tgc ggt gaa atg gcg cgt      240
Val Ser Thr Gln Thr Lys Asp Ile Asn Ala Cys Gly Glu Met Ala Arg
 65                  70                  75                  80 atc cag atg cag gaa ctg atc aaa aac tgc aaa gaa ttt ggc gtc gaa      288
Ile Gln Met Gln Glu Leu Ile Lys Asn Cys Lys Glu Phe Gly Val Glu
             85                  90                  95 ctg tat gac ctg aat cac ccg tat cag ggg atc gtc cac gta atg ggg      336
Leu Tyr Asp Leu Asn His Pro Tyr Gln Gly Ile Val His Val Met Gly
            100                 105                 110 ccg gaa cag ggc gtc acc ttg ccg ggg atg acc att gtc tgc ggc gac      384
Pro Glu Gln Gly Val Thr Leu Pro Gly Met Thr Ile Val Cys Gly Asp
            115                 120                 125 tcg cat acc gcc acc cac ggc gcg ttt ggc gca ctg gcc ttt ggt atc      432
Ser His Thr Ala Thr His Gly Ala Phe Gly Ala Leu Ala Phe Gly Ile
        130                 135                 140 ggc act tcc gaa gtt gaa cac gta ctg gca acg caa acc ctg aaa cag      480
Gly Thr Ser Glu Val Glu His Val Leu Ala Thr Gln Thr Leu Lys Gln
145                 150                 155                 160 ggc cgc gca aaa acc atg aaa att gaa gtc cag ggc aaa gcc gcg ccg      528
Gly Arg Ala Lys Thr Met Lys Ile Glu Val Gln Gly Lys Ala Ala Pro
                165                 170                 175 ggc att acc gca aaa gat atc gtg ctg gca att atc ggt aaa acc ggt      576
Gly Ile Thr Ala Lys Asp Ile Val Leu Ala Ile Ile Gly Lys Thr Gly
            180                 185                 190 agc gca ggc ggc acc ggg cat gtg gtg gag ttt tgc ggc gaa gca atc      624
Ser Ala Gly Gly Thr Gly His Val Val Glu Phe Cys Gly Glu Ala Ile
        195                 200                 205 cgt gat tta agc atg gaa ggt cgt atg acc ctg tgc aat atg gca atc      672
Arg Asp Leu Ser Met Glu Gly Arg Met Thr Leu Cys Asn Met Ala Ile
210                 215                 220 gaa atg ggc gca aaa gcc ggt ctg gtt gca ccg gac gaa acc acc ttt      720
Glu Met Gly Ala Lys Ala Gly Leu Val Ala Pro Asp Glu Thr Thr Phe
225                 230                 235                 240 aac tat gtc aaa ggc cgt ctg cat gcg ccg aaa ggc aaa gat ttc gac      768
Asn Tyr Val Lys Gly Arg Leu His Ala Pro Lys Gly Lys Asp Phe Asp
                245                 250                 255 gac gcc gtt gcc tac tgg aaa acc ctg caa acc gac gaa ggc gca act      816
Asp Ala Val Ala Tyr Trp Lys Thr Leu Gln Thr Asp Glu Gly Ala Thr
            260                 265                 270 ttc gat acc gtt gtc act ctg caa gca gaa gaa att tca ccg cag gtc      864
Phe Asp Thr Val Val Thr Leu Gln Ala Glu Glu Ile Ser Pro Gln Val
        275                 280                 285 acc tgg ggc acc aat ccc ggc cag gtg att tcc gtg aac gac aat att      912
Thr Trp Gly Thr Asn Pro Gly Gln Val Ile Ser Val Asn Asp Asn Ile
        290                 295                 300 ccc gat ccg gct tcg ttt gcc gat ccg gtt gaa cgc gcg tcg gca gaa      960
Pro Asp Pro Ala Ser Phe Ala Asp Pro Val Glu Arg Ala Ser Ala Glu
305                 310                 315                 320 aaa gcg ctg gcc tat atg ggg ctg aaa ccg ggt att ccg ctg acc gaa     1008
Lys Ala Leu Ala Tyr Met Gly Leu Lys Pro Gly Ile Pro Leu Thr Glu
                325                 330                 335 gtg gct atc gac aaa gtg ttt atc ggt tcc tgt acc aac tcg cgc att     1056
Val Ala Ile Asp Lys Val Phe Ile Gly Ser Cys Thr Asn Ser Arg Ile
            340                 345                 350
```

```
gaa gat tta cgc gcg gca gcg gag atc gcc aaa ggg cga aaa gtc gcg     1104
Glu Asp Leu Arg Ala Ala Ala Glu Ile Ala Lys Gly Arg Lys Val Ala
        355                 360                 365 cca ggc gtg cag gca ctg gtg gtt ccc ggc tct ggc ccg gta aaa gcc     1152
Pro Gly Val Gln Ala Leu Val Val Pro Gly Ser Gly Pro Val Lys Ala
370                 375                 380 cag gcg gaa gcg gaa ggt ctg gat aaa atc ttt att gaa gcc ggt ttt     1200
Gln Ala Glu Ala Glu Gly Leu Asp Lys Ile Phe Ile Glu Ala Gly Phe
385                 390                 395                 400 gaa tgg cgc ttg cct ggc tgc tca atg tgt ctg gcg atg aac aac gac     1248
Glu Trp Arg Leu Pro Gly Cys Ser Met Cys Leu Ala Met Asn Asn Asp
                405                 410                 415 cgt ctg aat ccg ggc gaa cgt tgt gcc tcc acc agc aac cgt aac ttt     1296
Arg Leu Asn Pro Gly Glu Arg Cys Ala Ser Thr Ser Asn Arg Asn Phe
        420                 425                 430 gaa ggc cgc cag ggg cgc ggc ggg cgc acg cat ctg gtc agc ccg gca     1344
Glu Gly Arg Gln Gly Arg Gly Gly Arg Thr His Leu Val Ser Pro Ala
435                 440                 445 atg gct gcc gct gct gct gtg acc gga cat ttc gcc gac att cgc aac     1392
Met Ala Ala Ala Ala Ala Val Thr Gly His Phe Ala Asp Ile Arg Asn
450                 455                 460 att aaa taa                                                         1401
Ile Lys
465

<210> SEQ ID NO 92
<211> LENGTH: 466
<212> TYPE: PRT
<213> ORGANISM: Escherichia coli

<400> SEQUENCE: 92

Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
            20                  25                  30

His Glu Val Thr Ser Pro Gln Ala Phe Asp Gly Leu Arg Ala His Gly
        35                  40                  45

Arg Pro Val Arg Gln Pro Gly Lys Thr Phe Ala Thr Met Asp His Asn
    50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
            100                 105                 110

Pro Glu Gln Gly Val Thr Leu Pro Gly Met Thr Ile Val Cys Gly Asp
        115                 120                 125

Ser His Thr Ala Thr His Gly Ala Phe Gly Ala Leu Ala Phe Gly Ile
    130                 135                 140

Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
            180                 185                 190

Ser Ala Gly Gly Thr Gly His Val Val Glu Phe Cys Gly Glu Ala Ile
        195                 200                 205

Arg Asp Leu Ser Met Glu Gly Arg Met Thr Leu Cys Asn Met Ala Ile
```

```
            210                 215                 220
Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
                245                 250                 255

Asp Ala Val Ala Tyr Trp Lys Thr Leu Gln Thr Asp Glu Gly Ala Thr
                260                 265                 270

Phe Asp Thr Val Val Thr Leu Gln Ala Glu Glu Ile Ser Pro Gln Val
            275                 280                 285

Thr Trp Gly Thr Asn Pro Gly Gln Val Ile Ser Val Asn Asp Asn Ile
290                 295                 300

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
                325                 330                 335

Val Ala Ile Asp Lys Val Phe Ile Gly Ser Cys Thr Asn Ser Arg Ile
            340                 345                 350

Glu Asp Leu Arg Ala Ala Ala Glu Ile Ala Lys Gly Arg Lys Val Ala
            355                 360                 365

Pro Gly Val Gln Ala Leu Val Val Pro Gly Ser Gly Pro Val Lys Ala
370                 375                 380

Gln Ala Glu Ala Glu Gly Leu Asp Lys Ile Phe Ile Glu Ala Gly Phe
385                 390                 395                 400

Glu Trp Arg Leu Pro Gly Cys Ser Met Cys Leu Ala Met Asn Asn Asp
                405                 410                 415

Arg Leu Asn Pro Gly Glu Arg Cys Ala Ser Thr Ser Asn Arg Asn Phe
                420                 425                 430

Glu Gly Arg Gln Gly Arg Gly Gly Arg Thr His Leu Val Ser Pro Ala
            435                 440                 445

Met Ala Ala Ala Ala Val Thr Gly His Phe Ala Asp Ile Arg Asn
            450                 455                 460

Ile Lys
465

<210> SEQ ID NO 93
<211> LENGTH: 606
<212> TYPE: DNA
<213> ORGANISM: Escherichia coli
<220> FEATURE:
<221> NAME/KEY: CDS
<222> LOCATION: (1)..(606)

<400> SEQUENCE: 93 atg gca gag aaa ttt atc aaa cac aca ggc ctg gtg gtt ccg ctg gat       48
Met Ala Glu Lys Phe Ile Lys His Thr Gly Leu Val Val Pro Leu Asp
1               5                   10                  15 gcc gcc aat gtc gat acc gat gca atc atc ccg aaa cag ttt ttg cag       96
Ala Ala Asn Val Asp Thr Asp Ala Ile Ile Pro Lys Gln Phe Leu Gln
                20                  25                  30 aaa gtg acc cgt acg ggt ttt ggc gcg cat ctg ttt aac gac tgg cgt      144
Lys Val Thr Arg Thr Gly Phe Gly Ala His Leu Phe Asn Asp Trp Arg
            35                  40                  45 ttt ctg gat gaa aaa ggc caa cag cca aac ccg gac ttc gtg ctg aac      192
Phe Leu Asp Glu Lys Gly Gln Gln Pro Asn Pro Asp Phe Val Leu Asn
        50                  55                  60 ttc ccg cag tat cag ggc gct tcc att ttg ctg gca cga gaa aac ttc      240
Phe Pro Gln Tyr Gln Gly Ala Ser Ile Leu Leu Ala Arg Glu Asn Phe
65                  70                  75                  80
```

```
ggc tgt ggc tct tcg cgt gag cac gcg ccc tgg gca ttg acc gac tac      288
Gly Cys Gly Ser Ser Arg Glu His Ala Pro Trp Ala Leu Thr Asp Tyr
            85                  90                  95 ggt ttt aaa gtg gtg att gcg ccg agt ttt gct gac atc ttc tac ggc      336
Gly Phe Lys Val Val Ile Ala Pro Ser Phe Ala Asp Ile Phe Tyr Gly
           100                 105                 110 aat agc ttt aac aac cag ctg ctg ccg gtg aaa tta agc gat gca gaa      384
Asn Ser Phe Asn Asn Gln Leu Leu Pro Val Lys Leu Ser Asp Ala Glu
           115                 120                 125 gtg gac gaa ctg ttt gcg ctg gtg aaa gct aat ccg ggg atc cat ttc      432
Val Asp Glu Leu Phe Ala Leu Val Lys Ala Asn Pro Gly Ile His Phe
130                 135                 140 gac gtg gat ctg gaa gcg caa gag gtg aaa gcg gga gag aaa acc tat      480
Asp Val Asp Leu Glu Ala Gln Glu Val Lys Ala Gly Glu Lys Thr Tyr
145                 150                 155                 160 cgc ttt acc atc gat gcc ttc cgc cgc cac tgc atg atg aac ggt ctg      528
Arg Phe Thr Ile Asp Ala Phe Arg Arg His Cys Met Met Asn Gly Leu
           165                 170                 175 gac agt att ggg ctt acc ttg cag cac gac gac gcc att gcc gct tat      576
Asp Ser Ile Gly Leu Thr Leu Gln His Asp Asp Ala Ile Ala Ala Tyr
           180                 185                 190 gaa gca aaa caa cct gcg ttt atg aat taa                              606
Glu Ala Lys Gln Pro Ala Phe Met Asn
           195                 200

<210> SEQ ID NO 94
<211> LENGTH: 201
<212> TYPE: PRT
<213> ORGANISM: Escherichia coli

<400> SEQUENCE: 94

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Leu Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu His Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200
```

<210> SEQ ID NO 95
<211> LENGTH: 264
<212> TYPE: DNA
<213> ORGANISM: Escherichia coli
<220> FEATURE:
<221> NAME/KEY: CDS
<222> LOCATION: (1)..(264)

<400> SEQUENCE: 95

```
atg atg caa cat cag gtc aat gta tcg gct cgc ttc aat cca gaa acc        48
Met Met Gln His Gln Val Asn Val Ser Ala Arg Phe Asn Pro Glu Thr
1               5                   10                  15 tta gaa cgt gtt tta cgc gtg gtg cgt cat cgt ggt ttc cac gtc tgc        96
Leu Glu Arg Val Leu Arg Val Val Arg His Arg Gly Phe His Val Cys
            20                  25                  30 tca atg aat atg gcc gcc gcc agc gat gca caa aat ata aat atc gaa       144
Ser Met Asn Met Ala Ala Ala Ser Asp Ala Gln Asn Ile Asn Ile Glu
        35                  40                  45 ttg acc gtt gcc agc cca cgg tcg gtc gac tta ctg ttt agt cag tta       192
Leu Thr Val Ala Ser Pro Arg Ser Val Asp Leu Leu Phe Ser Gln Leu
    50                  55                  60 aat aaa ctg gtg gac gtc gca cac gtt gcc atc tgc cag agc aca acc       240
Asn Lys Leu Val Asp Val Ala His Val Ala Ile Cys Gln Ser Thr Thr
65                  70                  75                  80 aca tca caa caa atc cgc gcc tga                                       264
Thr Ser Gln Gln Ile Arg Ala
                85
```

<210> SEQ ID NO 96
<211> LENGTH: 87
<212> TYPE: PRT
<213> ORGANISM: Escherichia coli

<400> SEQUENCE: 96

```
Met Met Gln His Gln Val Asn Val Ser Ala Arg Phe Asn Pro Glu Thr
1               5                   10                  15

Leu Glu Arg Val Leu Arg Val Val Arg His Arg Gly Phe His Val Cys
            20                  25                  30

Ser Met Asn Met Ala Ala Ala Ser Asp Ala Gln Asn Ile Asn Ile Glu
        35                  40                  45

Leu Thr Val Ala Ser Pro Arg Ser Val Asp Leu Leu Phe Ser Gln Leu
    50                  55                  60

Asn Lys Leu Val Asp Val Ala His Val Ala Ile Cys Gln Ser Thr Thr
65                  70                  75                  80

Thr Ser Gln Gln Ile Arg Ala
                85
```

<210> SEQ ID NO 97
<211> LENGTH: 582
<212> TYPE: DNA
<213> ORGANISM: Escherichia coli
<220> FEATURE:
<221> NAME/KEY: CDS
<222> LOCATION: (1)..(582)

<400> SEQUENCE: 97

```
ttg ttg tta aaa caa ctg tcg gat cgt aaa cct gcg gat tgc gtc gtg        48
Leu Leu Leu Lys Gln Leu Ser Asp Arg Lys Pro Ala Asp Cys Val Val
1               5                   10                  15 acc aca gat gtg ggg cag cac cag atg tgg gct gcg cag cac atc gcc        96
Thr Thr Asp Val Gly Gln His Gln Met Trp Ala Ala Gln His Ile Ala
            20                  25                  30
```

| | | | | | | | | | | | | | | | | |
|---|---|---|---|---|---|---|---|---|---|---|---|---|---|---|---|---|
| cac | act | cgc | ccg | gaa | aat | ttc | atc | acc | tcc | agc | ggt | tta | ggt | acc | atg | 144 |
| His | Thr | Arg | Pro | Glu | Asn | Phe | Ile | Thr | Ser | Ser | Gly | Leu | Gly | Thr | Met | |
| | | 35 | | | | | 40 | | | | | 45 | | | | |
| ggt | ttt | ggt | tta | ccg | gcg | gcg | gtt | ggc | gca | caa | gtc | gcg | cga | ccg | aac | 192 |
| Gly | Phe | Gly | Leu | Pro | Ala | Ala | Val | Gly | Ala | Gln | Val | Ala | Arg | Pro | Asn | |
| | 50 | | | | | 55 | | | | | 60 | | | | | |
| gat | acc | gtt | gtc | tgt | atc | tcc | ggt | gac | ggc | tct | ttc | atg | atg | aat | gtg | 240 |
| Asp | Thr | Val | Val | Cys | Ile | Ser | Gly | Asp | Gly | Ser | Phe | Met | Met | Asn | Val | |
| 65 | | | | | 70 | | | | | 75 | | | | | 80 | |
| caa | gag | ctg | ggc | acc | gta | aaa | cgc | aag | cag | tta | ccg | ttg | aaa | atc | gtc | 288 |
| Gln | Glu | Leu | Gly | Thr | Val | Lys | Arg | Lys | Gln | Leu | Pro | Leu | Lys | Ile | Val | |
| | | | | 85 | | | | | 90 | | | | | 95 | | |
| tta | ctc | gat | aac | caa | cgg | tta | ggg | atg | gtt | cga | caa | tgg | cag | caa | ctg | 336 |
| Leu | Leu | Asp | Asn | Gln | Arg | Leu | Gly | Met | Val | Arg | Gln | Trp | Gln | Gln | Leu | |
| | | | 100 | | | | | 105 | | | | | 110 | | | |
| ttt | ttt | cag | gaa | cga | tac | agc | gaa | acc | acc | ctt | act | gat | aac | ccc | gat | 384 |
| Phe | Phe | Gln | Glu | Arg | Tyr | Ser | Glu | Thr | Thr | Leu | Thr | Asp | Asn | Pro | Asp | |
| | | | 115 | | | | | 120 | | | | | 125 | | | |
| ttc | ctc | atg | tta | gcc | agc | gcc | ttc | ggc | atc | cat | ggc | caa | cac | atc | acc | 432 |
| Phe | Leu | Met | Leu | Ala | Ser | Ala | Phe | Gly | Ile | His | Gly | Gln | His | Ile | Thr | |
| | 130 | | | | | 135 | | | | | 140 | | | | | |
| cgg | aaa | gac | cag | gtt | gaa | gcg | gca | ctc | gac | acc | atg | ctg | aac | agt | gat | 480 |
| Arg | Lys | Asp | Gln | Val | Glu | Ala | Ala | Leu | Asp | Thr | Met | Leu | Asn | Ser | Asp | |
| 145 | | | | | 150 | | | | | 155 | | | | | 160 | |
| ggg | cca | tac | ctg | ctt | cat | gtc | tca | atc | gac | gaa | ctt | gag | aac | gtc | tgg | 528 |
| Gly | Pro | Tyr | Leu | Leu | His | Val | Ser | Ile | Asp | Glu | Leu | Glu | Asn | Val | Trp | |
| | | | | 165 | | | | | 170 | | | | | 175 | | |
| ccg | ctg | gtg | ccg | cct | ggc | gcc | agt | aat | tca | gaa | atg | ttg | gag | aaa | tta | 576 |
| Pro | Leu | Val | Pro | Pro | Gly | Ala | Ser | Asn | Ser | Glu | Met | Leu | Glu | Lys | Leu | |
| | | | 180 | | | | | 185 | | | | | 190 | | | |
| tca | tga | | | | | | | | | | | | | | | 582 |
| Ser | | | | | | | | | | | | | | | | |

<210> SEQ ID NO 98
<211> LENGTH: 193
<212> TYPE: PRT
<213> ORGANISM: Escherichia coli

<400> SEQUENCE: 98

Leu Leu Leu Lys Gln Leu Ser Asp Arg Lys Pro Ala Asp Cys Val Val
1               5                   10                  15

Thr Thr Asp Val Gly Gln His Gln Met Trp Ala Ala Gln His Ile Ala
            20                  25                  30

His Thr Arg Pro Glu Asn Phe Ile Thr Ser Ser Gly Leu Gly Thr Met
        35                  40                  45

Gly Phe Gly Leu Pro Ala Ala Val Gly Ala Gln Val Ala Arg Pro Asn
    50                  55                  60

Asp Thr Val Val Cys Ile Ser Gly Asp Gly Ser Phe Met Met Asn Val
65                  70                  75                  80

Gln Glu Leu Gly Thr Val Lys Arg Lys Gln Leu Pro Leu Lys Ile Val
                85                  90                  95

Leu Leu Asp Asn Gln Arg Leu Gly Met Val Arg Gln Trp Gln Gln Leu
            100                 105                 110

Phe Phe Gln Glu Arg Tyr Ser Glu Thr Thr Leu Thr Asp Asn Pro Asp
        115                 120                 125

Phe Leu Met Leu Ala Ser Ala Phe Gly Ile His Gly Gln His Ile Thr
    130                 135                 140

Arg Lys Asp Gln Val Glu Ala Ala Leu Asp Thr Met Leu Asn Ser Asp
145                 150                 155                 160

Gly Pro Tyr Leu Leu His Val Ser Ile Asp Glu Leu Glu Asn Val Trp
                165                 170                 175

Pro Leu Val Pro Pro Gly Ala Ser Asn Ser Glu Met Leu Glu Lys Leu
            180                 185                 190

Ser

<210> SEQ ID NO 99
<211> LENGTH: 291
<212> TYPE: DNA
<213> ORGANISM: Escherichia coli
<220> FEATURE:
<221> NAME/KEY: CDS
<222> LOCATION: (1)..(291)

<400> SEQUENCE: 99

| atg | caa | aac | aca | act | cat | gac | aac | gta | att | ctg | gag | ctc | acc | gtt | cgc | 48 |
| Met | Gln | Asn | Thr | Thr | His | Asp | Asn | Val | Ile | Leu | Glu | Leu | Thr | Val | Arg | |
| 1   |     |     |     | 5   |     |     |     |     | 10  |     |     |     |     | 15  |     | |

| aac | cat | ccg | ggc | gta | atg | acc | cac | gtt | tgt | ggc | ctt | ttt | gcc | cgc | cgc | 96 |
| Asn | His | Pro | Gly | Val | Met | Thr | His | Val | Cys | Gly | Leu | Phe | Ala | Arg | Arg | |
|     |     |     | 20  |     |     |     |     | 25  |     |     |     |     | 30  |     |     | |

| gct | ttt | aac | gtt | gaa | ggc | att | ctt | tgt | ctg | ccg | att | cag | gac | agc | gac | 144 |
| Ala | Phe | Asn | Val | Glu | Gly | Ile | Leu | Cys | Leu | Pro | Ile | Gln | Asp | Ser | Asp | |
|     |     |     |     | 35  |     |     |     |     | 40  |     |     |     |     | 45  |     | |

| aaa | agc | cat | atc | tgg | cta | ctg | gtc | aat | gac | gac | cag | cgt | ctg | gag | cag | 192 |
| Lys | Ser | His | Ile | Trp | Leu | Leu | Val | Asn | Asp | Asp | Gln | Arg | Leu | Glu | Gln | |
|     |     | 50  |     |     |     |     | 55  |     |     |     |     | 60  |     |     |     | |

| atg | ata | agc | caa | atc | gat | aag | ctg | gaa | gat | gtc | gtg | aaa | gtg | cag | cgt | 240 |
| Met | Ile | Ser | Gln | Ile | Asp | Lys | Leu | Glu | Asp | Val | Val | Lys | Val | Gln | Arg | |
| 65  |     |     |     |     | 70  |     |     |     |     | 75  |     |     |     |     | 80  | |

| aat | cag | tcc | gat | ccg | acg | atg | ttt | aac | aag | atc | gcg | gtg | ttt | ttt | cag | 288 |
| Asn | Gln | Ser | Asp | Pro | Thr | Met | Phe | Asn | Lys | Ile | Ala | Val | Phe | Phe | Gln | |
|     |     |     |     | 85  |     |     |     |     | 90  |     |     |     |     | 95  |     | |

| taa | | | | | | | | | | | | | | | | 291 |

<210> SEQ ID NO 100
<211> LENGTH: 96
<212> TYPE: PRT
<213> ORGANISM: Escherichia coli

<400> SEQUENCE: 100

Met Gln Asn Thr Thr His Asp Asn Val Ile Leu Glu Leu Thr Val Arg
1               5                   10                  15

Asn His Pro Gly Val Met Thr His Val Cys Gly Leu Phe Ala Arg Arg
            20                  25                  30

Ala Phe Asn Val Glu Gly Ile Leu Cys Leu Pro Ile Gln Asp Ser Asp
        35                  40                  45

Lys Ser His Ile Trp Leu Leu Val Asn Asp Asp Gln Arg Leu Glu Gln
    50                  55                  60

Met Ile Ser Gln Ile Asp Lys Leu Glu Asp Val Val Lys Val Gln Arg
65                  70                  75                  80

Asn Gln Ser Asp Pro Thr Met Phe Asn Lys Ile Ala Val Phe Phe Gln
                85                  90                  95

<210> SEQ ID NO 101
<211> LENGTH: 1689
<212> TYPE: DNA
<213> ORGANISM: Escherichia coli
<220> FEATURE:
<221> NAME/KEY: CDS
<222> LOCATION: (1)..(1689)

<400> SEQUENCE: 101

| | | | | | | | | | | | | | | | | |
|---|---|---|---|---|---|---|---|---|---|---|---|---|---|---|---|---|
| atg | gca | agt | tcg | ggc | aca | aca | tcg | acg | cgt | aag | cgc | ttt | acc | ggc | gca | 48 |
| Met | Ala | Ser | Ser | Gly | Thr | Thr | Ser | Thr | Arg | Lys | Arg | Phe | Thr | Gly | Ala | |
| 1 | | | | 5 | | | | | 10 | | | | | 15 | | |
| gaa | ttt | atc | gtt | cat | ttc | ctg | gaa | cag | cag | ggc | att | aag | att | gtg | aca | 96 |
| Glu | Phe | Ile | Val | His | Phe | Leu | Glu | Gln | Gln | Gly | Ile | Lys | Ile | Val | Thr | |
| | | | 20 | | | | | 25 | | | | | 30 | | | |
| ggc | att | ccg | ggc | ggt | tct | atc | ctg | cct | gtt | tac | gat | gcc | tta | agc | caa | 144 |
| Gly | Ile | Pro | Gly | Gly | Ser | Ile | Leu | Pro | Val | Tyr | Asp | Ala | Leu | Ser | Gln | |
| | | 35 | | | | | 40 | | | | | 45 | | | | |
| agc | acg | caa | atc | cgc | cat | att | ctg | gcc | cgt | cat | gaa | cag | ggc | gcg | ggc | 192 |
| Ser | Thr | Gln | Ile | Arg | His | Ile | Leu | Ala | Arg | His | Glu | Gln | Gly | Ala | Gly | |
| | 50 | | | | | 55 | | | | | 60 | | | | | |
| ttt | atc | gct | cag | gga | atg | gcg | cgc | acc | gac | ggt | aaa | ccg | gcg | gtc | tgt | 240 |
| Phe | Ile | Ala | Gln | Gly | Met | Ala | Arg | Thr | Asp | Gly | Lys | Pro | Ala | Val | Cys | |
| 65 | | | | | 70 | | | | | 75 | | | | | 80 | |
| atg | gcc | tgt | agc | gga | ccg | ggt | gcg | act | aac | ctg | gtg | acc | gcc | att | gcc | 288 |
| Met | Ala | Cys | Ser | Gly | Pro | Gly | Ala | Thr | Asn | Leu | Val | Thr | Ala | Ile | Ala | |
| | | | | 85 | | | | | 90 | | | | | 95 | | |
| gat | gcg | cgg | ctg | gac | tcc | atc | ccg | ctg | att | tgc | atc | act | ggt | cag | gtt | 336 |
| Asp | Ala | Arg | Leu | Asp | Ser | Ile | Pro | Leu | Ile | Cys | Ile | Thr | Gly | Gln | Val | |
| | | | | 100 | | | | | 105 | | | | | 110 | | |
| ccc | gcc | tcg | atg | atc | ggc | acc | gac | gcc | ttc | cag | gaa | gtg | gac | acc | tac | 384 |
| Pro | Ala | Ser | Met | Ile | Gly | Thr | Asp | Ala | Phe | Gln | Glu | Val | Asp | Thr | Tyr | |
| | | | 115 | | | | | 120 | | | | | 125 | | | |
| ggc | atc | tct | atc | ccc | atc | acc | aaa | cac | aac | tat | ctg | gtc | aga | cat | atc | 432 |
| Gly | Ile | Ser | Ile | Pro | Ile | Thr | Lys | His | Asn | Tyr | Leu | Val | Arg | His | Ile | |
| | | 130 | | | | | 135 | | | | | 140 | | | | |
| gaa | gaa | ctc | ccg | cag | gtc | atg | agc | gat | gcc | ttc | cgc | att | gcg | caa | tca | 480 |
| Glu | Glu | Leu | Pro | Gln | Val | Met | Ser | Asp | Ala | Phe | Arg | Ile | Ala | Gln | Ser | |
| 145 | | | | | 150 | | | | | 155 | | | | | 160 | |
| ggc | cgc | cca | ggc | ccg | gtg | tgg | ata | gac | att | cct | aag | gat | gtg | caa | acg | 528 |
| Gly | Arg | Pro | Gly | Pro | Val | Trp | Ile | Asp | Ile | Pro | Lys | Asp | Val | Gln | Thr | |
| | | | | 165 | | | | | 170 | | | | | 175 | | |
| gca | gtt | ttt | gag | att | gaa | aca | cag | ccc | gct | atg | gca | gaa | aaa | gcc | gcc | 576 |
| Ala | Val | Phe | Glu | Ile | Glu | Thr | Gln | Pro | Ala | Met | Ala | Glu | Lys | Ala | Ala | |
| | | | | 180 | | | | | 185 | | | | | 190 | | |
| gcc | ccc | gcc | ttt | agc | gaa | gaa | agc | att | cgt | gac | gca | gcg | gcg | atg | att | 624 |
| Ala | Pro | Ala | Phe | Ser | Glu | Glu | Ser | Ile | Arg | Asp | Ala | Ala | Ala | Met | Ile | |
| | | 195 | | | | | 200 | | | | | 205 | | | | |
| aac | gct | gcc | aaa | cgc | ccg | gtg | ctt | tat | ctg | ggc | ggc | ggt | gtg | atc | aat | 672 |
| Asn | Ala | Ala | Lys | Arg | Pro | Val | Leu | Tyr | Leu | Gly | Gly | Gly | Val | Ile | Asn | |
| 210 | | | | | 215 | | | | | 220 | | | | | | |
| gcg | ccc | gca | cgg | gtg | cgt | gaa | ctg | gcg | gag | aaa | gcg | caa | ctg | cct | acc | 720 |
| Ala | Pro | Ala | Arg | Val | Arg | Glu | Leu | Ala | Glu | Lys | Ala | Gln | Leu | Pro | Thr | |
| 225 | | | | | 230 | | | | | 235 | | | | | 240 | |
| acc | atg | act | tta | atg | gcg | ctg | ggc | atg | ttg | cca | aaa | gcg | cat | ccg | ttg | 768 |
| Thr | Met | Thr | Leu | Met | Ala | Leu | Gly | Met | Leu | Pro | Lys | Ala | His | Pro | Leu | |
| | | | | 245 | | | | | 250 | | | | | 255 | | |
| tcg | ctg | ggt | atg | ctg | ggg | atg | cac | ggc | gtg | cgc | agc | acc | aac | tat | att | 816 |
| Ser | Leu | Gly | Met | Leu | Gly | Met | His | Gly | Val | Arg | Ser | Thr | Asn | Tyr | Ile | |
| | | | 260 | | | | | 265 | | | | | 270 | | | |
| ttg | cag | gag | gcg | gat | ttg | ttg | ata | gtg | ctc | ggt | gcg | cgt | ttt | gat | gac | 864 |
| Leu | Gln | Glu | Ala | Asp | Leu | Leu | Ile | Val | Leu | Gly | Ala | Arg | Phe | Asp | Asp | |
| | | 275 | | | | | 280 | | | | | 285 | | | | |
| cgg | gcg | att | ggc | aaa | acc | gag | cag | ttc | tgt | ccg | aat | gcc | aaa | atc | att | 912 |
| Arg | Ala | Ile | Gly | Lys | Thr | Glu | Gln | Phe | Cys | Pro | Asn | Ala | Lys | Ile | Ile | |
| | 290 | | | | | 295 | | | | | 300 | | | | | |
| cat | gtc | gat | atc | gac | cgt | gca | gag | ctg | ggt | aaa | atc | aag | cag | ccg | cac | 960 |

```
His Val Asp Ile Asp Arg Ala Glu Leu Gly Lys Ile Lys Gln Pro His
305                 310                 315                 320 gtg gcg att cag gcg gat gtt gat gac gtg ctg gcg cag ttg atc ccg      1008
Val Ala Ile Gln Ala Asp Val Asp Asp Val Leu Ala Gln Leu Ile Pro
                    325                 330                 335 ctg gtg gaa gcg caa ccg cgt gca gag tgg cac cag ttg gta gcg gat      1056
Leu Val Glu Ala Gln Pro Arg Ala Glu Trp His Gln Leu Val Ala Asp
                340                 345                 350 ttg cag cgt gag ttt ccg tgt cca atc ccg aaa gcg tgc gat ccg tta      1104
Leu Gln Arg Glu Phe Pro Cys Pro Ile Pro Lys Ala Cys Asp Pro Leu
            355                 360                 365 agc cat tac ggc ctg atc aac gcc gtt gcc gcc tgt gtc gat gac aat      1152
Ser His Tyr Gly Leu Ile Asn Ala Val Ala Ala Cys Val Asp Asp Asn
        370                 375                 380 gca att atc acc acc gac gtt ggt cag cat cag atg tgg acc gcg caa      1200
Ala Ile Ile Thr Thr Asp Val Gly Gln His Gln Met Trp Thr Ala Gln
385                 390                 395                 400 gct tat ccg ctc aat cgc cca cgc cag tgg ctg acc tcc ggt ggg ctg      1248
Ala Tyr Pro Leu Asn Arg Pro Arg Gln Trp Leu Thr Ser Gly Gly Leu
                405                 410                 415 ggc acg atg ggt ttt ggc ctg cct gcg gcg att ggc gct gcg ctg gcg      1296
Gly Thr Met Gly Phe Gly Leu Pro Ala Ala Ile Gly Ala Ala Leu Ala
                420                 425                 430 aac ccg gat cgc aaa gtg ttg tgt ttc tcc ggc gac ggc agc ctg atg      1344
Asn Pro Asp Arg Lys Val Leu Cys Phe Ser Gly Asp Gly Ser Leu Met
            435                 440                 445 atg aat att cag gag atg gcg acc gcc agt gaa aat cag ctg gat gtc      1392
Met Asn Ile Gln Glu Met Ala Thr Ala Ser Glu Asn Gln Leu Asp Val
        450                 455                 460 aaa atc att ctg atg aac aac gaa gcg ctg ggg ctg gtg cat cag caa      1440
Lys Ile Ile Leu Met Asn Asn Glu Ala Leu Gly Leu Val His Gln Gln
465                 470                 475                 480 cag agt ctg ttc tac gag caa ggc gtt ttt gcc gcc acc tat ccg ggc      1488
Gln Ser Leu Phe Tyr Glu Gln Gly Val Phe Ala Ala Thr Tyr Pro Gly
                485                 490                 495 aaa atc aac ttt atg cag att gcc gcc gga ttc ggc ctc gaa acc tgt      1536
Lys Ile Asn Phe Met Gln Ile Ala Ala Gly Phe Gly Leu Glu Thr Cys
                500                 505                 510 gat ttg aat aac gaa gcc gat ccg cag gct tca ttg cag gaa atc atc      1584
Asp Leu Asn Asn Glu Ala Asp Pro Gln Ala Ser Leu Gln Glu Ile Ile
            515                 520                 525 aat cgc cct ggc ccg gcg ctg atc cat gtg cgc att gat gcc gaa gaa      1632
Asn Arg Pro Gly Pro Ala Leu Ile His Val Arg Ile Asp Ala Glu Glu
        530                 535                 540 aaa gtt tac ccg atg gtg ccg cca ggt gcg gcg aat act gaa atg gtg      1680
Lys Val Tyr Pro Met Val Pro Pro Gly Ala Ala Asn Thr Glu Met Val
545                 550                 555                 560 ggg gaa taa                                                          1689
Gly Glu <210> SEQ ID NO 102
<211> LENGTH: 562
<212> TYPE: PRT
<213> ORGANISM: Escherichia coli

<400> SEQUENCE: 102

Met Ala Ser Ser Gly Thr Thr Ser Thr Arg Lys Arg Phe Thr Gly Ala
1               5                   10                  15

Glu Phe Ile Val His Phe Leu Glu Gln Gln Gly Ile Lys Ile Val Thr
                20                  25                  30
```

-continued

```
Gly Ile Pro Gly Gly Ser Ile Leu Pro Val Tyr Asp Ala Leu Ser Gln
         35                  40                  45

Ser Thr Gln Ile Arg His Ile Leu Ala Arg His Glu Gln Gly Ala Gly
 50                      55                  60

Phe Ile Ala Gln Gly Met Ala Arg Thr Asp Gly Lys Pro Ala Val Cys
 65                  70                  75                  80

Met Ala Cys Ser Gly Pro Gly Ala Thr Asn Leu Val Thr Ala Ile Ala
                 85                  90                  95

Asp Ala Arg Leu Asp Ser Ile Pro Leu Ile Cys Ile Thr Gly Gln Val
            100                 105                 110

Pro Ala Ser Met Ile Gly Thr Asp Ala Phe Gln Glu Val Asp Thr Tyr
        115                 120                 125

Gly Ile Ser Ile Pro Ile Thr Lys His Asn Tyr Leu Val Arg His Ile
    130                 135                 140

Glu Glu Leu Pro Gln Val Met Ser Asp Ala Phe Arg Ile Ala Gln Ser
145                 150                 155                 160

Gly Arg Pro Gly Pro Val Trp Ile Asp Ile Pro Lys Asp Val Gln Thr
                165                 170                 175

Ala Val Phe Glu Ile Glu Thr Gln Pro Ala Met Ala Glu Lys Ala Ala
            180                 185                 190

Ala Pro Ala Phe Ser Glu Glu Ser Ile Arg Asp Ala Ala Ala Met Ile
        195                 200                 205

Asn Ala Ala Lys Arg Pro Val Leu Tyr Leu Gly Gly Gly Val Ile Asn
    210                 215                 220

Ala Pro Ala Arg Val Arg Glu Leu Ala Glu Lys Ala Gln Leu Pro Thr
225                 230                 235                 240

Thr Met Thr Leu Met Ala Leu Gly Met Leu Pro Lys Ala His Pro Leu
                245                 250                 255

Ser Leu Gly Met Leu Gly Met His Gly Val Arg Ser Thr Asn Tyr Ile
            260                 265                 270

Leu Gln Glu Ala Asp Leu Leu Ile Val Leu Gly Ala Arg Phe Asp Asp
        275                 280                 285

Arg Ala Ile Gly Lys Thr Glu Gln Phe Cys Pro Asn Ala Lys Ile Ile
    290                 295                 300

His Val Asp Ile Asp Arg Ala Glu Leu Gly Lys Ile Lys Gln Pro His
305                 310                 315                 320

Val Ala Ile Gln Ala Asp Val Asp Val Leu Ala Gln Leu Ile Pro
                325                 330                 335

Leu Val Glu Ala Gln Pro Arg Ala Glu Trp His Gln Leu Val Ala Asp
            340                 345                 350

Leu Gln Arg Glu Phe Pro Cys Pro Ile Pro Lys Ala Cys Asp Pro Leu
        355                 360                 365

Ser His Tyr Gly Leu Ile Asn Ala Val Ala Ala Cys Val Asp Asp Asn
    370                 375                 380

Ala Ile Ile Thr Thr Asp Val Gly Gln His Gln Met Trp Thr Ala Gln
385                 390                 395                 400

Ala Tyr Pro Leu Asn Arg Pro Arg Gln Trp Leu Thr Ser Gly Gly Leu
                405                 410                 415

Gly Thr Met Gly Phe Gly Leu Pro Ala Ala Ile Gly Ala Ala Leu Ala
            420                 425                 430

Asn Pro Asp Arg Lys Val Leu Cys Phe Ser Gly Asp Gly Ser Leu Met
        435                 440                 445

Met Asn Ile Gln Glu Met Ala Thr Ala Ser Glu Asn Gln Leu Asp Val
    450                 455                 460
```

```
Lys Ile Ile Leu Met Asn Asn Glu Ala Leu Gly Leu Val His Gln Gln
465                 470                 475                 480

Gln Ser Leu Phe Tyr Glu Gln Gly Val Phe Ala Ala Thr Tyr Pro Gly
            485                 490                 495

Lys Ile Asn Phe Met Gln Ile Ala Ala Gly Phe Gly Leu Glu Thr Cys
                500                 505                 510

Asp Leu Asn Asn Glu Ala Asp Pro Gln Ala Ser Leu Gln Glu Ile Ile
            515                 520                 525

Asn Arg Pro Gly Pro Ala Leu Ile His Val Arg Ile Asp Ala Glu Glu
        530                 535                 540

Lys Val Tyr Pro Met Val Pro Pro Gly Ala Ala Asn Thr Glu Met Val
545                 550                 555                 560

Gly Glu

<210> SEQ ID NO 103
<211> LENGTH: 2577
<212> TYPE: DNA
<213> ORGANISM: Clostridium acetobutylicum
<220> FEATURE:
<221> NAME/KEY: CDS
<222> LOCATION: (1)..(2577)

<400> SEQUENCE: 103 atg aaa gtt aca aat caa aaa gaa cta aaa caa aag cta aat gaa ttg      48
Met Lys Val Thr Asn Gln Lys Glu Leu Lys Gln Lys Leu Asn Glu Leu
1               5                   10                  15 aga gaa gcg caa aag aag ttt gca acc tat act caa gag caa gtt gat      96
Arg Glu Ala Gln Lys Lys Phe Ala Thr Tyr Thr Gln Glu Gln Val Asp
                20                  25                  30 aaa att ttt aaa caa tgt gcc ata gcc gca gct aaa gaa aga ata aac     144
Lys Ile Phe Lys Gln Cys Ala Ile Ala Ala Ala Lys Glu Arg Ile Asn
            35                  40                  45 tta gct aaa tta gca gta gaa gaa aca gga ata ggt ctt gta gaa gat     192
Leu Ala Lys Leu Ala Val Glu Glu Thr Gly Ile Gly Leu Val Glu Asp
        50                  55                  60 aaa att ata aaa aat cat ttt gca gca gaa tat ata tac aat aaa tat     240
Lys Ile Ile Lys Asn His Phe Ala Ala Glu Tyr Ile Tyr Asn Lys Tyr
65                  70                  75                  80 aaa aat gaa aaa act tgt ggc ata ata gac cat gac gat tct tta ggc     288
Lys Asn Glu Lys Thr Cys Gly Ile Ile Asp His Asp Asp Ser Leu Gly
                85                  90                  95 ata aca aag gtt gct gaa cca att gga att gtt gca gcc ata gtt cct     336
Ile Thr Lys Val Ala Glu Pro Ile Gly Ile Val Ala Ala Ile Val Pro
            100                 105                 110 act act aat cca act tcc aca gca att ttc aaa tca tta att tct tta     384
Thr Thr Asn Pro Thr Ser Thr Ala Ile Phe Lys Ser Leu Ile Ser Leu
        115                 120                 125 aaa aca aga aac gca ata ttc ttt tca cca cat cca cgt gca aaa aaa     432
Lys Thr Arg Asn Ala Ile Phe Phe Ser Pro His Pro Arg Ala Lys Lys
    130                 135                 140 tct aca att gct gca gca aaa tta att tta gat gca gct gtt aaa gca     480
Ser Thr Ile Ala Ala Ala Lys Leu Ile Leu Asp Ala Ala Val Lys Ala
145                 150                 155                 160 gga gca cct aaa aat ata ata ggc tgg ata gat gag cca tca ata gaa     528
Gly Ala Pro Lys Asn Ile Ile Gly Trp Ile Asp Glu Pro Ser Ile Glu
                165                 170                 175 ctt tct caa gat ttg atg agt gaa gct gat ata ata tta gca aca gga     576
Leu Ser Gln Asp Leu Met Ser Glu Ala Asp Ile Ile Leu Ala Thr Gly
            180                 185                 190
```

```
ggt cct tca atg gtt aaa gcg gcc tat tca tct gga aaa cct gca att        624
Gly Pro Ser Met Val Lys Ala Ala Tyr Ser Ser Gly Lys Pro Ala Ile
        195                 200                 205 ggt gtt gga gca gga aat aca cca gca ata ata gat gag agt gca gat        672
Gly Val Gly Ala Gly Asn Thr Pro Ala Ile Ile Asp Glu Ser Ala Asp
210                 215                 220 ata gat atg gca gta agc tcc ata att tta tca aag act tat gac aat        720
Ile Asp Met Ala Val Ser Ser Ile Ile Leu Ser Lys Thr Tyr Asp Asn
225                 230                 235                 240 gga gta ata tgc gct tct gaa caa tca ata tta gtt atg aat tca ata        768
Gly Val Ile Cys Ala Ser Glu Gln Ser Ile Leu Val Met Asn Ser Ile
            245                 250                 255 tac gaa aaa gtt aaa gag gaa ttt gta aaa cga gga tca tat ata ctc        816
Tyr Glu Lys Val Lys Glu Glu Phe Val Lys Arg Gly Ser Tyr Ile Leu
        260                 265                 270 aat caa aat gaa ata gct aaa ata aaa gaa act atg ttt aaa aat gga        864
Asn Gln Asn Glu Ile Ala Lys Ile Lys Glu Thr Met Phe Lys Asn Gly
    275                 280                 285 gct att aat gct gac ata gtt gga aaa tct gct tat ata att gct aaa        912
Ala Ile Asn Ala Asp Ile Val Gly Lys Ser Ala Tyr Ile Ile Ala Lys
290                 295                 300 atg gca gga att gaa gtt cct caa act aca aag ata ctt ata ggc gaa        960
Met Ala Gly Ile Glu Val Pro Gln Thr Thr Lys Ile Leu Ile Gly Glu
305                 310                 315                 320 gta caa tct gtt gaa aaa agc gag ctg ttc tca cat gaa aaa cta tca       1008
Val Gln Ser Val Glu Lys Ser Glu Leu Phe Ser His Glu Lys Leu Ser
            325                 330                 335 cca gta ctt gca atg tat aaa gtt aag gat ttt gat gaa gct cta aaa       1056
Pro Val Leu Ala Met Tyr Lys Val Lys Asp Phe Asp Glu Ala Leu Lys
        340                 345                 350 aag gca caa agg cta ata gaa tta ggt gga agt gga cac acg tca tct       1104
Lys Ala Gln Arg Leu Ile Glu Leu Gly Gly Ser Gly His Thr Ser Ser
    355                 360                 365 tta tat ata gat tca caa aac aat aag gat aaa gtt aaa gaa ttt gga       1152
Leu Tyr Ile Asp Ser Gln Asn Asn Lys Asp Lys Val Lys Glu Phe Gly
370                 375                 380 tta gca atg aaa act tca agg aca ttt att aac atg cct tct tca cag       1200
Leu Ala Met Lys Thr Ser Arg Thr Phe Ile Asn Met Pro Ser Ser Gln
385                 390                 395                 400 gga gca agc gga gat tta tac aat ttt gcg ata gca cca tca ttt act       1248
Gly Ala Ser Gly Asp Leu Tyr Asn Phe Ala Ile Ala Pro Ser Phe Thr
            405                 410                 415 ctt gga tgc ggc act tgg gga gga aac tct gta tcg caa aat gta gag       1296
Leu Gly Cys Gly Thr Trp Gly Gly Asn Ser Val Ser Gln Asn Val Glu
        420                 425                 430 cct aaa cat tta tta aat att aaa agt gtt gct gaa aga agg gaa aat       1344
Pro Lys His Leu Leu Asn Ile Lys Ser Val Ala Glu Arg Arg Glu Asn
    435                 440                 445 atg ctt tgg ttt aaa gtg cca caa aaa ata tat ttt aaa tat gga tgt       1392
Met Leu Trp Phe Lys Val Pro Gln Lys Ile Tyr Phe Lys Tyr Gly Cys
450                 455                 460 ctt aga ttt gca tta aaa gaa tta aaa gat atg aat aag aaa aga gcc       1440
Leu Arg Phe Ala Leu Lys Glu Leu Lys Asp Met Asn Lys Lys Arg Ala
465                 470                 475                 480 ttt ata gta aca gat aaa gat ctt ttt aaa ctt gga tat gtt aat aaa       1488
Phe Ile Val Thr Asp Lys Asp Leu Phe Lys Leu Gly Tyr Val Asn Lys
            485                 490                 495 ata aca aag gta cta gat gag ata gat att aaa tac agt ata ttt aca       1536
Ile Thr Lys Val Leu Asp Glu Ile Asp Ile Lys Tyr Ser Ile Phe Thr
        500                 505                 510
```

```
gat att aaa tct gat cca act att gat tca gta aaa aaa ggt gct aaa     1584
Asp Ile Lys Ser Asp Pro Thr Ile Asp Ser Val Lys Lys Gly Ala Lys
            515                 520                 525 gaa atg ctt aac ttt gaa cct gat act ata atc tct att ggt ggt gga     1632
Glu Met Leu Asn Phe Glu Pro Asp Thr Ile Ile Ser Ile Gly Gly Gly
        530                 535                 540 tcg cca atg gat gca gca aag gtt atg cac ttg tta tat gaa tat cca     1680
Ser Pro Met Asp Ala Ala Lys Val Met His Leu Leu Tyr Glu Tyr Pro
545                 550                 555                 560 gaa gca gaa att gaa aat cta gct ata aac ttt atg gat ata aga aag     1728
Glu Ala Glu Ile Glu Asn Leu Ala Ile Asn Phe Met Asp Ile Arg Lys
                565                 570                 575 aga ata tgc aat ttc cct aaa tta ggt aca aag gcg att tca gta gct     1776
Arg Ile Cys Asn Phe Pro Lys Leu Gly Thr Lys Ala Ile Ser Val Ala
            580                 585                 590 att cct aca act gct ggt acc ggt tca gag gca aca cct ttt gca gtt     1824
Ile Pro Thr Thr Ala Gly Thr Gly Ser Glu Ala Thr Pro Phe Ala Val
        595                 600                 605 ata act aat gat gaa aca gga atg aaa tac cct tta act tct tat gaa     1872
Ile Thr Asn Asp Glu Thr Gly Met Lys Tyr Pro Leu Thr Ser Tyr Glu
610                 615                 620 ttg acc cca aac atg gca ata ata gat act gaa tta atg tta aat atg     1920
Leu Thr Pro Asn Met Ala Ile Ile Asp Thr Glu Leu Met Leu Asn Met
625                 630                 635                 640 cct aga aaa tta aca gca gca act gga ata gat gca tta gtt cat gct     1968
Pro Arg Lys Leu Thr Ala Ala Thr Gly Ile Asp Ala Leu Val His Ala
                645                 650                 655 ata gaa gca tat gtt tcg gtt atg gct acg gat tat act gat gaa tta     2016
Ile Glu Ala Tyr Val Ser Val Met Ala Thr Asp Tyr Thr Asp Glu Leu
            660                 665                 670 gcc tta aga gca ata aaa atg ata ttt aaa tat ttg cct aga gcc tat     2064
Ala Leu Arg Ala Ile Lys Met Ile Phe Lys Tyr Leu Pro Arg Ala Tyr
        675                 680                 685 aaa aat ggg act aac gac att gaa gca aga gaa aaa atg gca cat gcc     2112
Lys Asn Gly Thr Asn Asp Ile Glu Ala Arg Glu Lys Met Ala His Ala
690                 695                 700 tct aat att gcg ggg atg gca ttt gca aat gct ttc tta ggt gta tgc     2160
Ser Asn Ile Ala Gly Met Ala Phe Ala Asn Ala Phe Leu Gly Val Cys
705                 710                 715                 720 cat tca atg gct cat aaa ctt ggg gca atg cat cac gtt cca cat gga     2208
His Ser Met Ala His Lys Leu Gly Ala Met His His Val Pro His Gly
                725                 730                 735 att gct tgt gct gta tta ata gaa gaa gtt att aaa tat aac gct aca     2256
Ile Ala Cys Ala Val Leu Ile Glu Glu Val Ile Lys Tyr Asn Ala Thr
            740                 745                 750 gac tgt cca aca aag caa aca gca ttc cct caa tat aaa tct cct aat     2304
Asp Cys Pro Thr Lys Gln Thr Ala Phe Pro Gln Tyr Lys Ser Pro Asn
        755                 760                 765 gct aag aga aaa tat gct gaa att gca gag tat ttg aat tta aag ggt     2352
Ala Lys Arg Lys Tyr Ala Glu Ile Ala Glu Tyr Leu Asn Leu Lys Gly
770                 775                 780 act agc gat acc gaa aag gta aca gcc tta ata gaa gct att tca aag     2400
Thr Ser Asp Thr Glu Lys Val Thr Ala Leu Ile Glu Ala Ile Ser Lys
785                 790                 795                 800 tta aag ata gat ttg agt att cca caa aat ata agt gcc gct gga ata     2448
Leu Lys Ile Asp Leu Ser Ile Pro Gln Asn Ile Ser Ala Ala Gly Ile
                805                 810                 815 aat aaa aaa gat ttt tat aat acg cta gat aaa atg tca gag ctt gct     2496
Asn Lys Lys Asp Phe Tyr Asn Thr Leu Asp Lys Met Ser Glu Leu Ala
            820                 825                 830
```

-continued

```
ttt gat gac caa tgt aca aca gct aat cct agg tat cca ctt ata agt    2544
Phe Asp Asp Gln Cys Thr Thr Ala Asn Pro Arg Tyr Pro Leu Ile Ser
        835                 840                 845 gaa ctt aag gat atc tat ata aaa tca ttt taa                        2577
Glu Leu Lys Asp Ile Tyr Ile Lys Ser Phe
        850                 855
```

<210> SEQ ID NO 104
<211> LENGTH: 858
<212> TYPE: PRT
<213> ORGANISM: Clostridium acetobutylicum

<400> SEQUENCE: 104

```
Met Lys Val Thr Asn Gln Lys Glu Leu Lys Gln Lys Leu Asn Glu Leu
1               5                   10                  15

Arg Glu Ala Gln Lys Lys Phe Ala Thr Tyr Thr Gln Glu Gln Val Asp
            20                  25                  30

Lys Ile Phe Lys Gln Cys Ala Ile Ala Ala Lys Glu Arg Ile Asn
        35                  40                  45

Leu Ala Lys Leu Ala Val Glu Glu Thr Gly Ile Gly Leu Val Glu Asp
    50                  55                  60

Lys Ile Ile Lys Asn His Phe Ala Ala Glu Tyr Ile Tyr Asn Lys Tyr
65                  70                  75                  80

Lys Asn Glu Lys Thr Cys Gly Ile Ile Asp His Asp Asp Ser Leu Gly
                85                  90                  95

Ile Thr Lys Val Ala Glu Pro Ile Gly Ile Val Ala Ala Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Phe Phe Ser Pro His Pro Arg Ala Lys Lys
    130                 135                 140

Ser Thr Ile Ala Ala Ala Lys Leu Ile Leu Asp Ala Ala Val Lys Ala
145                 150                 155                 160

Gly Ala Pro Lys Asn Ile Ile Gly Trp Ile Asp Glu Pro Ser Ile Glu
                165                 170                 175

Leu Ser Gln Asp Leu Met Ser Glu Ala Asp Ile Ile Leu Ala Thr Gly
            180                 185                 190

Gly Pro Ser Met Val Lys Ala Ala Tyr Ser Ser Gly Lys Pro Ala Ile
        195                 200                 205

Gly Val Gly Ala Gly Asn Thr Pro Ala Ile Ile Asp Glu Ser Ala Asp
    210                 215                 220

Ile Asp Met Ala Val Ser Ser Ile Ile Leu Ser Lys Thr Tyr Asp Asn
225                 230                 235                 240

Gly Val Ile Cys Ala Ser Glu Gln Ser Ile Leu Val Met Asn Ser Ile
                245                 250                 255

Tyr Glu Lys Val Lys Glu Glu Phe Val Lys Arg Gly Ser Tyr Ile Leu
            260                 265                 270

Asn Gln Asn Glu Ile Ala Lys Ile Lys Glu Thr Met Phe Lys Asn Gly
        275                 280                 285

Ala Ile Asn Ala Asp Ile Val Gly Lys Ser Ala Tyr Ile Ile Ala Lys
    290                 295                 300

Met Ala Gly Ile Glu Val Pro Gln Thr Thr Lys Ile Leu Ile Gly Glu
305                 310                 315                 320

Val Gln Ser Val Glu Lys Ser Glu Leu Phe Ser His Glu Lys Leu Ser
                325                 330                 335

Pro Val Leu Ala Met Tyr Lys Val Lys Asp Phe Asp Glu Ala Leu Lys
```

```
                        340                 345                 350
Lys Ala Gln Arg Leu Ile Glu Leu Gly Gly Ser Gly His Thr Ser Ser
                355                 360                 365
Leu Tyr Ile Asp Ser Gln Asn Asn Lys Asp Lys Val Lys Glu Phe Gly
            370                 375                 380
Leu Ala Met Lys Thr Ser Arg Thr Phe Ile Asn Met Pro Ser Ser Gln
385                 390                 395                 400
Gly Ala Ser Gly Asp Leu Tyr Asn Phe Ala Ile Ala Pro Ser Phe Thr
                405                 410                 415
Leu Gly Cys Gly Thr Trp Gly Gly Asn Ser Val Ser Gln Asn Val Glu
            420                 425                 430
Pro Lys His Leu Leu Asn Ile Lys Ser Val Ala Glu Arg Arg Glu Asn
            435                 440                 445
Met Leu Trp Phe Lys Val Pro Gln Lys Ile Tyr Phe Lys Tyr Gly Cys
        450                 455                 460
Leu Arg Phe Ala Leu Lys Glu Leu Lys Asp Met Asn Lys Lys Arg Ala
465                 470                 475                 480
Phe Ile Val Thr Asp Lys Asp Leu Phe Lys Leu Gly Tyr Val Asn Lys
                485                 490                 495
Ile Thr Lys Val Leu Asp Glu Ile Asp Ile Lys Tyr Ser Ile Phe Thr
            500                 505                 510
Asp Ile Lys Ser Asp Pro Thr Ile Asp Ser Val Lys Lys Gly Ala Lys
            515                 520                 525
Glu Met Leu Asn Phe Glu Pro Asp Thr Ile Ile Ser Ile Gly Gly Gly
        530                 535                 540
Ser Pro Met Asp Ala Ala Lys Val Met His Leu Leu Tyr Glu Tyr Pro
545                 550                 555                 560
Glu Ala Glu Ile Glu Asn Leu Ala Ile Asn Phe Met Asp Ile Arg Lys
                565                 570                 575
Arg Ile Cys Asn Phe Pro Lys Leu Gly Thr Lys Ala Ile Ser Val Ala
            580                 585                 590
Ile Pro Thr Thr Ala Gly Thr Gly Ser Glu Ala Thr Pro Phe Ala Val
            595                 600                 605
Ile Thr Asn Asp Glu Thr Gly Met Lys Tyr Pro Leu Thr Ser Tyr Glu
        610                 615                 620
Leu Thr Pro Asn Met Ala Ile Ile Asp Thr Glu Leu Met Leu Asn Met
625                 630                 635                 640
Pro Arg Lys Leu Thr Ala Ala Thr Gly Ile Asp Ala Leu Val His Ala
                645                 650                 655
Ile Glu Ala Tyr Val Ser Val Met Ala Thr Asp Tyr Thr Asp Glu Leu
            660                 665                 670
Ala Leu Arg Ala Ile Lys Met Ile Phe Lys Tyr Leu Pro Arg Ala Tyr
            675                 680                 685
Lys Asn Gly Thr Asn Asp Ile Glu Ala Arg Glu Lys Met Ala His Ala
        690                 695                 700
Ser Asn Ile Ala Gly Met Ala Phe Ala Asn Ala Phe Leu Gly Val Cys
705                 710                 715                 720
His Ser Met Ala His Lys Leu Gly Ala Met His His Val Pro His Gly
                725                 730                 735
Ile Ala Cys Ala Val Leu Ile Glu Glu Val Ile Lys Tyr Asn Ala Thr
            740                 745                 750
Asp Cys Pro Thr Lys Gln Thr Ala Phe Pro Gln Tyr Lys Ser Pro Asn
            755                 760                 765
```

```
Ala Lys Arg Lys Tyr Ala Glu Ile Ala Glu Tyr Leu Asn Leu Lys Gly
        770                 775                 780

Thr Ser Asp Thr Glu Lys Val Thr Ala Leu Ile Glu Ala Ile Ser Lys
785                 790                 795                 800

Leu Lys Ile Asp Leu Ser Ile Pro Gln Asn Ile Ser Ala Ala Gly Ile
                805                 810                 815

Asn Lys Lys Asp Phe Tyr Asn Thr Leu Asp Lys Met Ser Glu Leu Ala
                820                 825                 830

Phe Asp Asp Gln Cys Thr Thr Ala Asn Pro Arg Tyr Pro Leu Ile Ser
                835                 840                 845

Glu Leu Lys Asp Ile Tyr Ile Lys Ser Phe
    850                 855

<210> SEQ ID NO 105
<211> LENGTH: 1398
<212> TYPE: DNA
<213> ORGANISM: Leptospira interrogans
<220> FEATURE:
<221> NAME/KEY: CDS
<222> LOCATION: (1)..(1398)

<400> SEQUENCE: 105 atg aag aca atg ttc gaa aaa att tgg gaa gat cat cta gtc gga gaa    48
Met Lys Thr Met Phe Glu Lys Ile Trp Glu Asp His Leu Val Gly Glu
1               5                   10                  15 cta gat gct gga tcc tat cta atc tat ata gat cgc cat ctc att cat    96
Leu Asp Ala Gly Ser Tyr Leu Ile Tyr Ile Asp Arg His Leu Ile His
            20                  25                  30 gaa gtt aca agt cct cag gcg ttt gaa gga ctt aaa ctt gca ggc aga   144
Glu Val Thr Ser Pro Gln Ala Phe Glu Gly Leu Lys Leu Ala Gly Arg
        35                  40                  45 aag gtt cgt cgt cct gaa gct act ttt gcc aca atg gat cat aac gtt   192
Lys Val Arg Arg Pro Glu Ala Thr Phe Ala Thr Met Asp His Asn Val
    50                  55                  60 tct act aga aca cgt gat tta agt ctg gcc gat cct gtt tcc gca att   240
Ser Thr Arg Thr Arg Asp Leu Ser Leu Ala Asp Pro Val Ser Ala Ile
65                  70                  75                  80 caa atg cag act tta aaa aag aac tgc gac gaa aac gga atc cgc gtt   288
Gln Met Gln Thr Leu Lys Lys Asn Cys Asp Glu Asn Gly Ile Arg Val
                85                  90                  95 tat gat ttt caa aac cct gac caa gga atc att cac gta atc gct cct   336
Tyr Asp Phe Gln Asn Pro Asp Gln Gly Ile Ile His Val Ile Ala Pro
            100                 105                 110 gaa atg gga ctg act cat cct gga atg aca atc gta tgc gga gat tct   384
Glu Met Gly Leu Thr His Pro Gly Met Thr Ile Val Cys Gly Asp Ser
        115                 120                 125 cat act tct aca cac ggt gcg ttt ggt gcg ctt gct ttc ggg atc gga   432
His Thr Ser Thr His Gly Ala Phe Gly Ala Leu Ala Phe Gly Ile Gly
    130                 135                 140 acc agc gaa gta gag cac gtt ctt gcg act caa acc tta gtt caa aaa   480
Thr Ser Glu Val Glu His Val Leu Ala Thr Gln Thr Leu Val Gln Lys
145                 150                 155                 160 aga gca aaa aca atg gag att aga gtc gat gga aaa ctt tcc gat aag   528
Arg Ala Lys Thr Met Glu Ile Arg Val Asp Gly Lys Leu Ser Asp Lys
                165                 170                 175 gtc aca gca aaa gac atc att ctt gcg atc att gga aaa att gga acc   576
Val Thr Ala Lys Asp Ile Ile Leu Ala Ile Ile Gly Lys Ile Gly Thr
            180                 185                 190 gca ggt gcg aca ggt tat gtg atc gaa tat aga ggt tct gca att caa   624
Ala Gly Ala Thr Gly Tyr Val Ile Glu Tyr Arg Gly Ser Ala Ile Gln
        195                 200                 205
```

| | | | | | | | | | | | | | | | |
|---|---|---|---|---|---|---|---|---|---|---|---|---|---|---|---|
| gcc | ctc | agt | atg | gaa | gct | aga | atg | act | att | tgt | aat | atg | tct | atc | gaa | 672 |
| Ala | Leu | Ser | Met | Glu | Ala | Arg | Met | Thr | Ile | Cys | Asn | Met | Ser | Ile | Glu |
| 210 | | | | 215 | | | | | 220 | | | | | | |

| gcg | gga | gct | aga | gca | ggt | tta | atc | gca | cca | gat | gaa | act | act | ttt | aat | 720 |
| Ala | Gly | Ala | Arg | Ala | Gly | Leu | Ile | Ala | Pro | Asp | Glu | Thr | Thr | Phe | Asn |
| 225 | | | | | 230 | | | | | 235 | | | | | 240 |

| tat | att | caa | gga | aag | gac | ttt | tct | cca | aaa | gga | gtc | gaa | tgg | gat | ctt | 768 |
| Tyr | Ile | Gln | Gly | Lys | Asp | Phe | Ser | Pro | Lys | Gly | Val | Glu | Trp | Asp | Leu |
| | | | | 245 | | | | | 250 | | | | | 255 | |

| gcg | gtc | aaa | aaa | tgg | aaa | cac | tat | gta | acg | gac | gaa | ggt | gct | aaa | ttt | 816 |
| Ala | Val | Lys | Lys | Trp | Lys | His | Tyr | Val | Thr | Asp | Glu | Gly | Ala | Lys | Phe |
| | | 260 | | | | | 265 | | | | | 270 | | | |

| gat | aga | acc | gta | att | ctt | cat | gca | gat | gaa | atc | gct | cct | atg | gta | act | 864 |
| Asp | Arg | Thr | Val | Ile | Leu | His | Ala | Asp | Glu | Ile | Ala | Pro | Met | Val | Thr |
| | | 275 | | | | | 280 | | | | | 285 | | | |

| tgg | gga | act | tct | ccc | agt | cag | gtt | gtt | tcg | ata | aaa | gga | gtc | gtt | cca | 912 |
| Trp | Gly | Thr | Ser | Pro | Ser | Gln | Val | Val | Ser | Ile | Lys | Gly | Val | Val | Pro |
| | 290 | | | | | 295 | | | | | 300 | | | | |

| gat | cca | aaa | gat | gca | aat | gat | ccg | gtg | gaa | aaa | att | gga | att | gag | tct | 960 |
| Asp | Pro | Lys | Asp | Ala | Asn | Asp | Pro | Val | Glu | Lys | Ile | Gly | Ile | Glu | Ser |
| 305 | | | | | 310 | | | | | 315 | | | | | 320 |

| gcg | ctt | aaa | tat | atg | gat | ctc | aaa | tcg | ggc | cag | aag | ata | gaa | gac | att | 1008 |
| Ala | Leu | Lys | Tyr | Met | Asp | Leu | Lys | Ser | Gly | Gln | Lys | Ile | Glu | Asp | Ile |
| | | | | 325 | | | | | 330 | | | | | 335 | |

| tca | att | aat | aaa | gtg | ttt | atc | ggt | tcc | tgt | act | aat | tct | aga | atc | gaa | 1056 |
| Ser | Ile | Asn | Lys | Val | Phe | Ile | Gly | Ser | Cys | Thr | Asn | Ser | Arg | Ile | Glu |
| | | | 340 | | | | | 345 | | | | | 350 | | |

| gat | tta | aga | gcg | gcc | gct | gct | acc | gta | aaa | gga | aaa | aaa | gtt | tcc | tct | 1104 |
| Asp | Leu | Arg | Ala | Ala | Ala | Ala | Thr | Val | Lys | Gly | Lys | Lys | Val | Ser | Ser |
| | | 355 | | | | | 360 | | | | | 365 | | | |

| aag | gtt | cag | gcg | att | gtg | gtt | ccc | ggt | tca | ggc | aga | gtc | aaa | cgt | cag | 1152 |
| Lys | Val | Gln | Ala | Ile | Val | Val | Pro | Gly | Ser | Gly | Arg | Val | Lys | Arg | Gln |
| | 370 | | | | | 375 | | | | | 380 | | | | |

| gcg | gaa | caa | gaa | ggt | ctg | gat | aaa | att | ttt | acc | gcg | gcc | ggt | ttt | gaa | 1200 |
| Ala | Glu | Gln | Glu | Gly | Leu | Asp | Lys | Ile | Phe | Thr | Ala | Ala | Gly | Phe | Glu |
| 385 | | | | | 390 | | | | | 395 | | | | | 400 |

| tgg | aga | aat | cca | ggc | tgt | tct | atg | tgt | ctt | gcg | atg | aac | gac | gac | gta | 1248 |
| Trp | Arg | Asn | Pro | Gly | Cys | Ser | Met | Cys | Leu | Ala | Met | Asn | Asp | Asp | Val |
| | | | | 405 | | | | | 410 | | | | | 415 | |

| tta | gaa | ccg | gga | gat | cgt | tgt | gct | tct | act | tct | aac | cga | aac | ttt | gaa | 1296 |
| Leu | Glu | Pro | Gly | Asp | Arg | Cys | Ala | Ser | Thr | Ser | Asn | Arg | Asn | Phe | Glu |
| | | | 420 | | | | | 425 | | | | | 430 | | |

| ggt | cgt | caa | gga | aaa | ggt | gga | aga | acc | cat | cta | gta | gga | ccg | gaa | atg | 1344 |
| Gly | Arg | Gln | Gly | Lys | Gly | Gly | Arg | Thr | His | Leu | Val | Gly | Pro | Glu | Met |
| | | 435 | | | | | 440 | | | | | 445 | | | |

| gcc | gcc | gcc | gcg | gct | atc | gaa | ggc | cat | ttt | gtg | gat | att | cga | aac | tgg | 1392 |
| Ala | Ala | Ala | Ala | Ala | Ile | Glu | Gly | His | Phe | Val | Asp | Ile | Arg | Asn | Trp |
| 450 | | | | | 455 | | | | | 460 | | | | | |

| aaa | taa | | | | | | | | | | | | | | | 1398 |
| Lys | |
| 465 | |

<210> SEQ ID NO 106
<211> LENGTH: 465
<212> TYPE: PRT
<213> ORGANISM: Leptospira interrogans

<400> SEQUENCE: 106

| Met | Lys | Thr | Met | Phe | Glu | Lys | Ile | Trp | Glu | Asp | His | Leu | Val | Gly | Glu |
|---|---|---|---|---|---|---|---|---|---|---|---|---|---|---|---|
| 1 | | | | 5 | | | | | 10 | | | | | 15 | |

-continued

```
Leu Asp Ala Gly Ser Tyr Leu Ile Tyr Ile Asp Arg His Leu Ile His
             20                  25                  30
Glu Val Thr Ser Pro Gln Ala Phe Glu Gly Leu Lys Leu Ala Gly Arg
         35                  40                  45
Lys Val Arg Arg Pro Glu Ala Thr Phe Ala Thr Met Asp His Asn Val
 50                  55                  60
Ser Thr Arg Thr Arg Asp Leu Ser Leu Ala Asp Pro Val Ser Ala Ile
 65                  70                  75                  80
Gln Met Gln Thr Leu Lys Lys Asn Cys Asp Glu Asn Gly Ile Arg Val
                 85                  90                  95
Tyr Asp Phe Gln Asn Pro Asp Gln Gly Ile Ile His Val Ile Ala Pro
             100                 105                 110
Glu Met Gly Leu Thr His Pro Gly Met Thr Ile Val Cys Gly Asp Ser
         115                 120                 125
His Thr Ser Thr His Gly Ala Phe Gly Ala Leu Ala Phe Gly Ile Gly
     130                 135                 140
Thr Ser Glu Val Glu His Val Leu Ala Thr Gln Thr Leu Val Gln Lys
145                 150                 155                 160
Arg Ala Lys Thr Met Glu Ile Arg Val Asp Gly Lys Leu Ser Asp Lys
                 165                 170                 175
Val Thr Ala Lys Asp Ile Ile Leu Ala Ile Ile Gly Lys Ile Gly Thr
             180                 185                 190
Ala Gly Ala Thr Gly Tyr Val Ile Glu Tyr Arg Gly Ser Ala Ile Gln
         195                 200                 205
Ala Leu Ser Met Glu Ala Arg Met Thr Ile Cys Asn Met Ser Ile Glu
     210                 215                 220
Ala Gly Ala Arg Ala Gly Leu Ile Ala Pro Asp Glu Thr Thr Phe Asn
225                 230                 235                 240
Tyr Ile Gln Gly Lys Asp Phe Ser Pro Lys Gly Val Glu Trp Asp Leu
                 245                 250                 255
Ala Val Lys Lys Trp Lys His Tyr Val Thr Asp Glu Gly Ala Lys Phe
             260                 265                 270
Asp Arg Thr Val Ile Leu His Ala Asp Glu Ile Ala Pro Met Val Thr
         275                 280                 285
Trp Gly Thr Ser Pro Ser Gln Val Val Ser Ile Lys Gly Val Val Pro
     290                 295                 300
Asp Pro Lys Asp Ala Asn Asp Pro Val Glu Lys Ile Gly Ile Glu Ser
305                 310                 315                 320
Ala Leu Lys Tyr Met Asp Leu Lys Ser Gly Gln Lys Ile Glu Asp Ile
                 325                 330                 335
Ser Ile Asn Lys Val Phe Ile Gly Ser Cys Thr Asn Ser Arg Ile Glu
             340                 345                 350
Asp Leu Arg Ala Ala Ala Thr Val Lys Gly Lys Lys Val Ser Ser
         355                 360                 365
Lys Val Gln Ala Ile Val Val Pro Gly Ser Gly Arg Val Lys Arg Gln
     370                 375                 380
Ala Glu Gln Glu Gly Leu Asp Lys Ile Phe Thr Ala Ala Gly Phe Glu
385                 390                 395                 400
Trp Arg Asn Pro Gly Cys Ser Met Cys Leu Ala Met Asn Asp Asp Val
                 405                 410                 415
Leu Glu Pro Gly Asp Arg Cys Ala Ser Thr Ser Asn Arg Asn Phe Glu
             420                 425                 430
Gly Arg Gln Gly Lys Gly Gly Arg Thr His Leu Val Gly Pro Glu Met
         435                 440                 445
```

```
Ala Ala Ala Ala Ala Ile Glu Gly His Phe Val Asp Ile Arg Asn Trp
    450                 455                 460
Lys
465

<210> SEQ ID NO 107
<211> LENGTH: 621
<212> TYPE: DNA
<213> ORGANISM: Leptospira interrogans
<220> FEATURE:
<221> NAME/KEY: CDS
<222> LOCATION: (1)..(621)

<400> SEQUENCE: 107 atg aaa ccc ttt act ata tta aat gga att gcc gcc tta ctg gac aga      48
Met Lys Pro Phe Thr Ile Leu Asn Gly Ile Ala Ala Leu Leu Asp Arg
1               5                   10                  15 ccc aac gtg gat acg gat cag atc att cca aaa caa ttt tta cgg aag      96
Pro Asn Val Asp Thr Asp Gln Ile Ile Pro Lys Gln Phe Leu Arg Lys
                20                  25                  30 ata gaa cga acc ggt ttc gga gtt cat ctg ttt cac gat tgg aga tac     144
Ile Glu Arg Thr Gly Phe Gly Val His Leu Phe His Asp Trp Arg Tyr
            35                  40                  45 tta gac gac gcg ggt acc aaa ctc aat cct gat ttt tcc ctc aat caa     192
Leu Asp Asp Ala Gly Thr Lys Leu Asn Pro Asp Phe Ser Leu Asn Gln
    50                  55                  60 gaa cga tat aag gga gct tct atc ctt atc acc aga gat aac ttt ggt     240
Glu Arg Tyr Lys Gly Ala Ser Ile Leu Ile Thr Arg Asp Asn Phe Gly
65                  70                  75                  80 tgt gga tct tcc aga gaa cac gct cct tgg gct tta gaa gac tac ggg     288
Cys Gly Ser Ser Arg Glu His Ala Pro Trp Ala Leu Glu Asp Tyr Gly
                85                  90                  95 ttt agg gca atc att gct cct tct tac gcg gat att ttt ttc aac aac     336
Phe Arg Ala Ile Ile Ala Pro Ser Tyr Ala Asp Ile Phe Phe Asn Asn
            100                 105                 110 tgc ttt aaa aac gga atg ctt cca gtc att tta aaa tcg gaa gaa gta     384
Cys Phe Lys Asn Gly Met Leu Pro Val Ile Leu Lys Ser Glu Glu Val
    115                 120                 125 gaa gag ctg ttc cat ttg gtt tcg act aac gta gga gcg aaa gtc ata     432
Glu Glu Leu Phe His Leu Val Ser Thr Asn Val Gly Ala Lys Val Ile
130                 135                 140 gtg gat ctg gac aaa caa act gta acc gga ccg act gga aaa ata tat     480
Val Asp Leu Asp Lys Gln Thr Val Thr Gly Pro Thr Gly Lys Ile Tyr
145                 150                 155                 160 tat ttt gaa gtg gat tct ttt cgt aaa tac tgt ctt tat aac gga ctt     528
Tyr Phe Glu Val Asp Ser Phe Arg Lys Tyr Cys Leu Tyr Asn Gly Leu
                165                 170                 175 gat gac ata ggt cta act cta aaa caa gaa agt aaa att gga gag ttt     576
Asp Asp Ile Gly Leu Thr Leu Lys Gln Glu Ser Lys Ile Gly Glu Phe
            180                 185                 190 gaa aaa aag cag aaa gaa gtt gaa cct tgg tta tac gcc ata taa         621
Glu Lys Lys Gln Lys Glu Val Glu Pro Trp Leu Tyr Ala Ile
    195                 200                 205

<210> SEQ ID NO 108
<211> LENGTH: 206
<212> TYPE: PRT
<213> ORGANISM: Leptospira interrogans

<400> SEQUENCE: 108

Met Lys Pro Phe Thr Ile Leu Asn Gly Ile Ala Ala Leu Leu Asp Arg
1               5                   10                  15
```

```
Pro Asn Val Asp Thr Asp Gln Ile Ile Pro Lys Gln Phe Leu Arg Lys
            20                  25                  30

Ile Glu Arg Thr Gly Phe Gly Val His Leu Phe His Asp Trp Arg Tyr
         35                  40                  45

Leu Asp Asp Ala Gly Thr Lys Leu Asn Pro Asp Phe Ser Leu Asn Gln
 50                  55                  60

Glu Arg Tyr Lys Gly Ala Ser Ile Leu Ile Thr Arg Asp Asn Phe Gly
 65                  70                  75                  80

Cys Gly Ser Ser Arg Glu His Ala Pro Trp Ala Leu Glu Asp Tyr Gly
                 85                  90                  95

Phe Arg Ala Ile Ile Ala Pro Ser Tyr Ala Asp Ile Phe Phe Asn Asn
             100                 105                 110

Cys Phe Lys Asn Gly Met Leu Pro Val Ile Leu Lys Ser Glu Glu Val
         115                 120                 125

Glu Glu Leu Phe His Leu Val Ser Thr Asn Val Gly Ala Lys Val Ile
130                 135                 140

Val Asp Leu Asp Lys Gln Thr Val Thr Gly Pro Thr Gly Lys Ile Tyr
145                 150                 155                 160

Tyr Phe Glu Val Asp Ser Phe Arg Lys Tyr Cys Leu Tyr Asn Gly Leu
                 165                 170                 175

Asp Asp Ile Gly Leu Thr Leu Lys Gln Glu Ser Lys Ile Gly Glu Phe
             180                 185                 190

Glu Lys Lys Gln Lys Glu Val Glu Pro Trp Leu Tyr Ala Ile
        195                 200                 205

<210> SEQ ID NO 109
<211> LENGTH: 1077
<212> TYPE: DNA
<213> ORGANISM: Leptospira interrogans
<220> FEATURE:
<221> NAME/KEY: CDS
<222> LOCATION: (1)..(1077)

<400> SEQUENCE: 109 atg aag aat gta gca gta ctt tca gga gac gga atc gga ccg gaa gtc      48
Met Lys Asn Val Ala Val Leu Ser Gly Asp Gly Ile Gly Pro Glu Val
 1               5                  10                  15 atg gag ata gcc atc tcc gtt ttg aaa aag gct ctc ggt gca aaa gtt      96
Met Glu Ile Ala Ile Ser Val Leu Lys Lys Ala Leu Gly Ala Lys Val
             20                  25                  30 tcc gag ttt caa ttt aaa gaa gga ttt gta ggt gga atc gca atc gat     144
Ser Glu Phe Gln Phe Lys Glu Gly Phe Val Gly Gly Ile Ala Ile Asp
         35                  40                  45 aaa act gga cac cca ctt cca ccg gaa act ctt aaa cta tgt gaa gaa     192
Lys Thr Gly His Pro Leu Pro Pro Glu Thr Leu Lys Leu Cys Glu Glu
 50                  55                  60 tct tcc gca att ctt ttc gga agt gtg gga ggt cct aaa tgg gaa aca     240
Ser Ser Ala Ile Leu Phe Gly Ser Val Gly Gly Pro Lys Trp Glu Thr
 65                  70                  75                  80 ctc cct ccg gaa aaa caa ccg gaa cga ggg gca ctt cta cct ttg aga     288
Leu Pro Pro Glu Lys Gln Pro Glu Arg Gly Ala Leu Leu Pro Leu Arg
                 85                  90                  95 aaa cat ttt gat cta ttt gca aac tta aga cct gcg atc att tat cca     336
Lys His Phe Asp Leu Phe Ala Asn Leu Arg Pro Ala Ile Ile Tyr Pro
             100                 105                 110 gag ttg aaa aat gct tct cca gtt cgt tct gat att att gga aac gga     384
Glu Leu Lys Asn Ala Ser Pro Val Arg Ser Asp Ile Ile Gly Asn Gly
         115                 120                 125
```

-continued

| | | | | | | | | | | | | | | | |
|---|---|---|---|---|---|---|---|---|---|---|---|---|---|---|---|
| tta | gat | att | ctc | ata | tta | aga | gag | tta | acc | gga | gga | att | tat | ttt | gga | 432 |
| Leu | Asp | Ile | Leu | Ile | Leu | Arg | Glu | Leu | Thr | Gly | Gly | Ile | Tyr | Phe | Gly | |
| | 130 | | | | 135 | | | | 140 | | | | | | | |

```
tta gat att ctc ata tta aga gag tta acc gga gga att tat ttt gga    432
Leu Asp Ile Leu Ile Leu Arg Glu Leu Thr Gly Gly Ile Tyr Phe Gly
    130             135             140 caa cca aaa gga aga gaa gga tca ggt cag gaa gaa ttt gca tac gac    480
Gln Pro Lys Gly Arg Glu Gly Ser Gly Gln Glu Glu Phe Ala Tyr Asp
145             150              155                 160 acg atg aag tat tcc aga aga gaa atc gaa agg att gct aaa gtc gca    528
Thr Met Lys Tyr Ser Arg Arg Glu Ile Glu Arg Ile Ala Lys Val Ala
                165             170              175 ttc cag gcg gcc aga aaa aga aat aat aaa gtg act agt atc gat aaa    576
Phe Gln Ala Ala Arg Lys Arg Asn Asn Lys Val Thr Ser Ile Asp Lys
            180             185              190 gca aac gtc ttg act act tcc gtt ttt tgg aag gaa gta gta atc gaa    624
Ala Asn Val Leu Thr Thr Ser Val Phe Trp Lys Glu Val Val Ile Glu
        195             200              205 ttg cat aag aaa gaa ttt tca gac gtc caa ttg aat cat ctt tat gtg    672
Leu His Lys Lys Glu Phe Ser Asp Val Gln Leu Asn His Leu Tyr Val
    210             215              220 gac aat gcg gcg atg cag tta atc gta aat ccg aaa caa ttc gac gtg    720
Asp Asn Ala Ala Met Gln Leu Ile Val Asn Pro Lys Gln Phe Asp Val
225             230              235                 240 gtt ctt tgt gag aat atg ttt ggt gat att ctt tcg gac gag gct tcc    768
Val Leu Cys Glu Asn Met Phe Gly Asp Ile Leu Ser Asp Glu Ala Ser
                245             250              255 atc att acg ggt tca atc gga atg ctt cct tct gcc tct ctt tcc gaa    816
Ile Ile Thr Gly Ser Ile Gly Met Leu Pro Ser Ala Ser Leu Ser Glu
            260             265              270 tct gga ttt gga ttg tat gaa cct tct ggt ggt tct gcg ccg gac ata    864
Ser Gly Phe Gly Leu Tyr Glu Pro Ser Gly Gly Ser Ala Pro Asp Ile
        275             280              285 gcc gga aaa gga gtg gca aat ccg att gct caa gta ttg agt gcg gcg    912
Ala Gly Lys Gly Val Ala Asn Pro Ile Ala Gln Val Leu Ser Ala Ala
    290             295              300 ttg atg tta cgt tat tct ttt tct atg gaa gaa gaa gca aac aag ata    960
Leu Met Leu Arg Tyr Ser Phe Ser Met Glu Glu Glu Ala Asn Lys Ile
305             310              315                 320 gaa acc gcc gtg cgt aaa acg att gcc tcc gga aaa aga acc aga gac   1008
Glu Thr Ala Val Arg Lys Thr Ile Ala Ser Gly Lys Arg Thr Arg Asp
                325             330              335 ata gcg gaa gta gga tct acg atc gta gga act aaa gaa atc ggt caa   1056
Ile Ala Glu Val Gly Ser Thr Ile Val Gly Thr Lys Glu Ile Gly Gln
            340             345              350 ttg atc gaa tcc ttt ctc taa                                        1077
Leu Ile Glu Ser Phe Leu
        355

<210> SEQ ID NO 110
<211> LENGTH: 358
<212> TYPE: PRT
<213> ORGANISM: Leptospira interrogans

<400> SEQUENCE: 110

Met Lys Asn Val Ala Val Leu Ser Gly Asp Gly Ile Gly Pro Glu Val
1               5                   10                  15

Met Glu Ile Ala Ile Ser Val Leu Lys Lys Ala Leu Gly Ala Lys Val
            20                  25                  30

Ser Glu Phe Gln Phe Lys Glu Gly Phe Val Gly Gly Ile Ala Ile Asp
        35                  40                  45

Lys Thr Gly His Pro Leu Pro Pro Glu Thr Leu Lys Leu Cys Glu Glu
    50                  55                  60
```

```
Ser Ser Ala Ile Leu Phe Gly Ser Val Gly Gly Pro Lys Trp Glu Thr
65              70                  75                  80

Leu Pro Pro Glu Lys Gln Pro Glu Arg Gly Ala Leu Leu Pro Leu Arg
            85                  90                  95

Lys His Phe Asp Leu Phe Ala Asn Leu Arg Pro Ala Ile Ile Tyr Pro
                100                 105                 110

Glu Leu Lys Asn Ala Ser Pro Val Arg Ser Asp Ile Ile Gly Asn Gly
            115                 120                 125

Leu Asp Ile Leu Ile Leu Arg Glu Leu Thr Gly Gly Ile Tyr Phe Gly
130                 135                 140

Gln Pro Lys Gly Arg Glu Gly Ser Gly Gln Glu Glu Phe Ala Tyr Asp
145                 150                 155                 160

Thr Met Lys Tyr Ser Arg Arg Glu Ile Glu Arg Ile Ala Lys Val Ala
                165                 170                 175

Phe Gln Ala Ala Arg Lys Arg Asn Asn Lys Val Thr Ser Ile Asp Lys
                180                 185                 190

Ala Asn Val Leu Thr Thr Ser Val Phe Trp Lys Glu Val Val Ile Glu
            195                 200                 205

Leu His Lys Lys Glu Phe Ser Asp Val Gln Leu Asn His Leu Tyr Val
210                 215                 220

Asp Asn Ala Ala Met Gln Leu Ile Val Asn Pro Lys Gln Phe Asp Val
225                 230                 235                 240

Val Leu Cys Glu Asn Met Phe Gly Asp Ile Leu Ser Asp Glu Ala Ser
                245                 250                 255

Ile Ile Thr Gly Ser Ile Gly Met Leu Pro Ser Ala Ser Leu Ser Glu
                260                 265                 270

Ser Gly Phe Gly Leu Tyr Glu Pro Ser Gly Gly Ser Ala Pro Asp Ile
                275                 280                 285

Ala Gly Lys Gly Val Ala Asn Pro Ile Ala Gln Val Leu Ser Ala Ala
            290                 295                 300

Leu Met Leu Arg Tyr Ser Phe Ser Met Glu Glu Ala Asn Lys Ile
305                 310                 315                 320

Glu Thr Ala Val Arg Lys Thr Ile Ala Ser Gly Lys Arg Thr Arg Asp
                325                 330                 335

Ile Ala Glu Val Gly Ser Thr Val Gly Thr Lys Glu Ile Gly Gln
                340                 345                 350

Leu Ile Glu Ser Phe Leu
            355

<210> SEQ ID NO 111
<211> LENGTH: 1122
<212> TYPE: DNA
<213> ORGANISM: Leptospira interrogans
<220> FEATURE:
<221> NAME/KEY: CDS
<222> LOCATION: (1)..(1122)

<400> SEQUENCE: 111 atg gtt gct gaa ttg acc gca tta cgc gat caa att gat gaa gtc gat     48
Met Val Ala Glu Leu Thr Ala Leu Arg Asp Gln Ile Asp Glu Val Asp
1               5                   10                  15 aaa gcg ctg ctg aat tta tta gcg aag cgt ctg gaa ctg gtt gct gaa     96
Lys Ala Leu Leu Asn Leu Leu Ala Lys Arg Leu Glu Leu Val Ala Glu
            20                  25                  30 gtg ggc gag gtg aaa agc cgc ttt gga ctg cct att tat gtt ccg gag    144
Val Gly Glu Val Lys Ser Arg Phe Gly Leu Pro Ile Tyr Val Pro Glu
        35                  40                  45
```

-continued

| | | |
|---|---|---|
| cgc gag gca tct atg ttg gcc tcg cgt cgt gca gag gcg gaa gct ctg<br>Arg Glu Ala Ser Met Leu Ala Ser Arg Arg Ala Glu Ala Glu Ala Leu<br>  50                          55                      60 | 192 |
| ggt gta ccg cca gat ctg att gag gat gtt ttg cgt cgg gtg atg cgt<br>Gly Val Pro Pro Asp Leu Ile Glu Asp Val Leu Arg Arg Val Met Arg<br>65                   70                      75                 80 | 240 |
| gaa tct tac tcc agt gaa aac gac aaa gga ttt aaa aca ctt tgt ccg<br>Glu Ser Tyr Ser Ser Glu Asn Asp Lys Gly Phe Lys Thr Leu Cys Pro<br>                    85                      90                 95 | 288 |
| tca ctg cgt ccg gtg gtt atc gtc ggc ggt ggc ggt cag atg gga cgc<br>Ser Leu Arg Pro Val Val Ile Val Gly Gly Gly Gly Gln Met Gly Arg<br>           100                      105                 110 | 336 |
| ctg ttc gag aag atg ctg acc ctc tcg ggt tat cag gtg cgg att ctg<br>Leu Phe Glu Lys Met Leu Thr Leu Ser Gly Tyr Gln Val Arg Ile Leu<br>       115                      120                     125 | 384 |
| gag caa cat gac tgg gat cga gcg gct gat att gtt gcc gat gcc gga<br>Glu Gln His Asp Trp Asp Arg Ala Ala Asp Ile Val Ala Asp Ala Gly<br>130                        135                      140 | 432 |
| atg gtg att gtt agt gtg cca atc cac gtt act gag caa gtt att ggc<br>Met Val Ile Val Ser Val Pro Ile His Val Thr Glu Gln Val Ile Gly<br>145                        150                      155               160 | 480 |
| aaa tta ccg cct tta ccg aaa gat tgt att ctg gtc gat ctg gca tca<br>Lys Leu Pro Pro Leu Pro Lys Asp Cys Ile Leu Val Asp Leu Ala Ser<br>                165                      170                     175 | 528 |
| gtg aaa aat ggg cca tta cag gcc atg ctg gtg gcg cat gat ggt ccg<br>Val Lys Asn Gly Pro Leu Gln Ala Met Leu Val Ala His Asp Gly Pro<br>               180                      185                     190 | 576 |
| gtg ctg ggg cta cac ccg atg ttc ggt ccg gac agc ggt agc ctg gca<br>Val Leu Gly Leu His Pro Met Phe Gly Pro Asp Ser Gly Ser Leu Ala<br>       195                      200                     205 | 624 |
| aag caa gtt gtg gtc tgg tgt gat gga cgt aaa ccg gaa gca tac caa<br>Lys Gln Val Val Val Trp Cys Asp Gly Arg Lys Pro Glu Ala Tyr Gln<br>210                        215                      220 | 672 |
| tgg ttt ctg gag caa att cag gtc tgg ggc gct cgg ctg cat cgt att<br>Trp Phe Leu Glu Gln Ile Gln Val Trp Gly Ala Arg Leu His Arg Ile<br>225                        230                      235               240 | 720 |
| agc gcc gtc gag cac gat cag aat atg gcg ttt att cag gca ctg cgc<br>Ser Ala Val Glu His Asp Gln Asn Met Ala Phe Ile Gln Ala Leu Arg<br>               245                      250                     255 | 768 |
| cac ttt gct act ttt gct tac ggg ctg cac ctg gca gaa gaa aat gtt<br>His Phe Ala Thr Phe Ala Tyr Gly Leu His Leu Ala Glu Glu Asn Val<br>           260                      265                     270 | 816 |
| cag ctt gag caa ctt ctg gcg ctc tct tcg ccg att tac cgc ctt gag<br>Gln Leu Glu Gln Leu Leu Ala Leu Ser Ser Pro Ile Tyr Arg Leu Glu<br>       275                      280                     285 | 864 |
| ctg gcg atg gtc ggg cga ctg ttt gct cag gat ccg cag ctt tat gcc<br>Leu Ala Met Val Gly Arg Leu Phe Ala Gln Asp Pro Gln Leu Tyr Ala<br>290                        295                      300 | 912 |
| gac atc att atg tcg tca gag cgt aat ctg gcg tta atc aaa cgt tac<br>Asp Ile Ile Met Ser Ser Glu Arg Asn Leu Ala Leu Ile Lys Arg Tyr<br>305                        310                      315               320 | 960 |
| tat aag cgt ttc ggc gag gcg att gag ttg ctg gag cag ggc gat aag<br>Tyr Lys Arg Phe Gly Glu Ala Ile Glu Leu Leu Glu Gln Gly Asp Lys<br>               325                      330                     335 | 1008 |
| cag gcg ttt att gac agt ttc cgc aag gtg gag cac tgg ttc ggc gat<br>Gln Ala Phe Ile Asp Ser Phe Arg Lys Val Glu His Trp Phe Gly Asp<br>               340                      345                     350 | 1056 |
| tac gca cag cgt ttt cag agt gaa agc cgc gtg tta ttg cgt cag gcg<br>Tyr Ala Gln Arg Phe Gln Ser Glu Ser Arg Val Leu Leu Arg Gln Ala<br>       355                      360                     365 | 1104 |

```
aat gac aat cgc cag taa                                              1122
Asn Asp Asn Arg Gln
    370
```

<210> SEQ ID NO 112
<211> LENGTH: 373
<212> TYPE: PRT
<213> ORGANISM: Leptospira interrogans

<400> SEQUENCE: 112

```
Met Val Ala Glu Leu Thr Ala Leu Arg Asp Gln Ile Asp Glu Val Asp
1               5                   10                  15

Lys Ala Leu Leu Asn Leu Leu Ala Lys Arg Leu Glu Leu Val Ala Glu
            20                  25                  30

Val Gly Glu Val Lys Ser Arg Phe Gly Leu Pro Ile Tyr Val Pro Glu
        35                  40                  45

Arg Glu Ala Ser Met Leu Ala Ser Arg Arg Ala Glu Ala Glu Ala Leu
    50                  55                  60

Gly Val Pro Pro Asp Leu Ile Glu Asp Val Leu Arg Arg Val Met Arg
65                  70                  75                  80

Glu Ser Tyr Ser Ser Glu Asn Asp Lys Gly Phe Lys Thr Leu Cys Pro
                85                  90                  95

Ser Leu Arg Pro Val Val Ile Val Gly Gly Gly Gln Met Gly Arg
            100                 105                 110

Leu Phe Glu Lys Met Leu Thr Leu Ser Gly Tyr Gln Val Arg Ile Leu
        115                 120                 125

Glu Gln His Asp Trp Asp Arg Ala Ala Asp Ile Val Ala Asp Ala Gly
    130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
                165                 170                 175

Val Lys Asn Gly Pro Leu Gln Ala Met Leu Val Ala His Asp Gly Pro
            180                 185                 190

Val Leu Gly Leu His Pro Met Phe Gly Pro Asp Ser Gly Ser Leu Ala
        195                 200                 205

Lys Gln Val Val Trp Cys Asp Gly Arg Lys Pro Glu Ala Tyr Gln
    210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                245                 250                 255

His Phe Ala Thr Phe Ala Tyr Gly Leu His Leu Ala Glu Glu Asn Val
            260                 265                 270

Gln Leu Glu Gln Leu Leu Ala Leu Ser Ser Pro Ile Tyr Arg Leu Glu
        275                 280                 285

Leu Ala Met Val Gly Arg Leu Phe Ala Gln Asp Pro Gln Leu Tyr Ala
    290                 295                 300

Asp Ile Ile Met Ser Ser Glu Arg Asn Leu Ala Leu Ile Lys Arg Tyr
305                 310                 315                 320

Tyr Lys Arg Phe Gly Glu Ala Ile Glu Leu Leu Glu Gln Gly Asp Lys
                325                 330                 335

Gln Ala Phe Ile Asp Ser Phe Arg Lys Val Glu His Trp Phe Gly Asp
            340                 345                 350

Tyr Ala Gln Arg Phe Gln Ser Glu Ser Arg Val Leu Leu Arg Gln Ala
        355                 360                 365
```

```
Asn Asp Asn Arg Gln
    370
```